US011268072B2

(12) United States Patent
Gruszka et al.

(10) Patent No.: US 11,268,072 B2
(45) Date of Patent: Mar. 8, 2022

(54) **COMPOSITION OF MATTER: ENGINEERING OF *ESCHERICHIA COLI* PHAGE K1E**

(71) Applicant: The Charles Stark Draper Laboratory, Inc., Cambridge, MA (US)

(72) Inventors: Sarah Gruszka, Cambridge, MA (US); Jason Holder, Swampscott, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 0 days.

(21) Appl. No.: 16/510,643

(22) Filed: Jul. 12, 2019

(65) Prior Publication Data

US 2019/0330599 A1 Oct. 31, 2019

Related U.S. Application Data

(60) Division of application No. 16/204,817, filed on Nov. 29, 2018, now abandoned, which is a continuation of application No. 15/908,235, filed on Feb. 28, 2018, now Pat. No. 10,174,295.

(60) Provisional application No. 62/539,932, filed on Aug. 1, 2017.

(51) Int. Cl.

*C12N 7/00* (2006.01)
*C12N 15/70* (2006.01)
*C12Q 1/70* (2006.01)
*C12Q 1/18* (2006.01)

(52) U.S. Cl.

CPC ............... *C12N 7/00* (2013.01); *C12N 15/70* (2013.01); *C12Q 1/18* (2013.01); *C12Q 1/70* (2013.01); *C12N 2795/10021* (2013.01); *C12N 2795/10031* (2013.01); *C12N 2795/10221* (2013.01); *C12N 2795/10231* (2013.01); *C12N 2795/10243* (2013.01)

(58) Field of Classification Search

CPC ................................ C12N 7/00; C12N 15/70; C12N 2795/10021; C12N 2795/10031; C12N 2795/10221; C12N 2795/10231; C12N 2795/10243; C12Q 1/18; C12Q 1/70

See application file for complete search history.

(56) References Cited

U.S. PATENT DOCUMENTS 6,322,783 B1 11/2001 Takahashi
6,331,425 B1 12/2001 Taylor et al.
8,603,950 B2 * 12/2013 Bowers .................. C07K 16/22 506/26
10,174,293 B1 1/2019 Gruszka et al.
10,174,294 B1 1/2019 Mcbrine et al.
10,202,610 B2 * 2/2019 McBrine .............. C07K 14/005
10,329,539 B1 6/2019 Mcbrine et al.
10,494,638 B2 * 12/2019 Holder ................... C12N 15/86
10,815,535 B2 * 10/2020 Holder .............. B01L 3/502761
2003/0216338 A1 11/2003 Merril et al.
2012/0143024 A1 6/2012 Phillips et al.
2013/0122549 A1 5/2013 Lu et al.
2014/0302487 A1 10/2014 Koeris et al.
2016/0186147 A1 * 6/2016 Cady ....................... C12P 19/34 435/91.41
2017/0044502 A1 2/2017 Koeris et al.
2017/0268031 A1 9/2017 Nitin et al.
2017/0283779 A1 10/2017 Holder et al.
2017/0298456 A1 * 10/2017 Holder ..................... C12Q 1/70
2018/0155721 A1 * 6/2018 Lu .................... G01N 33/56916
2018/0223291 A1 8/2018 Holder et al.
2019/0249236 A1 * 8/2019 Su'etsugu ................ C12N 9/12
2020/0115727 A1 * 4/2020 Su'etsugu .............. C12N 15/10

FOREIGN PATENT DOCUMENTS

WO WO-0100234 A2 * 1/2001 ............ A61K 39/00
WO WO-2004/041156 A2 5/2004
WO WO-2016100389 A1 * 6/2016 ............... C12N 7/00
WO WO-2018/148410 A1 8/2018

OTHER PUBLICATIONS

GenScript: Restriction Enzyme Map Analysis, https://www.genscript.com/tools/restriction-enzyme-map-analysis; Accessed Apr. 20, 2020; Available Apr. 22, 2017.*

Zhang Y, Werling U, Edelmann W. Seamless Ligation Cloning Extract (SLiCE) cloning method. Methods Mol Biol. 2014; 1116:235-44.*

Dalhoff A. Differences between bacteria grown in vitro and in vivo. J Antimicrob Chemother. Jan. 1985;15 Suppl A:175-95. (Year: 1985).*

"In vitro". Wikipedia.org. Accessed Jan. 27, 2021. (Year: 2021).*

Pires DP, Cleto S, Sillankorva S, Azeredo J, Lu TK. Genetically Engineered Phages: a Review of Advances over the Last Decade. Microbiol Mol Biol Rev. Jun. 1, 2016;80(3):523-43. doi: 10.1128/MMBR.00069-15. PMID: 27250768; PMCID: PMC4981678. (Year: 2016).*

Garamella J, Marshall R, Rustad M, Noireaux V. The All *E. coli* TX-TL Toolbox 2.0: A Platform for Cell-Free Synthetic Biology. ACS Synth Biol. Apr. 15, 2016;5(4):344-55. Epub Feb. 9, 2016. (Year: 2016).*

Shin J, Jardine P, Noireaux V. Genome replication, synthesis, and assembly of the bacteriophage T7 in a single cell-free reaction. ACS Synth Biol. Sep. 21, 2012;1(9):408-13. Epub Jul. 10, 2012. (Year: 2012).*

Ando H, Lemire S, Pires DP, Lu TK. Engineering Modular Viral Scaffolds for Targeted Bacterial Population Editing. Cell Syst. Sep. 23, 2015;1(3):187-196. (Year: 2015).*

(Continued)

*Primary Examiner* — Rachel B Gill
(74) *Attorney, Agent, or Firm* — Foley & Lardner, LLP

(57) ABSTRACT

The present disclosure provides compositions including recombinant K1E bacteriophages, methods for making the same, and uses thereof. The recombinant K1E bacteriophages disclosed herein are useful for the identification and/or antibiotic susceptibility profiling of specific bacterial strains/species present in a sample.

3 Claims, 38 Drawing Sheets

Specification includes a Sequence Listing.

(56) References Cited

OTHER PUBLICATIONS

Stammen S, Schuller F, Dietrich S, Gamer M, Biedendieck R, Jahn D. Application of *Escherichia coli* phage K1E DNA-dependent RNA polymerase for in vitro RNA synthesis and in vivo protein production in Bacillus megaterium. Appl Microbiol Biotechnol. Sep. 2010;88(2):529-39. Epub Jul. 2, 2010. (Year: 2010).*

Pires DP, Cleto S, Sillankorva S, Azeredo J, Lu TK. Genetically Engineered Phages: a Review of Advances over the Last Decade. Microbiol Mol Biol Rev. Jun. 1, 2016;80(3):523-43. (Year: 2016).*

Caschera F. Bacterial cell-free expression technology to in vitro systems engineering and optimization. Synth Syst Biotechnol. Aug. 7, 2017;2(2):97-104. (Year: 2017).*

Engler C, Kandzia R, Marillonnet S. A one pot, one step, precision cloning method with high throughput capability. PLoS One. 2008; 3(11):e3647. Epub Nov. 5, 2008. (Year: 2008).*

Stummeyer K, Schwarzer D, Claus H, Vogel U, Gerardy-Schahn R, Mühlenhoff M. Evolution of bacteriophages infecting encapsulated bacteria: lessons from *Escherichia coli* K1-specific phages. Mol Microbiol. Jun. 2006;60(5):1123-35. doi: 10.1111/j.1365-2958.2006.05173.x. PMID: 16689790. (Year: 2006).*

Sun ZZ, Yeung E, Hayes CA, Noireaux V, Murray RM. Linear DNA for rapid prototyping of synthetic biological circuits in an *Escherichia coli* based TX-TL cell-free system. ACS Synth Biol. Jun. 20, 2014;3(6):387-97. Epub Dec. 4, 2013. (Year: 2013).*

New England Biolabs. NEBuilder® HiFi DNA Assembly Master Mix/NEBuilder HiFi DNA Assembly Cloning Kit: Instruction Manual. Ver. 1.2, Dec. 2015. (Year: 2015).*

Tikh IB, Samuelson JC. Leveraging modern DNA assembly techniques for rapid, markerless genome modification. Biol Methods Protoc. Dec. 27, 2016;1(1):bpw004. (Year: 2016).*

Haq IU, Chaudhry WN, Akhtar MN, Andleeb S, Qadri I. Bacteriophages and their implications on future biotechnology: a review. Virol J. Jan. 10, 2012;9:9. (Year: 2012).*

Ando, et al., "Engineering Modular Viral Scaffolds for Targeted Bacterial Population Editing", Cell Systems; Sep. 23, 2015; pp. 187-196; Elsevier Inc.

Chen,et. al., "Development of Engineered Bacteriophages for *Escherichia coli* Detection and High-Throughput Antibiotic Resistance Determination". ACS Sensors; 2017 pp. 484-489.

Dow et al., "Acoustic Seperation in Plastic Microfluidics for rapid detection of bacteria in blood using engineered bacteriophage" Lab on a Chip 2018; pp. 923-932.

*Escherichia coli* (Migula) Castellani and Chalmers (ATCC 700973 ™ ). Accessed online Apr. 23, 2018. ATCC Product catalog.

*Escherichia coli* (Migula) Castellani and Chalmers (ATCC? 11775 ™). Accessed on line Apr. 23, 2018. ATCC Product catalog.

International Search Report and Written Opinion for PCT/US2018/044634 dated Oct. 25, 2018.

New England Biolabs, Inc. "Pfl F 1". Nov. 2013. Accessed at https ://web .archive.org/web/20131102121559/https://www.neb.com/ products/r0595-pflfi.

Notice of Allowance on U.S. Appl. No. 15/908,235 dated Sep. 6, 2018.

Stummeyer K, Schwarzer D, Claus H, Vogel U, Gerardy-Schahn R, Muhlenhoff M. Evolution of bacteriophages infecting encapsulated bacteria: lessons from *Escherichia coli* K1-specific phages. Mol Microbial. Jun. 2006;60(5):1123-35.

U.S. Office Action for U.S. Appl. No. 15/908,235, dated Apr. 26, 2018.

Zhang et al., "The use of a Novel NanoLuc-Based Reporter Phage for the Detection of *Escherichia coli* O157:H7" Scientific Reports.

* cited by examiner

Figure 2

SEQ ID NO: 2

>Nanoluc insert with K1E homology to PflF1 cut site Gibson Assembly of PflFI upstream - SD_nanoluc - PflFI downstream AACACCTGCGGCTTAATTGTAAAGACGAAGGAGATTCAACATGGTCTTCACACTCGAAGATTTCGTTGGGGAC
TGGCGACAGACAGCCGGCTACAACCTGGACCAAGTCCTTGAACAGGGAGGTGTGTCCAGTTTGTTTCAGAAT
CTCGGGGTGTCCGTAACTCCGATCCAAAGGATTGTCCTGAGCGGTGAAAATGGGCTGAAGATCGACATCCAT
GTCATCATCCCGTATGAAGGTCTGAGCGGCGACCAAATGGGCCAGATCGAAAAAATTTTTAAGGTGGTGTAC
CCTGTGGATGATCATCACTTTAAGGTGATCCTGCACTATGGCACACTGGTAATCGACGGGGTTACGCCGAACA
TGATCGACTATTTCGGACGGCCGTATGAAGGCATCGCCGTGTTCGACGGCAAAAAGATCACTGTAACAGGGA
CCCTGTGGAACGGCAACAAAATTATCGACGAGCGCCTGATCAACCCCGACGGCTCCCTGCTGTTCCGAGTAAC
CATCAACGGAGTGACCGGCTGGCGGCTGTGCGAACGCATTCTGGCGTAAAGGTCAATAGTGCTTAACAAACA
CT

Figure 3(A)

SEQ ID NO: 3

>K1E_nanoluc_PflFI_recombined_genome Enterobacteria phage K1E, complete genome

TCTCGCCCTCGCCCTCGCCGGATTTTCCCCATATGGGGCCGCGCTGCGGTTGGCTTGGGGATTGGGCTAGGCT
GGGCCGTCTTCAACCTGCTGCCGCAGGAAGCTCGATGGGTTGGCTGAGGGTTGCCGAGGGCTGCGCTTAGTG
GTACACAAGTAGAACGCCTAGGAAGCGCTAGGGCACGCCTTAGTGTTGGACAAGGTGATTGCCTTAGTGCAA
CCGTTTAGGGCTTACACAGGCCGTTTTAGGGCAATTCCTGAGTGTTTGACAGGGTGTGAGGGTGTGGGCTATC
TGTTCGTTTCGCTACGCTTCACTCACTGCTCCTCACTTCGCTGTCGCTCGCTACACTGCCTGTCGTGTACCTTAG
GTTATTCCTTGAGGGATGGCTTAGGTTAGCCTTAGTGGGCTACCTTAGTTAAAGCCTTAGTGCTTAGCTTAGTA
TCAACTTAGTAGTGTACCTTAGTTAGTCTTAGTGCCAGACCTTAGTGATTGCATAGCTAAAGCTATAAGATGCA
ATTAGGTCGCGGTCGGTAGACCGCTGAGAGTAGGTAATAGTGATAAGATGCAGTAGGAGGAACACCAGAAA
CCTAGCCATCCTAGCCTATCCTAGCTCTGTATCTATTGCTTTCCTTAGTCTCACATGTTAGACAACCTAGGTTTAT
CTTAGTAGTTGTGACATGTATCACATAAATAATCTATCTTAGTTAAATTTAGTGTTGACACAGGCAATCAACAG
ATATACATTAGCAATCACTGAGACGGACCTAGCAAGCTGTCTCAGGTTATAAGTAGGAGAATTGATGCGTAG
GCCGTAGCTAGCGGATGTAGTCGCATGAAGGCTTGAGCAAGGGGCCGTTTAATACCTTCTTCCTCTGGAGACA
AAGCTTATAACATTGCTCTTTAACAATTTGCTTAGTGTAACCTATGTATGCCGTGGTTAATTACTTATTGAATGA
GGAATTAACTATGAATTATGAAGAAATGTATGAAGTCTATTTCGACTCATTAGATGAAGGCGAAGAAGCATTA
TCCTACGCTGAGTTTGTGGAGGCTTTATCATGATTCTGAATAACCGTGAACTGTCCGTTCTCTTCACTCTGTTAT
GCTACATGATTCGTAATAACGAATTACTTACAGATGACGAGATGGCACTATATCACCGCTTTCTTAACGAAGGT
TGGACAGATACAGTTAACCAGAAACGTGACTTGATGAAGGAGTTAAGTAATGATTCAGTTGACTGAAGACCA
ACTAAAGCAACTCTTAGTCGACGCGTGGTTTGCTGGTCATGAAACCTCGCAATACACGCCTAACTCTTACGGTG
ATGCTAACAGATATGCACGCTCTACATTAAAGGAGGTTAAAGAGGATGTATCAGCATGAGGTTTTCTTCGAAT
CAGCTAGTGAAGCTATCCGCTTCCATGATGATATGATGCAAGCTGGCGTAGGTGTTGATGTGTATCACTATTT
GATAGATTACGACACTGAATATCACCGAGTTACCTTAGTATCTGAGTATGACAACCAAGTCATTACTGAGTATC
TAGGTAGTGAAGATTATGATTACGATGAAGTAATCACAACAAATCTCTAAATTAACTATTGACAGCCACGGCA
TACAAGGCTACATTAAGCATCAAGACGGCGACGTCTTTAAACATCCCGCTCTTTAACAATCTGGCTAGTGCCTT
GGTAGGCTAACTACTTACTAAGGTGAACTATGAACTACTGCGACATCGCTCACGAATTACGCATGGAACGTGA
GAAACAAGAGAAGCGGATTATCAAGAAGATGGCTGTACTGCTTGCACACTATAAGGCAGACAAACAGCCAAC
ACATGATGAGTTCGTGGACTTCTGTAACATGTATCTTAATGTGAGTAAGGCCACTGGTTACAGATGGCTTAAA
GCACTGAATGATGGAGAATTGTAGCAATAAGCCAGCTTAATAGCTGGCCTATCAAGGCACTAACCTAGCTCTT
TAACAATCCGGTTTGTGTCTTGATAGGCTTACTAACAAAGGTGAACTATCATGACTAACGCACAACGTAAACG
CTATGATGCATTGCAAGAGAAACTTGCTGTTGCTTATGCCGCTTGGCAAGCTAACACAGACAAGAGCAAACAC
GATAAACTTTATAGTAAAGTGGTTGCAATTAATGCTAAAATAGATAAACTTGTGAATAGTATCTTATAAGATAG
TTGCTGGCACTAGCCAGCCTATCAAGGCACAAGCCACGCTCTTTTAACAATATGGGTAGTCGCTTCTTAGTCTG
GATAGGTTAAACCTAGGGTATTCTTTTGAGTGCCCTATAATGTAACCTAACTAACTAATGAGGATTAAATCATG
GAACGCAATGCTAACGCTTACTACAATCTTCTGGCTGCAACTGTTGAAGCATTCAACGAGCGCATTCAGTACG
ATGAGATCCGCGAAGGTGATGATTACTCTGATGCACTACATGAGGTTGTAGACAGCAATGTTCCAGTTTATTA
CAGCGAAATCTTTACTGTGATGGCTGCTGATGGCATTGATATTGAATTTGAGGATGCAGGTTTGATTCCTGATA
CGAAGGATGTAACCAAGATTCTACAAGCTCGCATCTATGAGTCTCTTTATAATGATGTACCAAATGATAGTGAT
GTAGTTTGGTATGAAGACGAGGAAGAATAAAGATGGAAAGGCAATATAACTTCATCTTCTCAGACGGTGTAA
CCCTGAAATGTTCCTTACGATTTGCGCAGATTCGTGAGGAAGTGCTAGGTACTACATACAAACTATTTAGCTGA
CACTATAAGAGAAGGCTTAACAAGGCGTTGCTACGGTAGCGCCTGATTAAACTTTCACTTACTAGGAGTTAAG
ACTATGGATTTAGATAGCATCATTATGGCATTTGCTCTTATTGGCTTAAGCTGGTGCTCCTATCACCTTTACCGT
GAGTTCTTATTTGATAAAGCTAAACGCAAACTAAGAAAGGAAGGCGGTAACTACCTCTGTGTAAGAGGCGGT

Figure 3(B)

TTAGTCGAATATATTGCACCTAACGGCACGGAATGCGCCATTAACAAAGATGCATTTATAGAAACGTGGCATT
ACATCAAGTAACTAGCCTATAGCCTGCCTGTGTGGGCTATGTGATATTTACTTACACTATATAAGGTGACTATT
ATGACTACTGAAAACACCCTTCTGTCTGTTCGTGAAGCTGCAACCGCTGAAATCAAGCAGCACTTAGACAATAT
CGGCACTTCTTACATCAAAGTTGGCGCTTGTCTGAATGAATTACGCGGTGATTTCGAAGGTCAAAAAGACTTTT
TAGCTTATGTAGAATCAGAGTTCGGCATCAAGAAGGCACAATGCTACAAGCTGATGAGTGTAGCCCGTGTCTT
TGAAGGAGACGAACGCTTTAAAGGTGTGGCTATGCGTGTAATGCTGGCGCTTGTTCCTTTCGCTGATGAAAAT
ATAATCATGGAGAAGGCCGCAGAACTCGCCGCAGATGGCAAGCTGGACACTAACGCCGTAAACGCCCTGATT
GAGACTAAGAAAGAGATAAAGGCCGAAACGGTACAATCTAAGGCTGAGGCAGTAAAACCGCAGGAGAACGC
GACTGAGGCCGCAGAATCACAGGAAATGCAAGCGCCGCAGGTAGTGCCACCCGCGAGCGAGCAGGAGGCCG
ACGAATCAGCACCATGGGAAGAGGAAAGCAAGCCGGAAGCGCCAAAGGCAGCGCCGCTGGATAACACGGCT
AATACCGAAAACGCCGCTATGGCTAGCCTCTTAGCACAAATTAAGGCACTGACTGAGCAATTACAGGCAGCTA
ATGACCGCATCGCCTCCTTAAGTAGCGCACGCGAAAGCAAGAAGGCAGCCGCACCTATGCTGCCGCAATTCAA
ATCTTCCTGCTTCTATGCTCGCTTAGGGTTAAGCGCTGAGGAGGCAACGAAGAAAACAGCAGTTAACAAGGC
GCGCCGCGAACTGGTTAAGCTAGGCTACGGTGAAGGACATGAAGCATGGCCCTTAATCTCTGAGGCAGTAGA
AGAGTTGACTAAGTAACCTTATCGGTGGCATCTCCTTAGGTGTCACCTATTAAGGTTTCTTTCACTAGGAGTAA
ACAAGATGCAAGACCTACACGCTATTCAACTTCAACTTGAAGAAGAAATGTTTAACGGCGGCATCCGTCGCTT
TGAAGCGGACCAACAACGCCAGATTGCATCCGGTAATGAATCAGACACGGCATGGAATCGCCGCTTATTGTCC
GAACTAATCGCACCTATGGCGGAAGGTATTCAGGCTTACAAGGAAGAATACGAAGGCAAGAGAGGTCGTGC
ACCACGTGCATTAGCTTTCATTAACTGCGTAGGAAACGAAGTGGCAGCATATATCACCATGAAAATCGTTATG
GATATGCTGAATACAGACGTTACCTTACAAGCTATCGCTATGAATGTAGCAGACCGCATCGAGGACCAAGTAC
GTTTTAGCAAGCTGGAAGGTCACGCAGCTAAGTACTTTGAGAAAGTGAAGAAGTCGCTTAAGGCTAGCAAGA
CTAAATCTTATCGTCATGCGCACAACGTAGCGGTAGTAGCTGAGAAATCTGTTGCTGACCGTGACGCGGATTT
CTCCCGTTGGGAGGCATGGCCTAAAGACACCTTGCTGCAAATCGGTATGACCTTGCTCGAAATATTGGAGAAT
AGTGTATTCTTCAATGGTCAACCTGTCTTCCTTCGTACCTTGCGCACTAACGGCGGAAAGCATGGTGTTTACTA
TTTACAGACCAGTGAACATGTTGGCGAGTGGATAACTGCATTTAAGGAACATGTAGCGCAGCTCAGCCCTGCC
TATGCACCTTGCGTTATACCTCCCCGCCCTTGGGTATCACCTTTTAACGGTGGGTTTCATACTGAGAAAGTAGC
AAGCCGTATTCGTCTGGTAAAAGGCAATCGTGAGCACGTCCGCAAGCTGACCAAAAAGCAAATGCCAGCCGT
TTATAAGGCTGTTAACGCTTTGCAGGCAACTAAGTGGCAGGTTAATAAAGAGGTTTTACAGGTTGTGGAGGA
CGTTATACGTCTAGACCTCGGCTATGGTGTACCTTCCTTTAAACCACTCATCGACCGTGAGAACAAGCCAGCTA
ATCCGGTGCCGTTAGAGTTCCAGCACCTGCGAGGCCGTGAACTGAAAGAAATGTTAACACCGGAACAATGGC
AAGCCTTCATCAACTGGAAAGGTGAATGCACCAAGCTGTATACCGCTGAGACTAAGCGCGGCAGCAAATCGG
CGGCGACCGTCCGCATGGTAGGGCAGGCCCGTAAATACAGCCAATTTGACGCAATATACTTCGTGTATGCTCT
GGACAGCCGCAGCCGCGTCTACGCGCAATCTAGCACGCTCTCTCCGCAATCAAACGACTTAGGCAAGGCATTG
CTCCGTTTTACCGAAGGGCAGCGTCTTGATAGCGCTGAGGCGCTTAAGTGGTTTTTGGTGAACGGGGCTAATA
ACTGGGGTTGGGATAAGAAAACTTTTGACGTGCGCACCGCTAACGTGCTGGATAGTGAATTTCAAGACATGT
GCCGCGACATTGCAGCGGATCCGCTGACCTTCACTCAATGGGTAAATGCCGACTCCCCTTACGGCTTCCTTGCA
TGGTGCTTTGAATATGCGCGTTATCTGGATGCACTGGATGAAGGCACGCAAGACCAATTCATGACGCACCTCC
CAGTCCATCAAGATGGTAGTTGTTCTGGTATCCAGCACTACAGTGCTATGCTACGCGATGCAGTAGGTGCGAA
AGCAGTAAACCTTAAGCCCTCTGACTCTCCTCAAGATATTTATGGTGCCGTTGCGCAGGTAGTAATTCAGAAG
AATTATGCATACATGAATGCAGAGGATGCGGAAACCTTCACTTCTGGCAGCGTGACTTTAACAGGTGCGGAAC
TGCGTAGTATGGCTAGTGCGTGGGATATGATAGGAATCACTCGCGGCCTGACCAAAAAGCCCGTAATGACAC
TACCTTATGGCAGCACACGTCTAACCTGCCGTGAGTCAGTGATTGATTATATCGTTGATTTAGAAGAAAAAGA
GGCCCAACGGGCTATTGCGGAAGGGCGTACCGCCAATCCTGTACACCCTTTTGATAATGACCGTAAAGACAGC
CTGACACCTAGCGCAGCTTATAACTATATGACAGCTTTAATCTGGCCTTCTATCTCGGAAGTGGTTAAAGCCCC
TATAGTGGCAATGAAAATGATTCGTCAGCTTGCACGTTTCGCAGCTAAAAGAAACGAAGGCTTAGAATATCCC
TTACCAACTGGCTTCATCTTGCAACAAAAGATAATGGCTACCGATATGCTCCGCGTATCCACTTGCTTGATGGG
TGAAATCAAGATGAGTCTCCAGATTGAAACAGATGTAGTTGATGAAACGGCAATGATGGGTGCGGCTGCTCC

Figure 3(C)

TAACTTCGTCCATGGTCACGATGCTAGCCACCTGATTCTGACTGTATGTGACCTAGTGGATAAAGGTATTACAT
CCGTTGCAGTCATCCATGATTCTTTCGGTACTCATGCAGGACGTACCGCAGACCTGCGGGATAGCTTAAGGGA
AGAAATGGTTAAGATGTATCAAAACCATAATGCCCTGCAAAACCTGCTAGATGTGCACGAAGAGCGTTGGTTA
GTAGACACCGGAATCCAAGTACCAGAGCAAGGGGAGTTTGACCTTAACGAAATCTTAGTTTCAGACTATTGTT
TCGCATAATATTAATAGGCCATTCCTTCGGGAGTGGCTTTCTTTTACCTACTACCTGTAACATTTCATTAACATA
AAACGTGTCTCACATGTGAGACTTTATTTACCGGACACTATAGGATAGCCGTCGGAGACGGGAAAGAAAGGG
AAGATAAAGGATATAAAGGAAGTAATAGGTATTAAAGGTTATATAGGTTATCTAGGAATACCTATTACCTTCT
TCCTTCCTCTTATTACCACTTAGAGGAAGGGCAGACCTAGGTTGTCTCACATGTGAGACTTCGTATTTACCGGA
CAGTATAGATAAGATTAACTCACTTTGGAGATTTAACCATGCGTAACTTTGAGAAGATGACCCGTAAAGCTAA
CCGTTTTGACATGGAAGAAGGGCAGAAGAAAGGCAAGAAGCTGAATAAACCTGTCCGTGACCGTGCATCTAA
ACGCGCAGCGTGGGAGTTCTAAGTTATGGCTAAATACAGAATCAAGACCTGTTTAAATAGTCACGGGCAAGA
GTGTTACATAGTGCAACGTAAAGTATTAGGCTTAATATGGGTCACATGTATGATGCCTATTGGATATACTGATA
CAGAGGCTATCTTCTGCACCGAAAGGGATGCAAAGCAGTTTATCTCTAAGCGTAGAAAAGCTGACTCTTATCA
ACCCAGAACTATTAAGGTGAACTAATGGCTATTATTAATAACATCCCGTGTCCTGCTTGTCAGAAGAATGGAC
ACGATAAATCCGGCAACCACCTCATGATATTTGATGATGGTGCTGGCTATTGCAACCGTGGTCACTTCCATGAT
AATGGCAAGCCCTACTATCACAAGCCAGAGGGTGGCATCGAGATAACCGAATTGCCTATTACTGGCAATATCA
AATATACACCTTCTCAATTCAAAGAGATGGAGAAGGAAGGGAAGATAAGCGACCCTAAGTTGCGCGCCATCG
CACTTGGTGGTATGCGTATGAAAGACCGTTGGGAGGTCATGAATGAGCAAGAAAGGGCAGACCAAGAAGCA
GAGTGGAAACTTGATGTTGAATGGTTCCTCACGCTTAAGCGTAAGAACCTTGTGTCCCGTCACATTCGAGGTG
ACATCGCAGCAATGTACGATGTGCGCGTTGGACACGATGAAGAGGGAAGAGTCAACCGTCACTATTATCCAC
GATATGAAAAGGGTGTGCTTGTTGGAGCAAAATGCCGGACGTTGCCGAAGGATTTTAAGTTCGGACACCTAG
GTAAACTCTTTGGTATGCAAGACCTTTTCGGTATGAATACTTTGTCTCACGTGTTAGACAAGGGAAGACGAAA
GGATTGCTTGCTTATTGTGGGCGGCGAACTGGATGCACTAGCAGCACAGCAAATGCTCCTTGATTCTGCCAAG
GGTACTAAGTGGGAAGGCCAGCCTTACCATGTATGGTCTGCCAATAAAGGTGAGTCTTGCCTTGAAGAGATA
GTGCAAAACCGTGAGCACATAGCCCAATTCAAGAAGATTATATGGGGCTTTGATGGCGACGAGGTGGGGCA
GAAGCAGAACCAACAAGCTGCTCGCCTGTTTCCTGGCAAATCCTACATCCTCGAATATCCCTCTGGTTGCAAAG
ATGCTAACAAGGCATTGATGGCTGGCAAGGCTAAAGAGTTTGTTGATGCTTGGTTTAATGCCAAGTCATCTGA
TGAAGTCTTTGGTAGCCAGATTAAATCTATCGCATCTCAAAGGGATAAGCTCAAGGCTGCACGTCCAGAGCAA
GGACTATCATGGCCTTGGCCTAAGCTGAACAAGGTAACGCTAGGTATTCGTAAGAACCAGCTTATCATTGTAG
GTGCAGGCTCTGGTGTAGGTAAGACTGAGTTCCTTCGTGAAGTAGTTAAGCACCTCATTGAAGAACACGGTG
AATCTGTAGGCATCATTTCTACAGAAGACCCGATGGTCAAGGTGTCCCGTGCTTTTATCGGCAAGTGGATTGA
TAAGCGTATTGAGTTACCGCCAACCAACGACCCGAAAGAAGACGGATACCGTGAGGTGTTCGACTACACCGA
GGAAGAAGCTAACGCTGCCATTGATTATGTGGCTGATACAGGAAAGTTATTTGTGGCTGACCTAGAAGGCGA
CTATTCTATGGAGAAGGTAGAGCAAACTTGCCTAGAGTTTGAGGCTATGGGCATTTCTAATATCATCATTGATA
ACTTAACGGGGATTAAATTAGATGAGCGTGCTTTTGGTGGGAAGGTTGGTGCACTTGATGAATGCGTCAAAC
GAATTGGTACTATCAAAGACCGACATGCGGTTACGATTTTCCTTGTCTCTCACCTTACACGTCCTCCGGCAAAC
CGTACCCAACACGAAGAAGGTGGCGAAGTTATCCTTTCTGACTTCCGAGGCTCAGGCGCTATCGGATTCTGGG
CATCTTACGCCTTGGGGATTGAGCGTAATACAAGAGCTGAAACGCTTGACGAAAGGACTACCACGTACATCTC
ATGTGTCAAAGACCGCGACCAAGGTATCTGGACTGGAACCAAGGTCATGCTTAAGGGTGACATTCAAACCGG
ACGTTTAATGGAACCACAAGCCCGTACTAAGTCATTTGATACAGGTGAAGCAAGGCAACAAGAAGTGCCGGA
TTTACCGGACACTATAGAAGAGACAACCTTTGACGATGAACAGGAGTTTTAATGGAAATTATTAAACCAGTAT
TGAATATCGGTATTGAGATCCTATTCATGCTTGTGATCGCAGATTATGCTGCACGATATGGATTCAAGAAAGCT
GTGAAACTTATCGTTGCATCTGGTTTTCTTATGTCAATGTTCTTTATTGTAACACGCCTTATCTAGTGTATTTATC
AGGGCTTGTCTCACATGTGAGACAGGCTCTTATTAAGTACATTAAATAACTGGAGATTGATTATGTATAGATTA
GTATTGAATGTAGGTGATTATGTTCGTAACATCAATGAAGCCTCACGTCGTTATCGTTGCCGTGGTGTAGTGG
CTCGTGTAAGTGAGAACATGTATCATGTAGAATATGAGGATGGTATTAAGGCTTCTTACCACAAGAAAACAGC
ACATAAATATCTTGAAAAGATTGTAGAGATAAACAATCAATGTAAGTGCATACATGATGAGGTTTGCGATAAA

Figure 3(D)

TGTGCTCGCCAGATGCTTAAGAATTTCCTAGCTCCTCTTTATTATGGTGCTGGTCCTCAAACACTAGCAGAGTA
CATGGCAGAAAAGAAAACCACACTCAAGAAAGAGCGTCGCAATGTAATCACTGGTAAGACTCAAAGTGAAAT
GATTAAGCAATGTGGCACTGCATTAGGTGTTACACAGTTCAATACTCGTGCATTGGGTAAATCCACAGGGCAA
GCTATGGTGAAAATTGGTGAAGCTATGATGCACCCAAATGTGCCTGTGCGAATCTTGGATGTTGACCATGCAA
TCACAGAGCATGGCACACCACGGCGTGTAGCTAATAATCATTTCGCCGACACTATAGAAGGTATTATTCGTAA
GCAAGGGTTGAAGGGTCTTCACATCTTAAATGGTGAAGAATTACTGTACCTACCTATCGTTACTGAAGAAACC
TACGTGAATATCTAAGGAGTTAATCATGACTAAGGTATTAATTTATATGCGTGGACCTCATAAATGCTATGCAG
TTGTAGCACCAGATGGTGTCAAGACATATGGTACTTCAAAGGGGTTTGCATTAATAGGTGCCAGTCTTAGTGC
AAGTTTTCAGATGGAACTTTTCGGTCATTGGACTGAAAAAGAGTTCCGTGAGGAGTTTAATGTAATCGGCAGC
TTTATGGTGAAACATGCAAAATAAACACAGTCTTAAGATGTTTGATGGTCACGAAGACCTGCAAGCACAAATT
ACTAACCAAGCCTTCCTGTTTGCACAGTTAACTATGGCTGAAGCAAAGAAGAATAGCCTGACGCGCGAGCAAG
TTATCAAAGAGGCAACTTGGGAGCCACACCAAGGCAAATACATGGGCCAGAAATTAACTGTAACACGCAGTC
GATAAGTAAAGGGTTGTCTCACACGTGAGACAGCCTTTCATCATATTGATTGGAGGTGCATTATGCCACGTGA
TTATGATTCTGATTGGGATTTCCAAGATTCAATGAACTCAAAACCTGAACGTTCAGATGACTACTACGAAACAG
AGGCAATGTATGAAAGCTATTAAAGTCAGTAAGGTTTGCTCTTGCGGTAAAGGTTATCGCAGTCGTATTGATG
GTAAGTGTGGGCATTGCAGGTCTAAGAAAGAGGCTGCTTTGTTTGATAAGTACCACAATGAATTAGCATATAA
CTATCCTCATCTAACACCTAATTCTTTATTAGGACTTGGTTATAGGGTTAAATACTTTGGAGCAATCTATGAAAT
CAATTGATTGGAAGAAGGAAGCAGAAGGCCGCATCTTAGTGATGGATTCTGAGGCTAAAGGCCTGCTGGATG
CTATCCGATATGGCCACCGCGAAGATGTGCACATCATTTGCTGCATGGATTTGCTTACTACAGAGGAGTTCCTC
TTCTTTGACCCATACGAGATGCGTGACCCTGAAGCAAGAGAACGCCTAAAAGAATGGGAAGGCCATCAAGAT
GGAACATTGGTTGACGGTGTTAACTTCCTTAAACACTGCGAAGCCATCGTCTCACAGAACTTCCTAGGGTACG
ACGGCCTTCTATTTGAGAAAGCATTCCCTGATATCTGGAAAGGCTTTAACTATACCGAGAGACGCGGCAAGGG
CAGACTCCGCGCTGACCTGTGTCCGGTACGCGTCATGGATACGCTGGTCATGAGTCGCCTGTTAAACCCCGAT
AGACGCCTCCCTCCGCAAGCATACGCCAAAGGCATGGGTAACGTAGCCCCTCACTCAATTGAGGCGCACGGC
ATTCGTATAGGCCGTTATAAGCCGGAGAACGAGGATTGGTCTAAACTAACTGACCACATGGTACATCGTGTAC
GCGAGGACGTGGCGATAGGCCGTGACCTATTCCTCTGGCTATTTAACGGAGAATGGACGGAGCACAAACGCC
GTGGCGTGAATAAACGCACTGGCCTAGGTATTGAGACAGCCTTCCACATGGAGTCCATTGTGGCGCTGGAGA
TGAGCCGTCAGGCCGAGCGTGGATTCCGTCTGGATATAGATAAAGCATTAGCACGATGCGAGGAATTGGACG
CTAAGATTGATGAGACAGTCGCAGCGTTCCGTCCGCACATGCCTATGCGTATCAAGTCTAAACCTTTTAAACCG
GAAGAAAAGAATGAAGTATGCCAACGCGCAAATGAGTATGGAGCTAGCAACAATATACCTACTGTCCTTGAC
CCCTCTCACTTTCTTCACGCAGAGAGACGAGGAGATCGCAAGACAGTATGGAGTGTCACTACTAAGTCTGGTG
ATTGGTCGGCTAGCGTCAAGAAAGACTTTCCTCACCTTAGAGGAAACCGTAATGACACGCCAAGCATCAAGTG
GATTGGCGCTTACTCGCCTGTTACTTTCGAAGAGATTCCCTTGGGTAACAGGGATACAGTTAAGCAAGTGCTC
TATGATTATGGATGGAAAGGTGTTGAATTTAACGATACCGAGCAAGCGCATCTCGATGAGCATGGCGTATTAC
CCAAGCCTTGGAGTGGGAAGATAAATGAAAAGTCCCTTACTTTATGGCAAGAGAGAGCCGCACGTGAAGGTA
AAACAGTCCCTGATTGGTGCTTGGGTATCGCTGCATGGTACATACTCGTATCCCGTCGTGGTCAGATCCTCAAC
CGTGGTGACGTTGAAGCCTTCGACCAGAAGGGGGTGTGGCCTTCGCAAGCTGGTATACGAAAGTGTCGCGGC
CTTGTACCTGTAGCATTTAACAAGGAGTTAGGAATCAATGCGCAGCAATACTACGAAAGGTACGGATGCTGG
CCTACGTCAGACAAGGATGACGGAGAATGGCGTGTGCCAGCTATTGCTATTAGTATTGGAACTTCTACGTTCC
GTATGCGTCATCGTAACGTGGTTAATATTCCTGCCCGTGGTTTGTATCCTTTACGTGATTTATTCATAGCCGGTA
AAGGTAAGCTAATCCTTGGTTGTGATGGTGCTGGTCTTGAACTACGTGTACTGTCTCACTTCATGAATGACCCT
GAATATCAAGATATTGTACTGCATGGTGACATTCACACCCATAATCAAATGAAGGCTGGTCTTCCTAAGCGTG
ACATGGCGAAGACATTTATATATGCCTTCCTATATGGGTCTGGTATAGCTAACCTTGCAGCAGTATGTGGTGTT
ACTGAGGAAGAAATGGAGGAAGTTGTGGCAAGATTTGAGGTTGAACTACCATCTCTTGCACGTCTTCGTGAG
AATGTTATCGCACAAGGTAACAAGTTTGGCTACCTACAAGCACCTGATGGTCATTGGGGTCGCATCCGTATGT
CTGGTGGTGAACTTAAAGAGCACACTATGCTTAACGTACTACTCCAGATGACTGGTTCTCTGTGTATGAAATAC
GCATTGGTCAGAGCGTTTGCAGTGATGCGCAAGGAAGGTGTGGCCTTAGATAGCATGGGAAACCCTTGCGGT

Figure 3(E)

ATAGCTAACGTGCACGATGAAATCCAGATGGAAGTCCCTGAAGATGAGGTCTTGTATCTCAACTACGACTTGC
CTTTCACCTTAGAAGGGTTCGAAACAGAGAAGGCTGCTGTGAAAGCAGTGTTCGATGCAGAGGAGAAACGTG
TTCATGTGGATTCTGAAGGACGTATGTGGTCTGCTGCAAATCTCGTTAGCGTTGATGCTGATGCTGGTGTACTT
CATTGCCAGCGTCGCTATCACCGTGCAGGGCATATCATTGCCGACGCAATGACTTGGGCGGGTCAGTATCTGA
AGATGCGTTGTCCGATGGCAGGTGAGTATAAGATTGGTGCAAGTTGGAAGGAAACACACTGATGGACAGGTT
TGATATTGTTTGCCTATTCTCCACCTTCTTTCTTATATTCCTTATGCTTGCTTGCTATGGAAGTATGCGATTAGAT
ATACCTGATGAAGAGGAGGGTTACGATTGATGCAGGCATCTTTTATTATTCTTGGAGTCATATTATTTATGGTA
GTATTCTGGGCTTTCTCTGGCATTGACCCAGATTGTGATGGTAACTACGACTGAGTTATACTCAAGGTCACTTA
CGAGTGGCCTTTATGAATAACTTATTCCTACTTATTTTGTCTAACATGATTTACTGGACACTATAGAAGGAAAG
CCTAGGTAATCTAGGTTTATAAGGTAGTATAGGTAATTAAATAAATATAGGAGATATAAATATGTCTATGGTA
ACTACTCTGGTATTCGTGGCTCAATACTTTCGTGGTCTTGCTAATAAGTTCAAGTCCAAGGCTATCAAAGCTATT
GAGGCTCGCATCGAAGCAGTACAGGCAGAGCAAGTTAAAGTTGAAGAACATCGTAGTTCTCAAATGATTGAC
TGTCATAACCGCTACTATGCATCTCGTGATGAACTAAATGCACGTCAAGTCAAAGAGGTAGAAGATATGCTGG
CACGTCACCAGCAAGAGCGTGACAGCCTGAAAGCTGAATTTGAAGAGAACAAGGCATCAATTGCTCTTGTAA
ATCAAGCTGCATCTGACAGCCTGAAGAAAGAGATTGTTATGCTGGAAATAGAACTGGACAACTTGACTAAATA
AGGAGTTATGATGGAAGAAGTGATTCAAGCTAAACATGTAGGTATCATCTTTCGTGACCTAGAGCAGCGTAA
AGTTGCAGGTCACACTCGTCTGGCTAAAGAAGACGATACAGCAATCACTACTGTGGAACAAGCAGATGCCTAT
CGTGGTCCAGAGTTTACTCAAGGTGAAACTTGTCATCAATTGAGCCTTTCACTTTGTGACACTATGGCTAGTGT
AAATGTACAAGAGGTTGAAGATGGTGAATGTGTTAGTTATGTCTACCCTCTCGATACTATTGCACGTATTAAG
GTAGTTCATAAGTAATTACTGGACACTATAGAACAATAGGTCGGCTTAGTTCGGCCTATGATTGTAAAGTGTC
GTTGATGTTGAACCATTGTGCACCTTGCACAACCCGATACCGTATCGGGCTTTCTAGTGAGCACATGCTTGTGC
TCAGTACAAAGCTAACTGACAATAGGAGACTAAATAAATGGCACGTGGTGATTTCGATTTTGGTGCTTCCGTA
TCTAAAGCTGAAGGTAAAGTCTTTAAGAATCCAGAAGTAGGTGATCATGAAGCAGTAATCTCTGGCATCATTC
ATGTTGGTTCCTTCCAAGACATCTTTAAGAAAGGTAATACCACTGAAGTTAAGAAGCCAGCAAACTTTGTTCTG
GTTAAGATTGTCCTGATGGGTGACGATGACAAGAACGAAGATGGTTCTCGCATGGAACAATGGATGGCTGTG
CCTCTGAAGTCTGGTGATAAGGCAACACTGACTAAGTTCCTGAATGCAGTTGACCCTAAAGAGTTGCTGGGTG
GCTTCGATGATTTTATCGGTGAATGTCTGACTGCAACTATGGTTGGCTCTGGCGACAAGAATGATGATGGTAC
TTTCAAGTATGTTAACTGGAAAGGCTTTGGCGGTATGCCTGATAAGTTGAAGAAGCTTGTACTGGCTCAGGTA
GAAGAGGAAGGTCTGTCTATGACAGGTCATATCACCTTCGACAAGCTGACCAAAGAAATCATTGATGACATCC
CAGCTAACTTGGTACGTCAATACTTCCTGAACGAGACACCTCGTGGTAAGAACCTGTCTGTTGCTGGCTCTCAC
GTAGAAGCTATTATCAAAGCTGCTCGTGAAGAAGACCCTGAATGGAAGAAGGCTAAGAAGAAAGACGAGGA
AGATGCTACCCCAGCTAATCGTAAATCTCTGGATACTGGTGAGTCTGTTCCGCAGGAAGTACCTGAAGCAGAA
GATACGCCTGCACCGGAGATGGATGAGGACGCGGAATATTAAGGAGAACGGATGAAAGTACAAATCGTAAC
TCTGCATTGCAAGAAAGGAATCACCACACTTGGCGGCAATACTTTTCACTCCTTCTCTGAAGGGGAGACATAC
GCCGACCTTCACTATATCTGGCGTGACGGGCAGCACGTGGTGAACTACAGCGACCCTGCGACTGGTAAACGC
CACGGCGTGTCGCTTCCGGCGCACGACATTGCTCAGGTGAACACAGTTTTATAAAGTCTCACGTGTGAGACAA
ATCGGTGTCCGGTATTTACTGGACACTATAGAAGAGAAGAATTTTAATCGGCGATAATGCCATAACCAACAAA
AGGAGAATTTAATATGTTCAAGATTGAAACTATCGTAAACCGTGTTGTTAAAGGTGCTGCTCTGGTATCCGTTG
AGTCTTTCATTATCGTCGATGAAGCTGATCAACTGGTAGCTGGTACTAAGGCTTACGATACCCGTGAAGAAGC
TCAGGCTAAGATTGACAGCATGGGTAACTTCGCTGCTGGTCTGGAGTTTGCTCGTGCTTGCTTCCCTGAGCAG
GCTGACAAAGCCCAGATCGGTAAGGCTAACATCGTAGCTGAATATCTGGATTGGATTGCTGCTGGTAAACCA
GTGAAAGAAGTTAAAGCTGCTGAAGAAGCTGAAGCTCCGGCAGTAGAAGTGTCTGCACCGGAAGCTCCGGTT
AGCGAAGAGGAAGAGTTTTGATAATAGCAGGTGTAGCCTCTGTTAGTCCTAGTTGACTATCACGCTCACCTCA
TCTAATGCCCTGTCTGCCTTAGTGTAGGCAGGGTCTTTTGCGTAATAGTTATTGGAGAATGAATTATGCCGACT
ATTGAATCTCGAATTGAACTGGACATTAGCTACAATGCAATCACCAGACAGTATATTGGGGTTGCCTATGATTA
CAAAACTGGTGAGAAGCTAGTGGAGGTGAGACAATGGGATGACTATTGGTTAAGACAGAACCTCCATGATGC
GGTGTCCTCCTTCTTGAAGGAGTGGCCTACATGCGACCAAACTTCGACTTCGGAGCTACAGTATCGGAAGACA

Figure 3(F)

ATAATCTCATCCTGTGGCCAACTGAAGGTAATCGAATCGCTTTAATAGATGCTGATATGTTACCCTACATCGTA
GGTTATACAATCAGTGACATGACTTATTTACGAGCCACAACTCGTGTTAAGTCAGGACAAGTCCCATCAATCAA
AGATACACCTGAGTGTAAGCAAGCATGTGACCGTGTGAACTCCTTGCTTAACTCTTGGGTGTATGCAGCAGAG
TGTGATGCAGCTAAGCTATTCATGACGAAATCAGAAGCTAACTTCCGTGTCCGCCTAGCATTCACAAAGCCTTA
TAAGGGTCAACGTAAGACCGAGAAGCCTCCGTTCTTCTATGAATTGCGAGAGCATCTCTTAGAGGTTCACGGT
GCAATCTTGGCAGATGGTGAGGAAGCTGATGACCTCATGAGCATCGCACAATGGGATAGCCACCGCCGCTTC
CAGCAAGATACAGGTAACGAGTTCGCTATCGGTAGTCCAGAGCATAAAGCATTCTCTGATACTTGCATCGTTT
CCTTAGATAAGGATTTGATGATTGTTCCCGGTTGGCATCTACAGCCGGGTCAAGAGAAGAAGTGGGTAGAGC
CTATGGGCTGGCTTGAGCTACGCCGTAAGGTTAATGGGCAAGTCAAAGATCTAAAAGGTGCTGGCCTCATGTT
CCACTATGCACAGATGATTATCGGTGATGATATTGATAACTATGCTGGCATACCAGGTCGTGGTGCTAAATAT
GCCTATGATCTTCTCAAAGATTGTAAGACAGAGAAAGAGTTGTACATGGCAGTGCTGGGTGCTTACAAGGCTA
AGTTCGGGCATGGACAAGTTAAAATTAAGAATTACCGAGGTGGTTATCGTATCGGCAAAGCCTTTGACCTAAT
GCTTGAGTGTGGTCGCTTAGCTCACATGGCAAGATTCAAGGGTGATATATGGCGAGCCGATAAGAACCCAAT
CTTGTGGGGAGATGAAGGATGGCTACAAAGTTAAAAGCATCTGAAGTTGCTGCTTATAAGAAAGAGTTGCTA
GAGAAGCAGGGCTGGAAATGTCCTATTTGTGGAGCACCTCTTAAAGCAGTGGCCGAGATTAACCGAGTACTA
GACCATTGCCATCGCAGAGGTTACTGTAGAGCGGTACTCTGTCGTGGGTGCAATGGCGGTATCGGGAAGATA
GAAAACCTAGTAAAGACTTATTGTAAGGCTGGGGATAATGAGTATTTCATTATCAAGACATTGCGAAACATTG
CAGATTATCTAGACTTACATAGTAAGCCTCAGACTGATAAGATTTATCATAAACATCAAACGGAGGCAGAGAA
GCGCGAGGCTAAGAACCGTAAGGCACGCCTTGCTTATGCAAGAAAGAAGAAGGAGGTTAAAGTTGGGTAAG
CTTCGCAGCTTGTACAAAGACTCCGAGGTACTTGATGCAATCGAGCAAGCTACCGACGAGAAAGGTAATGTTA
ATTACAATGAGATGGCACGGATATTATCGTGCCACCCTGTGGGTAAGAAGATTACCCGCCAGTTGGCTAGATA
CTGGCATGGTCAATTCAAGAAGACCAAGAAGAATGGTGATTACTACCAGACCCTTCTGCAAGAGGATAAGCG
TATCAAGGAAGAGCGTAAGCTCAGGACTCCTGACCGCTACGAGGATTTGGCTATTGTACCATTGCCTGACTCG
CCTCATCGAAGTGTACTGGTAATCCCTGATACCCATGCACCGTATGAGCACCCAGATACCTTAGAGTTCCTTGC
AGCAGTGGCAGCACGTTACCGTCCTGATACGGTGGTTCATCTTGGAGATGAGGCAGACAAACATGCCTTATCG
TTCCACGATTCGGACCCAAATCTGGACAGTGCTGGCATGGAGTTAGAGAAGGCCCGTGTCTTTATGCATAAAT
TACACAAGATGTTTCCTGTGATGCGCCTGTGTCATTCTAATCACGGCTCTATGCACTTCCGTAAGGCAAGCGCC
AAAGGTATTCCTGTACAATATCTGCGTACCTATCGTGAAGTCTTCTTTCCGCATGGGGGTGGCGACCAGTGGG
ATTGGCAGCATACACACGTTCTTGAGTTGCCGAATGGTGAACAGGTTGCATTTAAGCATCAACCCGCAGGCTC
AGTCTTAGCAGATGCAGCGCATGAGCGCATGAACTTAGTGTGCGGTCACTTGCATGGTAAGATGTCGGTGGA
GTATGCACGTAATACACATGAACAGTATTGGGCTGTGCAGGGCGGCTGTTTGATTGATGAGTCATCTCGTGCA
TTTGCCTATGGTCGTGAGTCCAAATACAAGCCAGCATTAGGTTGTGTGGTTATTCTGGAGGGTGTGCCGCACA
TTGTCCCGATGCAGACCAATAGTGACAATCGCTGGATTGGTAAGATTTAGTTGACACTATAGAACAAAGGGTA
GGTATTAGCTTACCCTTGATTGTATAGTGAATGGAGGAATTAATATGTCACAATATGTATGTGAGAAATGCGG
CAATCGATATGATAACTGCACCTGTGATTATAATAAAGGTAAAAGGATTAAATCAGGTGATTATGTTATACGA
CGTGCAGGCTGCCGCGACCCAGAGTGGGGCAGGGTGTGTAAACTATTAGGCAAGAAATCAGATGCAACATTC
AAAGTTATAAAGGATGAGTCTGTCGGCAGCGCCATTATACTTGAAGGTATCGAAAAGCGAGAATGGTATGCA
CCTTATTTCGAGAGAGTGGCAACCCCACCAGTTGTACCTGAGTCTAATAACTCAAACGATAATATGGTTACGCA
ACCTAAGCACTACGAGTTCTTCGATGGGGTAGAGGCAATCACTATCATTGCTCGTAGTATGACCGAGAAGCAA
TTTGCTGGATATTGCATGGGTAATGCTTTGAAGTATCGTCTGCGTGCAGGGAAGAAATTCAACACGGAAGAA
GACCTGAAGAAAGCAGACTACTACAAAGAGCTATTCCAGAAGCATCGTCACGAATGTATTGATGAGGATATTT
AATATGGAAGGTAAACTGTATAGAGGGTACTTCGGTAACTTATATAAAGTAAGCCCTCGCGGTTTTGTATTGA
CCTCTGATGATGAAGGTGCAATGTGGTTCCTAAGTGCCTATGGTTCTGACTTAGCATACTTTAAAGAGGCAAT
AGTTAAAGGTGTGATGAAGGAGGTGAAATGAATATCTTCCAATTCCTAGGTCTTCCAGAAGACCACCGCAATC
ACCCATTCATGCTGGTGAAACATCGCGGTGAAGTACCTGAGAAGAAATTAACTTTTCCATGTTATGCACAGGT
AAAACGAGATGGTATATTTAGTGCTGTGGTTGTTCGCAACGATGGTGTCGTTGGTGTCTTTGGACGCACTGGA
AAGAAACTGGCTAACACGGAAACCTTGGAAGAATCTTATTCAGCTTTCCCTACTGGCATTTATCTCGGTGAGTT

Figure 3(G)

GCAATCTATGGCTATTGATGTCTACCTTGAAGCACTTTCTGGAGTAGTTAACCCTAACCGCACTGAGCCACTGG
ATTTCATAGGCCAGCAGATTAAAGACAACCTGTATATTGACTTCTTCGATATGTTAACTATTAAGGCATTCCAT
GATGGATTCACTGATGTTTCTTATCTCAAACGTTACGATGCTTTACATCGTCGCATCGGCGCTCATCTTAGCGG
GCACAACGCTATCCTTCCTATTACTCCTTGCCATAATGAGCGAGAAGTTGAAGCGTTTGCGCAAGAGCAAATA
GATGCAGGCCGAGAGGGTGCTGTGTTCAAACTGGACTGCGATTATGAAGCAGGCCACAAAGGTTATCGTCAA
ACTAAGATTGTACGCATGGTGTCTTATGACCTAACCTGTATTGGTTGGGAAGAGGGTAAAGGAAAATACAAG
GGTAAGGTTGCTAACCTGATCTTTAAATGGAAAGGAGGCAAGTCTGTTAAGGCTATGCTGGGTCGTGGCTGG
TCGCATGAGGATGCAGCCCAAATGTATCACGATATTAAACACGGTGGCGAACTGAACGTCATTGGGAAAATCT
TCGCTGTCAAGGCGTTGCAGGAATCTAGCAAGGGAGTCCTGAGACTTCCCAAGGTTTCTGAGTTGCGCCACGA
TAAGGAGGTTCCTGATGTCTATTGATTTGAACGAAGAGCAGCTTGAATTGTTAATAGAAGCCATTGAGCAATA
CTATTACATGTGTGGCTATCAATCAGAAGAACTAGACTCCTTATATTCACAATTAAAAGGAGGTTAATTATGTC
TTTTGATTCTATGAAGGCAACTCGTGCGGTTGAGGTAGCAGAGGCTATCTTCGAAACTTTATCCTGTGGTATG
GAAGTACCATATACTTTACTGGCTGATGCAGAAGAGCTTGGTCTTTCTATAGAGGCCATCCAAGAGAAGGTTG
AGGAACTCTATGGTACAGACGAAGAAGAAACCGACGATTTCATTTGAGGGTATGGAGATGCTTGAGATGATT
CTCAAGCCTTCTTCTCCGAAGGTGACTAAGACTCACGAAGAATTAATCGTAGATGAAGTGAAGCGTTACATAA
TGGATTGTGTCAGAGCACAACTGGTGGTCCAATGATACGTCCAGCTTCATTCTTAGATATTCCTGAGATTATAA
ACCTTGGGAATAAGTACGTGGAAGAGGAAGTCAAGGTTGTAGCCCATCACTCAGCCTCATGGAATGCAGAAC
AAAGCGCACATAACCTTTGTGCATCTCTTAGTAGAGAAGATTTATTCCTATGGGTGGCTGTAGATGAAGGGCA
GATTGTAGGTTTTCTGTGGGCCGGCTATCATGAGTTAGCCCCTTGGACACCTGTAAGAGTTGCATCTGACATTC
TCTTTTATATTGTACCAGAGAAGCGAGGGACACTGCTCGGTATGCGCCTCATCAAAGCCTTGAAGCAATGGGC
TAATGATAGTGGGTGTTCCGAGGTCCGCCTGTCTATCGCTTCTGGTATTAATGAAGAACGTGTCGGACGTATG
TATAAGCGACTTGGCTTTGAACAGTTTGGCACTGTGTATAACCTGAAGTTCTAAGGAGATCACATGGGTATTG
TAAAGAAAGCATTTAAGGCTGTCGGTCTTGCTCAAGATGCACCGCGTATTGAAGCCAAGGTTCCTGCTCAGCA
GCTTGAGCGTAAGCCTGAGACTGAAGCTGAAGATATACAGATTGGTGCAGGTGGTGATGATGCGACTGCATC
TGCAAAAGGTAAGCGCGGGCTTGTCCGTCCGGTAGCTTCTAGCTTGAAGGTGTAATATGAAACAGAGCACAG
ATTTGGAGTATGGAGGTAAGCGGTCTAAGATACCTAAGCTATGGGAGAAGTTCTCCACTAAACGTAGCTCTTT
CCTTGATAGGGCGAAGCATTACTCCAAATTAACCTTGCCCTATCTGATGAATGACAAAGGTGATAACGAGACT
TCGCAGAACGGATGGCAAGGTGTAGGTGCTCAGGCAACTAACCACCTAGCCAACAAGCTAGCGCAAGTGCTA
TTCCCTGCACAGCGCTCCTTCTTCCGTGTAGACCTAACTGCACAAGGTGAGAAGGTTCTTAATCAGCGTGGCCT
GAAGAAGACAGAGCTAGCTACTATCTTTGCTCAAGTGGAAACACGGGCAATGAAAGAGTTAGAGCAACGTCA
ATTCCGGCCTGCTGTAGTAGAAGCATTCAAGCATCTTATTGTTGCTGGTAGCTGTATGCTATACAAGCCAAGCA
AAGGTGCAATCAGTGCAATCCCAATGCATCACTATGTAGTTAATCGTGACACTAATGGCGACCTGTTAGACAT
TATCTTACTGCAAGAAAAAATCCTTGCGTACATTTGACCCTGCTACACGTGCTGTAGTAGAGGTTGGCTTGAAAG
GTAAGAAATGCAAGGAAGATGACAGCATTAAGCTGTACACACATGCTAAGTATCTTGGTGAGGGTTTTTGGG
AACTCAAGCAATCTGCTGATGATATCCCTGTTGGTAAGGTAAGTAAAATCAAATCAGAAAAGCTACCATTTATC
CCGCTAACTTGGAAGCGAAGCTATGGTGAGGATTGGGGTCGTCCTTTAGCAGAGGATTACTCCGGTGATTTAT
TCGTTATCCAATTCTTATCTGAAGCAGTTGCCCGTGGTGCTGCACTGATGGCAGACATTAAGTACCTGATTCGT
CCGGGTGCTCAGACTGATGTTGACCACTTTGTTAACTCTGGCACTGGTGAGGTTGTCACTGGTGTAGAAGAAG
ATATCCATATTGTACAGTTAGGTAAGTACGCAGACCTCACACCTATTAGCGCGGTTCTAGAGGTATACACTCGC
CGTATCGGTGTAGTCTTCATGATGGAGACAATGACACGTCGTGACGCTGAACGTGTTACTGCTGTAGAAATCC
AGCGAGATGCGTTAGAAATTGAGCAGAACATGGGTGGTGTATATTCCCTCTTTGCTACTACTATGCAATCGCC
AGTAGCGATGTGGGGTCTGCTGGAGGCAGGAGACTCCTTCACTAGTGACCTAGTGGACCCTGTGATTATCAC
AGGTATTGAAGCTTTAGGACGCATGGCTGAGTTGGATAAACTGGCAAACTTTGCTCAGTACATGTCACTGCCA
TTACAATGGCCTGAGCCTGTACTAGCTGCTGTGAAATGGCCTGACTATATGGATTGGGTACGAGGTCAAATCT
CTGCTGAACTGCCGTTCCTTAAATCGGCTGAAGAGATGGAACAAGAACAGGAAGCACAGATGCAAGCACAGC
AAGCACAGATGCTTGAAGAAGGTGTGGCTAAGGCCGTGCCGGGTGTAATTCAACAAGAACTTAAGGAGGCG
TAATGTCTTTCTCATTTACTGAACCGTCAACCACTCATCCTACTGCTGAAGAAAATCCGGTAGAAACCAAGGAG

Figure 3(H)

GTAACAACTGATGCTGCTACTACTGATGTTCCTGCTGATGCTGGCACTGCTGTACAAGATGACAATGCTGGTG
CACAATCTACTGAAGACGCCGGAGGAGAAGCTTCTGGACAGCCTTCAGAAGAAGGAGACAATGGCGGAGAG
AATGGTGAATCTAAGCCAGATGATACCGCGACCGACACTGAGGAAGTGCAGTACTTCTTCGGAGAATATGAA
GTAACAGTAGATATACCACAGGATGTTACGGATAGCCTTAAAGAGAAGGGTATTGATGCTAAGCAGGTTGCC
AAGGAACTCTATGCCAAAGATGGCAAGTTTGAGCTGTCTGATGCAACCAAGCAGAAATTGTATGATGCTTTTG
GCAAGTTTGCGGTAGATGCTTACCTGTCAGGTCTTAAGGCTCAAAATGAAGCCTTCTTCCTGAAAGAAGCCAA
CGCAGCTAAAGAGTTGGAAGCAGCTAATACCCAACGCTTCTCTGATGTTTCTAAGGAAATTGGTGGAGAAGA
AGGTTGGTCCCGTCTTGAGGCGTGGGCGCTTGAAACGCTATCCAATGACGAACTCACGGCATTCAATGCGGT
GATGGAGTCTGGCAACCAATACCTCCAGCAATATGCTGTGCGTGAACTAGAAAGCCGCCGTAAAGCTGCACA
GGGTGATGACAAGCCAAACTTGATTGAGCCATCTGCACCTGCTGCCGCATCTGAGGATAATGGACCTCTGTCT
CGCGAGCAGTATCTCCGTGAGATGATGACGCTGGGTTCCCGCTTCGGTACAGACAAGAAAGCTGCTGCTGAG
TATCAGGCTAAGCTGGATGCTCGCCGCCGTGCGGGTATGGCTCGCGGACTTTAATCAGTATTTACTGGACACT
ATAGAAGGGAGAAATGTCTCCCTAAATTATCAATTTGATTTATAAGGAGGTTTATTAATGTCTACGCCGAATAA
CCTGACCAACGTTGCAGTTTCCGCTTCCGGTGAGGTAGACAGCCTTCTCATTGAGAAATTCAATGGTAAGGTA
AATGAGCAGTACCTGAAAGGTGAGAATATCATGTCTTACTTCGATGTTCAGACTGTAACTGGTACTAACACTG
TAAGCAACAAGTACTTGGGTGAAACCGAGTTGCAGGTTCTAGCACCGGGCCAGTCTCCGGCTGCAACCTCCAC
TCAGGCCGATAAAAACCAGCTGGTAATTGATGCCACTGTTATCGCGCGTAACACCGTTGCACACCTGCATGAT
GTACAGGGTGATATTGACAGCCTGAAACCGAAGCTGGCTACCAACCAAGCTAAGCAGCTTAAGAAGATGGAA
GACGAGATGCTTATTCAGCAGATGCTGCTGGGCGGTATTGCCAACACTCAGGCCAAGCGCACAAATCCTCGTG
TGAAAGGTCATGGCTTCTCTGTAAACGTAGAGGTCAATGAAGGAGAAGCACTGGTTAACCCACAGTATGTAA
TGGCAGCTGTAGAGTTTGCTCTGGAGCAGCAGCTTGAGCAGGAAGTTGATATCTCTGATGTAGCTATTCTGAT
GCCATGGCGTTACTTCAACGTACTGCGTGACGCAGACCGTATTGTTGATAAGAGCTACACGATTAGCCAGTCC
GGTGCTACTATCCAGGGCTTCGTACTGTCTTCCTACAATTGTCCGGTGATCCCGTCTAACCGCTTCCCTAAATAT
TCTCAGGGGCAGAAACATCACCTTTTGTCTAACGAAGATAACGGCTATCGTTATGACCCGATTGCAGAAATGA
ACGGTGCTATCGCTGTTCTGTTCACTGCTGATGCATTGCTGGTTGGTCGCTCTATCGACGTAATTGGTGATATC
TTCTATGAGAAGAAAGAGAAGACCTACTACATCGACACCTTCATGTCAGAAGGTGCAATCCCTGACCGTTGGG
AGGCTGTGTCGGTTGTTACTACCAAGCGTCAAAGCACTGGAGCAGTTGACTCTGGTAATGCTGCACAGCACAC
TCAGGTTCTGAACCGTGCACAGCGCAAAGCTGTCTACGTTAAGAATGCTGCCCCTGCAGGTGCTTTCGCTGCT
GCTAGCTTGTCTGCTGAAGACTTGGTTGCTGCTGTACGTGCAGTGATGGCTAATGACATTAAGCCGACTGCAA
TGAAACCTACTGAGTAATACCTATGCCCTATCTACCTTGCGTAGGTAGGGTTCTTTTTGTTAGGAGGATTCATG
CCTGTAATTAGACAAACCAGTAAAGTAGGACATATGATGGAAGATGTGGCCTTCCAGATTATTGATAGTAAGC
TGGAAGCGGTAAACTTGTGTATGCGAGCTATTGGTCGTGAGGGTGTGGATTCTCTCGACTCAGGTGACTTGG
ACGCAGAAGATGCAAGCAAGATGATCGACATCGTATCCCAGCGATTCCAGTACAACAAAGGAGGTGGCTGGT
GGTTCAATCGTGAACCAAACTGGCAGATTGCACCTGATACCAATGGTGAAGTCAATCTACCTAACAACTGCCT
AGCAGTATTGCAGTGTTATGCTTTGGGTGAGAAGAAAGTACCCATGACTATGCGAGCAGGTAAGCTCTACTCT
ACATGGAGTCATACCTTTGATATGCGTAAGCATGTGAATGCTAATGGTATGATTCGTCTTACCTTACTTACCTTA
CTTCCATATGAGCATCTACCTACTAGTGTAATGCAGGCTATTGCCTATCAAGCTGCTGTAGAGTTTATTGTGTCT
AAGGATGCAGATCAGACTAAGCTAGCCACTGCACAGCAGATTGCCACTCAGCTTCTAATGGATGTGCAATCAG
AACAAATGTCACAAAAGCGATTGAATATGCTTGTACATAATCCTACGCAGCGTCAGTTCGGTATTATGGCAGG
TGGTTCTCAGAATGTACCTGCTTACTCTCATTCACCATATGACAGTTGGGCACTTCGTCCGTGGGAGGATCGTT
AATGGAAGTACAAGGTTCATTAGGGAGGCAAATCCAAGGGATTAGCCAGCAACCTCCAGCGGTACGTCTTGA
TGGTCAATGTACGACTATGGTGAACATGGTCCCTGATGTAGTGAATGGAACTCAATCCCGCATGGGTACAACT
CACATTGCTAAGCTCTTGGATGAAGGTACAGATAATATGGCAACGCACCATTATCGCAGGGGTGAGGGGGAT
GAAGAGTATTTCTTCACCTTAAAGAAGGGGCAAGTGCCAGAGATATTTGATAAGCATGGACGCAAGTGCAAT
GTCATCTCTCAAGATGCACCTATGACCTACCTTTCTGAAGTTGTTAACCCTAGGGAAGATGTGCAATTCATGAC
TATAGCTGATGTTACTTTTATGCTTAACCGTAGGAAAGTGGTTAAAGTTAGTAATAGGAAGTCACCTAAAGTT
GGAGATAAAGCCATTGTGTTTTGTGCATATGGTCAATACGGTACATCTTATTCTATCATAATTAATGGAACTAC

Figure 3(I)

AGCTGCTAGTTTTAAAACACCAGATGGGGGAAGTGCAGAACATGTTGAACAAATACGAACGGAACGTATCAC
TTCTGAATTGTACTCCAAGTTGCAGCAATGGAGTGGTGTGAATGACTATGAAATACAAAGAGATGGTACGAG
CATATTTATAGAGAGACGCGATGGTAAAAGTTTCACAGTAACAACTACCGATGGTGCAAAAGGTAAGGACTT
AGTGGCTATCAAGAATAAAGTTAGCTCTACTGACCTACTCCCTTCTCGTGCGCCTGCTGGTTATAAAGTACAAG
TGTGGCCTACTGGCAGCAAACCTGAGTCTCGTTACTGGCTGCAAGCTGAGCCTAAAGAGGGAAACCTTGTGTC
TTGGAAAGAAACAATAGCTGCTGATGTATTACTTGGGTTTGATAAAGGCACAATGCCTTACATTATTGAACGT
ACAGGTATCATCGACGGCATAGCTCAATTCAAGATAAGACAAGGTGATTGGGAAGATCGTAAAGTAGGGGAT
GACTTGACTAACCCTATGCCCTCTTTTATTGATGAGGAAGTACCCCAGACAATAGGTGGAATGTTCATGGTGC
AGAACCGCCTATGCTTTACAGCAGGTGAAGCGGTTATTGCTTCTCGTACATCATACTTCTTCGATTTCTTTCGTT
ATACGGTTATCTCTGCATTGGCAACTGACCCATTTGATATTTTCTCAGATGCGAGTGAAGTCTACCAGCTAAAA
CATGCAGTGACCTTAGATGGCGCTACCGTATTGTTCTCTGATAAGTCACAATTCATACTGCCAGGAGATAAGCC
TTTAGAGAAGTCAAATGCATTGCTTAAGCCTGTTACAACATTTGAAGTGAACAATAAAGTGAAGCCAGTAGTA
ACTGGTGAATCGGTAATGTTTGCCACTAATGATGGTTCTTACTCTGGTGTACGAGAGTTCTATACGGACTCTTA
TAGTGACACTAAGAAGGCACAAGCAATCACAAGTCATGTGAATAAACTCATCGAAGGTAACATTACCAACATG
GCAGCAAGCACCAATGTCAATAGGCTACTTGTCACTACTGATAAGTATCGTAACATAATTTACTGCTATGATTG
GTTATGGCAAGGTACAGACCGTGTACAATCAGCATGGCATGTATGGGAGTGGCCTATGGGTACAAAGGTGCG
AGGTATGTTTTATTCTGGTGAATTACTTTATCTACTCCTTGAGCGAGGCGATGGCGTCTATCTGGAGAAGATG
GACATGGGTGATGCACTAACCTATGGTTTGAATGACCGCATCAGAATGGATAGGCAAGCAGAGTTGATCTTC
AAGCATTTTAAAGCAGAAGATGAATGGATATCTGAACCACTTCCTTGGACTCCTACTAACCCAGAACTTTTGGA
TTGCATCTTAATAGAAGGGTGGGATTCATATATTGGAGGTTCTTTCCTGTTCAAATATAAACCTAGTGATAACA
CCTTGTCTACAACCTTTGACATGCATGATGATAACCACGTAAAAGCGAAGGTTATTGTTGGTCAGATTTACCCT
CAAGAGTTTGAACCTACACCTGTAGTTATCAGAGATAGGCAAGACCGTGTATCCTATATTGATGTACCTGTTGT
GGGGTTGGTTCACCTTAATCTTGATATGTATCCTGATTTCTCCGTGGAAGTTAAGAATGTGAAGAGTGGTAAA
GTACGCAGGGTGCTAGCGTCAAACCGTATAGGTGGTGCTCTCAACAACACAGTAGGTTATGTTGAACCAAGG
GAGGGTGTCTTCAGATTCCCACTGAGGGCTAAGAGTACGGATGCTGTTTATCGTATTATTGTAGAATCACCTC
ATACATTCCAGCTTCGCGATATTGAGTGGGAAGGGAGCTACAATCCAACCAAAAGGAGGGTCTAATGGCTAT
AGGTTCAGCCGTTATGGCTGGTATGTCTTCTATTGGTAGCATGTTTGCAGGCAGTGGTGCAGCAGCCGCTGCT
GGAGGTGCTGCCGCAGGTGGCGGAGGTTTGCTAGGTTCACTAGGTGGATTCCTAAGTGGCTCCACTGCTGGT
TTCTCTAATGCTGGCCTTCTTGGTGCTGGCCTTCAAGGGTTAGGCTTGATTGGTGATCTATTTGGTGGAAGTGA
TGAAGCCAAGGCGATGAAGAAAGCACAAGAAGAGCAATGGCGGCAGCAGCTTATTGCTACACAAGAGGCGT
ACAAGACAGTGGCAGACGCAGAACGTTCTGCTGCTAAACAATATCATGCAGATGCAATCAGTAATCAGGCTTC
ACTGCTACAGCAGCGAGCACAGGTTGCATTACTTGCTGGGGCTACTGGTACTGGTGGTAATTCTGTGTCCTCT
ATGCTTAATGACTTAGCAGCAGATGGCGGCAGGAACCAGAGTACCATCATTGATAACTATGAGAATCAGAAG
ATTAATTTCACCAACCAACTTAAGTCTATCCAACGTGGTGGTCAGATGCAGATGCGTGAGTTTAAGAAGCCTTC
TGCTATGAGTACCTTGGTTCAAGGTATTCCAAGTCTGGCATCTGCCTATGTAACTGGTAGTAAGTCTGGCAAG
GCATTGGGTAAAGCCTTAACTGATTCTCGTACATATTCATCTGGAACAAGAGGTATTTAATGGCAATTGAGCG
ACAAGCAGTACAAGGTCTGCCACAAGTGCAGGCCACTTCTCCTAATGTCATGACCTTTGCACCTCAACAAGTG
GGAGGTGTGGAGGCTGGCGTGGCTTCTACCTCCGGTAGTAGGTTTATCGAAGACCTTATTCGTGCAGCCAGC
AGTGTGGCTGATGTTACCACTGGTATCCTTAATCAGAAGATTGAGGAAGATAAGGTTGTTCAAATGGAACGG
GCATATAACGGACTAATGCCTTCTGAGGATGCAACTCGTGGTGGCGCTCGTGCTAACATGCTTGTCAAAGCTC
AACTGCTAGCTAATGATGAAGCAGCACGAATGAAAGACATGGCTACTCGTTTCCAAGGGACGGATGACGAGT
GGACACAACTTATGGTTGACTCTCGTAATGAGATGCAGAATAAGCTGTTCCAGCAATACCCTGAGTTGCAAGG
TGACAAAGATACTATGCGTATGGTCACTAATGTCTTCCAAGAACAGCAGCCTCAGATTTGGGCTACACGAACC
CAGCATAAACTTGACCGTGAACAAGCAGACCGGGAGGATACCTTTGACGGGCGAGTGGCTTCTACTTGGGAT
CCTAATATTGACCCTGAAGCATCTGGCTATGCTTTACAGGAACGAATCCGCGAAGGTCTTACTCAAGGATTACT
ACCTGAACAGATGCACAAGAAGTTAGTCCAGCGAGCAATTTCACTTGCACAAGGCGGTGATGTTAGCATGGC
TGAAGCCCTGAAGTATGTGAAGGACGATAAGGGTGTTTCTGTTTATGCTAAGAATCCACAGCTTATCACAGCC

Figure 3(J)

ATCACTAGTGGTAATGCAGTTTGGGCTAGGAATAATGTAGCTGATGTAACTCGTATGTCTTTCGAAGTTAAAG
AATCATACCTTGCAGGTGATTTAACTGATGAAGAATTGTTGGAACGAGCACAGCACATTAATAATCTGACAGG
TAACTCTGTCTTCTCTAATCCAGAACTAGAGGCACTGATGCGCCAACGGGCTAAGCAGAATGCAGAGCTAGGT
GCAATGCAGGATATGCGACGTGAGCTTTACTCCGACCGCCTGACTGGCTTCCAAGGTAAGACTGATAAAGAG
AAGAAGGCTTACATTGATGTTATCAAACAGGATAGCCAACTTTATGCAGACCAGCAAATCAAACAACGTGGCT
TGGACCCTTACAGTCAAGAGGCTGAAGCTATTCGTGGTGCAGTGGAAGTGCAGCGCCTGCAATTCATGAACTC
CAAAGGTTTAGTGGATGATACCTTTGAATCTCGTATCAAGGCTATGGAATCCATGCTATCACCTGAGCACTTTG
CTAAAGGTGAACCACAGGAGTTAATGACCATTCGTCAGTTGTGGGAGCAGTTACCTGAAGAAAGTCGAGGTG
TCTTCGGTGACACTGTGAACGGTTATATGGATAACTACAATACTGCATTACAAATGGGAGAGACACCTTTGCA
GGCTGCAAGGTTTGCCCGTGAAGCACAGCAGAAATTCTCTCGTACTGAGAAGGAAACCAAGAAGTTCAACTC
CGCTATTGGAGATGCACTGGATGAGGTATCTGGTGCTGGCTGGTTTGATGGTAAAACCGAGGTGTCAGACTT
AGGTAAAGCTATTGCGGAAGAAGAGTTACGAGCTAAGGCCAATATGTTGTGGTCTAGCGGTATGCGTAACAT
GGATTCTATCAAGAAGGCTTTAATCACTTGGGGCAATAAACGCTACACTCAATCAGAGGATGCAAAGACTTCC
GGTGGCTATTTCATTAAAGGTGATTACACTTCTGCATCTGATATGCTTATGTCAGTTGGGAAAGGTGTAAACCC
TACCGATGTCCCTCTGGCGCTTGGTAGGTATGTAGAAACACAGATGCCAGAATTGAAGAAGGAGCTTCAAGA
GTGGGAAACTAAGGATGATGTGTACATTGATTACAATGAACAGAAAGGAACTTTTGTGATTCGTGCTGGTGC
AGCAGGTCGCCCTCTTTCTGGAGTAATCCCTGTAACTTCTTTGGATACCACTTCACTACTGGATTCTGCCTATCA
GAAGAAAGTAGAAGAACGAGATAAAGGCGAGTATGTTCATCCCTATCGTACAGATATCGGTGCACAAGAACC
AATGCCAGCTAAGCCAACTGCCAAAGATATTGGTAAATTAGGATTAGCTAACTTCCTCATGTCTTCTGCTTTTG
CTTCTGGTGAGAATCTACCTTCTAACTTCGAGATTAACTATCGAGGCAATATGCAACAATTCTATGACAAGCTA
GCTATGGATGAGAATAAAGATAAAGTTGGCTTTAATAAGGCAACTGGAACCTTTACTCCATATAAAGACGCTC
ACGGTGAGTCTATCGGTTACGGTCATTTCTTAACGGAAGAAGAGAAGCGAGACGGGTATATTAAGATTGGCG
ATGAACTAGTTCCCTATCGAGGGTCTATGTCTCAGCTTACAGAGAGTAAGGCTCGCGCTCTTATGGAGCAAGA
TGCTAGGAAGCATGTGCCTCCTACTCGTGACTGGAAGATTCCGTTTGACCAGATGCATCCTGCACAGCAACGT
GGCTTGATGGATTTAACCTACAATTTAGGTAAAGGTGGAATCCAGAACTCACCGCGTGCTCTTGCTGCATTCA
AAGCTGGTAAGCTTACGGAAGGCTTTATCGAAATGCTGGGTACTGCATCAAGTGAAGGTAAACGTATTCCGG
GCCTACTGAAGCGACGCGCTGAGGCATACAATATGGCAGCTGCTGGTGGTGTACCTAAGATCACAGAAGTGG
AGACGAGGGAAGATGGCTCTATGTGGGTTAAGTTTGGTGGACCTATGCCAGCAGGCTCTGTTTCTGCGTGGA
CGCATAAACGTATTGGAGCCGATGGCTGGTATCAGGTTTATGAGGCTGCACCTACCAAGTTAGCTAAAGACTC
TAAGGTAGGTAAAGTTAAATTGTAGTACCTAACTCAAGGCTTGTCTCACATGTGAGACAGGTCTTTATGATAG
GCACTATGGAGGAACTATGGAACAAGATATTAAGACTAATTGGGCTGGATATGTCCAGTCTACTCCTGAGCCG
TTTTCTATTGAGGCGGCTCCGGTATCGGCTCCTACGATACGCCAGCGTAATGAGTTACAAGAGCAAGTTCTTG
AAGCCAAAGCTGATGCGGACATCTTAGGTGCTGTAGGTGCTGCCTTCCAGAATGAATGGTTGGCATTCGGAG
GTAAGCGATGGTATGACCGTGCCACTGCTGATTTCACACCCCAACCTGACTTTGAAATCCAACCAGAGCAACG
TGAAGCACTACGTTTCAAATATGGTACGGATATGATGCAGACAATCACTGAGGGTGTTCGTTCTGAGGATGAA
TTGAACTTCCGTATTCAGAATGCTGATGAAGACCTTGAGCGCAATAAGCGCATTGCTCAGGCTGGATGGGCCG
GCTCTGTGGCAACGATTGGCGCTGCTGTGCTTGACCCAGTGGGTTGGGTTGCCTCTATTCCAACCGGTGGTGC
AGCTAAAGTTGGACTCGTAGGCCGTGCTGTGCGTGGCGCTATCGCCGCTGGCGTGAGTAATGCCGCTATTGA
ATCCGTATTGGTCCAAGGTGACATGACTCGTGATTTAGATGACATTATGGTAGCACTAGGTTCCGGTATGGCT
ATGGGTGGCGTTATTGGAGCTGTAGCGCGTGGTAGGGCCACTAAGCTCAGTGAGCAAGGGGATGACAGGGC
TGCGAGCATTGTGCGCAGTGCAGACGCAGGGGACCGCTATGTGCGTGCTGTTGCTGATGACAGTATCGGTGC
GATGCGTGTTAAGGGCGAAGAGGTACTCACTGAGGGTGCATTTGATATCTCTAGCAAAGGTGAAGATTTGCT
GAAAACCCTACAGCGGGAAGGTAATGCAATTGATATGACACCTCGCCGCTGGGCCGGAACTATGTCTGCCCTT
GGGACTGTCGTGCACTCCTCTCAGGATGCTAGTGTTCGTGGCCTCGGTGCTCGCCTGTTTGAGTCTCCGCAAG
GTTTAGGTATGCAAAAGGCATCTGCCAGTCTTATGCAGAATACCAACTTGAATCGACTGAAGTCTGCTGATAT
GAACCGTTTCAATGACGGGTTTGACTTATGGCTCAAAGAAAATAATATCAATCCAGTTGCAGGCCATACTAAC
TCTCACTATGTGCAGCAATATAATGAGAAGGTATGGGAAGCTGTACGCATCGGTATGGATGAGGCTACGCCT

Figure 3(K)

AAGTCTATCCGTATGGCAGCAGAGGGGCAGCAAGCTATGTATCGTGAAGCATTAGCATTACGTCAACGCTCTG
GTGAAGCTGGGTTTGAAAAGGTTAAAGCAGATGATAAGTACATGCCTGATATTTTTGACAGTATGAAGGCTC
GTCGTCAATTCGGTATGCACGATAAAGAAGATATCATTGAGTTATTCTCTCGTGCTTATCAGAACGGCGCTCGT
AAAATTCCAAAAGAAGTAGCGGATGAAATTGCACGAGCACAAGTAAACCGTGTTGTGGATGCCACTCTGACA
GGACGTATGAGTTTCGAAAAGGCTATGTCTGGTCAGACTAAAGCAGAGTATGAAGCAATAATGCGCAAGGCA
GGCTTCAGTGATGAAGAAATTGAAAAGATGGTAGAAGCTCTGGATAATAAAGAAACCAAAGATAATATCTCT
AACCGAGCTAAGATGAGTTTAGGCTTAGATGTTACTCAAGAGTACAATGGCATTCGTATGCGTGACTTTATGA
ATACTAACGTGGAAGAGTTAACAGATAACTACATGAAGGAAGCGGCAGGTGGTGCTGCCTTGGCTCGTCAAG
GTTTCTCTACCTATCAGGCTGCACTTAATGCAATTGACCTTGTAGAGCGAAATGCACGAAATGCAGCTAAAGA
TACAAAAGCACACGCACAATTTGAAGCGGAGTCTGCTAAGATTCGTCAATCAGAGCCTGATTACAAGAAGGC
ACAAGAGAAGATTGAAGAGCTAAAGAAGCGACTTAAATTGAAAGAGAAAGATGAAGCAGCAGGTCTGGCTA
TTGATGAAGAAATCCGTCAGATGCGAGAAGGGCTTCGCTTGATTATGGGTAAATCTATCGATGCAGACCCACA
GGCTTTGTCTACTAAAATGCTGCGTCGTGGTCGTGACATCACAGGCGTACTTCGCTTAGGTCAGATGGGTTTC
GCACAGCTAGGTGAACTTGCTAACTTCATGGGTGAGTTTGGTATTGCTGCAACCACTATAGCTTTAGGTAAGC
AATTCCGCTTTACATCTAAGGCTTTGCGGAGCGGTGATGGCTTCTTCCGAGATAAGAACTTGGCAGAAGTAGA
GAGGATGGTAGGTTACATTGGTGAGGATAACTGGCTAACAACCAAGGGTGCACGTCCAGATGAGTTTGGTGA
TGTAACCACAGTAAAAGGAATGATGGCTCACTTTGACCAATCCATGAACTCAATACGTCGTGCTCAAACCAAC
CTATCACTCTTCCGCATGGCACAGGGTTCTCTGGAGCGAATGACCAATAGGCAAATAGCTTTGTCTTTCATTGA
CCACCTTGAAGGCAAGAAGATTATTCCTCAGAAGAAACTGGAGGAACTTGGTCTTACTCAGGAGTTCATGACT
AACCTACAGAAGCACTATGATGCTAACTCTAAAGGTTCTGGCTTGCTTGGCTTTGATACAATGCCTTATGCCAT
GGGTGAAACTTTAGCTAATGCTATTCGTCGTAAGTCAGGTCTAATTATCCAACGTAACTTCATTGGTGATGAAG
GTATCTGGATGAACAAAGCACTAGGTAAGACATTTGCACAGCTTAAGTCATTCTCTCTTGTATCTGGTGAGAA
GCAATTTGGTCGAGGGATTCGCCACGATAAAATTGGTCTTGCTAAGAAGACAGCTTACGGGTTTGCTTTGGGT
TCAATAGTGTATGCGGCAAAAGCCTATGTGAACTCTATTGGGCGAGAAGACCAAGATGAATATTTGGAAGAG
AAGTTATCGCCTAAAGGGTTGGCCTTTGGTGCAATGGGTATGATGAGTACAACTGCTGTATTTAGTCTAGGTG
GAGATTTCTTAGGTGGCCTAGGTGTTCTACCTTCTGAGTTAGTACAATCCCGTTATGAGGCTGGCTTTCAGACT
AAAGGTTTGATAGACCAAATACCACTAGTAGGTGTTGGTCAAGATGCATATCGTTTAGCAGATTCTATAACTA
AATATGCAGAGGGTGATACAGAAGGTGTAGATGTGGCACGTAGGGCTTTACGCTTAGTGCCTCTAACTAATG
TAATAGGAATCCAGAACGCATTGCGTTATGGCTTAGATGAACTGGAGGATTGATGAGTTATACTTTCACAGAA
CATATAGCCAACGGTACGCAAGTAACCTATCCCTTTAGCTTTGCTGGCAGGGATAAAGGCTATCTTCGTGCCTC
AGATGTGATAGTGGAATCTCTTCAAGGTAACACTTGGATTGAGATTACATCTGGCTGGCAATTAACTGGTACG
CATCAAATCACTTTTGATGTAGCACCCGTTGCAGGTTTGAAGTTCCGTATTCGAAGGGAAGTACAAAAGGAAT
ATCCATACGCTGAGTTTGACCGTGGTGTTACCTTGGATATGAAGTCTTTAAATGGTTCTTTCATTCATATACTGG
AGATTACACAGGAGTTACTTGATGGGTTTTATCCAGAAGGATACTTCATTAAGCAGAATGTAAGCTGGGGCG
GCAATAAGATTACTGACCTAGCTGATGGTGAGAATCCAAAAGATGCAGTAAATAAATCACAGCTAGATGCTAT
CGACAAGAAGCATACTGATTGGAACTCTGCACAAGATATAGAGATTGCTGGTATTAAGAGAGGGATGGTGTC
TGGTGTGTCGCATCGAACTATTCCTTGGTATATGGTTGCCTCCGGTGGAGAGCAAATCATTCGACCACCTTACT
CATTTGATGATGCTATGGTGTTTATAAACGGTGTATTCCAGCATGAACTAGCAGGTGCAGTATCCGTGGGGTA
TGATGTTATAACCCTGTCCAAGCCATTACAGGCTGGGGATGAAGTTTATGTGCTTATCGGTAGTCGCTTAACCC
CACCTACAAGTGCGGATACTATCCTCTTTACACAAGCAGTGAGTGAAGGCACACAATCTATCGACATTGTAAC
GGCTTTCCAACGTCTTGATGTATACTTGGATGGCCTGTATCAACCTAATAATGCTTATGAAATCGTAGGGTCTA
CTATCACTTTCAGTGAGCCATTACCTGAGTGTGTCGTAAGTATGAAGCTACAACTAGTGTAAGGAGGTGAGAT
GATTAACTCCGAACTGGTAGATAGTGGTGTGAAGCTTGCGCCACCTGCATTAGTCTCAGGTGGGTACTTCCTC
GGTATCAGTTGGGATAATTGGGTGTTAATAGCAACATTCATTTATACCGTGTTGCAAATTGGAGACTGGTTTTA
TACCAAGATTAAACTATGGAGGAAGAACCGTGAGCGTCCACAATAAACATGCAGCTACAGAAGATGAGGTTG
GCATCCTGCATGGTGCTATTACCAAAATCTTTAATAAGAAAGCACAGGCAATACTGGACACTATAGAAGAAGA
CCCAGATGCAGCACTGCATTTAGTCTCTGGTAAAGACATTGGAGCTATGTGTAAGTGGGTTCTTGATAATGGT

Figure 3(L)

ATTACCGCTACACCTGCTGCACAGCAGGAGGAGTCCAAGCTATCTAAGCGCCTCAAGGCTATCCGAGAGGCAT
CAAGTGGCAAGATTATTCAATTCACTAAGGAGGATTGATGGCTAAGGCAAGAGAATCACAAGCGGAGGCTCT
TGCCAGATGGGAGATGCTACAGGAGTTACAGCAGACCTTTCCTTACACAGCGGAAGGTTTGCTTCTCTTTGCA
GACACAGTTATTCATAACTTAATTGCAGGCAACCCTCATCTGATTCGTATGCAGGCTGATATCTTGAAGTTCCT
ATTCTACGGACACAAGTATCGCCTCATCGAAGCGCCTCGTGGTATCGCTAAGACAACACTATCAGCAATCTATA
CAGTATTCCGTATCATTCATGAACCGCATAAGCGTATCATGGTTGTATCCCAAAACGCCAAGCGAGCAGAGGA
AATCGCAGGTTGGGTAGTTAAAATCTTCCGTGGCCTAGACTTTCTTGAGTTTATGCTACCGGACATCTACGCAG
GGGACCGTGCCTCAGTTAAGGCATTTGAGATTCATTACACCCTACGTGGCAGTGACAAGTCGCCTTCTGTGTCT
TGTTACTCAATCGAAGCAGGTATGCAGGGTGCGCGTGCAGATATCATCCTAGCAGATGACGTTGAGTCAATGC
AGAATGCTCGTACAGCGGCAGGACGTGCCTTGCTTGAGGAACTGACCAAGGAGTTTGAATCTATTAACCAGTT
TGGTGATATTATCTACCTTGGTACTCCTCAGAACGTAAACTCTATCTACAATAACCTACCTGCTCGTGGTTACTC
TGTTCGTATCTGGACTGCACGTTATCCCTCAGTGGAGCAGGAGCAATGCTATGGTGACTTCCTTGCACCTATGA
TTGTGCAGGATATGAAGGACAACCCAGCACTTCGCTCAGGGTATGGCTTGGATGGCAATAGTGGTGCCCCTT
GTGCACCTGAAATGTATGATGATGATGTGCTGATTGAGAAGGAAATCTCGCAGGGTGCGGCTAAGTTCCAGC
TTCAGTTCATGCTTAACACTCGCATGATGGATGCTGACCGCTATCCGCTACGCCTGAACAACCTCATCTTCACTT
CATTCGGTACAGAGGAAGTCCCTGTGATGCCTACGTGGAGCAATGATTCCATCAATATTATTGGCGATGCACC
GAAGTATGGCAATAAGCCTACAGACTTCATGTATCGACCTGTGGCTCGCCCGTATGAATGGGGCGCTGTCACT
CGTAAGATTATGTATATTGACCCTGCTGGTAAACACCTCTGCCAGCGTAAAACCCTCTTAATTCGGTGGAACTC
TCACTGAGACAATACCGAGCGAAGCCTGTTGCAATAACAGGAACGTGTAGAGACTAACTGTAAGGCCAAGCG
GTCTGAAACAGAGGGAGGCGCAAGCCTAAGATATAGTCCGACCTACTAGGTGACTAGTAGAAGTTAAAGTAG
CGAATTAACGTAACAATTGAAGGGAGTTAAATATGACAGAGCATAAAGTTTATCATATTCGTGTTGTTGGTGA
AACTGATGTAATGCAAGGTTATATTGGTGTAACCTCCGATATTAAGAAGCGTATGAGAGAGCACAAGTGTGC
AGGCCGTCTTTGTGATGGCCGCGAGTACGTTATCTTATTCACTGGTAGCAAAGAAGAGTGTTATGCACTAGAA
GAGAAGCTACGCCCACATGACAACATGGGTTGGAATAAGGGTAAAGGTGGTTATCGCAAAGCAGGTAACATC
GAGAAAGGTGAACGCATAAGTATTGCCACTGAAATCAAGAAAGGACAGCACTTGTCTGTTGCCACTGAGTTC
AAGAAAGGCATGACACCTTACAACAAAGGTACTGGCAAAGATTACATATTCACTTCTCCAGATGGTGAAGAGT
TTCTTGTAACTTGCATTACTGACTTCTGTAAAGAGCACAACCTAACACCTCAGAATATGCGTAAGGTGGCACGT
GGTTTACGTAAACACCACAAGGGTTGGCTCGCACGTCACGTTCAAACCGGGAGGTAAGAATGGGGATGAAAC
GGGTGTGGCTATCGTCTTCCTGCACGGCACATTCATTTATGTGTATCAGTGCTTTGGTGTGCCGGGAGGATAC
CGCGAATCGTCCCTGAATCGCATTGTGCAGGCCGCAAAGCAGGCAGGTGTTAAAGAGGTATTCATTGAAAAG
AACTTTGGTCATGGCGCGTTTGAGGCCGTTATAAAGCCATACTTTGAACGAGAGTGGCCTGTGACTCTGGAGG
AAGATTACGCCACCGGACAGAAAGAGTTGCGTATCATTGAAACACTAGAGCCACTAATGGCGGCCCACAGGC
TCATCTTCAACGCAGAGATGGTCAAGTCTGATTTTGAGTCGGTACAGCACTATCCGCTTGAGCTACGCATGTCA
TACAGCCTTTTCAATCAAATGTCGAACATCACGATTGAGAAGAACAGCCTACGACACGATGACCGCTTAGACG
CTCTGTATGGCGCTATACGGCAATTAACTTCTCAGATAGACTATGACGAGGTTACACGGATTAATCGCCTCAG
AGCGCAGGAGATGCGCGATTACATCCATGCTATGAACACACCTCACCTCCGTAGGGCAATGCTCTATGGAGAT
TATGGCACTGAGCGAAGAGTAACCAACACTTCCGTGGCTATGCAGCAAAGAGTATACGGTCAGAATTACAGG
AGTAAATCGGCAAGCAGAAATACACTTTCTGCAAGGATTTCAAGGACTTATTAATTACCGGACACTATAGAAG
GAAGGCCCAGATAATAAGAGAAATAACAAGGATAATATAGGTTAACCTAGGTTATATAGGTATTCCTTAGTAT
GGGTGTACTCCTGTACACCCTATTCCTTACTTCCTTACTATACTTACATAATAGGAGAGAGAGAGAGAGAGAAT
GTCTAATAGTTATAGTACACAACCTCTTACAGGTAAGTCTGCTCGTAAGCAGATACAACCTGTTAGTGAAGCCC
TTATGCTTCCTGTAGTTTACGAGGACACTGTTGAGAAGAAAGGTGATGTTATTAATGATGCCACCAAATCAGG
TAAGCAGAAAGGGGCCATGGTGTGTCTTGATACACATGATAACCTGGTTATTGCTATCGCAGTTGATGGCAAA
GAAGATTCCAATTGGTTGACAGCTAATAAAGCGGTCACTACTATTACCCCAGCTTAAGAGGAGAGTTACATGT
CTAAATATGGAACCGCAGGTACTGTTACTGGTCAGGCTTTTCGAGTAAAAACTGTACAAACCACTGCAACGGC
AATCCCTTTGCCTATTGTTGCTGAAGCAGACCTTAAGAAGAAAGATCATCCTATCAACATTAAACACCTCTCTG
GTAAACAGAAAGGTGCCATGGTTGCTGTAGAGAAAACAGACCAATCCTTGTACATCGCTATTGCACGTGGGA

Figure 3(M)

GTGAACCCACCGACAAGTGGGATGCAACTACTATGGAGTTGGACCCTGTAACACCTGCGGCTTAATTGTAAAG
ACGAAGGAGATTCAACATGGTCTTCACACTCGAAGATTTCGTTGGGGACTGGCGACAGACAGCCGGCTACAA
CCTGGACCAAGTCCTTGAACAGGGAGGTGTGTCCAGTTTGTTTCAGAATCTCGGGGTGTCCGTAACTCCGATC
CAAAGGATTGTCCTGAGCGGTGAAAATGGGCTGAAGATCGACATCCATGTCATCATCCCGTATGAAGGTCTG
AGCGGCGACCAAATGGGCCAGATCGAAAAAATTTTTAAGGTGGTGTACCCTGTGGATGATCATCACTTTAAG
GTGATCCTGCACTATGGCACACTGGTAATCGACGGGGTTACGCCGAACATGATCGACTATTTCGGACGGCCGT
ATGAAGGCATCGCCGTGTTCGACGGCAAAAAGATCACTGTAACAGGGACCCTGTGGAACGGCAACAAAATTA
TCGACGAGCGCCTGATCAACCCCGACGGCTCCCTGCTGTTCCGAGTAACCATCAACGGAGTGACCGGCTGGC
GGCTGTGCGAACGCATTCTGGCGTAAAGGTCAATAGTGCTTAACAAACACTTCAAGCGCCGTGAGTTCGCTTG
CCGTTGTGGGTGCGGTACATCCACAGTAGATGCTGAGTTACTACAGGTAGTCACAGATGTACGTGAGCACTTT
GGTGCTCCTGTAGTTATTACTTCTGGACACCGCTGTGCTAAGCACAATGCTAATGTGGGAGGTGCTAAGAACT
CCATGCATCTTACTGGTAAGGCTGCTGACATTAAGGTACAAGGTATTACACCTTACCGTGTATGGTCCTATCTA
ACAGCACGCTACCCCAATAAATATGGCATTGGGTCTTATCCTAATTTCACCCACATTGATGTAAGAGAGGGAT
GTGCACGATGGTAAGATGTATTGAATGGTGCGAGCGCATGGTTGCTCAAGCTGCCGAGGATGGCAACTATGA
TGACTGGAAGAACTACTCTGACTTGTTAGCTCAATGGAAAGGGAGATGCAATGAAAAAGCTGTTTAAGTCTAA
GAAAGTGGTAGGTGCACTGGTTGCACTAGTGATTGCTCTTGTTTCTGTAGGTCTTGGCGTAGACCTAGGTGAA
GGTGCGGAAGGTTCCGTCACTGACGTGGTATGCCAAGTAATCACCTGTGAATAAGGTGCTAGAGGTGGTAGC
AGGTCTTATTGGCCTGCTGCTTGCCGCTAAGAAGAAGAAGGAAGAGAAGGAGGCACAAAGTGAGGCGAATC
ATGCTAGCGACAATCCTGCTGATTGGTTCACTGATCACTTCAGGGTGTCAGACGGCGTTACCAGAGAATCCAA
AGGTGAAGCCTCTGAAGCCGACGCTTACGGCAGTCTACGAGGTGGACGATAAAGTCTGCTTCAGTAAGCCTG
ACGCTACAAAATTAGGTCTGTACATTCTCTCGCTAGAACGCGGGTATAATTAATACATAGTTTTATGTATCAGT
GTCTTACGATTTACTGGACACTATAGAAGAGATAAGATAGTGCCGTTCTTTTGAGCGGCCTATTACTAGCCAAT
CTTCATAGGGAGGGTTGGGAAGTAATAGGAGAGTATATGGCTAAGTTAACTAAACCCAAGACAACGGGCTTA
CTACATAGAGATACTGTACTAGCTACCTTATTAGATAATTTACTATCTAAAAGGCGTGTTACATTTGAAGGTGT
AGTTCCAAGTGAAGATACTAAAATTGAGATAGAAGTACCTACAGCATGGGATTTAGATTCTTCGTGGGCATCA
CTTGTATCATTAAGTACACCTACACTTTGTACAGCTTGGATTACTAAAGTGTCAGATACTAGATTAGAAGTACA
TGTGTTCCATACAGCACAAGTTGAAATAGACATAGATGTAGATGTTTACATTCTAGGTAAACACATTGTCAGTG
CGTAAGCACTGCTTTTCGCGCAACTTTTCTTAAAGGTTATCATGATGGTAGCCTTTCAGAAAAGGAGGTTACAT
GATTCAAAGACTAGGTTCTTCATTAGTTAAATTCAAGAGTAAAATAGCAGGTGCAATCTGGCGTAACTTGGAT
GACAAGCTCACCGAGGTTGTATCGCTTAAAGATTTTGGAGCCAAAGGTGATGGTAAGACAAACGACCAAGAT
GCAGTAAATGCAGCGATGGCTTCAGGTAAGAGAATTGACGGTGCTGGTGCTACTTACAAAGTATCATCTTTAC
CTGATATGGAGCGATTCTATAACACCCGCTTCGTATGGGAACGTTTAGCAGGTCAACCTCTTTACTATGTGAGT
AAAGGTTTTATCAATGGTGAACTCTATAAAATCACGGATAACCCTTATTACAATGCTTGGCCTCAAGACAAAGC
GTTTGTATATGAGAACGTGATATATGCACCTTACATGGGTAGCGACCGTCATGGTGTTAGTCGTCTGCATGTAT
CATGGGTTAAGTCTGGTGACGATGGTCAAACATGGTCTACTCCAGAGTGGTTAACTGATATGCATCCAGATTA
CCCTACAGTGAACTATCATTGTATGAGTATGGGTGTATGTCGCAACCGTCTGTTTGCCATGATTGAAACACGTA
CTTTAGCCAAGAACGAACTAACCAATTGTGCATTGTGGGATCGCCCTATGTCTCGTAGTCTGCATCTTACTGGT
GGTATCACTAAGGCTGCAAATCAGAGATATGCAACAATCCATGTACCTGATCACGGACTCTTCGTTGGTGATTT
TGTTAACTTCTCTAACTCTGCGGTAACAGGTGTATCTGGTGATATGAAGGTTGCAACAGTAATAGATAAGGAC
AACTTCACGGTTCTTACACCTAACCAGCAGACTTCAGATTTGAATAACGCTGGAAAGAATTGGCACATGGGTA
CTTCTTTCCATAAGTCTCCGTGGCGTAAGACAGATCTTGGTCTAATCCCTCGTGTCACAGAGGTGCATAGCTTT
GCTACTATTGATAACAATGGCTTTGTTATGGGCTATCATCAAGGTGATGTAGCTCCACGAGAAGTTGGGCTTTT
CTACTTCCCTGATGCTTTCAATAGCCCATCTAATTATGTTCGTCGTCAGATACCATCTGAGTATGAACCAGATGC
GGCAGAGCCATGCATCAAGTACTATGACGGTGTATTATACCTTATCACTCGTGGTACTCGTGGCGACCGACTA
GGAAGCTCTCTGCATCGTAGTAGAGATATAGGTCAGACTTGGGAGTCACTAAGATTTCCACATAATGTGCATC
ATACTACTTTACCGTTTGCTAAGGTAGGAGATGACCTTATTATGTTTGGTTCAGAACGTGCAGAAAATGAATG
GGAAGCAGGTGCACCAGATGATCGTTACAAGGCATCTTATCCTCGTACCTTCTATGCACGATTGAATGTAAAC

Figure 3(N)

AATTGGAATGCAGATGATATTGAATGGGTTAACATCACAGACCAAATCTATCAGGGTGACATTGTGAACTCTA
GTGTAGGTGTAGGTTCTGTTGTAGTTAAAGACAGCTTCATTTACTATATCTTTGGTGGTGAAAACCATTTCAAC
CCAATGACTTATGGTGACAACAAAGACAAAGACCCATTTAAAGGTCATGGACACCCTACTGATATATACTGCT
ATAAGATGCAGATTGCAAATGACAATCGTGTATCTCGTAAGTTTACATATGGTGCAACTCCAGGTCAAGCTAT
ACCTACTTTCATGGGTACTGATGGAATACGAAATATCCCTGCACCTTTGTATTTCTCAGATAACATTGTTACAGA
GGATACTAAAGTTGGACACTTAACACTTAAAGCAAGCACAAGTGCCAATATACGATCTGAAATGCAGATGGA
AGGTGAGTATGGCTTTATTGGCAAGTCTGTTCCAAAGGACAAACCAACAGGTCAACGTTTGATTATTTGTGGT
GGAGAAAGGACTTCATCATCTTCAGGTGCACAGATAACTTTGCACGGTTCTAATTCAAGTAAGGCTAAGCGTA
TCACTTATAACGGAAACGAGCACCTATTCCAAGGTGCACCAATCATGCCTGCTGTAGATAACCAGTTTGCTGCT
GGTGGACCTAGTAACCGATTCACTACCATCTACCTAGGCAGTGACCCTGTTACAACTTCAGATGCTGACCACAA
GTACGGTATCTCTAGTATTAATACCAAGGTGTTAAAGGCTTGGAGCAGGGTTGGTTTTAAACAGTATGGTTTG
AATAGTGAAGCAGAGAGGAACCTTGATAGCATACACTTCGGTGTCTTGGCTCAGGATATTGTAGCTGCTTTTG
AAGCTGAAGGGTTGGATGCCATTAAGTATGGAATTGTGTCCTTCGAAGAAGGTAGGTATGGTGTGAGATATA
GTGAAGTTCTAATCCTAGAGGCTGCCTATACTCGCCATCGTCTTGATAAATTAGAGGAGATGTATGCCACTAAT
AAAATCAGTTAAGCAATCTGCTGCACGCCAGAACACATAAGAACTTATACAATCAGGACGTGACCCTAAGCAG
GCATACGCCATTGCCAAGGATGTACAACGTCGTGCCATGAAGAAACCTTCTGCATCTTCTGCGTAAGCAGGTT
AATATCTTAGTGTACACAAGGGCAGACTTAGGTTTGCTCTTAGTGTAATCCAAGGAGGTAACATGCAAGAGGA
GAATTGGGATGTGTAATGTTGGATATGGAGAAGGTTGAACCTCAGTGTTGTACAAGGATTAACCAAAGTAAA
AATTTTGATATAGGCGTGTGTCAGCTCTCTCGCCCTCGCCCTCGCCGGATTTTCCCCATATGGGGCCGCGCTGC
GGTTGGCTTGGGGATTGGGCTAGGCTGGGCCGTCTTCAACCTGCTGCCGCAGGAAGCTCGATGGGTTGGCTG
AGGGTTGCCGAGGGCTGCGCTTAGTGGTACACAAGTAGAACGCCTAGGAAGCGCTAGGGCACGCCTTAGTGT
TGGACAAGGTGATTGCCTTAGTGCAACCGTTTAGGGCTTACACAGGCCGTTTTAGGGCAATTCCTGAGTGTTT
GACAGGGTGTGAGGGTGTGGGCTA

5'
ACGAAGGAGATTCAACATGGTCTTCACACTCGAAGATTTCGTTGGGGACTGGCGACAGA
CAGC 3'

(SEQ ID NO:4)

5'
GAGTAACCATCAACGGAGTGACCGGCTGGCGGCTGTGCGAACGCATTCTGGCGT
AAAGG 3' (SEQ ID NO: 5)

| Values shown are Tau | T7 | K1E |
|---|---|---|
| 10B | 2080.401 | .711 |
| K1 | .310 | 2687.814 |

Figure 10(A)

NCBI Reference Sequence: NC_007637.1 (SEQ ID NO: 1)

```
   1 tctcgccctc gccctcgccg gattttcccc atatggggcc gcgctgcggt tggcttgggg
  61 attgggctag gctgggccgt cttcaacctg ctgccgcagg aagctcgatg ggttggctga
 121 gggttgccga gggctgcgct tagtggtaca caagtagaac gcctaggaag cgctagggca
 181 cgccttagtg ttggacaagg tgattgcctt agtgcaaccg tttagggctt acacaggccg
 241 ttttagggca attcctgagt gtttgacagg gtgtgagggt gtgggctatc tgttcgtttc
 301 gctacgcttc actcactgct cctcacttcg ctgtcgctcg ctacactgcc tgtcgtgtac
 361 cttaggttat tccttgaggg atggcttagg ttagccttag tgggctacct tagttaaagc
 421 cttagtgctt agcttagtat caacttagta gtgtacctta gttagtctta gtgccagacc
 481 ttagtgattg catagctaaa gctataagat gcaattaggt cgcggtcggt agaccgctga
 541 gagtaggtaa tagtgataag atgcagtagg aggaacacca gaaacctagc catcctagcc
 601 tatcctagct ctgtatctat tgctttcctt agtctcacat gttagacaac ctaggtttat
 661 cttagtagtt gtgacatgta tcacataaat aatctatctt agttaaattt agtgttgaca
 721 caggcaatca acagatatac attagcaatc actgagacgg acctagcaag ctgtctcagg
 781 ttataagtag gagaattgat gcgtaggccg tagctagcgg atgtagtcgc atgaaggctt
 841 gagcaagggg ccgtttaata ccttcttcct ctggagacaa agcttataac attgctcttt
 901 aacaatttgc ttagtgtaac ctatgtatgc cgtggttaat tacttattga atgaggaatt
 961 aactatgaat tatgaagaaa tgtatgaagt ctatttcgac tcattagatg aaggcgaaga
1021 agcattatcc tacgctgagt ttgtggaggc tttatcatga ttctgaataa ccgtgaactg
1081 tccgttctct tcactctgtt atgctacatg attcgtaata acgaattact tacagatgac
1141 gagatggcac tatatcaccg ctttcttaac gaaggttgga cagatacagt taaccagaaa
1201 cgtgacttga tgaaggagtt aagtaatgat tcagttgact gaagaccaac taaagcaact
1261 cttagtcgac gcgtggtttg ctggtcatga aacctcgcaa tacacgccta actcttacgg
1321 tgatgctaac agatatgcac gctctacatt aaaggaggtt aaagaggatg tatcagcatg
1381 aggttttctt cgaatcagct agtgaagcta tccgcttcca tgatgatatg atgcaagctg
1441 gcgtaggtgt tgatgtgtat cactatttga tagattacga cactgaatat caccgagtta
1501 ccttagtatc tgagtatgac aaccaagtca ttactgagta tctaggtagt gaagattatg
1561 attacgatga agtaatcaca acaaatctct aaattaacta ttgacagcca cggcatacaa
1621 ggctacatta agcatcaaga cggcgacgtc tttaaacatc ccgctcttta acaatctggc
1681 tagtgccttg gtaggctaac tacttactaa ggtgaactat gaactactgc gacatcgctc
1741 acgaattacg catggaacgt gagaaacaag agaagcggat tatcaagaag atggctgtac
1801 tgcttgcaca ctataaggca gacaaacagc caacacatga tgagttcgtg gacttctgta
1861 acatgtatct taatgtgagt aaggccactg gttacagatg gcttaaagca ctgaatgatg
1921 gagaattgta gcaataagcc agcttaatag ctggcctatc aaggcactaa cctagctctt
1981 taacaatccg gtttgtgtct tgataggctt actaacaaag gtgaactatc atgactaacg
2041 cacaacgtaa acgctatgat gcattgcaag agaaacttgc tgttgcttat gccgcttggc
2101 aagctaacac agacaagagc aaacacgata aactttatag taaagtggtt gcaattaatg
2161 ctaaaataga taaacttgtg aatagtatct tataagatag ttgctggcac tagccagcct
2221 atcaaggcac aagccacgct cttttaacaa tatgggtagt cgcttcttag tctggatagg
2281 ttaaacctag ggtattcttt tgagtgccct ataatgtaac ctaactaact aatgaggatt
2341 aaatcatgga acgcaatgct aacgcttact acaatcttct ggctgcaact gttgaagcat
2401 tcaacgagcg cattcagtac gatgagatcc gcgaaggtga tgattactct gatgcactac
2461 atgaggttgt agacagcaat gttccagttt attacagcga aatctttact gtgatggctg
2521 ctgatggcat tgatattgaa tttgaggatg caggtttgat tcctgatacg aaggatgtaa
2581 ccaagattct acaagctcgc atctatgagt ctctttataa tgatgtacca aatgatagtg
2641 atgtagtttg gtatgaagac gaggaagaat aaagatggaa aggcaatata acttcatctt
2701 ctcagacggt gtaaccctga aatgttcctt acgatttgcg cagattcgtg aggaagtgct
2761 aggtactaca tacaaactat ttagctgaca ctataagaga aggcttaaca aggcgttgct
2821 acggtagcgc ctgattaaac tttcacttac taggagttaa gactatggat ttagatagca
2881 tcattatggc atttgctctt attggcttaa gctggtgctc ctatcacctt taccgtgagt
2941 tcttatttga taaagctaaa cgcaaactaa gaaaggaagg cggtaactac ctctgtgtaa
3001 gaggcggttt agtcgaatat attgcaccta acggcacgga atgcgccatt aacaaagatg
3061 catttataga aacgtggcat tacatcaagt aactagccta tagcctgcct gtgtgggcta
3121 tgtgatattt acttacacta tataaggtga ctattatgac tactgaaaac acccttctgt
3181 ctgttcgtga agctgcaacc gctgaaatca agcagcactt agacaatatc ggcacttctt
3241 acatcaaagt tggcgcttgt ctgaatgaat tacgcggtga tttcgaaggt caaaaagact
3301 ttttagctta tgtagaatca gagttcggca tcaagaaggc acaatgctac aagctgatga
```

Figure 10(B)

```
3361 gtgtagcccg tgtctttgaa ggagacgaac gctttaaagg tgtggctatg cgtgtaatgc
3421 tggcgcttgt tcctttcgct gatgaaaata taatcatgga gaaggccgca gaactcgccg
3481 cagatggcaa gctggacact aacgccgtaa acgccctgat tgagactaag aaagagataa
3541 aggccgaaac ggtacaatct aaggctgagg cagtaaaacc gcaggagaac gcgactgagg
3601 ccgcagaatc acaggaaatg caagcgccgc aggtagtgcc acccgcgagc gagcaggagg
3661 ccgacgaatc agcaccatgg gaagaggaaa gcaagccgga agcgccaaag gcagcgccgc
3721 tggataacac ggctaatacc gaaaacgccg ctatggctag cctcttagca caaattaagg
3781 cactgactga gcaattacag gcagctaatg accgcatcgc ctccttaagt agcgcacgcg
3841 aaagcaagaa ggcagccgca cctatgctgc cgcaattcaa atcttcctgc ttctatgctc
3901 gcttagggtt aagcgctgag gaggcaacga agaaaacagc agttaacaag gcgcgccgcg
3961 aactggttaa gctaggctac ggtgaaggac atgaagcatg gcccttaatc tctgaggcag
4021 tagaagagtt gactaagtaa ccttatcggt ggcatctcct taggtgtcac ctattaaggt
4081 ttctttcact aggagtaaac aagatgcaag acctacacgc tattcaactt caacttgaag
4141 aagaaatgtt taacggcggc atccgtcgct ttgaagcgga ccaacaacgc cagattgcat
4201 ccggtaatga atcagacacg gcatggaatc gccgcttatt gtccgaacta atcgcaccta
4261 tggcggaagg tattcaggct tacaaggaag aatacgaagg caagagaggt cgtgcaccac
4321 gtgcattagc tttcattaac tgcgtaggaa acgaagtggc agcatatatc accatgaaaa
4381 tcgttatgga tatgctgaat acagacgtta ccttacaagc tatcgctatg aatgtagcag
4441 accgcatcga ggaccaagta cgttttagca agctggaagg tcacgcagct aagtactttg
4501 agaaagtgaa gaagtcgctt aaggctagca agactaaatc ttatcgtcat gcgcacaacg
4561 tagcggtagt agctgagaaa tctgttgctg accgtgacgc ggatttctcc cgttgggagg
4621 catggcctaa agacaccttg ctgcaaatcg gtatgacctt gctcgaaata ttggagaata
4681 gtgtattctt caatggtcaa cctgtcttcc ttcgtacctt gcgcactaac ggcggaaagc
4741 atggtgttta ctatttacag accagtgaac atgttggcga gtggataact gcatttaagg
4801 aacatgtagc gcagctcagc cctgcctatg caccttgcgt tatacctccc cgcccttggg
4861 tatcaccttt taacggtggg tttcatactg agaaagtagc aagccgtatt cgtctggtaa
4921 aaggcaatcg tgagcacgtc cgcaagctga ccaaaaagca aatgccagcc gtttataagg
4981 ctgttaacgc tttgcaggca actaagtggc aggttaataa agaggtttta caggttgtgg
5041 aggacgttat acgtctagac ctcggctatg gtgtaccttc ctttaaacca ctcatcgacc
5101 gtgagaacaa gccagctaat ccggtgccgt tagagttcca gcacctgcga ggccgtgaac
5161 tgaaagaaat gttaacaccg gaacaatggc aagccttcat caactggaaa ggtgaatgca
5221 ccaagctgta taccgctgag actaagcgcg gcagcaaatc ggcggcgacc gtccgcatgg
5281 tagggcaggc ccgtaaatac agccaatttg acgcaatata cttcgtgtat gctctggaca
5341 gccgcagccg cgtctacgcg caatctagca cgctctctcc gcaatcaaac gacttaggca
5401 aggcattgct ccgttttacc gaagggcagc gtcttgatag cgctgaggcg cttaagtggt
5461 tttggtgaa cggggctaat aactggggtt gggataagaa aacttttgac gtgcgcaccg
5521 ctaacgtgct ggatagtgaa tttcaagaca tgtgccgcga cattgcagcg gatccgctga
5581 ccttcactca atgggtaaat gccgactccc cttacggctt ccttgcatgg tgctttgaat
5641 atgcgcgtta tctggatgca ctggatgaag gcacgcaaga ccaattcatg acgcacctcc
5701 cagtccatca agatggtagt tgttctggta tccagcacta cagtgctatg ctacgcgatg
5761 cagtaggtgc gaaagcagta aaccttaagc cctctgactc tcctcaagat atttatggtg
5821 ccgttgcgca ggtagtaatt cagaagaatt atgcatacat gaatgcagag gatgcggaaa
5881 ccttcacttc tggcagcgtg actttaacag gtgcggaact gcgtagtatg gctagtgcgt
5941 gggatatgat aggaatcact cgcggcctga ccaaaaagcc cgtaatgaca ctaccttatg
6001 gcagcacacg tctaacctgc cgtgagtcag tgattgatta tatcgttgat ttagaagaaa
6061 aagaggccca acgggctatt gcggaagggc gtaccgccaa tcctgtacac cctttgata
6121 atgaccgtaa agacagcctg acacctagcg cagcttataa ctatatgaca gctttaatct
6181 ggccttctat ctcggaagtg gttaaagccc ctatagtggc aatgaaaatg attcgtcagc
6241 ttgcacgttt cgcagctaaa agaaacgaag gcttagaata tcccttacca actggcttca
6301 tcttgcaaca aaagataatg gctaccgata tgctccgcgt atccacttgc ttgatgggtg
6361 aaatcaagat gagtctccag attgaaacag atgtagttga tgaaacggca atgatgggtg
6421 cggctgctcc taacttcgtc catggtcacg atgctagcca cctgattctg actgtatgtg
6481 acctagtgga taaaggtatt acatccgttg cagtcatcca tgattctttc ggtactcatg
6541 caggacgtac cgcagacctg cgggatagct taagggaaga aatggttaag atgtatcaaa
6601 accataatgc cctgcaaaac ctgctagatg tgcacgaaga gcgttggtta gtagacaccg
6661 gaatccaagt accagagcaa ggggagtttg accttaacga aatcttagtt tcagactatt
6721 gtttcgcata atattaatag gccattcctt cgggagtggc tttcttttac ctactacctg
6781 taacatttca ttaacataaa acgtgtctca catgtgagac tttatttacc ggacactata
6841 ggatagccgt cggagacggg aaagaaaggg aagataaagg atataaagga agtaataggt
6901 attaaaggtt atataggtta tctaggaata cctattacct tcttccttcc tcttattacc
```

Figure 10(C)

```
 6961 acttagagga agggcagacc taggttgtct cacatgtgag acttcgtatt taccggacag
 7021 tatagataag attaactcac tttggagatt taaccatgcg taactttgag aagatgaccc
 7081 gtaaagctaa ccgttttgac atggaagaag ggcagaagaa aggcaagaag ctgaataaac
 7141 ctgtccgtga ccgtgcatct aaacgcgcag cgtgggagtt ctaagttatg gctaaataca
 7201 gaatcaagac ctgtttaaat agtcacgggc aagagtgtta catagtgcaa cgtaaagtat
 7261 taggcttaat atgggtcaca tgtatgatgc ctattggata tactgataca gaggctatct
 7321 tctgcaccga aagggatgca aagcagttta tctctaagcg tagaaaagct gactcttatc
 7381 aacccagaac tattaaggtg aactaatggc tattattaat aacatcccgt gtcctgcttg
 7441 tcagaagaat ggacacgata aatccggcaa ccacctcatg atatttgatg atggtgctgg
 7501 ctattgcaac cgtggtcact tccatgataa tggcaagccc tactatcaca agccagaggg
 7561 tggcatcgag ataaccgaat tgcctattac tggcaatatc aaatatacac cttctcaatt
 7621 caaagagatg gagaaggaag ggaagataag cgaccctaag ttgcgcgcca tcgcacttgg
 7681 tggtatgcgt atgaaagacc gttgggaggt catgaatgag caagaaaggg cagaccaaga
 7741 agcagagtgg aaacttgatg ttgaatggtt cctcacgctt aagcgtaaga accttgtgtc
 7801 ccgtcacatt cgaggtgaca tcgcagcaat gtacgatgtg cgcgttggac acgatgaaga
 7861 gggaagagtc aaccgtcact attatccacg atatgaaaag ggtgtgcttg ttggagcaaa
 7921 atgccggacg ttgccgaagg atttaagtt cggacaccta ggtaaactct ttggtatgca
 7981 agacctttc ggtatgaata ctttgtctca cgtgttagac aagggaagac gaaaggattg
 8041 cttgcttatt gtgggcggcg aactggatgc actagcagca cagcaaatgc tccttgattc
 8101 tgccaagggt actaagtggg aaggccagcc ttaccatgta tggtctgcca ataaaggtga
 8161 gtcttgcctt gaagagatag tgcaaaaccg tgagcacata gcccaattca agaagattat
 8221 atggggcttt gatggcgacg aggtggggca gaagcagaac caacaagctg ctcgcctgtt
 8281 tcctggcaaa tcctacatcc tcgaatatcc ctctggttgc aaagatgcta acaaggcatt
 8341 gatggctggc aaggctaaag agtttgttga tgcttggttt aatgccaagt catctgatga
 8401 agtctttggt agccagatta aatctatcgc atctcaaagg gataagctca aggctgcacg
 8461 tccagagcaa ggactatcat ggccttggcc taagctgaac aaggtaacgc taggtattcg
 8521 taagaaccag cttatcattg taggtgcagg ctctggtgta ggtaagactg agttccttcg
 8581 tgaagtagtt aagcacctca ttgaagaaca cggtgaatct gtaggcatca tttctacaga
 8641 agacccgatg gtcaaggtgt cccgtgcttt tatcggcaag tggattgata agcgtattga
 8701 gttaccgcca accaacgacc cgaaagaaga cggataccgt gaggtgttcg actacaccga
 8761 ggaagaagct aacgctgcca ttgattatgt ggctgataca ggaaagttat ttgtggctga
 8821 cctagaaggc gactattcta tggagaaggt agagcaaact tgcctagagt ttgaggctat
 8881 gggcatttct aatatcatca ttgataactt aacggggatt aaattagatg agcgtgcttt
 8941 tggtgggaag gttggtgcac ttgatgaatg cgtcaaacga attggtacta tcaaagaccg
 9001 acatgcggtt acgattttcc ttgtctctca ccttacacgt cctccggcaa accgtaccca
 9061 acacgaagaa ggtggcgaag ttatcctttc tgacttccga ggctcaggcg ctatcggatt
 9121 ctgggcatct tacgccttgg ggattgagcg taatacaaga gctgaaacgc ttgacgaaag
 9181 gactaccacg tacatctcat gtgtcaaaga ccgcgaccaa ggtatctgga ctggaaccaa
 9241 ggtcatgctt aagggtgaca ttcaaaccgg acgtttaatg gaaccacaag cccgtactaa
 9301 gtcatttgat acaggtgaag caaggcaaca agaagtgccg gatttaccgg acactataga
 9361 agagacaacc tttgacgatg aacaggagtt ttaatggaaa ttattaaacc agtattgaat
 9421 atcggtattg agatcctatt catgcttgtg atcgcagatt atgctgcacg atatggattc
 9481 aagaaagctg tgaaacttat cgttgcatct ggttttctta tgtcaatgtt ctttattgta
 9541 acacgcctta tctagtgtat ttatcagggc ttgtctcaca tgtgagacag gctcttatta
 9601 agtacattaa ataactggag attgattatg tatagattag tattgaatgt aggtgattat
 9661 gttcgtaaca tcaatgaagc ctcacgtcgt tatcgttgcc gtggtgtagt ggctcgtgta
 9721 agtgagaaca tgtatcatgt agaatatgag gatggtatta aggcttctta ccacaagaaa
 9781 acagcacata aatatcttga aaagattgta gagataaaca atcaatgtaa gtgcatacat
 9841 gatgaggttt gcgataaatg tgctcgccag atgcttaaga atttcctagc tcctctttat
 9901 tatggtgctg gtcctcaaac actagcagag tacatggcag aaaagaaaac cacactcaag
 9961 aaagagcgtc gcaatgtaat cactggtaag actcaaagtg aaatgattaa gcaatgtggc
10021 actgcattag gtgttacaca gttcaatact cgtgcattgg gtaaatccac agggcaagct
10081 atggtgaaaa ttggtgaagc tatgatgcac ccaaatgtgc ctgtgcgaat cttggatgtt
10141 gaccatgcaa tcacagagca tggcacacca cggcgtgtag ctaataatca tttcgccgac
10201 actatagaag gtattattcg taagcaaggg ttgaagggtc ttcacatctt aaatggtgaa
10261 gaattactgt acctacctat cgttactgaa gaaacctacg tgaatatcta aggagttaat
10321 catgactaag gtattaattt atatgcgtgg acctcataaa tgctatgcag ttgtagcacc
10381 agatggtgtc aagacatatg gtacttcaaa ggggtttgca ttaataggtg ccagtcttag
10441 tgcaagtttt cagatggaac ttttcggtca ttggactgaa aaagagttcc gtgaggagtt
10501 taatgtaatc ggcagcttta tggtgaaaca tgcaaaataa acacagtctt aagatgtttg
```

Figure 10(D)

```
10561 atggtcacga agacctgcaa gcacaaatta ctaaccaagc cttcctgttt gcacagttaa
10621 ctatggctga agcaaagaag aatagcctga cgcgcgagca agttatcaaa gaggcaactt
10681 gggagccaca ccaaggcaaa tacatgggcc agaaattaac tgtaacacgc agtcgataag
10741 taaagggttg tctcacacgt gagacagcct ttcatcatat tgattggagg tgcattatgc
10801 cacgtgatta tgattctgat tgggatttcc aagattcaat gaactcaaaa cctgaacgtt
10861 cagatgacta ctacgaaaca gaggcaatgt atgaaagcta ttaaagtcag taaggtttgc
10921 tcttgcggta aaggttatcg cagtcgtatt gatggtaagt gtgggcattg caggtctaag
10981 aaagaggctg ctttgtttga taagtaccac aatgaattag catataacta tcctcatcta
11041 acacctaatt ctttattagg acttggttat agggttaaat actttggagc aatctatgaa
11101 atcaattgat tggaagaagg aagcagaagg ccgcatctta gtgatggatt ctgaggctaa
11161 aggcctgctg gatgctatcc gatatggcca ccgcgaagat gtgcacatca tttgctgcat
11221 ggatttgctt actacagagg agttcctctt ctttgaccca tacgagatgc gtgaccctga
11281 agcaagagaa cgcctaaaag aatgggaagg ccatcaagat ggaacattgg ttgacggtgt
11341 taacttcctt aaacactgcg aagccatcgt ctcacagaac ttcctagggt acgacggcct
11401 tctatttgag aaagcattcc ctgatatctg gaaaggcttt aactataccg agagacgcgg
11461 caagggcaga ctccgcgctg acctgtgtcc ggtacgcgtc atggatacgc tggtcatgag
11521 tcgcctgtta aaccccgata gacgcctccc tccgcaagca tacgccaaag gcatgggtaa
11581 cgtagcccct cactcaattg aggcgcacgg cattcgtata ggccgttata agccggagaa
11641 cgaggattgg tctaaactaa ctgaccacat ggtacatcgt gtacgcgagg acgtggcgat
11701 aggccgtgac ctattcctct ggctatttaa cggagaatgg acggagcaca aacgccgtgg
11761 cgtgaataaa cgcactggcc taggtattga gacagccttc cacatggagt ccattgtggc
11821 gctggagatg agccgtcagg ccgagcgtgg attccgtctg gatatagata aagcattagc
11881 acgatgcgag gaattggacg ctaagattga tgagacagtc gcagcgttcc gtccgcacat
11941 gcctatgcgt atcaagtcta aaccttttaa accggaagaa aagaatgaag tatgccaacg
12001 cgcaaatgag tatggagcta gcaacaatat acctactgtc cttgacccct ctcactttct
12061 tcacgcagag agacgaggag atcgcaagac agtatggagt gtcactacta agtctggtga
12121 ttggtcggct agcgtcaaga aagactttcc tcaccttaga ggaaaccgta atgacacgcc
12181 aagcatcaag tggattggcg cttactcgcc tgttactttc gaagagattc ccttgggtaa
12241 cagggataca gttaagcaag tgctctatga ttatggatgg aaaggtgttg aatttaacga
12301 taccgagcaa gcgcatctcg atgagcatgg cgtattaccc aagccttgga gtgggaagat
12361 aaatgaaaag tcccttactt tatggcaaga gagagccgca cgtgaaggta aaacagtccc
12421 tgattggtgc ttgggtatcg ctgcatggta catactcgta tcccgtcgtg gtcagatcct
12481 caaccgtggt gacgttgaag ccttcgacca gaagggggtg tggccttcgc aagctggtat
12541 acgaaagtgt cgcggccttg tacctgtagc atttaacaag gagttaggaa tcaatgcgca
12601 gcaatactac gaaaggtacg gatgctggcc tacgtcagac aaggatgacg gagaatggcg
12661 tgtgccagct attgctatta gtattggaac ttctacgttc cgtatgcgtc atcgtaacgt
12721 ggttaatatt cctgcccgtg gtttgtatcc tttacgtgat ttattcatag ccggtaaagg
12781 taagctaatc cttggttgtg atggtgctgg tcttgaacta cgtgtactgt ctcacttcat
12841 gaatgacccct gaatatcaag atattgtact gcatggtgac attcacaccc ataatcaaat
12901 gaaggctggt cttcctaagc gtgacatggc gaagacattt atatatgcct tcctatatgg
12961 gtctggtata gctaaccttg cagcagtatg tggtgttact gaggaagaaa tggaggaagt
13021 tgtggcaaga tttgaggttg aactaccatc tcttgcacgt cttcgtgaga atgttatcgc
13081 acaaggtaac aagtttggct acctacaagc acctgatggt cattggggtc gcatccgtat
13141 gtctggtggt gaacttaaag agcacactat gcttaacgta ctactccaga tgactggttc
13201 tctgtgtatg aaatacgcat tggtcagagc gtttgcagtg atgcgcaagg aaggtgtggc
13261 cttagatagc atgggaaacc cttgcggtat agctaacgtg cacgatgaaa tccagatgga
13321 agtccctgaa gatgaggtct tgtatctcaa ctacgacttg cctttcacct tagaagggtt
13381 cgaaacagag aaggctgctg tgaaagcagt gttcgatgca gaggagaaac gtgttcatgt
13441 ggattctgaa ggacgtatgt ggtctgctgc aaatctcgtt agcgttgatg ctgatgctgg
13501 tgtacttcat tgccagcgtc gctatcaccg tgcagggcat atcattgccg acgcaatgac
13561 ttgggcgggt cagtatctga agatgcgttg tccgatggca ggtgagtata agattggtgc
13621 aagttggaag gaaacacact gatggacagg tttgatattg tttgcctatt ctccaccttc
13681 tttcttatat tccttatgct tgcttgctat ggaagtatgc gattagatat acctgatgaa
13741 gaggagggtt acgattgatg caggcatctt ttattattct tggagtcata ttatttatgg
13801 tagtattctg ggctttctct ggcattgacc cagattgtga tggtaactac gactgagtta
13861 tactcaaggt cacttacgag tggcctttat gaataactta ttcctactta ttttgtctaa
13921 catgatttac tggacactat agaaggaaag cctaggtaat ctaggtttat aaggtagtat
13981 aggtaattaa ataaatatag gagatataaa tatgtctatg gtaactactc tggtattcgt
14041 ggctcaatac tttcgtggtc ttgctaataa gttcaagtcc aaggctatca aagctattga
14101 ggctcgcatc gaagcagtac aggcagagca agttaaagtt gaagaacatc gtagttctca
```

Figure 10(E)

```
14161 aatgattgac tgtcataacc gctactatgc atctcgtgat gaactaaatg cacgtcaagt
14221 caaagaggta gaagatatgc tggcacgtca ccagcaagag cgtgacagcc tgaaagctga
14281 atttgaagag aacaaggcat caattgctct tgtaaatcaa gctgcatctg acagcctgaa
14341 gaaagagatt gttatgctgg aaatagaact ggacaacttg actaaataag gagttatgat
14401 ggaagaagtg attcaagcta aacatgtagg tatcatcttt cgtgacctag agcagcgtaa
14461 agttgcaggt cacactcgtc tggctaaaga agacgataca gcaatcacta ctgtggaaca
14521 agcagatgcc tatcgtggtc cagagtttac tcaaggtgaa acttgtcatc aattgagcct
14581 ttcactttgt gacactatgg ctagtgtaaa tgtacaagag gttgaagatg gtgaatgtgt
14641 tagttatgtc taccctctcg atactattgc acgtattaag gtagttcata agtaattact
14701 ggacactata gaacaatagg tcggcttagt tcggcctatg attgtaaagt gtcgttgatg
14761 ttgaaccatt gtgcaccttg cacaacccga taccgtatcg ggctttctag tgagcacatg
14821 cttgtgctca gtacaaagct aactgacaat aggagactaa ataaatggca cgtggtgatt
14881 tcgattttgg tgcttccgta tctaaagctg aaggtaaagt ctttaagaat ccagaagtag
14941 gtgatcatga agcagtaatc tctggcatca ttcatgttgg ttccttccaa gacatcttta
15001 agaaaggtaa taccactgaa gttaagaagc cagcaaactt tgttctggtt aagattgtcc
15061 tgatgggtga cgatgacaag aacgaagatg gttctcgcat ggaacaatgg atggctgtgc
15121 ctctgaagtc tggtgataag gcaacactga ctaagttcct gaatgcagtt gaccctaaag
15181 agttgctggg tggcttcgat gattttatcg gtgaatgtct gactgcaact atggttggct
15241 ctggcgacaa gaatgatgat ggtactttca agtatgttaa ctggaaaggc tttggcggta
15301 tgcctgataa gttgaagaag cttgtactgg ctcaggtaga agaggaaggt ctgtctatga
15361 caggtcatat caccttcgac aagctgacca aagaaatcat tgatgacatc ccagctaact
15421 tggtacgtca atacttcctg aacgagacac ctcgtggtaa gaacctgtct gttgctggct
15481 ctcacgtaga agctattatc aaagctgctc gtgaagaaga ccctgaatgg aagaaggcta
15541 agaagaaaga cgaggaagat gctaccccag ctaatcgtaa atctctggat actggtgagt
15601 ctgttccgca ggaagtacct gaagcagaag atacgcctgc accggagatg gatgaggacg
15661 cggaatatta aggagaacgg atgaaagtac aaatcgtaac tctgcattgc aagaaaggaa
15721 tcaccacact tggcggcaat acttttcact ccttctctga aggggagaca tacgccgacc
15781 ttcactatat ctggcgtgac gggcagcacg tggtgaacta cagcgaccct gcgactggta
15841 aacgccacgg cgtgtcgctt ccggcgcacg acattgctca ggtgaacaca gttttataaa
15901 gtctcacgtg tgagacaaat cggtgtccgg tatttactgg acactataga agagaagaat
15961 tttaatcggc gataatgcca taaccaacaa aaggagaatt taatatgttc aagattgaaa
16021 ctatcgtaaa ccgtgttgtt aaaggtgctg ctctggtatc cgttgagtct ttcattatcg
16081 tcgatgaagc tgatcaactg gtagctggta ctaaggctta cgatacccgt gaagaagctc
16141 aggctaagat tgacagcatg ggtaacttcg ctgctggtct ggagtttgct cgtgcttgct
16201 tccctgagca ggctgacaaa gcccagatcg gtaaggctaa catcgtagct gaatatctgg
16261 attggattgc tgctggtaaa ccagtgaaag aagttaaagc tgctgaagaa gctgaagctc
16321 cggcagtaga agtgtctgca ccggaagctc cggttagcga agaggaagag ttttgataat
16381 agcaggtgta gcctctgtta gtcctagttg actatcacgc tcacctcatc taatgccctg
16441 tctgccttag tgtaggcagg gtcttttgcg taatagttat tggagaatga attatgccga
16501 ctattgaatc tcgaattgaa ctggacatta gctacaatgc aatcaccaga cagtatattg
16561 gggttgccta tgattacaaa actggtgaga agctagtgga ggtgagacaa tgggatgact
16621 attggttaag acagaacctc catgatgcgg tgtcctcctt cttgaaggag tggcctacat
16681 gcgaccaaac ttcgacttcg gagctacagt atcggaagac aataatctca tcctgtggcc
16741 aactgaaggt aatcgaatcg ctttaataga tgctgatatg ttaccctaca tcgtaggtta
16801 tacaatcagt gacatgactt atttacgagc cacaactcgt gttaagtcag gacaagtccc
16861 atcaatcaaa gatacacctg agtgtaagca agcatgtgac cgtgtgaact ccttgcttaa
16921 ctcttgggtg tatgcagcag agtgtgatgc agctaagcta ttcatgacga aatcagaagc
16981 taacttccgt gtccgcctag cattcacaaa gccttataag ggtcaacgta agaccgagaa
17041 gcctccgttc ttctatgaat tgcgagagca tctcttagag gttcacggtg caatcttggc
17101 agatggtgag gaagctgatg acctcatgag catcgcacaa tgggatagcc accgccgctt
17161 ccagcaagat acaggtaacg agttcgctat cggtagtcca gagcataaag cattctctga
17221 tacttgcatc gtttccttag ataaggattt gatgattgtt ccccggttggc atctacagcc
17281 gggtcaagag aagaagtggg tagagcctat gggctggctt gagctacgcc gtaaggttaa
17341 tgggcaagtc aaagatctaa aaggtgctgg cctcatgttc cactatgcac agatgattat
17401 cggtgatgat attgataact atgctggcat accaggtcgt ggtgctaaat atgcctatga
17461 tcttctcaaa gattgtaaga cagagaaaga gttgtacatg gcagtgctgg gtgcttacaa
17521 ggctaagttc gggcatggac aagttaaaat taagaattac cgaggtggtt atcgtatcgg
17581 caaagccttt gacctaatgc ttgagtgtgg tcgcttagct cacatggcaa gattcaaggg
17641 tgatatatgg cgagccgata agaacccaat cttgtgggga gatgaaggat ggctacaaag
17701 ttaaaagcat ctgaagttgc tgcttataag aaagagttgc tagagaagca gggctggaaa
```

Figure 10(F)

```
17761 tgtcctattt gtggagcacc tcttaaagca gtggccgaga ttaaccgagt actagaccat
17821 tgccatcgca gaggttactg tagagcggta ctctgtcgtg ggtgcaatgg cggtatcggg
17881 aagatagaaa acctagtaaa gacttattgt aaggctgggg ataatgagta tttcattatc
17941 aagacattgc gaaacattgc agattatcta gacttacata gtaagcctca gactgataag
18001 atttatcata aacatcaaac ggaggcagag aagcgcgagg ctaagaaccg taaggcacgc
18061 cttgcttatg caagaaagaa gaaggaggtt aaagttgggt aagcttcgca gcttgtacaa
18121 agactccgag gtacttgatg caatcgagca agctaccgac gagaaaggta atgttaatta
18181 caatgagatg gcacggatat tatcgtgcca ccctgtgggt aagaagatta cccgccagtt
18241 ggctagatac tggcatggtc aattcaagaa gaccaagaag aatggtgatt actaccagac
18301 ccttctgcaa gaggataagc gtatcaagga agagcgtaag ctcaggactc ctgaccgcta
18361 cgaggatttg gctattgtac cattgcctga ctcgcctcat cgaagtgtac tggtaatccc
18421 tgatacccat gcaccgtatg agcacccaga taccttagag ttccttgcag cagtggcagc
18481 acgttaccgt cctgatacgg tggttcatct tggagatgag gcagacaaac atgccttatc
18541 gttccacgat tcggacccaa atctggacag tgctggcatg gagttagaga aggcccgtgt
18601 ctttatgcat aaattacaca agatgtttcc tgtgatgcgc ctgtgtcatt ctaatcacgg
18661 ctctatgcac ttccgtaagg caagcgccaa aggtattcct gtacaatatc tgcgtaccta
18721 tcgtgaagtc ttctttccgc atggggggtgg cgaccagtgg gattggcagc atacacacgt
18781 tcttgagttg ccgaatggtg aacaggttgc atttaagcat caacccgcag gctcagtctt
18841 agcagatgca gcgcatgagc gcatgaactt agtgtgcggt cacttgcatg gtaagatgtc
18901 ggtggagtat gcacgtaata cacatgaaca gtattgggct gtgcagggcg gctgtttgat
18961 tgatgagtca tctcgtgcat ttgcctatgg tcgtgagtcc aaatacaagc cagcattagg
19021 ttgtgtggtt attctggagg gtgtgccgca cattgtcccg atgcagacca atagtgacaa
19081 tcgctggatt ggtaagattt agttgacact atagaacaaa gggtaggtat tagcttaccc
19141 ttgattgtat agtgaatgga ggaattaata tgtcacaata tgtatgtgag aaatgcggca
19201 atcgatatga taactgcacc tgtgattata ataaaggtaa aaggattaaa tcaggtgatt
19261 atgttatacg acgtgcaggc tgccgcgacc cagagtgggg cagggtgtgt aaactattag
19321 gcaagaaatc agatgcaaca ttcaaagtta taaaggatga gtctgtcggc agcgccatta
19381 tacttgaagg tatcgaaaag cgagaatggt atgcacctta tttcgagaga gtggcaaccc
19441 caccagttgt acctgagtct aataactcaa acgataatat ggttacgcaa cctaagcact
19501 acgagttctt cgatggggta gaggcaatca ctatcattgc tcgtagtatg accgagaagc
19561 aatttgctgg atattgcatg ggtaatgctt tgaagtatcg tctgcgtgca gggaagaaat
19621 tcaacacgga agaagacctg aagaaagcag actactacaa agagctattc cagaagcatc
19681 gtcacgaatg tattgatgag gatatttaat atggaaggta aactgtatag agggtacttc
19741 ggtaacttat ataaagtaag ccctcgcggt tttgtattga cctctgatga tgaaggtgca
19801 atgtggttcc taagtgccta tggttctgac ttagcatact ttaaagaggc aatagttaaa
19861 ggtgtgatga aggaggtgaa atgaatatct tccaattcct aggtcttcca gaagaccacc
19921 gcaatcaccc attcatgctg gtgaaacatc gcggtgaagt acctgagaag aaattaactt
19981 ttccatgtta tgcacaggta aaacgagatg gtatatttag tgctgtggtt gttcgcaacg
20041 atggtgtcgt tggtgtcttt ggacgcactg gaaagaaact ggctaacacg gaaaccttgg
20101 aagaatctta ttcagctttc cctactggca tttatctcgg tgagttgcaa tctatggcta
20161 ttgatgtcta ccttgaagca ctttctggag tagttaaccc taaccgcact gagccactgg
20221 atttcatagg ccagcagatt aaagacaacc tgtatattga cttcttcgat atgttaacta
20281 ttaaggcatt ccatgatgga ttcactgatg tttcttatct caaacgttac gatgctttac
20341 atcgtcgcat cggcgctcat cttagcgggc acaacgctat cctttcctatt actccttgcc
20401 ataatgagcg agaagttgaa gcgtttgcgc aagagcaaat agatgcaggc cgagagggtg
20461 ctgtgttcaa actggactgc gattatgaag caggccacaa aggttatcgt caaactaaga
20521 ttgtacgcat ggtgtcttat gacctaacct gtattggttg ggaagagggt aaaggaaaat
20581 acaagggtaa ggttgctaac ctgatcttta aatggaaagg aggcaagtct gttaaggcta
20641 tgctgggtcg tggctggtcg catgaggatg cagcccaaat gtatcacgat attaaacacg
20701 gtggcgaact gaacgtcatt gggaaaatct tcgctgtcaa ggcgttgcag gaatctagca
20761 agggagtcct gagacttccc aaggtttctg agttgcgcca cgataaggag gttcctgatg
20821 tctattgatt tgaacgaaga gcagcttgaa ttgttaatag aagccattga gcaatactat
20881 tacatgtgtg gctatcaatc agaagaacta gactccttat attcacaatt aaaaggaggt
20941 taattatgtc ttttgattct atgaaggcaa ctcgtgcggt tgaggtagca gaggctatct
21001 tcgaaacttt atcctgtggt atggaagtac catatacttt actggctgat gcagaagagc
21061 ttggtctttc tatagaggcc atccaagaga aggttgagga actctatggt acagacgaag
21121 aagaaaccga cgatttcatt tgagggtatg gagatgcttg agatgattct caagccttct
21181 tctccgaagg tgactaagac tcacgaagaa ttaatcgtag atgaagtgaa gcgttacata
21241 atggattgtg tcagagcaca actggtggtc caatgatacg tccagcttca ttcttagata
21301 ttcctgagat tataaacctt gggaataagt acgtggaaga ggaagtcaag gttgtagccc
```

Figure 10(G)

```
21361 atcactcagc ctcatggaat gcagaacaaa gcgcacataa cctttgtgca tctcttagta
21421 gagaagattt attcctatgg gtggctgtag atgaagggca gattgtaggt tttctgtggg
21481 ccggctatca tgagttagcc ccttggacac ctgtaagagt tgcatctgac attctctttt
21541 atattgtacc agagaagcga gggacactgc tcggtatgcg cctcatcaaa gccttgaagc
21601 aatgggctaa tgatagtggg tgttccgagg tccgcctgtc tatcgcttct ggtattaatg
21661 aagaacgtgt cggacgtatg tataagcgac ttggctttga acagtttggc actgtgtata
21721 acctgaagtt ctaaggagat cacatgggta ttgtaaagaa agcatttaag gctgtcggtc
21781 ttgctcaaga tgcaccgcgt attgaagcca aggttcctgc tcagcagctt gagcgtaagc
21841 ctgagactga agctgaagat atacagattg gtgcaggtgg tgatgatgcg actgcatctg
21901 caaaaggtaa gcgcgggctt gtccgtccgg tagcttctag cttgaaggtg taatatgaaa
21961 cagagcacag atttggagta tggaggtaag cggtctaaga tacctaagct atgggagaag
22021 ttctccacta aacgtagctc tttccttgat agggcgaagc attactccaa attaaccttg
22081 ccctatctga tgaatgacaa aggtgataac gagacttcgc agaacggatg gcaaggtgta
22141 ggtgctcagg caactaacca cctagccaac aagctagcgc aagtgctatt ccctgcacag
22201 cgctccttct tccgtgtaga cctaactgca caaggtgaga aggttcttaa tcagcgtggc
22261 ctgaagaaga cagagctagc tactatcttt gctcaagtgg aaacacgggc aatgaaagag
22321 ttagagcaac gtcaattccg gcctgctgta gtagaagcat tcaagcatct tattgttgct
22381 ggtagctgta tgctatacaa gccaagcaaa ggtgcaatca gtgcaatccc aatgcatcac
22441 tatgtagtta atcgtgacac taatggcgac ctgttagaca ttatcttact gcaagaaaaa
22501 tccttgcgta catttgaccc tgctacacgt gctgtagtag aggttggctt gaaaggtaag
22561 aaatgcaagg aagatgacag cattaagctg tacacacatg ctaagtatct tggtgagggt
22621 ttttgggaac tcaagcaatc tgctgatgat atccctgttg gtaaggtaag taaaatcaaa
22681 tcagaaaagc taccatttat cccgctaact tggaagcgaa gctatggtga ggattggggt
22741 cgtcctttag cagaggatta ctccggtgat ttattcgtta tccaattctt atctgaagca
22801 gttgcccgtg gtgctgcact gatggcagac attaagtacc tgattcgtcc gggtgctcag
22861 actgatgttg accactttgt taactctggc actggtgagg ttgtcactgg tgtagaagaa
22921 gatatccata ttgtacagtt aggtaagtac gcagacctca cacctattag cgcggttcta
22981 gaggtataca ctcgccgtat cggtgtagtc ttcatgatgg agacaatgac acgtcgtgac
23041 gctgaacgtg ttactgctgt agaaatccag cgagatgcgt tagaaattga gcagaacatg
23101 ggtggtgtat attccctctt tgctactact atgcaatcgc cagtagcgat gtggggtctg
23161 ctggaggcag gagactcctt cactagtgac ctagtggacc ctgtgattat cacaggtatt
23221 gaagctttag gacgcatggc tgagttggat aaactggcaa actttgctca gtacatgtca
23281 ctgccattac aatggcctga gcctgtacta gctgctgtga aatggcctga ctatatggat
23341 tgggtacgag gtcaaatctc tgctgaactg ccgttcctta aatcggctga agagatggaa
23401 caagaacagg aagcacagat gcaagcacag caagcacaga tgcttgaaga aggtgtggct
23461 aaggccgtgc cgggtgtaat tcaacaagaa cttaaggagg cgtaatgtct ttctcattta
23521 ctgaaccgtc aaccactcat cctactgctg aagaaaatcc ggtagaaacc aaggaggtaa
23581 caactgatgc tgctactact gatgttcctg ctgatgctgg cactgctgta caagatgaca
23641 atgctggtgc acaatctact gaagacgccg gaggagaagc ttctggacag ccttcagaag
23701 aaggagacaa tggcggagag aatggtgaat ctaagccaga tgataccgcg accgacactg
23761 aggaagtgca gtacttcttc ggagaatatg aagtaacagt agatatacca caggatgtta
23821 cggatagcct taaagagaag ggtattgatg ctaagcaggt tgccaaggaa ctctatgcca
23881 aagatggcaa gtttgagctg tctgatgcaa ccaagcagaa attgtatgat gcttttggca
23941 agtttgcggt agatgcttac ctgtcaggtc ttaaggctca aaatgaagcc ttcttcctga
24001 aagaagccaa cgcagctaaa gagttggaag cagctaatac ccaacgcttc tctgatgttt
24061 ctaaggaaat tggtggagaa gaaggttggt cccgtcttga ggcgtgggcg cttgaaacgc
24121 tatccaatga cgaactcacg gcattcaatg cggtgatgga gtctggcaac caatacctcc
24181 agcaatatgc tgtgcgtgaa ctagaaagcc gccgtaaagc tgcacagggt gatgacaagc
24241 caaacttgat tgagccatct gcacctgctg ccgcatctga ggataatgga cctctgtctc
24301 gcgagcagta tctccgtgag atgatgacgc tgggttcccg cttcggtaca gacaagaaag
24361 ctgctgctga gtatcaggct aagctggatg ctcgccgccg tgcgggtatg gctcgcggac
24421 tttaatcagt atttactgga cactatagaa gggagaaatg tctccctaaa ttatcaattt
24481 gatttataag gaggtttatt aatgtctacg ccgaataacc tgaccaacgt tgcagtttcc
24541 gcttccggtg aggtagacag ccttctcatt gagaaattca atggtaaggt aaatgagcag
24601 tacctgaaag gtgagaatat catgtcttac ttcgatgttc agactgtaac tggtactaac
24661 actgtaagca acaagtactt gggtgaaacc gagttgcagg ttctagcacc gggccagtct
24721 ccggctgcaa cctccactca ggccgataaa aaccagctgg taattgatgc cactgttatc
24781 gcgcgtaaca ccgttgcaca cctgcatgat gtacagggtg atattgacag cctgaaaccg
24841 aagctggcta ccaaccaagc taagcagctt aagaagatgg aagacgagat gcttattcag
24901 cagatgctgc tgggcggtat tgccaacact caggccaagc gcacaaatcc tcgtgtgaaa
```

Figure 10(H)

```
24961 ggtcatggct tctctgtaaa cgtagaggtc aatgaaggag aagcactggt taacccacag
25021 tatgtaatgg cagctgtaga gtttgctctg gagcagcagc ttgagcagga agttgatatc
25081 tctgatgtag ctattctgat gccatggcgt tacttcaacg tactgcgtga cgcagaccgt
25141 attgttgata agagctacac gattagccag tccggtgcta ctatccaggg cttcgtactg
25201 tcttcctaca attgtccggt gatcccgtct aaccgcttcc ctaaatattc tcaggggcag
25261 aaacatcacc ttttgtctaa cgaagataac ggctatcgtt atgaccccgat tgcagaaatg
25321 aacggtgcta tcgctgttct gttcactgct gatgcattgc tggttggtcg ctctatcgac
25381 gtaattggtg atatcttcta tgagaagaaa gagaagacct actacatcga caccttcatg
25441 tcagaaggtg caatccctga ccgttgggag gctgtgtcgg ttgttactac caagcgtcaa
25501 agcactggag cagttgactc tggtaatgct gcacagcaca ctcaggttct gaaccgtgca
25561 cagcgcaaag ctgtctacgt taagaatgct gcccctgcag gtgctttcgc tgctgctagc
25621 ttgtctgctg aagacttggt tgctgctgta cgtgcagtga tggctaatga cattaagccg
25681 actgcaatga aacctactga gtaataccta tgccctatct accttgcgta ggtagggttc
25741 tttttgttag gaggattcat gcctgtaatt agacaaacca gtaaagtagg acatatgatg
25801 gaagatgtgg ccttccagat tattgatagt aagctggaag cggtaaactt gtgtatgcga
25861 gctattggtc gtgagggtgt ggattctctc gactcaggtg acttggacgc agaagatgca
25921 agcaagatga tcgacatcgt atcccagcga ttccagtaca acaaaggagg tggctggtgg
25981 ttcaatcgtg aaccaaactg gcagattgca cctgatacca atggtgaagt caatctacct
26041 aacaactgcc tagcagtatt gcagtgttat gctttgggtg agaagaaagt acccatgact
26101 atgcgagcag gtaagctcta ctctacatgg agtcatacct ttgatatgcg taagcatgtg
26161 aatgctaatg gtatgattcg tcttacctta cttaccttac ttccatatga gcatctacct
26221 actagtgtaa tgcaggctat tgcctatcaa gctgctgtag agtttattgt gtctaaggat
26281 gcagatcaga ctaagctagc cactgcacag cagattgcca ctcagcttct aatggatgtg
26341 caatcagaac aaatgtcaca aaagcgattg aatatgcttg tacataatcc tacgcagcgt
26401 cagttcggta ttatggcagg tggttctcag aatgtacctg cttactctca ttcaccatat
26461 gacagttggg cacttcgtcc gtgggaggat cgttaatgga agtacaaggt tcattaggga
26521 ggcaaatcca agggattagc cagcaacctc cagcggtacg tcttgatggt caatgtacga
26581 ctatggtgaa catggtccct gatgtagtga atggaactca atcccgcatg ggtacaactc
26641 acattgctaa gctcttggat gaaggtacag ataatatggc aacgcaccat tatcgcaggg
26701 gtgaggggga tgaagagtat ttcttcacct taaagaaggg gcaagtgcca gagatatttg
26761 ataagcatgg acgcaagtgc aatgtcatct ctcaagatgc acctatgacc tacctttctg
26821 aagttgttaa ccctagggaa gatgtgcaat tcatgactat agctgatgtt acttttatgc
26881 ttaaccgtag gaaagtggtt aaagttagta ataggaagtc acctaaagtt ggagataaag
26941 ccattgtgtt ttgtgcatat ggtcaatacg gtacatctta ttctatcata attaatggaa
27001 ctacagctgc tagttttaaa acaccagatg gggaagtgc agaacatgtt gaacaaatac
27061 gaacggaacg tatcacttct gaattgtact ccaagttgca gcaatggagt ggtgtgaatg
27121 actatgaaat acaaagagat ggtacgagca tatttataga gagacgcgat ggtaaaagtt
27181 tcacagtaac aactaccgat ggtgcaaaag gtaaggactt agtggctatc aagaataaag
27241 ttagctctac tgacctactc ccttctcgtg cgcctgctgg ttataaagta caagtgtggc
27301 ctactggcag caaacctgag tctcgttact ggctgcaagc tgagcctaaa gagggaaacc
27361 ttgtgtcttg gaaagaaaca atagctgctg atgtattact tgggtttgat aaaggcacaa
27421 tgccttacat tattgaacgt acaggtatca tcgacggcat agctcaattc aagataagac
27481 aaggtgattg ggaagatcgt aaagtagggg atgacttgac taaccctatg ccctctttta
27541 ttgatgagga agtaccccag acaataggtg gaatgttcat ggtgcagaac cgcctatgct
27601 ttacagcagg tgaagcggtt attgcttctc gtacatcata cttcttcgat ttctttcgtt
27661 atacggttat ctctgcattg gcaactgacc catttgatat ttttctcagat gcgagtgaag
27721 tctaccagct aaaacatgca gtgaccttag atggcgctac cgtattgttc tctgataagt
27781 cacaattcat actgccagga gataagcctt tagagaagtc aaatgcattg cttaagcctg
27841 ttacaacatt tgaagtgaac aataaagtga agccagtagt aactggtgaa tcggtaatgt
27901 ttgccactaa tgatggttct tactctggtg tacgagagtt ctatacggac tcttatagtg
27961 acactaagaa ggcacaagca atcacaagtc atgtgaataa actcatcgaa ggtaacatta
28021 ccaacatggc agcaagcacc aatgtcaata ggctacttgt cactactgat aagtatcgta
28081 acataattta ctgctatgat tggttatggc aaggtacaga ccgtgtacaa tcagcatggc
28141 atgtatggga gtggcctatg ggtacaaagg tgcgaggtat gttttattct ggtgaattac
28201 tttatctact ccttgagcga ggcgatggcg tctatctgga gaagatggac atgggtgatg
28261 cactaaccta tggtttgaat gaccgcatca gaatggatag gcaagcagag ttgatcttca
28321 agcattttaa agcagaagat gaatggatat ctgaaccact tccttggact cctactaacc
28381 cagaactttt ggattgcatc ttaatagaag ggtgggattc atatattgga ggttctttcc
28441 tgttcaaata taaacctagt gataacacct tgtctacaac ctttgacatg catgatgata
28501 accacgtaaa agcgaaggtt attgttggtc agatttaccc tcaagagttt gaacctacac
```

Figure 10(I)

28561 ctgtagttat cagagatagg caagaccgtg tatcctatat tgatgtacct gttgtggggt
28621 tggttcacct taatcttgat atgtatcctg atttctccgt ggaagttaag aatgtgaaga
28681 gtggtaaagt acgcagggtg ctagcgtcaa accgtatagg tggtgctctc aacaacacag
28741 taggttatgt tgaaccaagg gagggtgtct tcagattccc actgagggct aagagtacgg
28801 atgctgttta tcgtattatt gtagaatcac ctcatacatt ccagcttcgc gatattgagt
28861 gggaagggag ctacaatcca accaaaagga gggtctaatg gctataggtt cagccgttat
28921 ggctggtatg tcttctattg gtagcatgtt tgcaggcagt ggtgcagcag ccgctgctgg
28981 aggtgctgcc gcaggtggcg gaggtttgct aggttcacta ggtggattcc taagtggctc
29041 cactgctggt ttctctaatg ctggccttct tggtgctggc cttcaagggt taggcttgat
29101 tggtgatcta tttggtggaa gtgatgaagc caaggcgatg aagaaagcac aagaagagca
29161 atggcggcag cagcttattg ctacacaaga ggcgtacaag acagtggcag acgcagaacg
29221 ttctgctgct aaacaatatc atgcagatgc aatcagtaat caggcttcac tgctacagca
29281 gcgagcacag gttgcattac ttgctggggc tactggtact ggtggtaatt ctgtgtcctc
29341 tatgcttaat gacttagcag cagatggcgg caggaaccag agtaccatca ttgataacta
29401 tgagaatcag aagattaatt tcaccaacca acttaagtct atccaacgtg gtggtcagat
29461 gcagatgcgt gagtttaaga agccttctgc tatgagtacc ttggttcaag gtattccaag
29521 tctggcatct gcctatgtaa ctggtagtaa gtctggcaag gcattgggta aagccttaac
29581 tgattctcgt acatattcat ctggaacaag aggtatttaa tggcaattga gcgacaagca
29641 gtacaaggtc tgccacaagt gcaggccact tctcctaatg tcatgacctt tgcacctcaa
29701 caagtgggag gtgtggaggc tggcgtggct tctacctccg gtagtaggtt tatcgaagac
29761 cttattcgtg cagccagcag tgtggctgat gttaccactg gtatccttaa tcagaagatt
29821 gaggaagata aggttgttca aatggaacgg gcatataacg gactaatgcc ttctgaggat
29881 gcaactcgtg gtggcgctcg tgctaacatg cttgtcaaag ctcaactgct agctaatgat
29941 gaagcagcac gaatgaaaga catggctact cgtttccaag ggacggatga cgagtggaca
30001 caacttatgg ttgactctcg taatgagatg cagaataagc tgttccagca ataccctgag
30061 ttgcaaggtg acaaagatac tatgcgtatg gtcactaatg tctttccaaga acagcagcct
30121 cagatttggg ctacacgaac ccagcataaa cttgaccgtg aacaagcaga ccgggaggat
30181 acctttgacg ggcgagtggc ttctacttgg gatcctaata ttgaccctga agcatctggc
30241 tatgctttac aggaacgaat ccgcgaaggt cttactcaag gattactacc tgaacagatg
30301 cacaagaagt tagtccagcg agcaatttca cttgcacaag gcggtgatgt tagcatggct
30361 gaagccctga agtatgtgaa ggacgataag ggtgtttctg tttatgctaa gaatccacag
30421 cttatcacag ccatcactag tggtaatgca gtttgggcta ggaataatgt agctgatgta
30481 actcgtatgt ctttcgaagt taaagaatca taccttgcag gtgatttaac tgatgaagaa
30541 ttgttggaac gagcacagca cattaataat ctgacaggta actctgtctt ctctaatcca
30601 gaactagagg cactgatgcg ccaacgggct aagcagaatg cagagctagg tgcaatgcag
30661 gatatgcgac gtgagcttta ctccgaccgc ctgactggct tccaaggtaa gactgataaa
30721 gagaagaagg cttacattga tgttatcaaa caggatagcc aactttatgc agaccagcaa
30781 atcaaacaac gtggcttgga cccttacagt caagaggctg aagctattcg tggtgcagtg
30841 gaagtgcagc gcctgcaatt catgaactcc aaaggtttag tggatgatac ctttgaatct
30901 cgtatcaagg ctatggaatc catgctatca cctgagcact ttgctaaagg tgaaccacag
30961 gagttaatga ccattcgtca gttgtgggag cagttacctg aagaaagtcg aggtgtcttc
31021 ggtgacactg tgaacggtta tatggataac tacaatactg cattacaaat gggagagaca
31081 cctttgcagg ctgcaaggtt tgcccgtgaa gcacagcaga aattctctcg tactgagaag
31141 gaaaccaaga agttcaactc cgctattgga gatgcactgg atgaggtatc tggtgctggc
31201 tggtttgatg gtaaaaccga ggtgtcagac ttaggtaaag ctattgcgga agaagagtta
31261 cgagctaagg ccaatatgtt gtggtctagc ggtatgcgta acatggattc tatcaagaag
31321 gctttaatca cttggggcaa taaacgctac actcaatcag aggatgcaaa gacttccggt
31381 ggctatttca ttaaaggtga ttacacttct gcatctgata tgcttatgtc agttgggaaa
31441 ggtgtaaacc ctaccgatgt ccctctggcg cttggtaggt atgtagaaac acagatgcca
31501 gaattgaaga aggagcttca agagtgggaa actaaggatg atgtgtacat tgattacaat
31561 gaacagaaag gaacttttgt gattcgtgct ggtgcagcag gtcgccctct ttctggagta
31621 atccctgtaa cttctttgga taccacttca ctactggatt ctgcctatca gaagaaagta
31681 gaagaacgag ataaaggcga gtatgttcat ccctatcgta cagatatcgg tgcacaagaa
31741 ccaatgccag ctaagccaac tgccaaagat attggtaaat taggattagc taacttcctc
31801 atgtcttctg cttttgcttc tggtgagaat ctaccttcta acttcgagat taactatcga
31861 ggcaatatgc aacaattcta tgacaagcta gctatggatg agaataaaga taaagttggc
31921 tttaataagg caactggaac ctttactcca tataaagacg ctcacggtga gtctatcggt
31981 tacggtcatt tcttaacgga agaagagaag cgagacgggt atattaagat tggcgatgaa
32041 ctagttccct atcgagggtc tatgtctcag cttacagaga gtaaggctcg cgctcttatg
32101 gagcaagatg ctaggaagca tgtgcctcct actcgtgact ggaagattcc gtttgaccag

Figure 10(J)

```
32161 atgcatcctg cacagcaacg tggcttgatg gatttaacct acaatttagg taaaggtgga
32221 atccagaact caccgcgtgc tcttgctgca ttcaaagctg gtaagcttac ggaaggcttt
32281 atcgaaatgc tgggtactgc atcaagtgaa ggtaaacgta ttccgggcct actgaagcga
32341 cgcgctgagg catacaatat ggcagctgct ggtggtgtac ctaagatcac agaagtggag
32401 acgagggaag atggctctat gtgggttaag tttggtggac ctatgccagc aggctctgtt
32461 tctgcgtgga cgcataaacg tattggagcc gatggctggt atcaggttta tgaggctgca
32521 cctaccaagt tagctaaaga ctctaaggta ggtaaagtta aattgtagta cctaactcaa
32581 ggcttgtctc acatgtgaga caggtcttta tgataggcac tatggaggaa ctatggaaca
32641 agatattaag actaattggg ctggatatgt ccagtctact cctgagccgt tttctattga
32701 ggcggctccg gtatcggctc ctacgatacg ccagcgtaat gagttacaag agcaagttct
32761 tgaagccaaa gctgatgcgg acatcttagg tgctgtaggt gctgccttcc agaatgaatg
32821 gttggcattc ggaggtaagc gatggtatga ccgtgccact gctgatttca caccccaacc
32881 tgactttgaa atccaaccag agcaacgtga agcactacgt ttcaaatatg gtacggatat
32941 gatgcagaca atcactgagg gtgttcgttc tgaggatgaa ttgaacttcc gtattcagaa
33001 tgctgatgaa gaccttgagc gcaataagcg cattgctcag gctggatggg ccggctctgt
33061 ggcaacgatt ggcgctgctg tgcttgaccc agtgggttgg gttgcctcta ttccaaccgg
33121 tggtgcagct aaagttggac tcgtaggccg tgctgtgcgt ggcgctatcg ccgctggcgt
33181 gagtaatgcc gctattgaat ccgtattggt ccaaggtgac atgactcgtg atttagatga
33241 cattatggta gcactaggtt ccggtatggc tatgggtggc gttattggag ctgtagcgcg
33301 tggtagggcc actaagctca gtgagcaagg ggatgacagg gctgcgagca ttgtgcgcag
33361 tgcagacgca ggggaccgct atgtgcgtgc tgttgctgat gacagtatcg gtgcgatgcg
33421 tgttaagggc gaagaggtac tcactgaggg tgcatttgat atctctagca aaggtgaaga
33481 tttgctgaaa accctacagc gggaaggtaa tgcaattgat atgacacctc gccgctgggc
33541 cggaactatg tctgcccttg ggactgtcgt gcactcctct caggatgcta gtgttcgtgg
33601 cctcggtgct cgcctgtttg agtctccgca aggtttaggt atgcaaaagg catctgccag
33661 tcttatgcag aataccaact tgaatcgact gaagtctgct gatatgaacc gtttcaatga
33721 cgggtttgac ttatggctca aagaaaataa tatcaatcca gttgcaggcc atactaactc
33781 tcactatgtg cagcaatata atgagaaggt atgggaagct gtacgcatcg gtatggatga
33841 ggctacgcct aagtctatcc gtatggcagc agagggggcag caagctatgt atcgtgaagc
33901 attagcatta cgtcaacgct ctggtgaagc tgggtttgaa aaggttaaag cagatgataa
33961 gtacatgcct gatattttg acagtatgaa ggctcgtcgt caattcggta tgcacgataa
34021 agaagatatc attgagttat tctctcgtgc ttatcagaac ggcgctcgta aaattccaaa
34081 agaagtagcg gatgaaattg cacgagcaca agtaaaccgt gttgtggatg ccactctgac
34141 aggacgtatg agtttcgaaa aggctatgtc tggtcagact aaagcagagt atgaagcaat
34201 aatgcgcaag gcaggcttca gtgatgaaga aattgaaaag atggtagaag ctctggataa
34261 taaagaaacc aaagataata tctctaaccg agctaagatg agtttaggct tagatgttac
34321 tcaagagtac aatggcattc gtatgcgtga ctttatgaat actaacgtgg aagagttaac
34381 agataactac atgaaggaag cggcaggtgg tgctgccttg gctcgtcaag gtttctctac
34441 ctatcaggct gcacttaatg caattgacct tgtagagcga aatgcacgaa atgcagctaa
34501 agatacaaaa gcacacgcac aatttgaagc ggagtctgct aagattcgtc aatcagagcc
34561 tgattacaag aaggcacaag agaagattga agagctaaag aagcgactta aattgaaaga
34621 gaaagatgaa gcagcaggtc tggctattga tgaagaaatc cgtcagatgc gagaagggct
34681 tcgcttgatt atgggtaaat ctatcgatgc agacccacag gctttgtcta ctaaaatgct
34741 gcgtcgtggt cgtgacatca caggcgtact tcgcttaggt cagatgggtt tcgcacagct
34801 aggtgaactt gctaacttca tgggtgagtt tggtattgct gcaaccacta tagctttagg
34861 taagcaattc cgctttacat ctaaggcttt gcggagcggt gatggcttct tccgagataa
34921 gaacttggca gaagtagaga ggatggtagg ttacattggt gaggataact ggctaacaac
34981 caagggtgca cgtccagatg agtttggtga tgtaaccaca gtaaaaggaa tgatggctca
35041 ctttgaccaa tccatgaact caatacgtcg tgctcaaacc aacctatcac tcttccgcat
35101 ggcacagggt tctctggagc gaatgaccaa taggcaaata gctttgtctt tcattgacca
35161 ccttgaaggc aagaagatta ttcctcagaa gaaactggag gaacttggtc ttactcagga
35221 gttcatgact aacctacaga agcactatga tgctaactct aaaggttctg gcttgcttgg
35281 ctttgataca atgccttatg ccatgggtga aactttagct aatgctattc gtcgtaagtc
35341 aggtctaatt atccaacgta acttcattgg tgatgaaggt atctggatga acaaagcact
35401 aggtaagaca tttgcacagc ttaagtcatt ctctcttgta tctggtgaga agcaatttgg
35461 tcgagggatt cgccacgata aaattggtct tgctaagaag acagcttacg ggtttgcttt
35521 gggttcaata gtgtatgcgg caaaagccta tgtgaactct attgggcgag aagaccaaga
35581 tgaatatttg gaagagaagt tatcgcctaa agggttggcc tttggtgcaa tgggtatgat
35641 gagtacaact gctgtattta gtctaggtgg agatttctta ggtggcctag gtgttctacc
35701 ttctgagtta gtacaatccc gttatgaggc tggctttcag actaaaggtt tgatagacca
```

Figure 10(K)

```
35761 aataccacta gtaggtgttg gtcaagatgc atatcgttta gcagattcta taactaaata
35821 tgcagagggt gatacagaag gtgtagatgt ggcacgtagg gctttacgct tagtgcctct
35881 aactaatgta ataggaatcc agaacgcatt gcgttatggc ttagatgaac tggaggattg
35941 atgagttata ctttcacaga acatatagcc aacggtacgc aagtaaccta tccctttagc
36001 tttgctggca gggataaagg ctatcttcgt gcctcagatg tgatagtgga atctcttcaa
36061 ggtaacactt ggattgagat tacatctggc tggcaattaa ctggtacgca tcaaatcact
36121 tttgatgtag cacccgttgc aggtttgaag ttccgtattc gaagggaagt acaaaaggaa
36181 tatccatacg ctgagtttga ccgtggtgtt accttggata tgaagtcttt aaatggttct
36241 ttcattcata tactggagat tacacaggag ttacttgatg ggttttatcc agaaggatac
36301 ttcattaagc agaatgtaag ctggggcggc aataagatta ctgacctagc tgatggtgag
36361 aatccaaaag atgcagtaaa taaatcacag ctagatgcta tcgacaagaa gcatactgat
36421 tggaactctg cacaagatat agagattgct ggtattaaga gagggatggt gtctggtgtg
36481 tcgcatcgaa ctattccttg gtatatggtt gcctccggtg gagagcaaat cattcgacca
36541 ccttactcat ttgatgatgc tatggtgttt ataaacggtg tattccagca tgaactagca
36601 ggtgcagtat ccgtggggta tgatgttata accctgtcca agccattaca ggctggggat
36661 gaagtttatg tgcttatcgg tagtcgctta accccaccta caagtgcgga tactatcctc
36721 tttacacaag cagtgagtga aggcacacaa tctatcgaca ttgtaacggc tttccaacgt
36781 cttgatgtat acttggatgg cctgtatcaa cctaataatg cttatgaaat cgtagggtct
36841 actatcactt tcagtgagcc attacctgag tgtgtcgtaa gtatgaagct acaactagtg
36901 taaggaggtg agatgattaa ctccgaactg gtagatagtg gtgtgaagct tgcgccacct
36961 gcattagtct caggtgggta cttcctcggt atcagttggg ataattgggt gttaatagca
37021 acattcattt ataccgtgtt gcaaattgga gactggtttt ataccaagat taaactatgg
37081 aggaagaacc gtgagcgtcc acaataaaca tgcagctaca gaagatgagg ttggcatcct
37141 gcatggtgct attaccaaaa tctttaataa gaaagcacag gcaatactgg acactataga
37201 agaagaccca gatgcagcac tgcatttagt ctctggtaaa gacattggag ctatgtgtaa
37261 gtgggttctt gataatggta ttaccgctac acctgctgca cagcaggagg agtccaagct
37321 atctaagcgc ctcaaggcta tccgagaggc atcaagtggc aagattattc aattcactaa
37381 ggaggattga tggctaaggc aagagaatca caagcggagg ctcttgccag atgggagatg
37441 ctacaggagt tacagcagac ctttccttac acagcggaag gtttgcttct ctttgcagac
37501 acagttattc ataacttaat tgcaggcaac cctcatctga ttcgtatgca ggctgatatc
37561 ttgaagttcc tattctacgg acacaagtat cgcctcatcg aagcgcctcg tggtatcgct
37621 aagacaacac tatcagcaat ctatacagta ttccgtatca ttcatgaacc gcataagcgt
37681 atcatggttg tatcccaaaa cgccaagcga gcagaggaaa tcgcaggttg ggtagttaaa
37741 atcttccgtg gcctagactt tcttgagttt atgctaccgg acatctacgc aggggaccgt
37801 gcctcagtta aggcatttga gattcattac accctacgtg gcagtgacaa gtcgccttct
37861 gtgtcttgtt actcaatcga agcaggtatg cagggtgcgc gtgcagatat catcctagca
37921 gatgacgttg agtcaatgca gaatgctcgt acagcggcag gacgtgcctt gcttgaggaa
37981 ctgaccaagg agtttgaatc tattaaccag tttggtgata ttatctacct tggtactcct
38041 cagaacgtaa actctatcta caataaccta cctgctcgtg gttactctgt tcgtatctgg
38101 actgcacgtt atccctcagt ggagcaggag caatgctatg gtgacttcct tgcacctatg
38161 attgtgcagg atatgaagga caacccagca cttcgctcag ggtatggctt ggatggcaat
38221 agtggtgccc cttgtgcacc tgaaatgtat gatgatgatg tgctgattga gaaggaaatc
38281 tcgcagggtg cggctaagtt ccagcttcag ttcatgctta acactcgcat gatggatgct
38341 gaccgctatc cgctacgcct gaacaacctc atcttcactt cattcggtac agaggaagtc
38401 cctgtgatgc ctacgtggag caatgattcc atcaatatta ttggcgatgc accgaagtat
38461 ggcaataagc ctacagactt catgtatcga cctgtggctc gcccgtatga atggggcgct
38521 gtcactcgta agattatgta tattgaccct gctggtaaac acctctgcca gcgtaaaacc
38581 ctcttaattc ggtggaactc tcactgagac aataccgagc gaagcctgtt gcaataacag
38641 gaacgtgtag agactaactg taaggccaag cggtctgaaa cagagggagg cgcaagccta
38701 agatatagtc cgacctacta ggtgactagt agaagttaaa gtagcgaatt aacgtaacaa
38761 ttgaagggag ttaaatatga cagagcataa agtttatcat attcgtgttg ttggtgaaac
38821 tgatgtaatg caaggttata ttggtgtaac ctccgatatt aagaagcgta tgagagagca
38881 caagtgtgca ggccgtcttt gtgatggccg cgagtacgtt atcttattca ctggtagcaa
38941 agaagagtgt tatgcactag aagagaagct acgcccacat gacaacatgg gttggaataa
39001 gggtaaaggt ggttatcgca aagcaggtaa catcgagaaa ggtgaacgca taagtattgc
39061 cactgaaatc aagaaaggac agcacttgtc tgttgccact gagttcaaga aaggcatgac
39121 accttacaac aaaggtactg gcaaagatta catattcact tctccagatg gtgaagagtt
39181 tcttgtaact tgcattactg acttctgtaa agagcacaac ctaacacctc agaatatgcg
39241 taaggtggca cgtggtttac gtaaacacca caagggttgg ctcgcacgtc acgttcaaac
39301 cgggaggtaa gaatggggat gaaacgggtg tggctatcgt cttcctgcac ggcacattca
```

Figure 10(L)

```
39361 tttatgtgta tcagtgcttt ggtgtgccgg gaggataccg cgaatcgtcc ctgaatcgca
39421 ttgtgcaggc cgcaaagcag gcaggtgtta aagaggtatt cattgaaaag aactttggtc
39481 atggcgcgtt tgaggccgtt ataaagccat actttgaacg agagtggcct gtgactctgg
39541 aggaagatta cgccaccgga cagaaagagt tgcgtatcat tgaaacacta gagccactaa
39601 tggcggccca caggctcatc ttcaacgcag agatggtcaa gtctgatttt gagtcggtac
39661 agcactatcc gcttgagcta cgcatgtcat acagcctttt caatcaaatg tcgaacatca
39721 cgattgagaa gaacagccta cgacacgatg accgcttaga cgctctgtat ggcgctatac
39781 ggcaattaac ttctcagata gactatgacg aggttacacg gattaatcgc ctcagagcgc
39841 aggagatgcg cgattacatc catgctatga acacacctca cctccgtagg gcaatgctct
39901 atggagatta tggcactgag cgaagagtaa ccaacacttc cgtggctatg cagcaaagag
39961 tatacggtca gaattacagg agtaaatcgg caagcagaaa tacactttct gcaaggattt
40021 caaggactta ttaattaccg gacactatag aaggaaggcc cagataataa gagaaataac
40081 aaggataata taggttaacc taggttatat aggtattcct tagtatgggt gtactcctgt
40141 acaccctatt ccttacttcc ttactatact tacataatag gagagagaga gagagagaat
40201 gtctaatagt tatagtacac aacctcttac aggtaagtct gctcgtaagc agatacaacc
40261 tgttagtgaa gcccttatgc ttcctgtagt ttacgaggac actgttgaga agaaaggtga
40321 tgttattaat gatgccacca aatcaggtaa gcagaaaggg gccatggtgt gtcttgatac
40381 acatgataac ctggttattg ctatcgcagt tgatggcaaa gaagattcca attggttgac
40441 agctaataaa gcggtcacta ctattacccc agcttaagag gagagttaca tgtctaaata
40501 tggaaccgca ggtactgtta ctggtcaggc ttttcgagta aaaactgtac aaaccactgc
40561 aacggcaatc cctttgccta ttgttgctga agcagacctt aagaagaaag atcatcctat
40621 caacattaaa cacctctctg gtaaacagaa aggtgccatg gttgctgtag agaaaacaga
40681 ccaatccttg tacatcgcta ttgcacgtgg gagtgaaccc accgacaagt gggatgcaac
40741 tactatggag ttggaccctg taacacctgc ggcttaattg taaagacgag gtcaatagtg
40801 cttaacaaac acttcaagcg ccgtgagttc gcttgccgtt gtgggtgcgg tacatccaca
40861 gtagatgctg agttactaca ggtagtcaca gatgtacgtg agcactttgg tgctcctgta
40921 gttattactt ctggacaccg ctgtgctaag cacaatgcta atgtgggagg tgctaagaac
40981 tccatgcatc ttactggtaa ggctgctgac attaaggtac aaggtattac accttaccgt
41041 gtatggtcct atctaacagc acgctacccc aataaatatg gcattgggtc ttatcctaat
41101 ttcacccaca ttgatgtaag agagggatgt gcacgatggt aagatgtatt gaatggtgcg
41161 agcgcatggt tgctcaagct gccgaggatg gcaactatga tgactggaag aactactctg
41221 acttgttagc tcaatggaaa gggagatgca atgaaaaagc tgtttaagtc taagaaagtg
41281 gtaggtgcac tggttgcact agtgattgct cttgtttctg taggtcttgg cgtagaccta
41341 ggtgaaggtg cggaaggttc cgtcactgac gtggtatgcc aagtaatcac ctgtgaataa
41401 ggtgctagag gtggtagcag gtcttattgg cctgctgctt gccgctaaga agaagaagga
41461 agagaaggag gcacaaagtg aggcgaatca tgctagcgac aatcctgctg attggttcac
41521 tgatcacttc agggtgtcag acggcgttac cagagaatcc aaaggtgaag cctctgaagc
41581 cgacgcttac ggcagtctac gaggtggacg ataaagtctg cttcagtaag cctgacgcta
41641 caaaattagg tctgtacatt ctctcgctag aacgcgggta taattaatac atagttttat
41701 gtatcagtgt cttacgattt actggacact atagaagaga taagatagtg ccgttctttt
41761 gagcggccta ttactagcca atcttcatag ggagggttgg gaagtaatag gagagtatat
41821 ggctaagtta actaaaccca agacaacggg cttactacat agagatactg tactagctac
41881 cttattagat aatttactat ctaaaaggcg tgttacattt gaaggtgtag ttccaagtga
41941 agatactaaa attgagatag aagtacctac agcatgggat ttagattctt cgtgggcatc
42001 acttgtatca ttaagtacac ctacactttg tacagcttgg attactaaag tgtcagatac
42061 tagattagaa gtacatgtgt tccatacagc acaagttgaa atagacatag atgtagatgt
42121 ttacattcta ggtaaacaca ttgtcagtgc gtaagcactg cttttcgcgc aacttttctt
42181 aaaggttatc atgatggtag cctttcagaa aaggaggtta catgattcaa agactaggtt
42241 cttcattagt taaattcaag agtaaaatag caggtgcaat ctggcgtaac ttggatgaca
42301 agctcaccga ggttgtatcg cttaaagatt ttggagccaa aggtgatggt aagacaaacg
42361 accaagatgc agtaaatgca gcgatggctt caggtaagag aattgacggt gctggtgcta
42421 cttacaaagt atcatcttta cctgatatgg agcgattcta taacacccgc ttcgtatggg
42481 aacgtttagc aggtcaacct ctttactatg tgagtaaagg ttttatcaat ggtgaactct
42541 ataaaatcac ggataaccct tattacaatg cttggcctca agacaaagcg tttgtatatg
42601 agaacgtgat atatgcacct tacatgggta gcgaccgtca tggtgttagt cgtctgcatg
42661 tatcatgggt taagtctggt gacgatggtc aaacatggtc tactccagag tggttaactg
42721 atatgcatcc agattaccct acagtgaact atcattgtat gagtatgggt gtatgtcgca
42781 accgtctgtt tgccatgatt gaaacacgta ctttagccaa gaacgaacta accaattgtg
42841 cattgtggga tcgccctatg tctcgtagtc tgcatcttac tggtggtatc actaaggctg
42901 caaatcagag atatgcaaca atccatgtac ctgatcacgg actcttcgtt ggtgattttg
```

Figure 10(M)

```
42961 ttaacttctc taactctgcg gtaacaggtg tatctggtga tatgaaggtt gcaacagtaa
43021 tagataagga caacttcacg gttcttacac ctaaccagca gacttcagat ttgaataacg
43081 ctggaaagaa ttggcacatg ggtacttctt tccataagtc tccgtggcgt aagacagatc
43141 ttggtctaat ccctcgtgtc acagaggtgc atagctttgc tactattgat aacaatggct
43201 ttgttatggg ctatcatcaa ggtgatgtag ctccacgaga agttgggctt ttctacttcc
43261 ctgatgcttt caatagccca tctaattatg ttcgtcgtca gataccatct gagtatgaac
43321 cagatgcggc agagccatgc atcaagtact atgacggtgt attatacctt atcactcgtg
43381 gtactcgtgg cgaccgacta ggaagctctc tgcatcgtag tagagatata ggtcagactt
43441 gggagtcact aagatttcca cataatgtgc atcatactac tttaccgttt gctaaggtag
43501 gagatgacct tattatgttt ggttcagaac gtgcagaaaa tgaatgggaa gcaggtgcac
43561 cagatgatcg ttacaaggca tcttatcctc gtaccttcta tgcacgattg aatgtaaaca
43621 attggaatgc agatgatatt gaatgggtta acatcacaga ccaaatctat cagggtgaca
43681 ttgtgaactc tagtgtaggt gtaggttctg ttgtagttaa agacagcttc atttactata
43741 tctttggtgg tgaaaaccat ttcaacccaa tgacttatgg tgacaacaaa gacaaagacc
43801 catttaaagg tcatggacac cctactgata tatactgcta taagatgcag attgcaaatg
43861 acaatcgtgt atctcgtaag tttacatatg gtgcaactcc aggtcaagct atacctactt
43921 tcatgggtac tgatggaata cgaaatatcc ctgcaccttt gtatttctca gataacattg
43981 ttacagagga tactaaagtt ggacacttaa cacttaaagc aagcacaagt gccaatatac
44041 gatctgaaat gcagatggaa ggtgagtatg gctttattgg caagtctgtt ccaaaggaca
44101 aaccaacagg tcaacgtttg attatttgtg gtggagaaag gacttcatca tcttcaggtg
44161 cacagataac tttgcacggt tctaattcaa gtaaggctaa gcgtatcact tataacggaa
44221 acgagcacct attccaaggt gcaccaatca tgcctgctgt agataaccag tttgctgctg
44281 gtggacctag taaccgattc actaccatct acctaggcag tgaccctgtt acaacttcag
44341 atgctgacca caagtacggt atctctagta ttaataccaa ggtgttaaag gcttggagca
44401 gggttggttt taaacagtat ggtttgaata gtgaagcaga gaggaacctt gatagcatac
44461 acttcggtgt cttggctcag gatattgtag ctgcttttga agctgaaggg ttggatgcca
44521 ttaagtatgg aattgtgtcc ttcgaagaag gtaggtatgg tgtgagatat agtgaagttc
44581 taatcctaga ggctgcctat actcgccatc gtcttgataa attagaggag atgtatgcca
44641 ctaataaaat cagttaagca atctgctgca cgccagaaca cataagaact tatacaatca
44701 ggacgtgacc ctaagcaggc atacgccatt gccaaggatg tacaacgtcg tgccatgaag
44761 aaaccttctg catcttctgc gtaagcaggt taatatctta gtgtacacaa gggcagactt
44821 aggtttgctc ttagtgtaat ccaaggaggt aacatgcaag aggagaattg ggatgtgtaa
44881 tgttggatat ggagaaggtt gaacctcagt gttgtacaag gattaaccaa agtaaaaatt
44941 ttgatatagg cgtgtgtcag ctctctcgcc ctcgccctcg ccggattttc cccatatggg
45001 gccgcgctgc ggttggcttg ggattgggc taggctgggc cgtcttcaac ctgctgccgc
45061 aggaagctcg atgggttggc tgagggttgc cgagggctgc gcttagtggt acacaagtag
45121 aacgcctagg aagcgctagg gcacgcctta gtgttggaca aggtgattgc cttagtgcaa
45181 ccgtttaggg cttacacagg ccgttttagg gcaattcctg agtgtttgac agggtgtgag
45241 ggtgtgggct a
```

COMPOSITION OF MATTER: ENGINEERING OF *ESCHERICHIA COLI* PHAGE K1E

CROSS-REFERENCE TO RELATED APPLICATIONS

This application is a divisional application of U.S. Ser. No. 16/204,817, filed Nov. 29, 2018, which application is a continuation of U.S. Ser. No. 15/908,235, filed Feb. 28, 2018, which application claims the benefit of and priority to U.S. Provisional Appl. No. 62/539,932, filed Aug. 1, 2017, the contents of all of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Feb. 27, 2018, is named 102590-0619_SL.txt and is 122,588 bytes in size.

TECHNICAL FIELD

The present technology relates generally to compositions including recombinant K1E bacteriophages, methods for making the same, and uses thereof. The recombinant K1E bacteriophages disclosed herein are useful for the identification and/or antibiotic susceptibility profiling of specific bacterial strains/species present in a sample.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE PRESENT TECHNOLOGY

In one aspect, the present disclosure provides a recombinant K1E bacteriophage nucleic acid sequence, wherein the nucleic acid sequence between (a) position 40,788 and 40,789 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In certain embodiments, the open reading frame of the heterologous nucleic acid sequence is operably linked to an expression control sequence that is capable of directing expression of the reporter protein. The expression control sequence may be an inducible promoter or a constitutive promoter. Additionally or alternatively, in some embodiments, the recombinant K1E bacteriophage nucleic acid sequence comprises a sequence selected from the group consisting of SEQ ID NO: 2, SEQ ID NO: 3, SEQ ID NO: 4, and SEQ ID NO: 5.

Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOκ, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa. Examples of chemiluminescent protein include, but are not limited to, β-galactosidase, horseradish peroxidase (HRP), or alkaline phosphatase. Examples of bioluminescent protein include, but are not limited to, Aequorin, firefly luciferase, *Renilla* luciferase, red luciferase, luxAB, or nanoluciferase. In some embodiments, the bioluminescent protein is nanoluciferase.

In one aspect, the present disclosure provides a vector comprising any of the recombinant K1E bacteriophage nucleic acid sequences disclosed herein, as well as bacterial host cells comprising the vectors of the present technology. In some embodiments, the bacterial host cell expresses K1 capsule genes. The bacterial host cell may be a natural or non-natural host for K1E bacteriophage.

In another aspect, the present disclosure provides a recombinant K1E bacteriophage comprising any of the recombinant K1E bacteriophage nucleic acid sequences of the present technology. Also provided herein are recombinant K1E bacteriophages comprising a nucleic acid sequence selected from the group consisting of SEQ ID NO: 2, SEQ ID NO: 3, SEQ ID NO: 4, and SEQ ID NO: 5. The recombinant K1E bacteriophage of the present technology specifically infects *E. coli* strains that express K1 capsule genes. In some embodiments, the *E. coli* strains that express K1 capsule genes are selected from the group consisting of ATCC #11775 and ATCC #700973.

In one aspect, the present disclosure provides a bacterial host cell comprising a recombinant K1E bacteriophage disclosed herein. In some embodiments, the bacterial host cell expresses K1 capsule genes. The bacterial host cell may be a natural or non-natural host for K1E bacteriophage.

In one aspect, the present disclosure provides a method for identifying at least one bacterial strain or species that expresses K1 capsule genes in a test sample obtained from a subject comprising (a) contacting the test sample comprising bacterial cells with a recombinant K1E bacteriophage of the present technology; and (b) detecting the expression of the reporter protein in recombinant K1E bacteriophage-infected bacterial cells, wherein detection of the reporter protein indicates the presence of at least one bacterial strain or species that expresses K1 capsule genes in the test sample. In some embodiments of the method, the expression of the reporter protein is measured in about 5, 10, 15, 20, 25, 30, 35, 40, 45, 50, 55, 60, 65, 70, 75, 80, 85, or 90 minutes after contacting the test sample comprising bacterial cells with the recombinant K1E bacteriophage.

In another aspect, the present disclosure provides a method for determining the antibiotic susceptibility of a bacterial strain or species in a test sample obtained from a subject comprising (a) contacting a plurality of test samples comprising bacterial cells with a recombinant K1E bacteriophage of the present technology and an antibiotic, wherein the plurality of test samples is derived from the subject; (b) detecting the expression of the reporter protein in recombinant K1E bacteriophage-infected bacterial cells in the plurality of test samples; and (c) determining that the antibiotic is effective in inhibiting the bacterial strain or species in a test sample when the reporter protein expression levels of the recombinant K1E phage-infected bacterial cells in the test sample are reduced relative to that observed in an untreated control sample comprising bacterial cells, wherein the untreated control sample is derived from the subject. In some embodiments, the bacterial strain or species in the test sample expresses K1 capsule genes. The expression of the reporter protein may be measured in about 5, 10, 15, 20, 25, 30, 35, 40, 45, 50, 55, 60, 65, 70, 75, 80, 85, or 90 minutes after contacting the plurality of test samples comprising bacterial cells with the recombinant K1E bacteriophage.

Additionally or alternatively, in some embodiments of the methods disclosed herein, the test sample is blood, sputum, mucus, lavage, saliva, or a swab obtained from the subject. In some embodiments, the subject is human.

In certain embodiments of the method, the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In one aspect, the present disclosure provides a method for making a recombinant K1E bacteriophage of the present technology comprising (a) contacting a non-recombinant K1E bacteriophage genome of SEQ ID NO: 1 comprising a single first recognition site with a first restriction enzyme in vitro under conditions where the first restriction enzyme cleaves the first recognition site to produce a cleaved non-recombinant K1E bacteriophage genome; and (b) recombining in vitro the cleaved non-recombinant K1E bacteriophage genome with a heterologous nucleic acid in the presence of a recombination system under conditions to produce a recombinant K1E bacteriophage genome, wherein the heterologous nucleic acid sequence comprises an open reading frame that encodes a bioluminescent protein, a fluorescent protein, a chemiluminescent protein, or any combination thereof. In some embodiments of the method, the first restriction enzyme is PflF1.

Additionally or alternatively, in some embodiments of the method disclosed herein, the cleaved non-recombinant K1E bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments, the method further comprises propagating the recombinant K1E bacteriophage genome in a bacterial host. The bacterial host may be a non-natural bacterial host cell or a natural bacterial host cell for K1E bacteriophage.

Additionally or alternatively, in some embodiments of the method, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Also disclosed herein are kits comprising one or more coded/labeled vials that contain the recombinant K1E bacteriophage of the present technology, instructions for use, and optionally at least one antibiotic.

BRIEF DESCRIPTION OF THE DRAWINGS

FIG. 2 shows the heterologous nucleic acid sequence (SEQ ID NO: 2) that was inserted into K1E phage genomic DNA that was cleaved with PflF1. The underlined sequences represent the homologous 5' and 3' flanking regions of the heterologous nucleic acid sequence.

FIGS. 3(A)-3(N) show the complete genome sequence of the recombinant NanoLuc® K1E phage (SEQ ID NO: 3).

FIGS. 10(A)-10(M) show the complete genome sequence of non-recombinant K1E phage (NCBI Reference Sequence: NC_007637; SEQ ID NO: 1).

DETAILED DESCRIPTION

Figure 1:
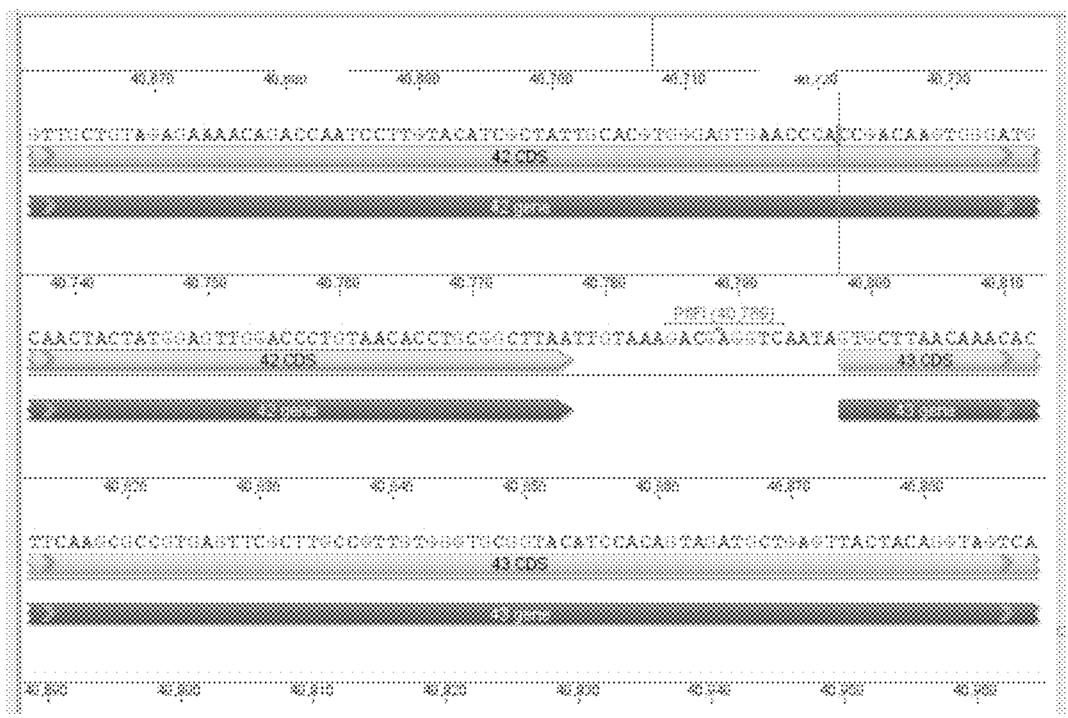
FIG. 1 shows the PflF1 restriction enzyme cleavage site within the K1E bacteriophage genome. PflF1 cleavage occurs between base pairs 40,788 and 40,789 of the K1E bacteriophage genome. Figure discloses SEQ ID NO: 8.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in* Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) *Antibodies, A Laboratory Manual*; Freshney (2005) *Culture of Animal Cells: A Manual of Basic Technique,* 5th edition; Gait ed. (1984) Oligonucleotide Synthesis; U.S. Pat. No. 4,683,195; Hames and Higgins eds. (1984) *Nucleic Acid Hybridization; Anderson* (1999) *Nucleic Acid* Hybridization; Hames and Higgins eds. (1984) Transcription and Translation; *Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, a "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to a nucleic acid of interest to initiate, regulate or otherwise control transcription of the nucleic acid of interest.

As used herein, a "phage genome" or "bacteriophage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion or an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, a "recombinant K1E bacteriophage" or "recombinant K1E phage" means a K1E bacteriophage whose genomic DNA comprises a heterologous nucleic acid sequence that encodes a bioluminescent protein, a fluorescent protein, a chromogenic protein, or any combination thereof.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some embodiments, the test sample is blood, sputum, mucus, lavage, or saliva. In certain embodiments, the test sample is a swab from a subject.

As used herein, the terms "subject," "individual," or "patient" are used interchangeably and refer to an individual organism, a vertebrate, a mammal, or a human. In certain embodiments, the individual, patient or subject is a human.

As used herein, a "vector" refers to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

Recombinant K1E Phage Compositions of the Present Technology

K1E is a 45,251 bp, lytic bacteriophage (NCBI Reference Sequence: NC 007637; see FIGS. 10(A)-10(M)) that infects numerous *E. coli* strains that express K1 capsule genes. K1E phage is of the T7 supergroup. The recombinant K1E bacteriophage of the present technology specifically infects *E. coli* strains that express K1 capsule genes. In some embodiments, the *E. coli* strains that express K1 capsule genes are selected from the group consisting of ATCC #11775, and ATCC #700973.

In one aspect, the present disclosure provides a recombinant K1E bacteriophage nucleic acid sequence, wherein the nucleic acid sequence between position 40,788 and 40,789 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof.

Also disclosed herein are recombinant K1E bacteriophages that comprise any recombinant K1E bacteriophage nucleic acid sequence disclosed herein. In some embodiments, the reporter protein(s) encoded by the heterologous nucleic acid sequence produces a detectable signal upon exposure to the appropriate stimuli, and the resulting signal permits detection of bacterial host cells infected by a recombinant K1E phage of the present technology.

In certain embodiments, the open reading frame encodes a reporter protein that serves as a marker that can be identified by screening bacterial host cells infected by a recombinant K1E phage of the present technology. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the K1E phage genome with no loss of endogenous K1E phage genomic sequence. In some embodiments, the heterologous nucleic acid sequence replaces an endogenous K1E phage genomic sequence. In certain embodiments, the heterologous nucleic acid sequence replaces an endogenous K1E phage genomic sequence that is less than the length of the heterologous nucleic acid sequence. Accordingly, in some embodiments, the length of the recombinant K1E phage genome is longer than the length of the wild-type K1E phage genome.

In certain embodiments, the open reading frame of the heterologous nucleic acid sequence encodes a reporter protein that confers a phenotype of interest on a host cell infected by a recombinant K1E phage of the present technology. In some embodiments, the phenotype of interest is the expression of the gene product encoded by the open reading frame of the heterologous nucleic acid sequence.

In certain embodiments, the open reading frame of the heterologous nucleic acid sequence is operably linked to an expression control sequence that is capable of directing expression of the open reading frame, wherein the open reading frame encodes a reporter protein (e.g., a bioluminescent protein, a fluorescent protein, a chemiluminescent protein, or any combination thereof). In some embodiments, the expression control sequence is located within the heterologous nucleic acid sequence. In other embodiments, the expression control sequence is located in the endogenous K1E phage genome sequence. For example, the open reading frame may be inserted into the K1E phage genome downstream of or in the place of an endogenous K1E phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous K1E phage promoter sequence, a phage promoter sequence that is non-endogenous to K1E phage, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include, but are not limited to, blue/UV fluorescent proteins (for example, TagBFP, Azurite, EBFP2, mKalamal, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid sequence comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type K1E bacteriophage and the bacterial host cell. Accordingly, detection of the epitope in a sample demonstrates the presence of a bacterial host cell infected by a recombinant K1E phage comprising a heterologous nucleic acid sequence, wherein the open reading frame of the heterologous nucleic acid sequence comprises the epitope. In other embodiments, the open reading frame of the heterologous nucleic acid sequence comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, the antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Also disclosed herein are recombinant K1E bacteriophages comprising any of the recombinant K1E bacteriophage nucleic acid sequences disclosed herein. In some embodiments, the recombinant K1E bacteriophages comprise a nucleic acid sequence selected from the group consisting of SEQ ID NO: 2, SEQ ID NO: 3, SEQ ID NO: 4, and SEQ ID NO: 5.

In another aspect, the present disclosure provides a vector comprising any of the recombinant K1E bacteriophage nucleic acid sequences disclosed herein, as well as bacterial host cells comprising the vectors of the present technology. In some embodiments, the bacterial host cell expresses K1 capsule genes. The bacterial host cell may be a natural or non-natural host for K1E bacteriophage.

The present disclosure also provides a bacterial host cell comprising a recombinant K1E bacteriophage disclosed herein. In some embodiments, the bacterial host cell expresses K1 capsule genes. The bacterial host cell may be a natural or non-natural host for K1E bacteriophage.

Methods of Making Recombinant K1E Bacteriophage of the Present Technology

In one aspect, the present disclosure provides methods for making a recombinant K1E bacteriophage of the present technology comprising (a) contacting a non-recombinant K1E bacteriophage genome of SEQ ID NO: 1 comprising a single first recognition site with a first restriction enzyme in vitro under conditions where the first restriction enzyme cleaves the first recognition site to produce a cleaved non-recombinant K1E bacteriophage genome; and (b) recombining in vitro the cleaved non-recombinant K1E bacteriophage genome with a heterologous nucleic acid in the presence of a recombination system under conditions to produce a recombinant K1E bacteriophage genome, wherein the heterologous nucleic acid sequence comprises an open reading frame that encodes a bioluminescent protein, a fluorescent protein, a chemiluminescent protein, or any combination thereof. The cleaved non-recombinant K1E bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment. In some embodiments, the first restriction enzyme is PflF1.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments, the methods further comprise propagating the recombinant K1E bacteriophage genome in a bacterial host. For example, the bacterial host may be transformed with the recombinant K1E bacteriophage genome via electroporation. The bacterial host may be a non-natural bacterial host cell or a natural bacterial host cell for K1E bacteriophage.

Additionally or alternatively, in some embodiments of the methods disclosed herein, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Bacterial Identification and Antibiotic Susceptibility Profiling Methods of the Present Technology Accurate identification of bacterial species within a biological sample informs the selection of suitable therapies for treating bacterial infections. The recombinant K1E bacteriophages disclosed herein may be used to identify bacteria present within a biological sample (e.g., whole blood, plasma, serum). Such methods entail contacting the biological sample with a recombinant K1E bacteriophage disclosed herein, and detecting the presence of bacterial host cells infected by the recombinant K1E phage, wherein the recombinant K1E phage comprises a heterologous nucleic acid sequence that encodes a detectable gene product, thereby leading to the identification of bacteria present within the biological sample.

Additionally or alternatively, the recombinant K1E bacteriophages disclosed herein, may be used in methods for profiling antibiotic susceptibility of bacteria present within a biological sample (e.g., whole blood, plasma, serum). These methods include (a) contacting the biological sample with an antibiotic and a recombinant K1E bacteriophage disclosed herein, (b) detecting the presence of bacterial host cells infected by the recombinant K1E phage, wherein the recombinant K1E phage comprises a heterologous nucleic acid sequence that encodes a detectable gene product, and (c) determining that the antibiotic is effective in inhibiting the bacteria present in the biological sample when the levels of recombinant K1E phage infected bacterial host cells are reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) contacting each sub-sample with at least one recombinant K1E bacteriophage disclosed herein, wherein each recombinant K1E bacteriophage comprises a heterologous nucleic acid sequence encoding one or more reporter genes, and (c) identifying at least one bacterial strain or species in the test sample by detecting the expression of the one or more reporter genes in recombinant K1E bacteriophage-infected bacterial cells. In certain embodiments, the at least one K1E bacteriophage comprises a nucleic acid sequence selected from the group consisting of SEQ ID NO: 2, SEQ ID NO: 3, SEQ ID NO: 4, and SEQ ID NO: 5. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes in recombinant K1E bacteriophage-infected bacterial cells, e.g., detectable expression of green fluorescence indicates the presence of bacterial species A in a test sample or sub-sample. In some embodiments, the absence of at least one bacterial strain or species is identified by the lack of detectable expression of the one or more reporter genes in recombinant K1E bacteriophage-infected bacterial cells, e.g., undetectable expression of green fluorescence indicates the lack of bacterial species A in a test sample or sub-sample.

In some embodiments, the at least one recombinant K1E bacteriophage infects a single species of bacteria. In certain embodiments, the at least one recombinant K1E bacteriophage infects two or more species of bacteria. By way of example, but not by way of limitation, in some embodiments, the species of bacteria that are infected include K1capsule gene expressing *E. coli* strains, such as ATCC #11775, and ATCC #700973.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90, 120 minutes or any time between any two of the preceding values after contacting a sub-sample with the at least one recombinant K1E bacteriophage disclosed herein.

The present disclosure also provides a method for identifying at least one bacterial strain or species that expresses K1 capsule genes in a test sample obtained from a subject comprising (a) contacting the test sample comprising bacterial cells with a recombinant K1E bacteriophage of the present technology; and (b) detecting the expression of the reporter protein in recombinant K1E bacteriophage-infected bacterial cells, wherein detection of the reporter protein indicates the presence of at least one bacterial strain or species that expresses K1 capsule genes in the test sample. In some embodiments of the method, the expression of the reporter protein is measured in about 5, 10, 15, 20, 25, 30, 35, 40, 45, 50, 55, 60, 65, 70, 75, 80, 85, 90 or 120 minutes after contacting the test sample comprising bacterial cells with the recombinant K1E bacteriophage.

Additionally or alternatively, in some embodiments of the methods disclosed herein, the test sample is blood, sputum, mucus, lavage, saliva, or a swab obtained from the subject. In some embodiments, the subject is human.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) contacting the plurality of sub-samples with a recombinant K1E bacteriophage disclosed herein and at least one antibiotic, wherein the recombinant K1E bacteriophage comprises a heterologous nucleic acid sequence encoding a reporter gene, and (c) detecting the expression of the reporter gene in recombinant K1E bacteriophage-infected bacterial cells in the presence of each antibiotic. In some embodiments, the method further comprises determining that the bacterial strain or species in the test sample is susceptible to an antibiotic if the reporter gene expression in the recombinant K1E bacteriophage-infected bacterial cells in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression in the recombinant K1E bacteriophage-infected bacterial cells in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample.

Additionally or alternatively, in some embodiments of the recombinant K1E bacteriophages of the present technology, the reporter gene is nanoluciferase. In certain embodiments, recombinant K1E bacteriophage comprises a nucleic acid sequence selected from the group consisting of SEQ ID NO: 2, SEQ ID NO: 3, SEQ ID NO: 4, and SEQ ID NO: 5.

Examples of antibiotics include one or more of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In some embodiments of the method, the differences in the reporter gene expression in the recombinant K1E bacteriophage-infected bacterial cells observed in the antibiotic treated sub-sample and the untreated control sub-sample is defined as Additionally or alternatively, in some embodiments of the method, the expression of the reporter gene is detected in about 5, 10, 15, 20, 25, 30, 35, 40, 45, 50, 55, 60, 65, 70, 75, 80, 85, 90, 120 minutes or any time between any two of the preceding values after contacting a sub-sample with a recombinant K1E bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant K1E bacteriophage, as intact non-bacterial cells (e.g., red blood cells) may quench reporter gene expression. In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample. In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In another aspect, the present disclosure provides a method for determining the antibiotic susceptibility of a bacterial strain or species in a test sample obtained from a subject comprising (a) contacting a plurality of test samples comprising bacterial cells with a recombinant K1E bacteriophage of the present technology and an antibiotic, wherein the plurality of test samples is derived from the subject; (b) detecting the expression of the reporter protein in recombinant K1E bacteriophage-infected bacterial cells in the plurality of test samples; and (c) determining that the antibiotic is effective in inhibiting the bacterial strain or species in a test sample when the reporter protein expression levels in recombinant K1E phage-infected bacterial cells in the test sample are reduced relative to that observed in an untreated control sample comprising bacterial cells, wherein the untreated control sample is derived from the subject. In some embodiments, the bacterial strain or species in the test sample expresses K1 capsule genes. The expression of the reporter protein may be measured in about 5, 10, 15, 20, 25, 30, 35, 40, 45, 50, 55, 60, 65, 70, 75, 80, 85, 90, or 120 minutes after contacting the plurality of test samples comprising bacterial cells with the recombinant K1E bacteriophage. In other embodiments, the method further comprises determining that the bacterial strain or species in the test sample is resistant to the antibiotic when the reporter protein expression levels of the recombinant K1E bacteriophage-infected bacterial cells in the test sample are comparable to that observed in an untreated control sample comprising bacterial cells, wherein the untreated control sample is derived from the subject.

In any of the above embodiments of the methods of the present technology, the test sample is blood, sputum, mucus, lavage, saliva, or a swab obtained from the subject. In some embodiments of the methods disclosed herein, the test sample is obtained from a mammalian subject, including, for example, farm animals, such as sheep, pigs, cows, and horses; pet animals, such as dogs and cats; and laboratory animals, such as rats, mice and rabbits. In one embodiment, the mammal subject is a human.

Kits

The present technology provides kits including the recombinant K1E bacteriophages disclosed herein for bacteria identification and antibiotic susceptibility profiling.

In one aspect, the kits of the present technology comprise one or more coded/labeled vials that contain a plurality of the recombinant K1E bacteriophages disclosed herein, and instructions for use. In some embodiments, each coded/labeled vial corresponds to a different recombinant K1E bacteriophage. In other embodiments, each coded/labeled vial corresponds to the same recombinant K1E bacteriophage. In some embodiments, the kits of the present technology comprise one or more coded/labeled vials that contain at least one recombinant K1E bacteriophage comprising a nucleic acid sequence selected from the group consisting of SEQ ID NO: 2, SEQ ID NO: 3, SEQ ID NO: 4, and SEQ ID NO: 5.

In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments, the kits further comprise vials containing natural or non-natural bacterial host cells. In some embodiments, the bacterial host cells are *E. coli*. In certain embodiments, the bacterial host cells are *E. coli* strain DH10B.

The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids of the recombinant K1E bacteriophages disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

The kits of the present technology may optionally comprise a recombination system that includes a 5'-3' exonuclease, a DNA polymerase, and a DNA ligase. For example, in one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the kits comprise a non-endogenous recombination system that includes a 3'-5' exonuclease, a DNA polymerase, and a DNA ligase.

EXAMPLES

Example 1: Design and Methods for Generating the Recombinant K1E Bacteriophages of the Present Technology This Example demonstrates that the methods of the present technology are useful for producing the recombinant K1E bacteriophages disclosed herein.

K1E bacteriophage DNA was extracted from a clarified lysate using the Zymo ZR Viral DNA kit (Cat. No. D3015) (Zymo Research, Irvine, Calif.). 150 ng of K1E bacteriophage DNA was digested with the restriction enzyme PflF1 (New England Biolabs, Ipswich, Mass.) according to the manufacturer's specifications. As shown in FIG. 1, the PflF1 restriction enzyme cleavage site is located between gene 42 and gene 43 of the K1E bacteriophage genome.

A gBlock (synthesized by Integrated DNA Technologies, Coralville, Iowa) containing the NanoLuc® gene flanked on each side by 25 bp of homology (see FIG. 2; SEQ ID NO: 2) to the viral genome was inserted into the PfLf1 cleavage site using the NEBuilder® (New England Biolabs, Ipswich, Mass.) kit according to the manufacturer's specifications. FIGS. 3(A)-3(N) show the complete nucleic acid sequence of the recombinant K1E bacteriophage.

2 μl of the assembly reaction was transformed into electrocompetent NEB10β cells (NEB C3030K) (New England Biolabs, Ipswich, Mass.). Cells were recovered in 450 μl of SOC medium and incubated for 1 hour at 37° C. After incubation, 250 μl of the transformation mixture was added to 3 ml of log-phase *E. coli* K1 cells (ATCC® 700973). The mixture was further incubated at 37° C. for an hour. After incubation, 1 ml of the culture was centrifuged at 10,000×g for 10 minutes and 100 μl of the supernatant was mixed with 100 μl of *E. coli* K1 cells and plated on LB agar with 3 ml 0.65% soft agar overlay. After incubation at 37° C. overnight, isolated plaques were selected and screened for NanoLuc® insertion by PCR using primers that flanked the NanoLuc® insertion site.

Figure 4:
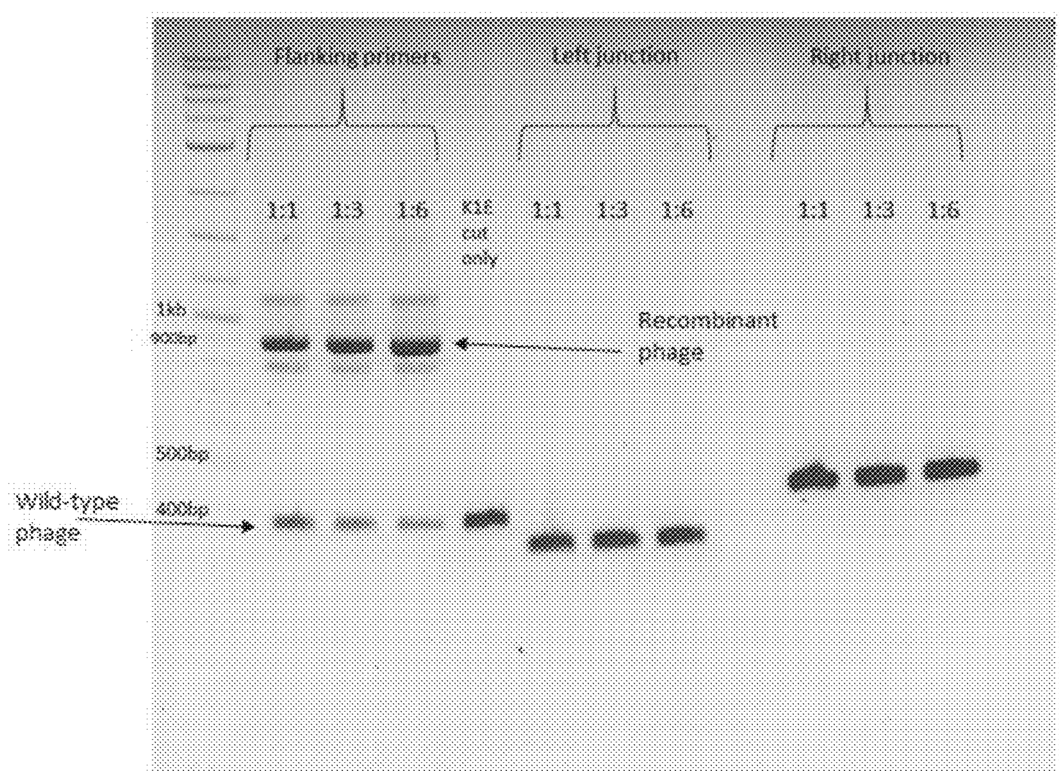
FIG. 4 shows the junctional and flanking PCR assays that tested for the presence of recombinant K1E bacteriophage.
Figure 5A:
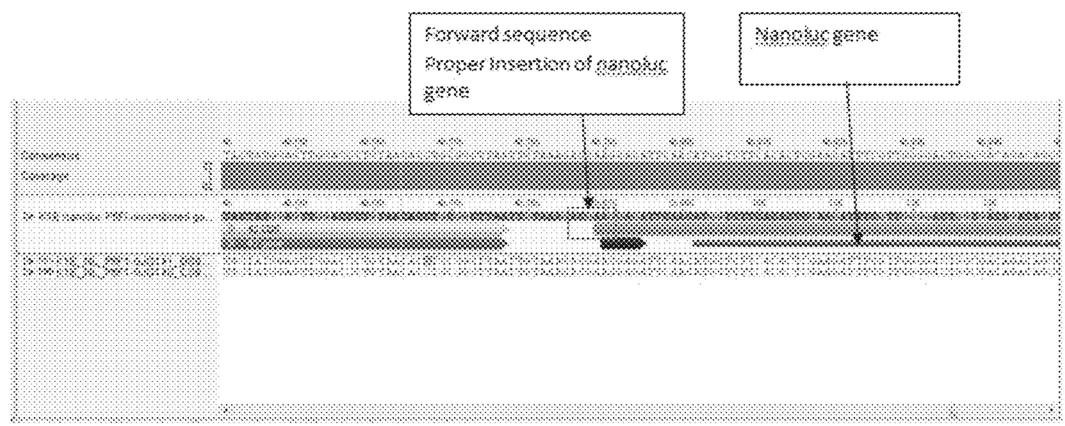
FIG. 5(A) shows the upstream junction sequence of the nanoluciferase insertion in the recombinant K1E phage genome (SEQ ID NO: 4). Figure also discloses SEQ ID NOS 9, 9, 10, and 9, respectively, in order of appearance.
Figure 5B:
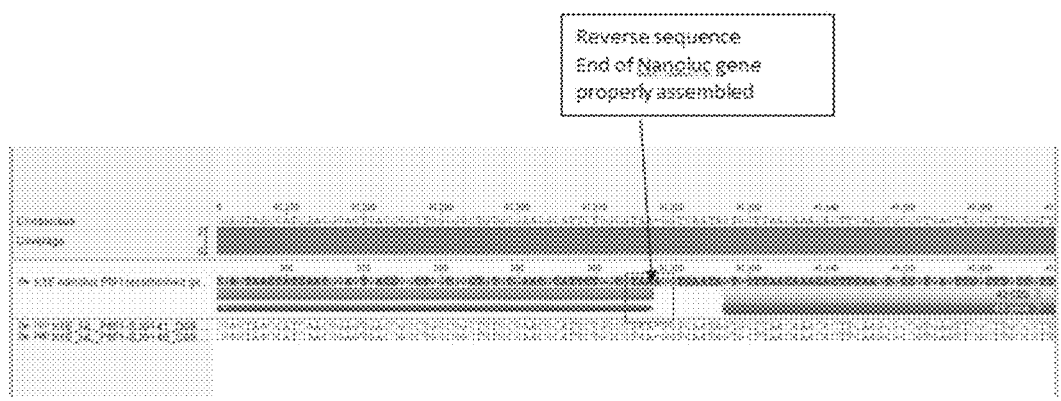
FIG. 5(B) shows the downstream junction sequence of the nanoluciferase insertion in the recombinant K1E phage genome (SEQ ID NO: 5). Figure also discloses SEQ ID NOS 11, 12, 11, and 11, respectively, in order of appearance.

Genotypic Analysis:

Primers flanking the PflF1 cleavage site were designed so as to assess the insertion of the NanoLuc® gene via PCR screening: Forward primer—CTTAAGAAGAAAGATCATCCTATCAAC (SEQ ID NO: 6) and Reverse primer—GTTCTTAGCACCTCCCACAT (SEQ ID NO: 7). Recombinant K1E phage with the proper NanoLuc® insertion yielded a 912 bp amplicon, whereas the wild type amplicon was 383 bp. See FIG. 4. The left and right junctions of the PCR products were sequenced in both forward and reverse directions to ensure the proper insertion of the nanoluciferase payload (see FIG. 5(A) and FIG. 5(B)).

Phenotypic Analysis:

NanoLuc® production was also evaluated by infecting *E. coli* K1 (ATCC® 700973) bacterial host cells with the recombinant K1E phage for 1 hour at 37° C. and measuring luminescence using the Nano-Glo® Luciferase Assay System (Promega Corp., Madison Wis.). Briefly, mutated and wild-type plaques were picked and used to infect host K1 *E. coli* cells for 1 hour. The K1 *E. coli* cells were assayed for NanoLuc® production with the Nano-Glo Luciferase Assay System (Promega Corp., Madison Wis.). See FIG. 6.

These results demonstrate that the methods of the present technology are useful for making the recombinant K1E bacteriophages disclosed herein. Accordingly, the methods disclosed herein are useful for generating recombinant K1E bacteriophages that can be used in the identification and/or antibiotic susceptibility profiling of specific bacterial strains/species (e.g., bacterial strains/species that express K1 capsule gene) present in a sample.

Example 2: Functional Activity of the Recombinant K1E Bacteriophages of the Present Technology This Example demonstrates that the recombinant K1E bacteriophages of the present technology are useful for the identification and/or antibiotic susceptibility profiling of specific bacterial strains/species (e.g., bacterial strains/species that express K1 capsule gene) present in a sample.

Figure 6:
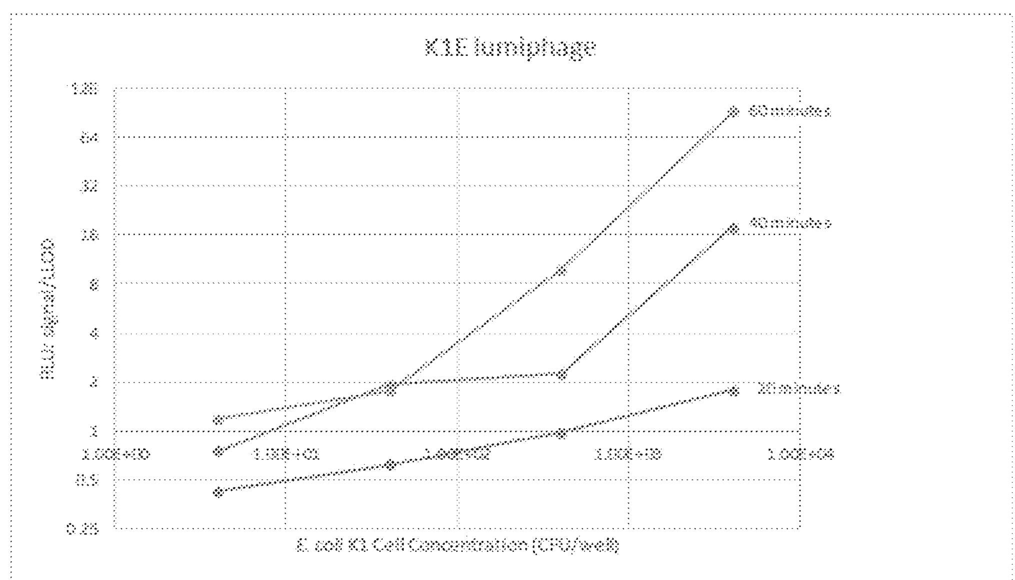
FIG. 6 shows the luminescence activity profile and sensitivity of the recombinant K1E phages of the present technology.

NanoLuc® signal production and sensitivity were evaluated by infecting *E. coli* K1 cells with the purified recombinant K1E lumiphage and measuring luminescence at 20, 40, 60 minutes. Briefly, bacterial cells were grown to mid log-phase growth in LB medium and serially diluted in log steps in a microtiter plate to obtain concentrations of $10^4$ bacteria/100W down to 1 bacterial cell/100 μl. K1E detector phage was added to each well at a constant concentration of $10^6$ phage/well. For each time point, luminescence was measured using the Nano-Glo® Luciferase Assay System (Promega Corp., Madison Wis.). FIG. 6 shows the luminescence activity profile and sensitivity of the recombinant K1E bacteriophage of the present technology. As shown in FIG. 6, the luminescence activity of the recombinant K1E bacteriophage-infected K1 bacterial host cells increased in both a host cell-dependent and time-dependent manner.

Figure 8:
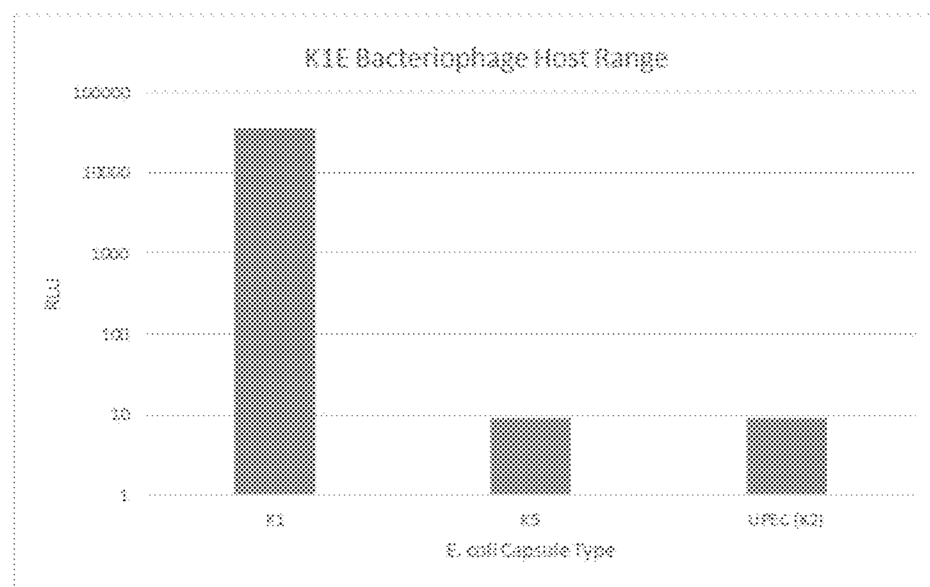
FIG. 8 shows the specific host range of the recombinant K1E phages of the present technology.

Plaques containing the recombinant K1E bacteriophages disclosed herein were used to infect a host population of K1, K5 and K2 capsule producing *E. coli* strains. FIG. 8 demonstrates that the K1E bacteriophage of the present technology specifically infects K1 capsule producing *E. coli* strains. The infected K1 bacterial host cells exhibited luminescence that was at least three orders of magnitude above the background level. See FIG. 8.

Figure 9:
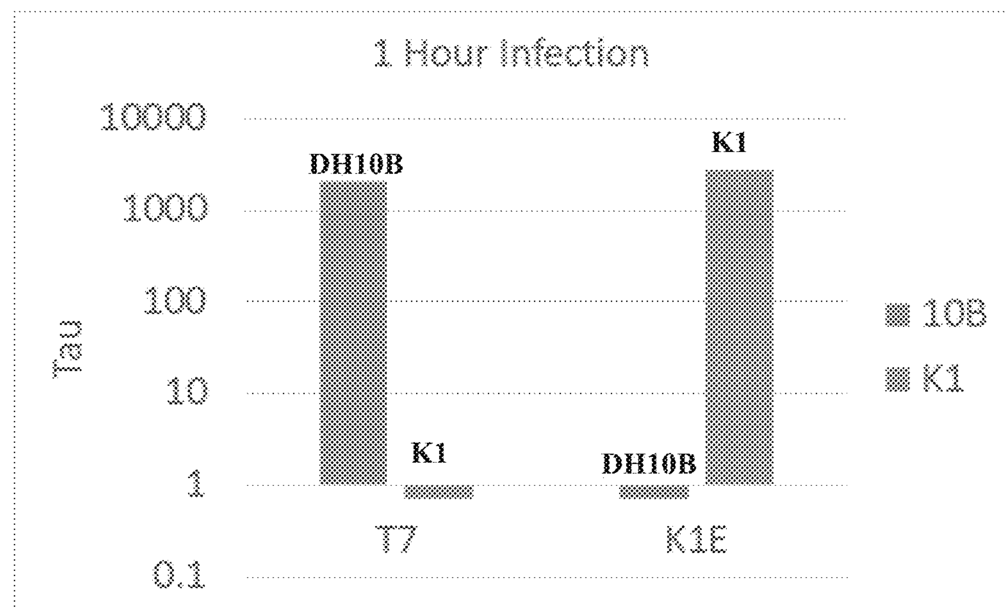
FIG. 9 shows that the recombinant NanoLuc® K1E phages of the present technology successfully infected an *E. coli* clinical isolate that was incapable of being infected with a recombinant nanoluciferase expressing T7 phage. An *E. coli* clinical isolate expressing K1 capsule genes was infected with the recombinant NanoLuc® K1E phages disclosed herein, and a recombinant NanoLuc® T7 phage for 1 hour.
Figure 11A:
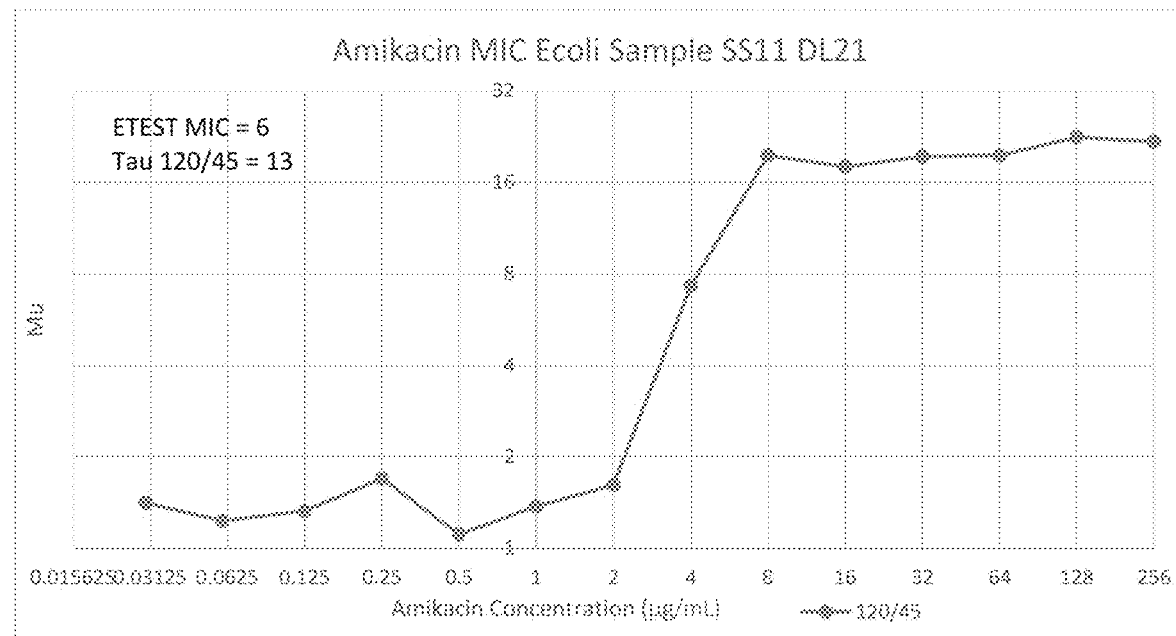
FIG. 11(A) shows the antibiotic susceptibility profile of an *E. coli* strain to amikacin using the recombinant K1E phages of the present technology.
Figure 11B:
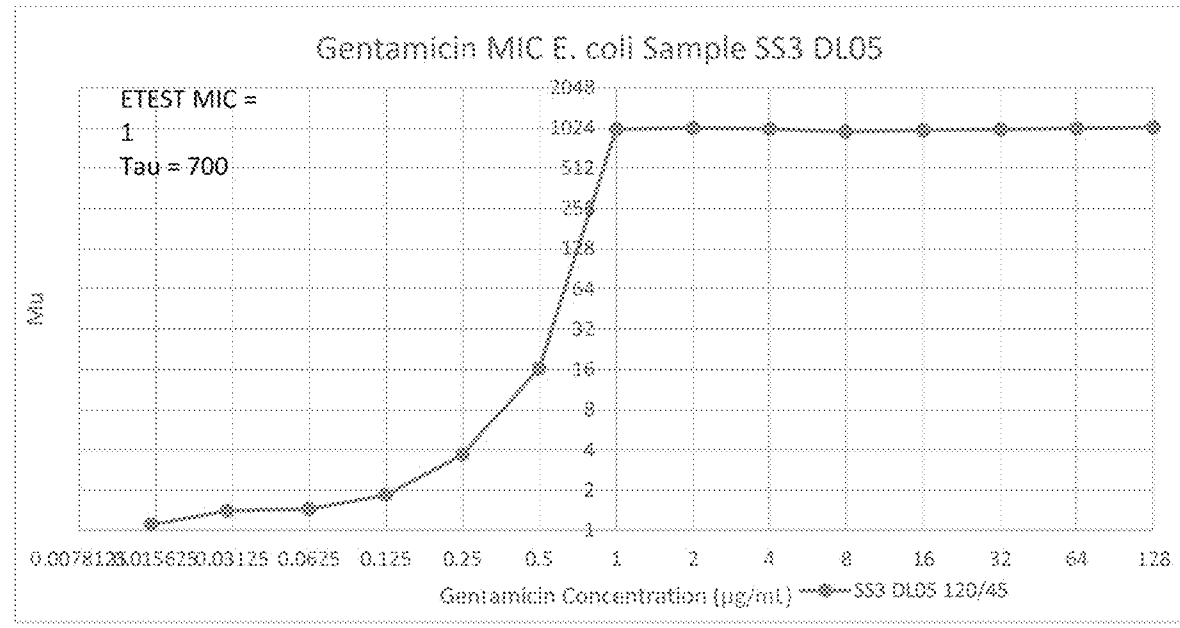
FIG. 11(B) shows the antibiotic susceptibility profile of an *E. coli* strain to gentamicin using the recombinant K1E phages of the present technology.
Figure 11C:
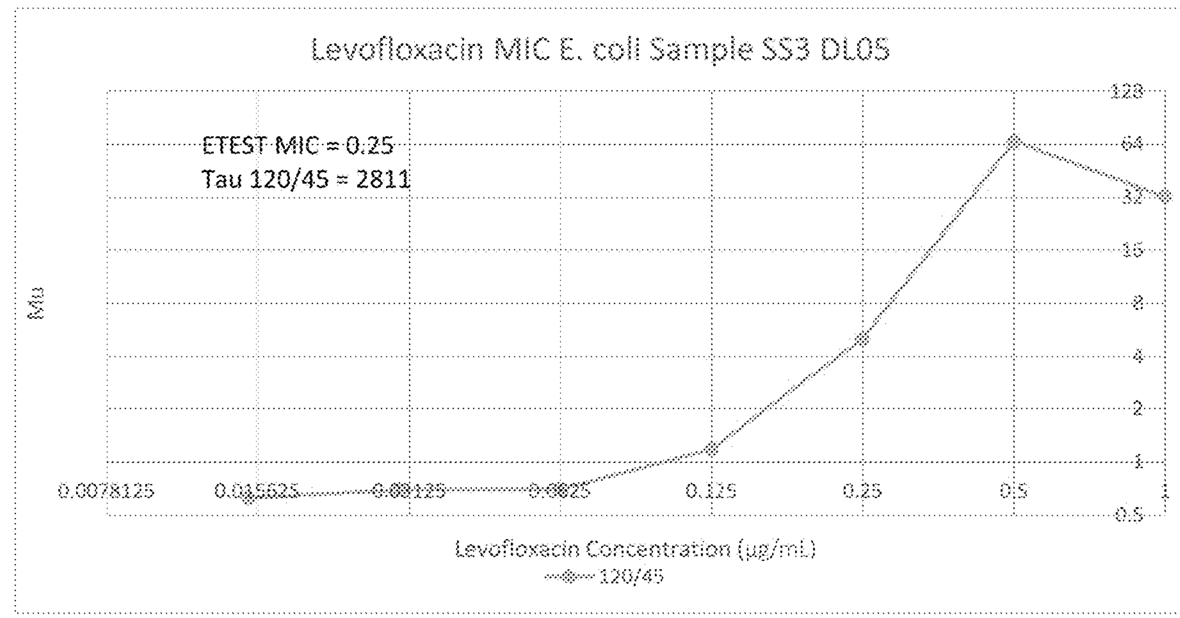
FIG. 11(C) shows the antibiotic susceptibility profile of an *E. coli* strain to levofloxacin using the recombinant K1E phages of the present technology.
Figure 11D:
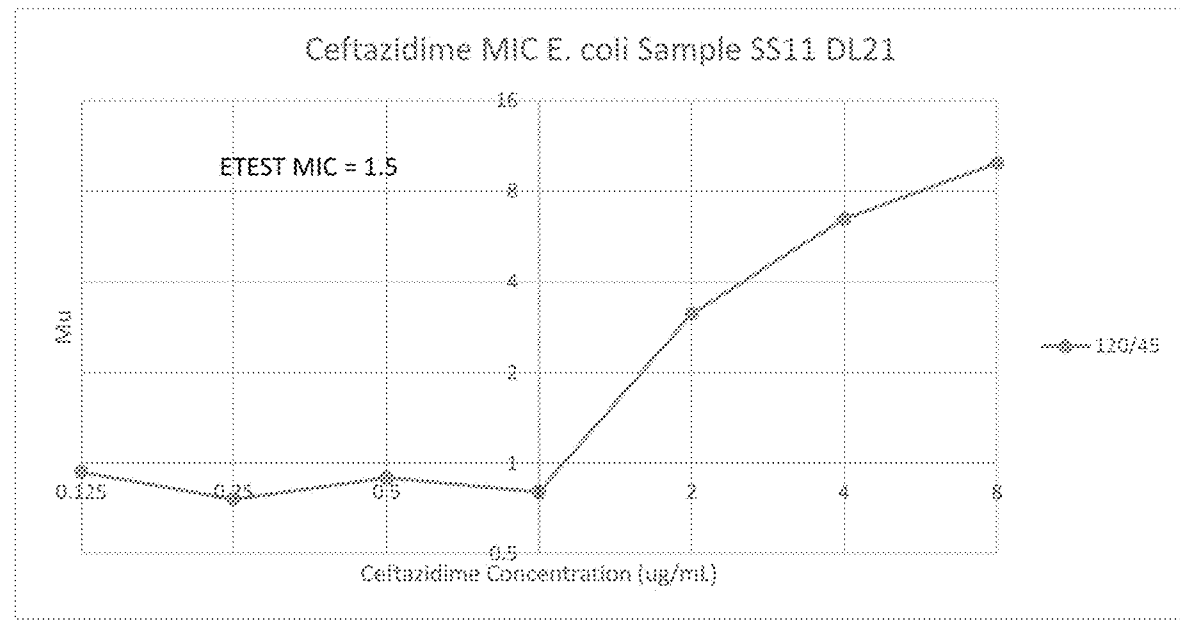
FIG. 11(D) shows the antibiotic susceptibility profile of an *E. coli* strain to ceftazidime using the recombinant K1E phages of the present technology.

As shown in FIG. 9, the recombinant NanoLuc® K1E phages of the present technology successfully infected a K1 capsule expressing *E. coli* isolate that was incapable of being infected with a recombinant nanoluciferase expressing T7 phage. Only K1 capsule expressing *E. coli* cells infected with the recombinant NanoLuc®K1E phages of the present technology exhibited an increase in relative luminescence units (RLU) during active infection (1 hour).

Figure 7:
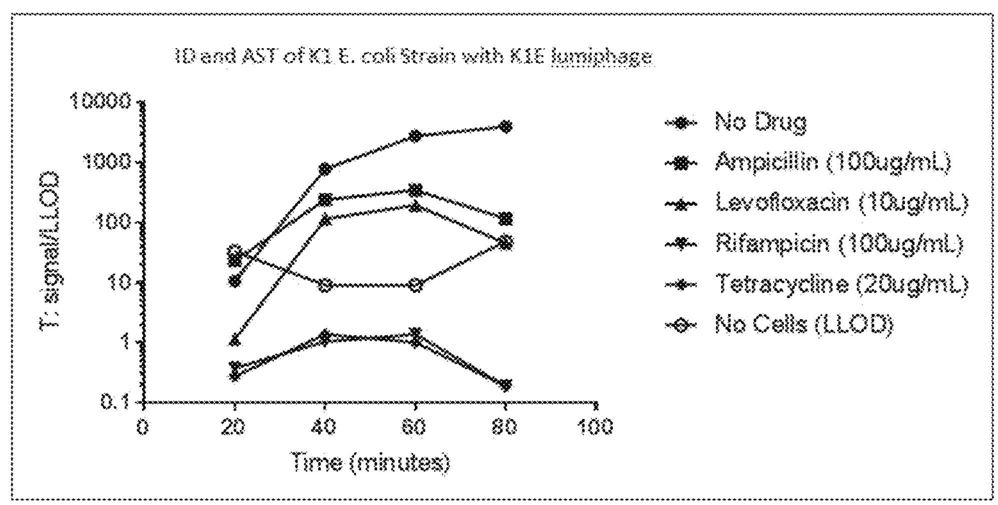
FIG. 7 shows antibiotic susceptibility profiling results using the recombinant K1E phages of the present technology.

FIG. 7 demonstrates that the recombinant K1E phages of the present technology are useful in identifying and profiling the antibiotic susceptibility of a bacterial strain that expresses K1 capsule genes in a test sample. For example, FIG. 7 demonstrates that the K1 capsule expressing *E. coli* in the test sample was sensitive to treatment with 100 μg/ml rifampicin and 20 μg/ml tetracycline.

These results demonstrate that the recombinant K1E bacteriophages of the present technology are useful for detecting target bacterial strains/species present in a sample. Accordingly, the recombinant K1E bacteriophages disclosed herein are useful for the identification and/or antibiotic susceptibility profiling of specific bacterial strains/species (e.g., bacterial strains/species that express K1 capsule gene) present in a sample.

Example 3: Antibiotic Susceptibility Profiling Using the Recombinant K1E Bacteriophages of the Present Technology Antibiotics were prepared by performing eleven 2-fold serial dilutions in Mueller Hinton Broth (Sigma, St. Louis, Mo.) in 96 well microtiter plates at a final volume of 100 μl. One column contained broth only and served as a no drug control.

Cells from an overnight growth blood culture in 25% human blood and 75% Tryptic Soy Broth TSB were diluted 1:10 in Mueller Hinton Broth. From this dilution, 5 μl of cells was added to each well of the antibiotic plate. Cells were pretreated with antibiotics (Ceftazidime, Gentamicin, Amikacin, and Levofloxacin) for 120 minutes at 37° C. After the 120 minute pretreatment, 10 μl of phage suspension comprising the recombinant K1E phage of the present technology (1E6 pfu/reaction well) was added to each well and incubated at 37° C. for 45 minutes. After infection with the phage, 50 μl of the reaction was added to 50 μl Nano Glo Luciferase Substrate (Promega, Madison, Wis.) in a luminescent plate and read in a luminometer. The minimal inhibitory concentration (MIC) of each sample was determined using the ETEST® method (Biomerieux, St. Louis, Mo.) according to the manufacturer's instructions. The differences in the reporter gene expression of the recombinant K1E bacteriophage observed in the antibiotic treated samples and the untreated control samples is defined as μ.

FIGS. 11(A)-11(D) demonstrate that the recombinant K1E bacteriophages of the present technology were effective in determining the antibiotic susceptibility profile of two different *E. coli* strains SS11 DL21 and SS3 DL05.

These results demonstrate that the recombinant K1E bacteriophages of the present technology are useful for determining the antibiotic susceptibility of a bacterial strain or species in a test sample. Accordingly, the recombinant K1E bacteriophages disclosed herein are useful for the identification and/or antibiotic susceptibility profiling of specific bacterial strains/species (e.g., bacterial strains/species that express K1 capsule genes) present in a sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for making a linear recombinant K1E bacteriophage genome of SEQ ID NO: 3 in vitro comprising (a) contacting a non-recombinant K1E bacteriophage genome of SEQ ID NO: 1 comprising a single PflF1 recognition site with PflF1 in vitro under conditions where PflF1 cleaves the PflF1 recognition site to produce a cleaved linear non-recombinant K1E bacteriophage genome; and (b) recombining in vitro the cleaved linear non-recombinant K1E bacteriophage genome with a heterologous nucleic acid of SEQ ID NO: 2 in the presence of 5'-3' exonuclease, a DNA polymerase, and a DNA ligase in an in vitro DNA assembly reaction under conditions to produce an in vitro generated linear recombinant K1E bacteriophage genome of SEQ ID NO: 3, wherein the in vitro DNA assembly reaction is devoid of biological extracts, wherein the cleaved linear non-recombinant K1E bacteriophage genome comprises a first cleaved linear bacteriophage genomic fragment and a second cleaved linear bacteriophage genomic fragment, wherein the heterologous nucleic acid comprises a 5' flanking region that is homologous to the 3' end of the first cleaved linear bacteriophage genomic fragment, and a 3' flanking region that is homologous to the 5' end of the second cleaved linear bacteriophage genomic fragment, wherein the 5' flanking region and the 3' flanking region of the heterologous nucleic acid do not comprise the single PflF1 recognition site, and wherein the in vitro generated linear recombinant K1E bacteriophage genome of SEQ ID NO: 3 is capable of producing non-endogenous bioluminescent protein that is functionally active when transformed into a bacterial host cell.

2. The method of claim 1, further comprising transforming the in vitro generated linear recombinant K1E bacteriophage genome in a bacterial host.

3. The method of claim 2, wherein the bacterial host is a non-natural bacterial host cell or a natural bacterial host cell for K1E bacteriophage.

* * * * *

SEQUENCE LISTING

```
<160> NUMBER OF SEQ ID NOS: 12

<210> SEQ ID NO 1
<211> LENGTH: 45251
<212> TYPE: DNA
```

<213> ORGANISM: Enterobacteria phage K1E

<400> SEQUENCE: 1

```
tctcgccctc gccctcgccg gattttcccc atatggggcc gcgctgcggt tggcttgggg     60
attgggctag gctgggccgt cttcaacctg ctgccgcagg aagctcgatg ggttggctga    120
gggttgccga gggctgcgct tagtggtaca caagtagaac gcctaggaag cgctagggca    180
cgccttagtg ttggacaagg tgattgcctt agtgcaaccg tttagggctt acacaggccg    240
ttttagggca attcctgagt gtttgacagg gtgtgagggt gtgggctatc tgttcgtttc    300
gctacgcttc actcactgct cctcacttcg ctgtcgctcg ctacactgcc tgtcgtgtac    360
cttaggttat tccttgaggg atggcttagg ttagccttag tgggctacct tagttaaagc    420
cttagtgctt agcttagtat caacttagta gtgtacctta gttagtctta gtgccagacc    480
ttagtgattg catagctaaa gctataagat gcaattaggt cgcggtcggt agaccgctga    540
gagtaggtaa tagtgataag atgcagtagg aggaacacca gaaacctagc catcctagcc    600
tatcctagct ctgtatctat tgctttcctt agtctcacat gttagacaac ctaggtttat    660
cttagtagtt gtgacatgta tcacataaat aatctatctt agttaaattt agtgttgaca    720
caggcaatca acagatatac attagcaatc actgagacgg acctagcaag ctgtctcagg    780
ttataagtag gagaattgat gcgtaggccg tagctagcgg atgtagtcgc atgaaggctt    840
gagcaagggg ccgtttaata ccttcttcct ctggagacaa agcttataac attgctcttt    900
aacaatttgc ttagtgtaac ctatgtatgc cgtggttaat tacttattga atgaggaatt    960
aactatgaat tatgaagaaa tgtatgaagt ctatttcgac tcattagatg aaggcgaaga   1020
agcattatcc tacgctgagt ttgtggaggc tttatcatga ttctgaataa ccgtgaactg   1080
tccgttctct tcactctgtt atgctacatg attcgtaata acgaattact tacagatgac   1140
gagatggcac tatatcaccg ctttcttaac gaaggttgga cagatacagt taaccagaaa   1200
cgtgacttga tgaaggagtt aagtaatgat tcagttgact gaagaccaac taaagcaact   1260
cttagtcgac gcgtggtttg ctggtcatga aacctcgcaa tacacgccta actcttacgg   1320
tgatgctaac agatatgcac gctctacatt aaaggaggtt aaagaggatg tatcagcatg   1380
aggttttctt cgaatcagct agtgaagcta tccgcttcca tgatgatatg atgcaagctg   1440
gcgtaggtgt tgatgtgtat cactatttga tagattacga cactgaatat caccgagtta   1500
ccttagtatc tgagtatgac aaccaagtca ttactgagta tctaggtagt gaagattatg   1560
attacgatga agtaatcaca acaaatctct aaattaacta ttgacagcca cggcatacaa   1620
ggctacatta agcatcaaga cggcgacgtc tttaaacatc ccgctcttta acaatctggc   1680
tagtgccttg gtaggctaac tacttactaa ggtgaactat gaactactgc gacatcgctc   1740
acgaattacg catggaacgt gagaaacaag agaagcggat tatcaagaag atggctgtac   1800
tgcttgcaca ctataaggca gacaaacagc caacacatga tgagttcgtg gacttctgta   1860
acatgtatct taatgtgagt aaggccactg gttacagatg gcttaaagca ctgaatgatg   1920
gagaattgta gcaataagcc agcttaatag ctggcctatc aaggcactaa cctagctctt   1980
taacaatccg gtttgtgtct tgataggctt actaacaaag gtgaactatc atgactaacg   2040
cacaacgtaa acgctatgat gcattgcaag agaaacttgc tgttgcttat gccgcttggc   2100
aagctaacac agacaagagc aaacacgata aactttatag taaagtggtt gcaattaatg   2160
ctaaaataga taaacttgtg aatagtatct tataagatag ttgctggcac tagccagcct   2220
atcaaggcac aagccacgct cttttaacaa tatgggtagt cgcttcttag tctggatagg   2280
```

```
ttaaacctag ggtattcttt tgagtgccct ataatgtaac ctaactaact aatgaggatt   2340
aaatcatgga acgcaatgct aacgcttact acaatcttct ggctgcaact gttgaagcat   2400
tcaacgagcg cattcagtac gatgagatcc gcgaaggtga tgattactct gatgcactac   2460
atgaggttgt agacagcaat gttccagttt attacagcga aatctttact gtgatggctg   2520
ctgatggcat tgatattgaa tttgaggatg caggtttgat tcctgatacg aaggatgtaa   2580
ccaagattct acaagctcgc atctatgagt ctctttataa tgatgtacca aatgatagtg   2640
atgtagtttg gtatgaagac gaggaagaat aaagatggaa aggcaatata acttcatctt   2700
ctcagacggt gtaaccctga aatgttcctt acgatttgcg cagattcgtg aggaagtgct   2760
aggtactaca tacaaactat ttagctgaca ctataagaga aggcttaaca aggcgttgct   2820
acggtagcgc ctgattaaac tttcacttac taggagttaa gactatggat ttagatagca   2880
tcattatggc atttgctctt attggcttaa gctggtgctc ctatcacctt taccgtgagt   2940
tcttatttga taaagctaaa cgcaaactaa gaaaggaagg cggtaactac ctctgtgtaa   3000
gaggcggttt agtcgaatat attgcaccta acggcacgga atgcgccatt aacaaagatg   3060
catttataga aacgtggcat tacatcaagt aactagccta tagcctgcct gtgtgggcta   3120
tgtgatattt acttacacta tataaggtga ctattatgac tactgaaaac acccttctgt   3180
ctgttcgtga agctgcaacc gctgaaatca agcagcactt agacaatatc ggcacttctt   3240
acatcaaagt tggcgcttgt ctgaatgaat tacgcggtga tttcgaaggt caaaaagact   3300
ttttagctta tgtagaatca gagttcggca tcaagaaggc acaatgctac aagctgatga   3360
gtgtagcccg tgtctttgaa ggagacgaac gctttaaagg tgtggctatg cgtgtaatgc   3420
tggcgcttgt tcctttcgct gatgaaaata taatcatgga gaaggccgca gaactcgccg   3480
cagatggcaa gctggacact aacgccgtaa acgccctgat tgagactaag aaagagataa   3540
aggccgaaac ggtacaatct aaggctgagg cagtaaaacc gcaggagaac gcgactgagg   3600
ccgcagaatc acaggaaatg caagcgccgc aggtagtgcc acccgcgagc gagcaggagg   3660
ccgacgaatc agcaccatgg gaagaggaaa gcaagccgga agcgccaaag gcagcgccgc   3720
tggataacac ggctaatacc gaaaacgccg ctatggctag cctcttagca caaattaagg   3780
cactgactga gcaattacag gcagctaatg accgcatcgc ctccttaagt agcgcacgcg   3840
aaagcaagaa ggcagccgca cctatgctgc cgcaattcaa atcttcctgc ttctatgctc   3900
gcttagggtt aagcgctgag gaggcaacga agaaaacagc agttaacaag gcgcgccgcg   3960
aactggttaa gctaggctac ggtgaaggac atgaagcatg gcccttaatc tctgaggcag   4020
tagaagagtt gactaagtaa ccttatcggt ggcatctcct taggtgtcac ctattaaggt   4080
ttctttcact aggagtaaac aagatgcaag acctacacgc tattcaactt caacttgaag   4140
aagaaatgtt taacggcggc atccgtcgct ttgaagcgga ccaacaacgc cagattgcat   4200
ccggtaatga atcagacacg gcatggaatc gccgcttatt gtccgaacta atcgcaccta   4260
tggcggaagg tattcaggct tacaaggaag aatacgaagg caagagaggt cgtgcaccac   4320
gtgcattagc tttcattaac tgcgtaggaa acgaagtggc agcatatatc accatgaaaa   4380
tcgttatgga tatgctgaat acagacgtta ccttacaagc tatcgctatg aatgtagcag   4440
accgcatcga ggaccaagta cgttttagca agctggaagg tcacgcagct aagtactttg   4500
agaaagtgaa gaagtcgctt aaggctagca agactaaatc ttatcgtcat gcgcacaacg   4560
tagcggtagt agctgagaaa tctgttgctg accgtgacgc ggatttctcc cgttgggagg   4620
```

-continued

```
catggcctaa agacaccttg ctgcaaatcg gtatgacctt gctcgaaata ttggagaata   4680
gtgtattctt caatggtcaa cctgtcttcc ttcgtacctt gcgcactaac ggcggaaagc   4740
atggtgttta ctatttacag accagtgaac atgttggcga gtggataact gcatttaagg   4800
aacatgtagc gcagctcagc cctgcctatg caccttgcgt tatacctccc cgcccttggg   4860
tatcaccttt taacggtggg tttcatactg agaaagtagc aagccgtatt cgtctggtaa   4920
aaggcaatcg tgagcacgtc cgcaagctga ccaaaaagca aatgccagcc gtttataagg   4980
ctgttaacgc tttgcaggca actaagtggc aggttaataa agaggtttta caggttgtgg   5040
aggacgttat acgtctagac ctcggctatg gtgtaccttc ctttaaacca ctcatcgacc   5100
gtgagaacaa gccagctaat ccggtgccgt tagagttcca gcacctgcga ggccgtgaac   5160
tgaaagaaat gttaacaccg gaacaatggc aagccttcat caactggaaa ggtgaatgca   5220
ccaagctgta taccgctgag actaagcgcg gcagcaaatc ggcggcgacc gtccgcatgg   5280
tagggcaggc ccgtaaatac agccaatttg acgcaatata cttcgtgtat gctctggaca   5340
gccgcagccg cgtctacgcg caatctagca cgctctctcc gcaatcaaac gacttaggca   5400
aggcattgct ccgttttacc gaagggcagc gtcttgatag cgctgaggcg cttaagtggt   5460
tttggtgaa cggggctaat aactggggtt gggataagaa aactttgac gtgcgcaccg   5520
ctaacgtgct ggatagtgaa tttcaagaca tgtgccgcga cattgcagcg gatccgctga   5580
ccttcactca atgggtaaat gccgactccc cttacggctt ccttgcatgg tgctttgaat   5640
atgcgcgtta tctggatgca ctggatgaag gcacgcaaga ccaattcatg acgcacctcc   5700
cagtccatca agatggtagt tgttctggta tccagcacta cagtgctatg ctacgcgatg   5760
cagtaggtgc gaaagcagta aaccttaagc cctctgactc tcctcaagat atttatggtg   5820
ccgttgcgca ggtagtaatt cagaagaatt atgcatacat gaatgcagag gatgcggaaa   5880
ccttcacttc tggcagcgtg actttaacag gtgcggaact gcgtagtatg gctagtgcgt   5940
gggatatgat aggaatcact cgcggcctga ccaaaaagcc cgtaatgaca ctaccttatg   6000
gcagcacacg tctaacctgc cgtgagtcag tgattgatta tatcgttgat ttagaagaaa   6060
aagaggccca acgggctatt gcggaagggc gtaccgccaa tcctgtacac ccttttgata   6120
atgaccgtaa agacagcctg acacctagcg cagcttataa ctatatgaca gctttaatct   6180
ggccttctat ctcggaagtg gttaaagccc ctatagtggc aatgaaaatg attcgtcagc   6240
ttgcacgttt cgcagctaaa agaaacgaag gcttagaata tcccttacca actggcttca   6300
tcttgcaaca aaagataatg gctaccgata tgctccgcgt atccacttgc ttgatgggtg   6360
aaatcaagat gagtctccag attgaaacag atgtagttga tgaaacggca atgatgggtg   6420
cggctgctcc taacttcgtc catggtcacg atgctagcca cctgattctg actgtatgtg   6480
acctagtgga taaaggtatt acatccgttg cagtcatcca tgattctttc ggtactcatg   6540
caggacgtac cgcagacctg cgggatagct taagggaaga aatggttaag atgtatcaaa   6600
accataatgc cctgcaaaac ctgctagatg tgcacgaaga gcgttggtta gtagacaccg   6660
gaatccaagt accagagcaa ggggagtttg accttaacga aatcttagtt tcagactatt   6720
gtttcgcata atattaatag gccattcctt cgggagtggc tttcttttac ctactacctg   6780
taacatttca ttaacataaa acgtgtctca catgtgagac tttatttacc ggacactata   6840
ggatagccgt cggagacggg aaagaaaggg aagataaagg atataaagga agtaataggt   6900
attaaaggtt atataggtta tctaggaata cctattacct tcttccttcc tcttattacc   6960
acttagagga agggcagacc taggttgtct cacatgtgag acttcgtatt taccggacag   7020
```

```
tatagataag attaactcac tttggagatt taaccatgcg taactttgag aagatgaccc   7080
gtaaagctaa ccgttttgac atggaagaag ggcagaagaa aggcaagaag ctgaataaac   7140
ctgtccgtga ccgtgcatct aaacgcgcag cgtgggagtt ctaagttatg gctaaataca   7200
gaatcaagac ctgtttaaat agtcacgggc aagagtgtta catagtgcaa cgtaaagtat   7260
taggcttaat atgggtcaca tgtatgatgc ctattggata tactgataca gaggctatct   7320
tctgcaccga aagggatgca aagcagttta tctctaagcg tagaaaagct gactcttatc   7380
aacccagaac tattaaggtg aactaatggc tattattaat aacatcccgt gtcctgcttg   7440
tcagaagaat ggacacgata aatccggcaa ccacctcatg atatttgatg atggtgctgg   7500
ctattgcaac cgtggtcact tccatgataa tggcaagccc tactatcaca agccagaggg   7560
tggcatcgag ataaccgaat tgcctattac tggcaatatc aaatatacac cttctcaatt   7620
caaagagatg gagaaggaag ggaagataag cgaccctaag ttgcgcgcca tcgcacttgg   7680
tggtatgcgt atgaaagacc gttgggaggt catgaatgag caagaaaggg cagaccaaga   7740
agcagagtgg aaacttgatg ttgaatggtt cctcacgctt aagcgtaaga accttgtgtc   7800
ccgtcacatt cgaggtgaca tcgcagcaat gtacgatgtg cgcgttggac acgatgaaga   7860
gggaagagtc aaccgtcact attatccacg atatgaaaag ggtgtgcttg ttggagcaaa   7920
atgccggacg ttgccgaagg attttaagtt cggacaccta ggtaaactct ttggtatgca   7980
agacctttc ggtatgaata ctttgtctca cgtgttagac aagggaagac gaaaggattg   8040
cttgcttatt gtgggcggcg aactggatgc actagcagca cagcaaatgc tccttgattc   8100
tgccaagggt actaagtggg aaggccagcc ttaccatgta tggtctgcca ataaaggtga   8160
gtcttgcctt gaagagatag tgcaaaaccg tgagcacata gcccaattca agaagattat   8220
atggggcttt gatggcgacg aggtggggca gaagcagaac caacaagctg ctcgcctgtt   8280
tcctggcaaa tcctacatcc tcgaatatcc ctctggttgc aaagatgcta acaaggcatt   8340
gatggctggc aaggctaaag agtttgttga tgcttggttt aatgccaagt catctgatga   8400
agtctttggt agccagatta aatctatcgc atctcaaagg gataagctca aggctgcacg   8460
tccagagcaa ggactatcat ggccttggcc taagctgaac aaggtaacgc taggtattcg   8520
taagaaccag cttatcattg taggtgcagg ctctggtgta ggtaagactg agttccttcg   8580
tgaagtagtt aagcacctca ttgaagaaca cggtgaatct gtaggcatca tttctacaga   8640
agacccgatg gtcaaggtgt cccgtgcttt tatcggcaag tggattgata agcgtattga   8700
gttaccgcca accaacgacc cgaaagaaga cggataccgt gaggtgttcg actacaccga   8760
ggaagaagct aacgctgcca ttgattatgt ggctgataca ggaaagttat ttgtggctga   8820
cctagaaggc gactattcta tggagaaggt agagcaaact tgcctagagt ttgaggctat   8880
gggcatttct aatatcatca ttgataactt aacggggatt aaattagatg agcgtgcttt   8940
tggtgggaag gttggtgcac ttgatgaatg cgtcaaacga attggtacta tcaaagaccg   9000
acatgcggtt acgattttcc ttgtctctca ccttacacgt cctccggcaa accgtaccca   9060
acacgaagaa ggtggcgaag ttatcctttc tgacttccga ggctcaggcg ctatcggatt   9120
ctgggcatct tacgccttgg ggattgagcg taatacaaga gctgaaacgc ttgacgaaag   9180
gactaccacg tacatctcat gtgtcaaaga ccgcgaccaa ggtatctgga ctggaaccaa   9240
ggtcatgctt aagggtgaca ttcaaaccgg acgtttaatg gaaccacaag cccgtactaa   9300
gtcatttgat acaggtgaag caaggcaaca agaagtgccg gatttaccgg acactataga   9360
```

```
agagacaacc tttgacgatg aacaggagtt ttaatggaaa ttattaaacc agtattgaat   9420
atcggtattg agatcctatt catgcttgtg atcgcagatt atgctgcacg atatggattc   9480
aagaaagctg tgaaacttat cgttgcatct ggttttctta tgtcaatgtt ctttattgta   9540
acacgcctta tctagtgtat ttatcagggc ttgtctcaca tgtgagacag gctcttatta   9600
agtacattaa ataactggag attgattatg tatagattag tattgaatgt aggtgattat   9660
gttcgtaaca tcaatgaagc ctcacgtcgt tatcgttgcc gtggtgtagt ggctcgtgta   9720
agtgagaaca tgtatcatgt agaatatgag gatggtatta aggcttctta ccacaagaaa   9780
acagcacata aatatcttga aaagattgta gagataaaca atcaatgtaa gtgcatacat   9840
gatgaggttt gcgataaatg tgctcgccag atgcttaaga atttcctagc tcctctttat   9900
tatggtgctg gtcctcaaac actagcagag tacatggcag aaaagaaaac cacactcaag   9960
aaagagcgtc gcaatgtaat cactggtaag actcaaagtg aaatgattaa gcaatgtggc  10020
actgcattag gtgttacaca gttcaatact cgtgcattgg gtaaatccac agggcaagct  10080
atggtgaaaa ttggtgaagc tatgatgcac ccaaatgtgc ctgtgcgaat cttggatgtt  10140
gaccatgcaa tcacagagca tggcacacca cggcgtgtag ctaataatca tttcgccgac  10200
actatagaag gtattattcg taagcaaggg ttgaagggtc ttcacatctt aaatggtgaa  10260
gaattactgt acctacctat cgttactgaa gaaacctacg tgaatatcta aggagttaat  10320
catgactaag gtattaattt atatgcgtgg acctcataaa tgctatgcag ttgtagcacc  10380
agatggtgtc aagacatatg gtacttcaaa ggggtttgca ttaataggtg ccagtcttag  10440
tgcaagtttt cagatggaac ttttcggtca ttggactgaa aaagagttcc gtgaggagtt  10500
taatgtaatc ggcagcttta tggtgaaaca tgcaaaataa acacagtctt aagatgtttg  10560
atggtcacga agacctgcaa gcacaaatta ctaaccaagc cttcctgttt gcacagttaa  10620
ctatggctga agcaaagaag aatagcctga cgcgcgagca agttatcaaa gaggcaactt  10680
gggagccaca ccaaggcaaa tacatgggcc agaaattaac tgtaacacgc agtcgataag  10740
taaagggttg tctcacacgt gagacagcct ttcatcatat tgattggagg tgcattatgc  10800
cacgtgatta tgattctgat tgggatttcc aagattcaat gaactcaaaa cctgaacgtt  10860
cagatgacta ctacgaaaca gaggcaatgt atgaaagcta ttaaagtcag taaggtttgc  10920
tcttgcggta aaggttatcg cagtcgtatt gatggtaagt gtgggcattg caggtctaag  10980
aaagaggctg ctttgtttga taagtaccac aatgaattag catataacta tcctcatcta  11040
acacctaatt ctttattagg acttggttat agggttaaat actttggagc aatctatgaa  11100
atcaattgat tggaagaagg aagcagaagg ccgcatctta gtgatggatt ctgaggctaa  11160
aggcctgctg gatgctatcc gatatggcca ccgcgaagat gtgcacatca tttgctgcat  11220
ggatttgctt actacagagg agttcctctt ctttgaccca tacgagatgc gtgaccctga  11280
agcaagagaa cgcctaaaag aatgggaagg ccatcaagat ggaacattgg ttgacggtgt  11340
taacttcctt aaacactgcg aagccatcgt ctcacagaac ttcctagggt acgacggcct  11400
tctatttgag aaagcattcc ctgatatctg gaaaggcttt aactataccg agagacgcgg  11460
caagggcaga ctccgcgctg acctgtgtcc ggtacgcgtc atggatacgc tggtcatgag  11520
tcgcctgtta aaccccgata gacgcctccc tccgcaagca tacgccaaag gcatgggtaa  11580
cgtagcccct cactcaattg aggcgcacgg cattcgtata ggccgttata agccggagaa  11640
cgaggattgg tctaaactaa ctgaccacat ggtacatcgt gtacgcgagg acgtggcgat  11700
aggccgtgac ctattcctct ggctatttaa cggagaatgg acggagcaca aacgccgtgg  11760
```

```
cgtgaataaa cgcactggcc taggtattga gacagccttc cacatggagt ccattgtggc  11820
gctggagatg agccgtcagg ccgagcgtgg attccgtctg gatatagata aagcattagc  11880
acgatgcgag gaattggacg ctaagattga tgagacagtc gcagcgttcc gtccgcacat  11940
gcctatgcgt atcaagtcta aaccttttaa accggaagaa aagaatgaag tatgccaacg  12000
cgcaaatgag tatggagcta gcaacaatat acctactgtc cttgacccct ctcactttct  12060
tcacgcagag agacgaggag atcgcaagac agtatggagt gtcactacta agtctggtga  12120
ttggtcggct agcgtcaaga aagactttcc tcaccttaga ggaaaccgta atgacacgcc  12180
aagcatcaag tggattggcg cttactcgcc tgttactttc gaagagattc ccttgggtaa  12240
cagggataca gttaagcaag tgctctatga ttatggatgg aaaggtgttg aatttaacga  12300
taccgagcaa gcgcatctcg atgagcatgg cgtattaccc aagccttgga gtgggaagat  12360
aaatgaaaag tcccttactt tatggcaaga gagagccgca cgtgaaggta aaacagtccc  12420
tgattggtgc ttgggtatcg ctgcatggta catactcgta tcccgtcgtg gtcagatcct  12480
caaccgtggt gacgttgaag ccttcgacca gaagggggtg tggccttcgc aagctggtat  12540
acgaaagtgt cgcggccttg tacctgtagc atttaacaag gagttaggaa tcaatgcgca  12600
gcaatactac gaaaggtacg gatgctggcc tacgtcagac aaggatgacg gagaatggcg  12660
tgtgccagct attgctatta gtattggaac ttctacgttc cgtatgcgtc atcgtaacgt  12720
ggttaatatt cctgcccgtg gtttgtatcc tttacgtgat ttattcatag ccggtaaagg  12780
taagctaatc cttggttgtg atggtgctgg tcttgaacta cgtgtactgt ctcacttcat  12840
gaatgaccct gaatatcaag atattgtact gcatggtgac attcacaccc ataatcaaat  12900
gaaggctggt cttcctaagc gtgacatggc gaagacattt atatatgcct tcctatatgg  12960
gtctggtata gctaaccttg cagcagtatg tggtgttact gaggaagaaa tggaggaagt  13020
tgtggcaaga tttgaggttg aactaccatc tcttgcacgt cttcgtgaga atgttatcgc  13080
acaaggtaac aagtttggct acctacaagc acctgatggt cattggggtc gcatccgtat  13140
gtctggtggt gaacttaaag agcacactat gcttaacgta ctactccaga tgactggttc  13200
tctgtgtatg aaatacgcat tggtcagagc gtttgcagtg atgcgcaagg aaggtgtggc  13260
cttagatagc atgggaaacc cttgcggtat agctaacgtg cacgatgaaa tccagatgga  13320
agtccctgaa gatgaggtct tgtatctcaa ctacgacttg cctttcacct tagaagggtt  13380
cgaaacagag aaggctgctg tgaaagcagt gttcgatgca gaggagaaac gtgttcatgt  13440
ggattctgaa ggacgtatgt ggtctgctgc aaatctcgtt agcgttgatg ctgatgctgg  13500
tgtacttcat tgccagcgtc gctatcaccg tgcagggcat atcattgccg acgcaatgac  13560
ttgggcgggt cagtatctga agatgcgttg tccgatggca ggtgagtata agattggtgc  13620
aagttggaag gaaacacact gatggacagg tttgatattg tttgcctatt ctccaccttc  13680
tttcttatat tccttatgct tgcttgctat ggaagtatgc gattagatat acctgatgaa  13740
gaggagggtt acgattgatg caggcatctt ttattattct tggagtcata ttatttatgg  13800
tagtattctg ggctttctct ggcattgacc cagattgtga tggtaactac gactgagtta  13860
tactcaaggt cacttacgag tggcctttat gaataactta ttcctactta ttttgtctaa  13920
catgatttac tggacactat agaaggaaag cctaggtaat ctaggtttat aaggtagtat  13980
aggtaattaa ataaatatag gagatataaa tatgtctatg gtaactactc tggtattcgt  14040
ggctcaatac tttcgtggtc ttgctaataa gttcaagtcc aaggctatca aagctattga  14100
```

-continued

```
ggctcgcatc gaagcagtac aggcagagca agttaaagtt gaagaacatc gtagttctca  14160
aatgattgac tgtcataacc gctactatgc atctcgtgat gaactaaatg cacgtcaagt  14220
caaagaggta gaagatatgc tggcacgtca ccagcaagag cgtgacagcc tgaaagctga  14280
atttgaagag aacaaggcat caattgctct tgtaaatcaa gctgcatctg acagcctgaa  14340
gaaagagatt gttatgctgg aaatagaact ggacaacttg actaaataag gagttatgat  14400
ggaagaagtg attcaagcta aacatgtagg tatcatcttt cgtgacctag agcagcgtaa  14460
agttgcaggt cacactcgtc tggctaaaga agacgataca gcaatcacta ctgtggaaca  14520
agcagatgcc tatcgtggtc cagagtttac tcaaggtgaa acttgtcatc aattgagcct  14580
ttcactttgt gacactatgg ctagtgtaaa tgtacaagag gttgaagatg gtgaatgtgt  14640
tagttatgtc taccctctcg atactattgc acgtattaag gtagttcata agtaattact  14700
ggacactata gaacaatagg tcggcttagt tcggcctatg attgtaaagt gtcgttgatg  14760
ttgaaccatt gtgcaccttg cacaacccga taccgtatcg ggctttctag tgagcacatg  14820
cttgtgctca gtacaaagct aactgacaat aggagactaa ataaatggca cgtggtgatt  14880
tcgattttgg tgcttccgta tctaaagctg aaggtaaagt ctttaagaat ccagaagtag  14940
gtgatcatga agcagtaatc tctggcatca ttcatgttgg ttccttccaa gacatcttta  15000
agaaaggtaa taccactgaa gttaagaagc cagcaaactt tgttctggtt aagattgtcc  15060
tgatgggtga cgatgacaag aacgaagatg gttctcgcat ggaacaatgg atggctgtgc  15120
ctctgaagtc tggtgataag gcaacactga ctaagttcct gaatgcagtt gaccctaaag  15180
agttgctggg tggcttcgat gattttatcg gtgaatgtct gactgcaact atggttggct  15240
ctggcgacaa gaatgatgat ggtactttca agtatgttaa ctggaaaggc tttggcggta  15300
tgcctgataa gttgaagaag cttgtactgg ctcaggtaga agaggaaggt ctgtctatga  15360
caggtcatat caccttcgac aagctgacca aagaaatcat tgatgacatc ccagctaact  15420
tggtacgtca atacttcctg aacgagacac ctcgtggtaa gaacctgtct gttgctggct  15480
ctcacgtaga agctattatc aaagctgctc gtgaagaaga ccctgaatgg aagaaggcta  15540
agaagaaaga cgaggaagat gctaccccag ctaatcgtaa atctctggat actggtgagt  15600
ctgttccgca ggaagtacct gaagcagaag atacgcctgc accggagatg gatgaggacg  15660
cggaatatta aggagaacgg atgaaagtac aaatcgtaac tctgcattgc aagaaaggaa  15720
tcaccacact tggcggcaat acttttcact ccttctctga aggggagaca tacgccgacc  15780
ttcactatat ctggcgtgac gggcagcacg tggtgaacta cagcgaccct gcgactggta  15840
aacgccacgg cgtgtcgctt ccggcgcacg acattgctca ggtgaacaca gttttataaa  15900
gtctcacgtg tgagacaaat cggtgtccgg tatttactgg acactataga agagaagaat  15960
tttaatcggc gataatgcca taaccaacaa aaggagaatt taatatgttc aagattgaaa  16020
ctatcgtaaa ccgtgttgtt aaaggtgctg ctctggtatc cgttgagtct ttcattatcg  16080
tcgatgaagc tgatcaactg gtagctggta ctaaggctta cgatacccgt gaagaagctc  16140
aggctaagat tgacagcatg ggtaacttcg ctgctggtct ggagtttgct cgtgcttgct  16200
tccctgagca ggctgacaaa gcccagatcg gtaaggctaa catcgtagct gaatatctgg  16260
attggattgc tgctggtaaa ccagtgaaag aagttaaagc tgctgaagaa gctgaagctc  16320
cggcagtaga agtgtctgca ccggaagctc cggttagcga agaggaagag ttttgataat  16380
agcaggtgta gcctctgtta gtcctagttg actatcacgc tcacctcatc taatgccctg  16440
tctgccttag tgtaggcagg gtcttttgcg taatagttat tggagaatga attatgccga  16500
```

```
ctattgaatc tcgaattgaa ctggacatta gctacaatgc aatcaccaga cagtatattg  16560
gggttgccta tgattacaaa actggtgaga agctagtgga ggtgagacaa tgggatgact  16620
attggttaag acagaacctc catgatgcgg tgtcctcctt cttgaaggag tggcctacat  16680
gcgaccaaac ttcgacttcg gagctacagt atcggaagac aataatctca tcctgtggcc  16740
aactgaaggt aatcgaatcg ctttaataga tgctgatatg ttaccctaca tcgtaggtta  16800
tacaatcagt gacatgactt atttacgagc cacaactcgt gttaagtcag gacaagtccc  16860
atcaatcaaa gatacacctg agtgtaagca agcatgtgac cgtgtgaact ccttgcttaa  16920
ctcttgggtg tatgcagcag agtgtgatgc agctaagcta ttcatgacga aatcagaagc  16980
taacttccgt gtccgcctag cattcacaaa gccttataag ggtcaacgta agaccgagaa  17040
gcctccgttc ttctatgaat tgcgagagca tctcttagag gttcacggtg caatcttggc  17100
agatggtgag gaagctgatg acctcatgag catcgcacaa tgggatagcc accgccgctt  17160
ccagcaagat acaggtaacg agttcgctat cggtagtcca gagcataaag cattctctga  17220
tacttgcatc gtttccttag ataaggattt gatgattgtt cccggttggc atctacagcc  17280
gggtcaagag aagaagtggg tagagcctat gggctggctt gagctacgcc gtaaggttaa  17340
tgggcaagtc aaagatctaa aggtgctggc cctcatgttc cactatgcac agatgattat  17400
cggtgatgat attgataact atgctggcat accaggtcgt ggtgctaaat atgcctatga  17460
tcttctcaaa gattgtaaga cagagaaaga gttgtacatg gcagtgctgg gtgcttacaa  17520
ggctaagttc gggcatggac aagttaaaat taagaattac cgaggtggtt atcgtatcgg  17580
caaagccttt gacctaatgc ttgagtgtgg tcgcttagct cacatggcaa gattcaaggg  17640
tgatatatgg cgagccgata agaacccaat cttgtgggga gatgaaggat ggctacaaag  17700
ttaaaagcat ctgaagttgc tgcttataag aaagagttgc tagagaagca gggctggaaa  17760
tgtcctattt gtggagcacc tcttaaagca gtggccgaga ttaaccgagt actagaccat  17820
tgccatcgca gaggttactg tagagcggta ctctgtcgtg ggtgcaatgg cggtatcggg  17880
aagatagaaa acctagtaaa gacttattgt aaggctgggg ataatgagta tttcattatc  17940
aagacattgc gaaacattgc agattatcta gacttacata gtaagcctca gactgataag  18000
atttatcata aacatcaaac ggaggcagag aagcgcgagg ctaagaaccg taaggcacgc  18060
cttgcttatg caagaaagaa gaaggaggtt aaagttgggt aagcttcgca gcttgtacaa  18120
agactccgag gtacttgatg caatcgagca agctaccgac gagaaaggta atgttaatta  18180
caatgagatg gcacggatat tatcgtgcca ccctgtgggt aagaagatta cccgccagtt  18240
ggctagatac tggcatggtc aattcaagaa gaccaagaag aatggtgatt actaccagac  18300
ccttctgcaa gaggataagc gtatcaagga agagcgtaag ctcaggactc ctgaccgcta  18360
cgaggatttg gctattgtac cattgcctga ctcgcctcat cgaagtgtac tggtaatccc  18420
tgatacccat gcaccgtatg agcacccaga taccttagag ttccttgcag cagtggcagc  18480
acgttaccgt cctgatacgg tggttcatct tggagatgag gcagacaaac atgccttatc  18540
gttccacgat tcggacccaa atctggacag tgctggcatg gagttagaga aggcccgtgt  18600
ctttatgcat aaattacaca agatgtttcc tgtgatgcgc ctgtgtcatt ctaatcacgg  18660
ctctatgcac ttccgtaagg caagcgccaa aggtattcct gtacaatatc tgcgtaccta  18720
tcgtgaagtc ttctttccgc atgggggtgg cgaccagtgg gattggcagc atacacacgt  18780
tcttgagttg ccgaatggtg aacaggttgc atttaagcat caacccgcag gctcagtctt  18840
```

-continued

```
agcagatgca gcgcatgagc gcatgaactt agtgtgcggt cacttgcatg gtaagatgtc  18900
ggtggagtat gcacgtaata cacatgaaca gtattgggct gtgcagggcg gctgtttgat  18960
tgatgagtca tctcgtgcat ttgcctatgg tcgtgagtcc aaatacaagc cagcattagg  19020
ttgtgtggtt attctggagg gtgtgccgca cattgtcccg atgcagacca atagtgacaa  19080
tcgctggatt ggtaagattt agttgacact atagaacaaa gggtaggtat tagcttaccc  19140
ttgattgtat agtgaatgga ggaattaata tgtcacaata tgtatgtgag aaatgcggca  19200
atcgatatga taactgcacc tgtgattata ataaaggtaa aaggattaaa tcaggtgatt  19260
atgttatacg acgtgcaggc tgccgcgacc cagagtgggg cagggtgtgt aaactattag  19320
gcaagaaatc agatgcaaca ttcaaagtta taaaggatga gtctgtcggc agcgccatta  19380
tacttgaagg tatcgaaaag cgagaatggt atgcacctta tttcgagaga gtggcaaccc  19440
caccagttgt acctgagtct aataactcaa acgataatat ggttacgcaa cctaagcact  19500
acgagttctt cgatggggta gaggcaatca ctatcattgc tcgtagtatg accgagaagc  19560
aatttgctgg atattgcatg ggtaatgctt tgaagtatcg tctgcgtgca gggaagaaat  19620
tcaacacgga agaagacctg aagaaagcag actactacaa agagctattc cagaagcatc  19680
gtcacgaatg tattgatgag gatatttaat atggaaggta aactgtatag agggtacttc  19740
ggtaacttat ataaagtaag ccctcgcggt tttgtattga cctctgatga tgaaggtgca  19800
atgtggttcc taagtgccta tggttctgac ttagcatact ttaaagaggc aatagttaaa  19860
ggtgtgatga aggaggtgaa atgaatatct tccaattcct aggtcttcca gaagaccacc  19920
gcaatcaccc attcatgctg gtgaaacatc gcggtgaagt acctgagaag aaattaactt  19980
ttccatgtta tgcacaggta aaacgagatg gtatatttag tgctgtggtt gttcgcaacg  20040
atggtgtcgt tggtgtcttt ggacgcactg gaaagaaact ggctaacacg gaaaccttgg  20100
aagaatctta ttcagctttc cctactggca tttatctcgg tgagttgcaa tctatggcta  20160
ttgatgtcta ccttgaagca ctttctggag tagttaaccc taaccgcact gagccactgg  20220
atttcatagg ccagcagatt aaagacaacc tgtatattga cttcttcgat atgttaacta  20280
ttaaggcatt ccatgatgga ttcactgatg tttcttatct caaacgttac gatgctttac  20340
atcgtcgcat cggcgctcat cttagcgggc acaacgctat ccttcctatt actccttgcc  20400
ataatgagcg agaagttgaa gcgtttgcgc aagagcaaat agatgcaggc cgagagggtg  20460
ctgtgttcaa actggactgc gattatgaag caggccacaa aggttatcgt caaactaaga  20520
ttgtacgcat ggtgtcttat gacctaacct gtattggttg ggaagagggt aaaggaaaat  20580
acaagggtaa ggttgctaac ctgatcttta aatggaaagg aggcaagtct gttaaggcta  20640
tgctgggtcg tggctggtcg catgaggatg cagcccaaat gtatcacgat attaaacacg  20700
gtggcgaact gaacgtcatt gggaaaatct tcgctgtcaa ggcgttgcag gaatctagca  20760
agggagtcct gagacttccc aaggtttctg agttgcgcca cgataaggag gttcctgatg  20820
tctattgatt tgaacgaaga gcagcttgaa ttgttaatag aagccattga gcaatactat  20880
tacatgtgtg gctatcaatc agaagaacta gactccttat attcacaatt aaaaggaggt  20940
taattatgtc ttttgattct atgaaggcaa ctcgtgcggt tgaggtagca gaggctatct  21000
tcgaaacttt atcctgtggt atggaagtac catatacttt actggctgat gcagaagagc  21060
ttggtctttc tatagaggcc atccaagaga aggttgagga actctatggt acagacgaag  21120
aagaaaccga cgatttcatt tgagggtatg gagatgcttg agatgattct caagccttct  21180
tctccgaagg tgactaagac tcacgaagaa ttaatcgtag atgaagtgaa gcgttacata  21240
```

```
atggattgtg tcagagcaca actggtggtc caatgatacg tccagcttca ttcttagata  21300

ttcctgagat tataaacctt gggaataagt acgtggaaga ggaagtcaag gttgtagccc  21360

atcactcagc ctcatggaat gcagaacaaa gcgcacataa cctttgtgca tctcttagta  21420

gagaagattt attcctatgg gtggctgtag atgaagggca gattgtaggt tttctgtggg  21480

ccggctatca tgagttagcc ccttggacac ctgtaagagt tgcatctgac attctctttt  21540

atattgtacc agagaagcga gggacactgc tcggtatgcg cctcatcaaa gccttgaagc  21600

aatgggctaa tgatagtggg tgttccgagg tccgcctgtc tatcgcttct ggtattaatg  21660

aagaacgtgt cggacgtatg tataagcgac ttggctttga acagtttggc actgtgtata  21720

acctgaagtt ctaaggagat cacatgggta ttgtaaagaa agcatttaag gctgtcggtc  21780

ttgctcaaga tgcaccgcgt attgaagcca aggttcctgc tcagcagctt gagcgtaagc  21840

ctgagactga agctgaagat atacagattg gtgcaggtgg tgatgatgcg actgcatctg  21900

caaaaggtaa gcgcgggctt gtccgtccgg tagcttctag cttgaaggtg taatatgaaa  21960

cagagcacag atttggagta tggaggtaag cggtctaaga tacctaagct atgggagaag  22020

ttctccacta aacgtagctc tttccttgat agggcgaagc attactccaa attaaccttg  22080

ccctatctga tgaatgacaa aggtgataac gagacttcgc agaacggatg gcaaggtgta  22140

ggtgctcagg caactaacca cctagccaac aagctagcgc aagtgctatt ccctgcacag  22200

cgctccttct tccgtgtaga cctaactgca caaggtgaga aggttcttaa tcagcgtggc  22260

ctgaagaaga cagagctagc tactatcttt gctcaagtgg aaacacgggc aatgaaagag  22320

ttagagcaac gtcaattccg gcctgctgta gtagaagcat tcaagcatct tattgttgct  22380

ggtagctgta tgctatacaa gccaagcaaa ggtgcaatca gtgcaatccc aatgcatcac  22440

tatgtagtta atcgtgacac taatggcgac ctgttagaca ttatcttact gcaagaaaaa  22500

tccttgcgta catttgaccc tgctacacgt gctgtagtag aggttggctt gaaaggtaag  22560

aaatgcaagg aagatgacag cattaagctg tacacacatg ctaagtatct tggtgagggt  22620

ttttgggaac tcaagcaatc tgctgatgat atccctgttg gtaaggtaag taaaatcaaa  22680

tcagaaaagc taccatttat cccgctaact tggaagcgaa gctatggtga ggattggggt  22740

cgtcctttag cagaggatta ctccggtgat ttattcgtta tccaattctt atctgaagca  22800

gttgcccgtg gtgctgcact gatggcagac attaagtacc tgattcgtcc gggtgctcag  22860

actgatgttg accactttgt taactctggc actggtgagg ttgtcactgg tgtagaagaa  22920

gatatccata ttgtacagtt aggtaagtac gcagacctca cacctattag cgcggttcta  22980

gaggtataca ctcgccgtat cggtgtagtc ttcatgatgg agacaatgac acgtcgtgac  23040

gctgaacgtg ttactgctgt agaaatccag cgagatgcgt tagaaattga gcagaacatg  23100

ggtggtgtat attccctctt tgctactact atgcaatcgc cagtagcgat gtggggtctg  23160

ctggaggcag gagactcctt cactagtgac ctagtggacc ctgtgattat cacaggtatt  23220

gaagctttag gacgcatggc tgagttggat aaactggcaa actttgctca gtacatgtca  23280

ctgccattac aatggcctga gcctgtacta gctgctgtga aatggcctga ctatatggat  23340

tgggtacgag gtcaaatctc tgctgaactg ccgttcctta aatcggctga agagatggaa  23400

caagaacagg aagcacagat gcaagcacag caagcacaga tgcttgaaga aggtgtggct  23460

aaggccgtgc cgggtgtaat tcaacaagaa cttaaggagg cgtaatgtct ttctcattta  23520

ctgaaccgtc aaccactcat cctactgctg aagaaaatcc ggtagaaacc aaggaggtaa  23580
```

-continued

```
caactgatgc tgctactact gatgttcctg ctgatgctgg cactgctgta caagatgaca  23640
atgctggtgc acaatctact gaagacgccg gaggagaagc ttctggacag ccttcagaag  23700
aaggagacaa tggcggagag aatggtgaat ctaagccaga tgataccgcg accgacactg  23760
aggaagtgca gtacttcttc ggagaatatg aagtaacagt agatatacca caggatgtta  23820
cggatagcct taaagagaag ggtattgatg ctaagcaggt tgccaaggaa ctctatgcca  23880
aagatggcaa gtttgagctg tctgatgcaa ccaagcagaa attgtatgat gcttttggca  23940
agtttgcggt agatgcttac ctgtcaggtc ttaaggctca aaatgaagcc ttcttcctga  24000
aagaagccaa cgcagctaaa gagttggaag cagctaatac ccaacgcttc tctgatgttt  24060
ctaaggaaat tggtggagaa gaaggttggt cccgtcttga ggcgtgggcg cttgaaacgc  24120
tatccaatga cgaactcacg gcattcaatg cggtgatgga gtctggcaac caatacctcc  24180
agcaatatgc tgtgcgtgaa ctagaaagcc gccgtaaagc tgcacagggt gatgacaagc  24240
caaacttgat tgagccatct gcacctgctg ccgcatctga ggataatgga cctctgtctc  24300
gcgagcagta tctccgtgag atgatgacgc tgggttcccg cttcggtaca gacaagaaag  24360
ctgctgctga gtatcaggct aagctggatg ctcgccgccg tgcgggtatg gctcgcggac  24420
tttaatcagt atttactgga cactatagaa gggagaaatg tctccctaaa ttatcaattt  24480
gatttataag gaggtttatt aatgtctacg ccgaataacc tgaccaacgt tgcagtttcc  24540
gcttccggtg aggtagacag ccttctcatt gagaaattca atggtaaggt aaatgagcag  24600
tacctgaaag gtgagaatat catgtcttac ttcgatgttc agactgtaac tggtactaac  24660
actgtaagca acaagtactt gggtgaaacc gagttgcagg ttctagcacc gggccagtct  24720
ccggctgcaa cctccactca ggccgataaa aaccagctgg taattgatgc cactgttatc  24780
gcgcgtaaca ccgttgcaca cctgcatgat gtacagggtg atattgacag cctgaaaccg  24840
aagctggcta ccaaccaagc taagcagctt aagaagatgg aagacgagat gcttattcag  24900
cagatgctgc tgggcggtat tgccaacact caggccaagc gcacaaatcc tcgtgtgaaa  24960
ggtcatggct tctctgtaaa cgtagaggtc aatgaaggag aagcactggt taacccacag  25020
tatgtaatgg cagctgtaga gtttgctctg gagcagcagc ttgagcagga agttgatatc  25080
tctgatgtag ctattctgat gccatggcgt tacttcaacg tactgcgtga cgcagaccgt  25140
attgttgata agagctacac gattagccag tccggtgcta ctatccaggg cttcgtactg  25200
tcttcctaca attgtccggt gatcccgtct aaccgcttcc ctaaatattc tcaggggcag  25260
aaacatcacc ttttgtctaa cgaagataac ggctatcgtt atgacccgat tgcagaaatg  25320
aacggtgcta tcgctgttct gttcactgct gatgcattgc tggttggtcg ctctatcgac  25380
gtaattggtg atatcttcta tgagaagaaa gagaagacct actacatcga caccttcatg  25440
tcagaaggtg caatccctga ccgttgggag gctgtgtcgg ttgttactac caagcgtcaa  25500
agcactggag cagttgactc tggtaatgct gcacagcaca ctcaggttct gaaccgtgca  25560
cagcgcaaag ctgtctacgt taagaatgct gcccctgcag gtgctttcgc tgctgctagc  25620
ttgtctgctg aagacttggt tgctgctgta cgtgcagtga tggctaatga cattaagccg  25680
actgcaatga aacctactga gtaataccta tgccctatct accttgcgta ggtagggttc  25740
tttttgttag gaggattcat gcctgtaatt agacaaacca gtaaagtagg acatatgatg  25800
gaagatgtgg ccttccagat tattgatagt aagctggaag cggtaaactt gtgtatgcga  25860
gctattggtc gtgagggtgt ggattctctc gactcaggtg acttggacgc agaagatgca  25920
agcaagatga tcgacatcgt atcccagcga ttccagtaca acaaaggagg tggctggtgg  25980
```

```
ttcaatcgtg aaccaaactg gcagattgca cctgatacca atggtgaagt caatctacct  26040
aacaactgcc tagcagtatt gcagtgttat gctttgggtg agaagaaagt acccatgact  26100
atgcgagcag gtaagctcta ctctacatgg agtcatacct ttgatatgcg taagcatgtg  26160
aatgctaatg gtatgattcg tcttacctta cttaccttac ttccatatga gcatctacct  26220
actagtgtaa tgcaggctat tgcctatcaa gctgctgtag agtttattgt gtctaaggat  26280
gcagatcaga ctaagctagc cactgcacag cagattgcca ctcagcttct aatggatgtg  26340
caatcagaac aaatgtcaca aaagcgattg aatatgcttg tacataatcc tacgcagcgt  26400
cagttcggta ttatggcagg tggttctcag aatgtacctg cttactctca ttcaccatat  26460
gacagttggg cacttcgtcc gtgggaggat cgttaatgga agtacaaggt tcattaggga  26520
ggcaaatcca agggattagc cagcaacctc cagcggtacg tcttgatggt caatgtacga  26580
ctatggtgaa catggtccct gatgtagtga atggaactca atcccgcatg ggtacaactc  26640
acattgctaa gctcttggat gaaggtacag ataatatggc aacgcaccat tatcgcaggg  26700
gtgaggggga tgaagagtat ttcttcacct taaagaaggg gcaagtgcca gagatatttg  26760
ataagcatgg acgcaagtgc aatgtcatct ctcaagatgc acctatgacc tacctttctg  26820
aagttgttaa ccctagggaa gatgtgcaat tcatgactat agctgatgtt acttttatgc  26880
ttaaccgtag gaaagtggtt aaagttagta ataggaagtc acctaaagtt ggagataaag  26940
ccattgtgtt ttgtgcatat ggtcaatacg gtacatctta ttctatcata attaatggaa  27000
ctacagctgc tagttttaaa acaccagatg gggaagtgc agaacatgtt gaacaaatac  27060
gaacggaacg tatcacttct gaattgtact ccaagttgca gcaatggagt ggtgtgaatg  27120
actatgaaat acaaagagat ggtacgagca tatttataga gagacgcgat ggtaaaagtt  27180
tcacagtaac aactaccgat ggtgcaaaag gtaaggactt agtggctatc aagaataaag  27240
ttagctctac tgacctactc ccttctcgtg cgcctgctgg ttataaagta caagtgtggc  27300
ctactggcag caaacctgag tctcgttact ggctgcaagc tgagcctaaa gagggaaacc  27360
ttgtgtcttg gaaagaaaca atagctgctg atgtattact tgggtttgat aaaggcacaa  27420
tgccttacat tattgaacgt acaggtatca tcgacggcat agctcaattc aagataagac  27480
aaggtgattg ggaagatcgt aaagtagggg atgacttgac taaccctatg ccctctttta  27540
ttgatgagga agtaccccag acaataggtg gaatgttcat ggtgcagaac cgcctatgct  27600
ttacagcagg tgaagcggtt attgcttctc gtacatcata cttcttcgat ttctttcgtt  27660
atacggttat ctctgcattg gcaactgacc catttgatat tttctcagat gcgagtgaag  27720
tctaccagct aaaacatgca gtgaccttag atggcgctac cgtattgttc tctgataagt  27780
cacaattcat actgccagga gataagcctt tagagaagtc aaatgcattg cttaagcctg  27840
ttacaacatt tgaagtgaac aataaagtga agccagtagt aactggtgaa tcggtaatgt  27900
ttgccactaa tgatggttct tactctggtg tacgagagtt ctatacggac tcttatagtg  27960
acactaagaa ggcacaagca atcacaagtc atgtgaataa actcatcgaa ggtaacatta  28020
ccaacatggc agcaagcacc aatgtcaata ggctacttgt cactactgat aagtatcgta  28080
acataattta ctgctatgat tggttatggc aaggtacaga ccgtgtacaa tcagcatggc  28140
atgtatggga gtggcctatg ggtacaaagg tgcgaggtat gttttattct ggtgaattac  28200
tttatctact ccttgagcga ggcgatggcg tctatctgga gaagatggac atgggtgatg  28260
cactaaccta tggtttgaat gaccgcatca gaatggatag gcaagcagag ttgatcttca  28320
```

```
agcattttaa agcagaagat gaatggatat ctgaaccact tccttggact cctactaacc  28380
cagaactttt ggattgcatc ttaatagaag ggtgggattc atatattgga ggttctttcc  28440
tgttcaaata taaacctagt gataacacct tgtctacaac ctttgacatg catgatgata  28500
accacgtaaa agcgaaggtt attgttggtc agatttaccc tcaagagttt gaacctacac  28560
ctgtagttat cagagatagg caagaccgtg tatcctatat tgatgtacct gttgtggggt  28620
tggttcacct taatcttgat atgtatcctg atttctccgt ggaagttaag aatgtgaaga  28680
gtggtaaagt acgcagggtg ctagcgtcaa accgtatagg tggtgctctc aacaacacag  28740
taggttatgt tgaaccaagg gagggtgtct tcagattccc actgagggct aagagtacgg  28800
atgctgttta tcgtattatt gtagaatcac ctcatacatt ccagcttcgc gatattgagt  28860
gggaagggag ctacaatcca accaaaagga gggtctaatg gctataggtt cagccgttat  28920
ggctggtatg tcttctattg gtagcatgtt tgcaggcagt ggtgcagcag ccgctgctgg  28980
aggtgctgcc gcaggtggcg gaggtttgct aggttcacta ggtggattcc taagtggctc  29040
cactgctggt ttctctaatg ctggccttct tggtgctggc cttcaagggt taggcttgat  29100
tggtgatcta tttggtggaa gtgatgaagc caaggcgatg aagaaagcac aagaagagca  29160
atggcggcag cagcttattg ctacacaaga ggcgtacaag acagtggcag acgcagaacg  29220
ttctgctgct aaacaatatc atgcagatgc aatcagtaat caggcttcac tgctacagca  29280
gcgagcacag gttgcattac ttgctggggc tactggtact ggtggtaatt ctgtgtcctc  29340
tatgcttaat gacttagcag cagatggcgg caggaaccag agtaccatca ttgataacta  29400
tgagaatcag aagattaatt tcaccaacca acttaagtct atccaacgtg gtggtcagat  29460
gcagatgcgt gagtttaaga agccttctgc tatgagtacc ttggttcaag gtattccaag  29520
tctggcatct gcctatgtaa ctggtagtaa gtctggcaag gcattgggta aagccttaac  29580
tgattctcgt acatattcat ctggaacaag aggtatttaa tggcaattga gcgacaagca  29640
gtacaaggtc tgccacaagt gcaggccact tctcctaatg tcatgacctt tgcacctcaa  29700
caagtgggag gtgtggaggc tggcgtggct tctacctccg gtagtaggtt tatcgaagac  29760
cttattcgtg cagccagcag tgtggctgat gttaccactg gtatccttaa tcagaagatt  29820
gaggaagata aggttgttca aatggaacgg gcatataacg gactaatgcc ttctgaggat  29880
gcaactcgtg gtggcgctcg tgctaacatg cttgtcaaag ctcaactgct agctaatgat  29940
gaagcagcac gaatgaaaga catggctact cgtttccaag ggacggatga cgagtggaca  30000
caacttatgg ttgactctcg taatgagatg cagaataagc tgttccagca ataccctgag  30060
ttgcaaggtg acaaagatac tatgcgtatg gtcactaatg tcttccaaga acagcagcct  30120
cagatttggg ctacacgaac ccagcataaa cttgaccgtg aacaagcaga ccgggaggat  30180
acctttgacg ggcgagtggc ttctacttgg gatcctaata ttgaccctga agcatctggc  30240
tatgctttac aggaacgaat ccgcgaaggt cttactcaag gattactacc tgaacagatg  30300
cacaagaagt tagtccagcg agcaatttca cttgcacaag gcggtgatgt tagcatggct  30360
gaagccctga agtatgtgaa ggacgataag ggtgtttctg tttatgctaa gaatccacag  30420
cttatcacag ccatcactag tggtaatgca gtttgggcta ggaataatgt agctgatgta  30480
actcgtatgt ctttcgaagt taaagaatca taccttgcag gtgatttaac tgatgaagaa  30540
ttgttggaac gagcacagca cattaataat ctgacaggta actctgtctt ctctaatcca  30600
gaactagagg cactgatgcg ccaacgggct aagcagaatg cagagctagg tgcaatgcag  30660
gatatgcgac gtgagcttta ctccgaccgc ctgactggct tccaaggtaa gactgataaa  30720
```

gagaagaagg cttacattga tgttatcaaa caggatagcc aactttatgc agaccagcaa 30780
atcaaacaac gtggcttgga cccttacagt caagaggctg aagctattcg tggtgcagtg 30840
gaagtgcagc gcctgcaatt catgaactcc aaaggtttag tggatgatac ctttgaatct 30900
cgtatcaagg ctatggaatc catgctatca cctgagcact ttgctaaagg tgaaccacag 30960
gagttaatga ccattcgtca gttgtgggag cagttacctg aagaaagtcg aggtgtcttc 31020
ggtgacactg tgaacggtta tatggataac tacaatactg cattacaaat gggagagaca 31080
cctttgcagg ctgcaaggtt tgcccgtgaa gcacagcaga aattctctcg tactgagaag 31140
gaaaccaaga agttcaactc cgctattgga gatgcactgg atgaggtatc tggtgctggc 31200
tggtttgatg gtaaaaccga ggtgtcagac ttaggtaaag ctattgcgga agaagagtta 31260
cgagctaagg ccaatatgtt gtggtctagc ggtatgcgta acatggattc tatcaagaag 31320
gctttaatca cttggggcaa taaacgctac actcaatcag aggatgcaaa gacttccggt 31380
ggctatttca ttaaaggtga ttacacttct gcatctgata tgcttatgtc agttgggaaa 31440
ggtgtaaacc ctaccgatgt ccctctggcg cttggtaggt atgtagaaac acagatgcca 31500
gaattgaaga aggagcttca agagtgggaa actaaggatg atgtgtacat tgattacaat 31560
gaacagaaag gaacttttgt gattcgtgct ggtgcagcag gtcgccctct ttctggagta 31620
atccctgtaa cttctttgga taccacttca ctactggatt ctgcctatca gaagaaagta 31680
gaagaacgag ataaaggcga gtatgttcat ccctatcgta cagatatcgg tgcacaagaa 31740
ccaatgccag ctaagccaac tgccaaagat attggtaaat taggattagc taacttcctc 31800
atgtcttctg cttttgcttc tggtgagaat ctaccttcta acttcgagat taactatcga 31860
ggcaatatgc aacaattcta tgacaagcta gctatggatg agaataaaga taaagttggc 31920
tttaataagg caactggaac ctttactcca tataaagacg ctcacggtga gtctatcggt 31980
tacggtcatt tcttaacgga agaagagaag cgagacgggt atattaagat tggcgatgaa 32040
ctagttccct atcgagggtc tatgtctcag cttacagaga gtaaggctcg cgctcttatg 32100
gagcaagatg ctaggaagca tgtgcctcct actcgtgact ggaagattcc gtttgaccag 32160
atgcatcctg cacagcaacg tggcttgatg gatttaacct acaatttagg taaaggtgga 32220
atccagaact caccgcgtgc tcttgctgca ttcaaagctg gtaagcttac ggaaggcttt 32280
atcgaaatgc tgggtactgc atcaagtgaa ggtaaacgta ttccgggcct actgaagcga 32340
cgcgctgagg catacaatat ggcagctgct ggtggtgtac ctaagatcac agaagtggag 32400
acgagggaag atggctctat gtgggttaag tttggtggac ctatgccagc aggctctgtt 32460
tctgcgtgga cgcataaacg tattggagcc gatggctggt atcaggttta tgaggctgca 32520
cctaccaagt tagctaaaga ctctaaggta ggtaaagtta aattgtagta cctaactcaa 32580
ggcttgtctc acatgtgaga caggtcttta tgataggcac tatggaggaa ctatggaaca 32640
agatattaag actaattggg ctggatatgt ccagtctact cctgagccgt tttctattga 32700
ggcggctccg gtatcggctc ctacgatacg ccagcgtaat gagttacaag agcaagttct 32760
tgaagccaaa gctgatgcgg acatcttagg tgctgtaggt gctgccttcc agaatgaatg 32820
gttggcattc ggaggtaagc gatggtatga ccgtgccact gctgatttca caccccaacc 32880
tgactttgaa atccaaccag agcaacgtga agcactacgt ttcaaatatg gtacggatat 32940
gatgcagaca atcactgagg gtgttcgttc tgaggatgaa ttgaacttcc gtattcagaa 33000
tgctgatgaa gaccttgagc gcaataagcg cattgctcag gctggatggg ccggctctgt 33060

```
ggcaacgatt ggcgctgctg tgcttgaccc agtgggttgg gttgcctcta ttccaaccgg  33120
tggtgcagct aaagttggac tcgtaggccg tgctgtgcgt ggcgctatcg ccgctggcgt  33180
gagtaatgcc gctattgaat ccgtattggt ccaaggtgac atgactcgtg atttagatga  33240
cattatggta gcactaggtt ccggtatggc tatgggtggc gttattggag ctgtagcgcg  33300
tggtagggcc actaagctca gtgagcaagg ggatgacagg gctgcgagca ttgtgcgcag  33360
tgcagacgca ggggaccgct atgtgcgtgc tgttgctgat gacagtatcg gtgcgatgcg  33420
tgttaagggc gaagaggtac tcactgaggg tgcatttgat atctctagca aaggtgaaga  33480
tttgctgaaa accctacagc gggaaggtaa tgcaattgat atgacacctc gccgctgggc  33540
cggaactatg tctgcccttg ggactgtcgt gcactcctct caggatgcta gtgttcgtgg  33600
cctcggtgct cgcctgtttg agtctccgca aggtttaggt atgcaaaagg catctgccag  33660
tcttatgcag aataccaact tgaatcgact gaagtctgct gatatgaacc gtttcaatga  33720
cgggtttgac ttatggctca aagaaaataa tatcaatcca gttgcaggcc atactaactc  33780
tcactatgtg cagcaatata atgagaaggt atgggaagct gtacgcatcg gtatggatga  33840
ggctacgcct aagtctatcc gtatggcagc agaggggcag caagctatgt atcgtgaagc  33900
attagcatta cgtcaacgct ctggtgaagc tgggtttgaa aaggttaaag cagatgataa  33960
gtacatgcct gatatttttg acagtatgaa ggctcgtcgt caattcggta tgcacgataa  34020
agaagatatc attgagttat tctctcgtgc ttatcagaac ggcgctcgta aaattccaaa  34080
agaagtagcg gatgaaattg cacgagcaca agtaaaccgt gttgtggatg ccactctgac  34140
aggacgtatg agtttcgaaa aggctatgtc tggtcagact aaagcagagt atgaagcaat  34200
aatgcgcaag gcaggcttca gtgatgaaga aattgaaaag atggtagaag ctctggataa  34260
taaagaaacc aaagataata tctctaaccg agctaagatg agtttaggct tagatgttac  34320
tcaagagtac aatggcattc gtatgcgtga ctttatgaat actaacgtgg aagagttaac  34380
agataactac atgaaggaag cggcaggtgg tgctgccttg gctcgtcaag gtttctctac  34440
ctatcaggct gcacttaatg caattgacct tgtagagcga aatgcacgaa atgcagctaa  34500
agatacaaaa gcacacgcac aatttgaagc ggagtctgct aagattcgtc aatcagagcc  34560
tgattacaag aaggcacaag agaagattga agagctaaag aagcgactta aattgaaaga  34620
gaaagatgaa gcagcaggtc tggctattga tgaagaaatc cgtcagatgc gagaagggct  34680
tcgcttgatt atgggtaaat ctatcgatgc agacccacag gctttgtcta ctaaaatgct  34740
gcgtcgtggt cgtgacatca caggcgtact tcgcttaggt cagatgggtt tcgcacagct  34800
aggtgaactt gctaacttca tgggtgagtt tggtattgct gcaaccacta tagctttagg  34860
taagcaattc cgctttacat ctaaggcttt gcggagcggt gatggcttct tccgagataa  34920
gaacttggca gaagtagaga ggatggtagg ttacattggt gaggataact ggctaacaac  34980
caagggtgca cgtccagatg agtttggtga tgtaaccaca gtaaaaggaa tgatggctca  35040
ctttgaccaa tccatgaact caatacgtcg tgctcaaacc aacctatcac tcttccgcat  35100
ggcacagggt tctctggagc gaatgaccaa taggcaaata gctttgtctt tcattgacca  35160
ccttgaaggc aagaagatta ttcctcagaa gaaactggag gaacttggtc ttactcagga  35220
gttcatgact aacctacaga agcactatga tgctaactct aaaggttctg gcttgcttgg  35280
ctttgataca atgccttatg ccatgggtga aactttagct aatgctattc gtcgtaagtc  35340
aggtctaatt atccaacgta acttcattgg tgatgaaggt atctggatga acaaagcact  35400
aggtaagaca tttgcacagc ttaagtcatt ctctcttgta tctggtgaga agcaatttgg  35460
```

```
tcgagggatt cgccacgata aaattggtct tgctaagaag acagcttacg ggtttgcttt  35520
gggttcaata gtgtatgcgg caaaagccta tgtgaactct attgggcgag aagaccaaga  35580
tgaatatttg gaagagaagt tatcgcctaa agggttggcc tttggtgcaa tgggtatgat  35640
gagtacaact gctgtattta gtctaggtgg agatttctta ggtggcctag gtgttctacc  35700
ttctgagtta gtacaatccc gttatgaggc tggctttcag actaaaggtt tgatagacca  35760
aataccacta gtaggtgttg gtcaagatgc atatcgttta gcagattcta taactaaata  35820
tgcagagggt gatacagaag gtgtagatgt ggcacgtagg gctttacgct tagtgcctct  35880
aactaatgta ataggaatcc agaacgcatt gcgttatggc ttagatgaac tggaggattg  35940
atgagttata ctttcacaga acatatagcc aacggtacgc aagtaaccta tccctttagc  36000
tttgctggca gggataaagg ctatcttcgt gcctcagatg tgatagtgga atctcttcaa  36060
ggtaacactt ggattgagat tacatctggc tggcaattaa ctggtacgca tcaaatcact  36120
tttgatgtag cacccgttgc aggtttgaag ttccgtattc gaagggaagt acaaaaggaa  36180
tatccatacg ctgagtttga ccgtggtgtt accttggata tgaagtcttt aaatggttct  36240
ttcattcata tactggagat tacacaggag ttacttgatg ggttttatcc agaaggatac  36300
ttcattaagc agaatgtaag ctggggcggc aataagatta ctgacctagc tgatggtgag  36360
aatccaaaag atgcagtaaa taaatcacag ctagatgcta tcgacaagaa gcatactgat  36420
tggaactctg cacaagatat agagattgct ggtattaaga gagggatggt gtctggtgtg  36480
tcgcatcgaa ctattccttg gtatatggtt gcctccggtg gagagcaaat cattcgacca  36540
ccttactcat ttgatgatgc tatggtgttt ataaacggtg tattccagca tgaactagca  36600
ggtgcagtat ccgtggggta tgatgttata accctgtcca agccattaca ggctggggat  36660
gaagtttatg tgcttatcgg tagtcgctta accccaccta caagtgcgga tactatcctc  36720
tttacacaag cagtgagtga aggcacacaa tctatcgaca ttgtaacggc tttccaacgt  36780
cttgatgtat acttggatgg cctgtatcaa cctaataatg cttatgaaat cgtagggtct  36840
actatcactt tcagtgagcc attacctgag tgtgtcgtaa gtatgaagct acaactagtg  36900
taaggaggtg agatgattaa ctccgaactg gtagatagtg gtgtgaagct tgcgccacct  36960
gcattagtct caggtgggta cttcctcggt atcagttggg ataattgggt gttaatagca  37020
acattcattt ataccgtgtt gcaaattgga gactggtttt ataccaagat taaactatgg  37080
aggaagaacc gtgagcgtcc acaataaaca tgcagctaca gaagatgagg ttggcatcct  37140
gcatggtgct attaccaaaa tctttaataa gaaagcacag gcaatactgg acactataga  37200
agaagaccca gatgcagcac tgcatttagt ctctggtaaa gacattggag ctatgtgtaa  37260
gtgggttctt gataatggta ttaccgctac acctgctgca cagcaggagg agtccaagct  37320
atctaagcgc ctcaaggcta tccgagaggc atcaagtggc aagattattc aattcactaa  37380
ggaggattga tggctaaggc aagagaatca caagcggagg ctcttgccag atgggagatg  37440
ctacaggagt tacagcagac ctttccttac acagcggaag gtttgcttct ctttgcagac  37500
acagttattc ataacttaat tgcaggcaac cctcatctga ttcgtatgca ggctgatatc  37560
ttgaagttcc tattctacgg acacaagtat cgcctcatcg aagcgcctcg tggtatcgct  37620
aagacaacac tatcagcaat ctatacagta ttccgtatca ttcatgaacc gcataagcgt  37680
atcatggttg tatcccaaaa cgccaagcga gcagaggaaa tcgcaggttg ggtagttaaa  37740
atcttccgtg gcctagactt tcttgagttt atgctaccgg acatctacgc aggggaccgt  37800
```

```
gcctcagtta aggcatttga gattcattac accctacgtg gcagtgacaa gtcgccttct  37860
gtgtcttgtt actcaatcga agcaggtatg cagggtgcgc gtgcagatat catcctagca  37920
gatgacgttg agtcaatgca gaatgctcgt acagcggcag gacgtgcctt gcttgaggaa  37980
ctgaccaagg agtttgaatc tattaaccag tttggtgata ttatctacct tggtactcct  38040
cagaacgtaa actctatcta caataaccta cctgctcgtg gttactctgt tcgtatctgg  38100
actgcacgtt atccctcagt ggagcaggag caatgctatg gtgacttcct tgcacctatg  38160
attgtgcagg atatgaagga caacccagca cttcgctcag ggtatggctt ggatggcaat  38220
agtggtgccc cttgtgcacc tgaaatgtat gatgatgatg tgctgattga gaaggaaatc  38280
tcgcagggtg cggctaagtt ccagcttcag ttcatgctta acactcgcat gatggatgct  38340
gaccgctatc cgctacgcct gaacaacctc atcttcactt cattcggtac agaggaagtc  38400
cctgtgatgc ctacgtggag caatgattcc atcaatatta ttggcgatgc accgaagtat  38460
ggcaataagc ctacagactt catgtatcga cctgtggctc gcccgtatga atggggcgct  38520
gtcactcgta agattatgta tattgaccct gctggtaaac acctctgcca gcgtaaaacc  38580
ctcttaattc ggtggaactc tcactgagac aataccgagc gaagcctgtt gcaataacag  38640
gaacgtgtag agactaactg taaggccaag cggtctgaaa cagagggagg cgcaagccta  38700
agatatagtc cgacctacta ggtgactagt agaagttaaa gtagcgaatt aacgtaacaa  38760
ttgaagggag ttaaatatga cagagcataa agtttatcat attcgtgttg ttggtgaaac  38820
tgatgtaatg caaggttata ttggtgtaac ctccgatatt aagaagcgta tgagagagca  38880
caagtgtgca ggccgtcttt gtgatggccg cgagtacgtt atcttattca ctggtagcaa  38940
agaagagtgt tatgcactag aagagaagct acgcccacat gacaacatgg gttggaataa  39000
gggtaaaggt ggttatcgca aagcaggtaa catcgagaaa ggtgaacgca taagtattgc  39060
cactgaaatc aagaaaggac agcacttgtc tgttgccact gagttcaaga aaggcatgac  39120
accttacaac aaaggtactg gcaaagatta catattcact tctccagatg gtgaagagtt  39180
tcttgtaact tgcattactg acttctgtaa agagcacaac ctaacacctc agaatatgcg  39240
taaggtggca cgtggtttac gtaaacacca caagggttgg ctcgcacgtc acgttcaaac  39300
cgggaggtaa gaatggggat gaaacgggtg tggctatcgt cttcctgcac ggcacattca  39360
tttatgtgta tcagtgcttt ggtgtgccgg gaggataccg cgaatcgtcc ctgaatcgca  39420
ttgtgcaggc cgcaaagcag gcaggtgtta aagaggtatt cattgaaaag aactttggtc  39480
atggcgcgtt tgaggccgtt ataaagccat actttgaacg agagtggcct gtgactctgg  39540
aggaagatta cgccaccgga cagaaagagt tgcgtatcat tgaaacacta gagccactaa  39600
tggcggccca caggctcatc ttcaacgcag agatggtcaa gtctgatttt gagtcggtac  39660
agcactatcc gcttgagcta cgcatgtcat acagcctttt caatcaaatg tcgaacatca  39720
cgattgagaa gaacagccta cgacacgatg accgcttaga cgctctgtat ggcgctatac  39780
ggcaattaac ttctcagata gactatgacg aggttacacg gattaatcgc ctcagagcgc  39840
aggagatgcg cgattacatc catgctatga acacacctca cctccgtagg gcaatgctct  39900
atggagatta tggcactgag cgaagagtaa ccaacacttc cgtggctatg cagcaaagag  39960
tatacggtca gaattacagg agtaaatcgg caagcagaaa tacactttct gcaaggattt  40020
caaggactta ttaattaccg gacactatag aaggaaggcc cagataataa gagaaataac  40080
aaggataata taggttaacc taggttatat aggtattcct tagtatgggt gtactcctgt  40140
acaccctatt ccttacttcc ttactatact tacataatag gagagagaga gagagagaat  40200
```

```
gtctaatagt tatagtacac aacctcttac aggtaagtct gctcgtaagc agatacaacc  40260
tgttagtgaa gcccttatgc ttcctgtagt ttacgaggac actgttgaga agaaaggtga  40320
tgttattaat gatgccacca aatcaggtaa gcagaaaggg gccatggtgt gtcttgatac  40380
acatgataac ctggttattg ctatcgcagt tgatggcaaa gaagattcca attggttgac  40440
agctaataaa gcggtcacta ctattacccc agcttaagag gagagttaca tgtctaaata  40500
tggaaccgca ggtactgtta ctggtcaggc ttttcgagta aaaactgtac aaaccactgc  40560
aacggcaatc cctttgccta ttgttgctga agcagacctt aagaagaaag atcatcctat  40620
caacattaaa cacctctctg gtaaacagaa aggtgccatg gttgctgtag agaaaacaga  40680
ccaatccttg tacatcgcta ttgcacgtgg gagtgaaccc accgacaagt gggatgcaac  40740
tactatggag ttggaccctg taacacctgc ggcttaattg taaagacgag gtcaatagtg  40800
cttaacaaac acttcaagcg ccgtgagttc gcttgccgtt gtgggtgcgg tacatccaca  40860
gtagatgctg agttactaca ggtagtcaca gatgtacgtg agcactttgg tgctcctgta  40920
gttattactt ctggacaccg ctgtgctaag cacaatgcta atgtgggagg tgctaagaac  40980
tccatgcatc ttactggtaa ggctgctgac attaaggtac aaggtattac accttaccgt  41040
gtatggtcct atctaacagc acgctacccc aataaatatg gcattgggtc ttatcctaat  41100
ttcacccaca ttgatgtaag agagggatgt gcacgatggt aagatgtatt gaatggtgcg  41160
agcgcatggt tgctcaagct gccgaggatg gcaactatga tgactggaag aactactctg  41220
acttgttagc tcaatggaaa gggagatgca atgaaaaagc tgtttaagtc taagaaagtg  41280
gtaggtgcac tggttgcact agtgattgct cttgtttctg taggtcttgg cgtagaccta  41340
ggtgaaggtg cggaaggttc cgtcactgac gtggtatgcc aagtaatcac ctgtgaataa  41400
ggtgctagag gtggtagcag gtcttattgg cctgctgctt gccgctaaga agaagaagga  41460
agagaaggag gcacaaagtg aggcgaatca tgctagcgac aatcctgctg attggttcac  41520
tgatcacttc agggtgtcag acggcgttac cagagaatcc aaaggtgaag cctctgaagc  41580
cgacgcttac ggcagtctac gaggtggacg ataaagtctg cttcagtaag cctgacgcta  41640
caaaattagg tctgtacatt ctctcgctag aacgcgggta taattaatac atagttttat  41700
gtatcagtgt cttacgattt actggacact atagaagaga taagatagtg ccgttctttt  41760
gagcggccta ttactagcca atcttcatag ggagggttgg gaagtaatag gagagtatat  41820
ggctaagtta actaaaccca agacaacggg cttactacat agagatactg tactagctac  41880
cttattagat aatttactat ctaaaaggcg tgttacattt gaaggtgtag ttccaagtga  41940
agatactaaa attgagatag aagtacctac agcatgggat ttagattctt cgtgggcatc  42000
acttgtatca ttaagtacac ctacactttg tacagcttgg attactaaag tgtcagatac  42060
tagattagaa gtacatgtgt tccatacagc acaagttgaa atagacatag atgtagatgt  42120
ttacattcta ggtaaacaca ttgtcagtgc gtaagcactg cttttcgcgc aacttttctt  42180
aaaggttatc atgatggtag cctttcagaa aaggaggtta catgattcaa agactaggtt  42240
cttcattagt taaattcaag agtaaaatag caggtgcaat ctggcgtaac ttggatgaca  42300
agctcaccga ggttgtatcg cttaaagatt ttggagccaa aggtgatggt aagacaaacg  42360
accaagatgc agtaaatgca gcgatggctt caggtaagag aattgacggt gctggtgcta  42420
cttacaaagt atcatcttta cctgatatgg agcgattcta taacacccgc ttcgtatggg  42480
aacgtttagc aggtcaacct ctttactatg tgagtaaagg ttttatcaat ggtgaactct  42540
```

-continued

```
ataaaatcac ggataaccct tattacaatg cttggcctca agacaaagcg tttgtatatg  42600
agaacgtgat atatgcacct tacatgggta gcgaccgtca tggtgttagt cgtctgcatg  42660
tatcatgggt taagtctggt gacgatggtc aaacatggtc tactccagag tggttaactg  42720
atatgcatcc agattaccct acagtgaact atcattgtat gagtatgggt gtatgtcgca  42780
accgtctgtt tgccatgatt gaaacacgta ctttagccaa gaacgaacta accaattgtg  42840
cattgtggga tcgccctatg tctcgtagtc tgcatcttac tggtggtatc actaaggctg  42900
caaatcagag atatgcaaca atccatgtac ctgatcacgg actcttcgtt ggtgattttg  42960
ttaacttctc taactctgcg gtaacaggtg tatctggtga tatgaaggtt gcaacagtaa  43020
tagataagga caacttcacg gttcttacac ctaaccagca gacttcagat ttgaataacg  43080
ctggaaagaa ttggcacatg ggtacttctt tccataagtc tccgtggcgt aagacagatc  43140
ttggtctaat ccctcgtgtc acagaggtgc atagctttgc tactattgat aacaatggct  43200
ttgttatggg ctatcatcaa ggtgatgtag ctccacgaga agttgggctt ttctacttcc  43260
ctgatgcttt caatagccca tctaattatg ttcgtcgtca gataccatct gagtatgaac  43320
cagatgcggc agagccatgc atcaagtact atgacggtgt attatacctt atcactcgtg  43380
gtactcgtgg cgaccgacta ggaagctctc tgcatcgtag tagagatata ggtcagactt  43440
gggagtcact aagatttcca cataatgtgc atcatactac tttaccgttt gctaaggtag  43500
gagatgacct tattatgttt ggttcagaac gtgcagaaaa tgaatgggaa gcaggtgcac  43560
cagatgatcg ttacaaggca tcttatcctc gtaccttcta tgcacgattg aatgtaaaca  43620
attggaatgc agatgatatt gaatgggtta acatcacaga ccaaatctat cagggtgaca  43680
ttgtgaactc tagtgtaggt gtaggttctg ttgtagttaa agacagcttc atttactata  43740
tctttggtgg tgaaaaccat ttcaacccaa tgacttatgg tgacaacaaa gacaaagacc  43800
catttaaagg tcatggacac cctactgata tatactgcta taagatgcag attgcaaatg  43860
acaatcgtgt atctcgtaag tttacatatg gtgcaactcc aggtcaagct atacctactt  43920
tcatgggtac tgatggaata cgaaatatcc ctgcaccttt gtatttctca gataacattg  43980
ttacagagga tactaaagtt ggacacttaa cacttaaagc aagcacaagt gccaatatac  44040
gatctgaaat gcagatggaa ggtgagtatg gctttattgg caagtctgtt ccaaaggaca  44100
aaccaacagg tcaacgtttg attatttgtg gtggagaaag gacttcatca tcttcaggtg  44160
cacagataac tttgcacggt tctaattcaa gtaaggctaa gcgtatcact tataacggaa  44220
acgagcacct attccaaggt gcaccaatca tgcctgctgt agataaccag tttgctgctg  44280
gtggacctag taaccgattc actaccatct acctaggcag tgaccctgtt acaacttcag  44340
atgctgacca caagtacggt atctctagta ttaataccaa ggtgttaaag gcttggagca  44400
gggttggttt taaacagtat ggtttgaata gtgaagcaga gaggaacctt gatagcatac  44460
acttcggtgt cttggctcag gatattgtag ctgcttttga agctgaaggg ttggatgcca  44520
ttaagtatgg aattgtgtcc ttcgaagaag gtaggtatgg tgtgagatat agtgaagttc  44580
taatcctaga ggctgcctat actcgccatc gtcttgataa attagaggag atgtatgcca  44640
ctaataaaat cagttaagca atctgctgca cgccagaaca cataagaact tatacaatca  44700
ggacgtgacc ctaagcaggc atacgccatt gccaaggatg tacaacgtcg tgccatgaag  44760
aaaccttctg catcttctgc gtaagcaggt taatatctta gtgtacacaa gggcagactt  44820
aggtttgctc ttagtgtaat ccaaggaggt aacatgcaag aggagaattg ggatgtgtaa  44880
tgttggatat ggagaaggtt gaacctcagt gttgtacaag gattaaccaa agtaaaaatt  44940
```

```
ttgatatagg cgtgtgtcag ctctctcgcc ctcgccctcg ccggattttc cccatatggg  45000

gccgcgctgc ggttggcttg gggattgggc taggctgggc cgtcttcaac ctgctgccgc  45060

aggaagctcg atgggttggc tgagggttgc cgagggctgc gcttagtggt acacaagtag  45120

aacgcctagg aagcgctagg gcacgcctta gtgttggaca aggtgattgc cttagtgcaa  45180

ccgtttaggg cttacacagg ccgttttagg gcaattcctg agtgtttgac agggtgtgag  45240

ggtgtgggct a                                                        45251
```

<210> SEQ ID NO 2
<211> LENGTH: 581
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
aacacctgcg gcttaattgt aaagacgaag gagattcaac atggtcttca cactcgaaga     60

tttcgttggg gactggcgac agacagccgg ctacaacctg gaccaagtcc ttgaacaggg    120

aggtgtgtcc agtttgtttc agaatctcgg ggtgtccgta actccgatcc aaaggattgt    180

cctgagcggt gaaaatgggc tgaagatcga catccatgtc atcatcccgt atgaaggtct    240

gagcggcgac caaatgggcc agatcgaaaa aatttttaag gtggtgtacc ctgtggatga    300

tcatcacttt aaggtgatcc tgcactatgg cacactggta atcgacgggg ttacgccgaa    360

catgatcgac tatttcggac ggccgtatga aggcatcgcc gtgttcgacg gcaaaaagat    420

cactgtaaca gggaccctgt ggaacggcaa caaaattatc gacgagcgcc tgatcaaccc    480

cgacggctcc ctgctgttcc gagtaaccat caacggagtg accggctggc ggctgtgcga    540

acgcattctg gcgtaaaggt caatagtgct taacaaacac t                        581
```

<210> SEQ ID NO 3
<211> LENGTH: 45780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
tctcgccctc gccctcgccg gattttcccc atatggggcc gcgctgcggt tggcttgggg     60

attgggctag gctgggccgt cttcaacctg ctgccgcagg aagctcgatg ggttggctga    120

gggttgccga gggctgcgct tagtggtaca caagtagaac gcctaggaag cgctagggca    180

cgccttagtg ttggacaagg tgattgcctt agtgcaaccg tttagggctt acacaggccg    240

ttttagggca attcctgagt gtttgacagg gtgtgagggt gtgggctatc tgttcgtttc    300

gctacgcttc actcactgct cctcacttcg ctgtcgctcg ctacactgcc tgtcgtgtac    360

cttaggttat tccttgaggg atggcttagg ttagccttag tgggctacct tagttaaagc    420

cttagtgctt agcttagtat caacttagta gtgtacctta gttagtctta gtgccagacc    480

ttagtgattg catagctaaa gctataagat gcaattaggt cgcggtcggt agaccgctga    540

gagtaggtaa tagtgataag atgcagtagg aggaacacca gaaacctagc catcctagcc    600

tatcctagct ctgtatctat tgctttcctt agtctcacat gttagacaac ctaggtttat    660

cttagtagtt gtgacatgta tcacataaat aatctatctt agttaaattt agtgttgaca    720
```

-continued

```
caggcaatca acagatatac attagcaatc actgagacgg acctagcaag ctgtctcagg    780
ttataagtag gagaattgat gcgtaggccg tagctagcgg atgtagtcgc atgaaggctt    840
gagcaagggg ccgtttaata ccttcttcct ctggagacaa agcttataac attgctcttt    900
aacaatttgc ttagtgtaac ctatgtatgc cgtggttaat tacttattga atgaggaatt    960
aactatgaat tatgaagaaa tgtatgaagt ctatttcgac tcattagatg aaggcgaaga   1020
agcattatcc tacgctgagt ttgtggaggc tttatcatga ttctgaataa ccgtgaactg   1080
tccgttctct tcactctgtt atgctacatg attcgtaata acgaattact tacagatgac   1140
gagatggcac tatatcaccg ctttcttaac gaaggttgga cagatacagt taaccagaaa   1200
cgtgacttga tgaaggagtt aagtaatgat tcagttgact gaagaccaac taaagcaact   1260
cttagtcgac gcgtggtttg ctggtcatga aacctcgcaa tacacgccta actcttacgg   1320
tgatgctaac agatatgcac gctctacatt aaaggaggtt aaagaggatg tatcagcatg   1380
aggttttctt cgaatcagct agtgaagcta tccgcttcca tgatgatatg atgcaagctg   1440
gcgtaggtgt tgatgtgtat cactatttga tagattacga cactgaatat caccgagtta   1500
ccttagtatc tgagtatgac aaccaagtca ttactgagta tctaggtagt gaagattatg   1560
attacgatga agtaatcaca acaaatctct aaattaacta ttgacagcca cggcatacaa   1620
ggctacatta agcatcaaga cggcgacgtc tttaaacatc ccgctcttta acaatctggc   1680
tagtgccttg gtaggctaac tacttactaa ggtgaactat gaactactgc gacatcgctc   1740
acgaattacg catggaacgt gagaaacaag agaagcggat tatcaagaag atggctgtac   1800
tgcttgcaca ctataaggca gacaaacagc caacacatga tgagttcgtg gacttctgta   1860
acatgtatct taatgtgagt aaggccactg gttacagatg gcttaaagca ctgaatgatg   1920
gagaattgta gcaataagcc agcttaatag ctggcctatc aaggcactaa cctagctctt   1980
taacaatccg gtttgtgtct tgataggctt actaacaaag gtgaactatc atgactaacg   2040
cacaacgtaa acgctatgat gcattgcaag agaaacttgc tgttgcttat gccgcttggc   2100
aagctaacac agacaagagc aaacacgata aactttatag taaagtggtt gcaattaatg   2160
ctaaaataga taaacttgtg aatagtatct tataagatag ttgctggcac tagccagcct   2220
atcaaggcac aagccacgct cttttaacaa tatgggtagt cgcttcttag tctggatagg   2280
ttaaacctag ggtattcttt tgagtgccct ataatgtaac ctaactaact aatgaggatt   2340
aaatcatgga acgcaatgct aacgcttact acaatcttct ggctgcaact gttgaagcat   2400
tcaacgagcg cattcagtac gatgagatcc gcgaaggtga tgattactct gatgcactac   2460
atgaggttgt agacagcaat gttccagttt attacagcga aatctttact gtgatggctg   2520
ctgatggcat tgatattgaa tttgaggatg caggtttgat tcctgatacg aaggatgtaa   2580
ccaagattct acaagctcgc atctatgagt ctctttataa tgatgtacca aatgatagtg   2640
atgtagtttg gtatgaagac gaggaagaat aaagatggaa aggcaatata acttcatctt   2700
ctcagacggt gtaaccctga aatgttcctt acgatttgcg cagattcgtg aggaagtgct   2760
aggtactaca tacaaactat ttagctgaca ctataagaga aggcttaaca aggcgttgct   2820
acggtagcgc ctgattaaac tttcacttac taggagttaa gactatggat ttagatagca   2880
tcattatggc atttgctctt attggcttaa gctggtgctc ctatcacctt taccgtgagt   2940
tcttatttga taaagctaaa cgcaaactaa gaaaggaagg cggtaactac ctctgtgtaa   3000
gaggcggttt agtcgaatat attgcaccta acggcacgga atgcgccatt aacaaagatg   3060
catttataga aacgtggcat tacatcaagt aactagccta tagcctgcct gtgtgggcta   3120
```

```
tgtgatattt acttacacta tataaggtga ctattatgac tactgaaaac acccttctgt   3180
ctgttcgtga agctgcaacc gctgaaatca agcagcactt agacaatatc ggcacttctt   3240
acatcaaagt tggcgcttgt ctgaatgaat tacgcggtga tttcgaaggt caaaaagact   3300
ttttagctta tgtagaatca gagttcggca tcaagaaggc acaatgctac aagctgatga   3360
gtgtagcccg tgtctttgaa ggagacgaac gctttaaagg tgtggctatg cgtgtaatgc   3420
tggcgcttgt tcctttcgct gatgaaaata taatcatgga gaaggccgca gaactcgccg   3480
cagatggcaa gctggacact aacgccgtaa acgccctgat tgagactaag aaagagataa   3540
aggccgaaac ggtacaatct aaggctgagg cagtaaaacc gcaggagaac gcgactgagg   3600
ccgcagaatc acaggaaatg caagcgccgc aggtagtgcc acccgcgagc gagcaggagg   3660
ccgacgaatc agcaccatgg gaagaggaaa gcaagccgga agcgccaaag gcagcgccgc   3720
tggataacac ggctaatacc gaaaacgccg ctatggctag cctcttagca caaattaagg   3780
cactgactga gcaattacag gcagctaatg accgcatcgc ctccttaagt agcgcacgcg   3840
aaagcaagaa ggcagccgca cctatgctgc cgcaattcaa atcttcctgc ttctatgctc   3900
gcttagggtt aagcgctgag gaggcaacga agaaaacagc agttaacaag gcgcgccgcg   3960
aactggttaa gctaggctac ggtgaaggac atgaagcatg gcccttaatc tctgaggcag   4020
tagaagagtt gactaagtaa ccttatcggt ggcatctcct taggtgtcac ctattaaggt   4080
ttctttcact aggagtaaac aagatgcaag acctacacgc tattcaactt caacttgaag   4140
aagaaatgtt taacggcggc atccgtcgct ttgaagcgga ccaacaacgc cagattgcat   4200
ccggtaatga atcagacacg gcatggaatc gccgcttatt gtccgaacta atcgcaccta   4260
tggcggaagg tattcaggct tacaaggaag aatacgaagg caagagaggt cgtgcaccac   4320
gtgcattagc tttcattaac tgcgtaggaa acgaagtggc agcatatatc accatgaaaa   4380
tcgttatgga tatgctgaat acagacgtta ccttacaagc tatcgctatg aatgtagcag   4440
accgcatcga ggaccaagta cgttttagca agctggaagg tcacgcagct aagtactttg   4500
agaaagtgaa gaagtcgctt aaggctagca agactaaatc ttatcgtcat gcgcacaacg   4560
tagcggtagt agctgagaaa tctgttgctg accgtgacgc ggatttctcc cgttgggagg   4620
catggcctaa agacaccttg ctgcaaatcg gtatgacctt gctcgaaata ttggagaata   4680
gtgtattctt caatggtcaa cctgtcttcc ttcgtacctt gcgcactaac ggcggaaagc   4740
atggtgttta ctatttacag accagtgaac atgttggcga gtggataact gcatttaagg   4800
aacatgtagc gcagctcagc cctgcctatg caccttgcgt tatacctccc cgcccttggg   4860
tatcaccttt taacggtggg tttcatactg agaaagtagc aagccgtatt cgtctggtaa   4920
aaggcaatcg tgagcacgtc cgcaagctga ccaaaaagca aatgccagcc gtttataagg   4980
ctgttaacgc tttgcaggca actaagtggc aggttaataa agaggtttta caggttgtgg   5040
aggacgttat acgtctagac ctcggctatg gtgtaccttc ctttaaacca ctcatcgacc   5100
gtgagaacaa gccagctaat ccggtgccgt tagagttcca gcacctgcga ggccgtgaac   5160
tgaaagaaat gttaacaccg gaacaatggc aagccttcat caactggaaa ggtgaatgca   5220
ccaagctgta taccgctgag actaagcgcg gcagcaaatc ggcggcgacc gtccgcatgg   5280
tagggcaggc ccgtaaatac agccaatttg acgcaatata cttcgtgtat gctctggaca   5340
gccgcagccg cgtctacgcg caatctagca cgctctctcc gcaatcaaac gacttaggca   5400
aggcattgct ccgttttacc gaagggcagc gtcttgatag cgctgaggcg cttaagtggt   5460
```

-continued

```
ttttggtgaa cggggctaat aactggggtt gggataagaa aacttttgac gtgcgcaccg   5520
ctaacgtgct ggatagtgaa tttcaagaca tgtgccgcga cattgcagcg gatccgctga   5580
ccttcactca atgggtaaat gccgactccc cttacggctt ccttgcatgg tgctttgaat   5640
atgcgcgtta tctggatgca ctggatgaag gcacgcaaga ccaattcatg acgcacctcc   5700
cagtccatca agatggtagt tgttctggta tccagcacta cagtgctatg ctacgcgatg   5760
cagtaggtgc gaaagcagta aaccttaagc cctctgactc tcctcaagat atttatggtg   5820
ccgttgcgca ggtagtaatt cagaagaatt atgcatacat gaatgcagag gatgcggaaa   5880
ccttcacttc tggcagcgtg actttaacag gtgcggaact gcgtagtatg gctagtgcgt   5940
gggatatgat aggaatcact cgcggcctga ccaaaaagcc cgtaatgaca ctaccttatg   6000
gcagcacacg tctaacctgc cgtgagtcag tgattgatta tatcgttgat ttagaagaaa   6060
aagaggccca acgggctatt gcggaagggc gtaccgccaa tcctgtacac ccttttgata   6120
atgaccgtaa agacagcctg acacctagcg cagcttataa ctatatgaca gctttaatct   6180
ggccttctat ctcggaagtg gttaaagccc ctatagtggc aatgaaaatg attcgtcagc   6240
ttgcacgttt cgcagctaaa agaaacgaag gcttagaata tcccttacca actggcttca   6300
tcttgcaaca aaagataatg gctaccgata tgctccgcgt atccacttgc ttgatgggtg   6360
aaatcaagat gagtctccag attgaaacag atgtagttga tgaaacggca atgatgggtg   6420
cggctgctcc taacttcgtc catggtcacg atgctagcca cctgattctg actgtatgtg   6480
acctagtgga taaaggtatt acatccgttg cagtcatcca tgattctttc ggtactcatg   6540
caggacgtac cgcagacctg cgggatagct taagggaaga aatggttaag atgtatcaaa   6600
accataatgc cctgcaaaac ctgctagatg tgcacgaaga gcgttggtta gtagacaccg   6660
gaatccaagt accagagcaa ggggagtttg accttaacga aatcttagtt tcagactatt   6720
gtttcgcata atattaatag gccattcctt cgggagtggc tttcttttac ctactacctg   6780
taacatttca ttaacataaa acgtgtctca catgtgagac tttatttacc ggacactata   6840
ggatagccgt cggagacggg aaagaaaggg aagataaagg atataaagga agtaataggt   6900
attaaaggtt atataggtta tctaggaata cctattacct tcttccttcc tcttattacc   6960
acttagagga agggcagacc taggttgtct cacatgtgag acttcgtatt taccggacag   7020
tatagataag attaactcac tttggagatt taaccatgcg taactttgag aagatgaccc   7080
gtaaagctaa ccgttttgac atggaagaag ggcagaagaa aggcaagaag ctgaataaac   7140
ctgtccgtga ccgtgcatct aaacgcgcag cgtgggagtt ctaagttatg gctaaataca   7200
gaatcaagac ctgtttaaat agtcacgggc aagagtgtta catagtgcaa cgtaaagtat   7260
taggcttaat atgggtcaca tgtatgatgc ctattggata tactgataca gaggctatct   7320
tctgcaccga aagggatgca aagcagttta tctctaagcg tagaaaagct gactcttatc   7380
aacccagaac tattaaggtg aactaatggc tattattaat aacatcccgt gtcctgcttg   7440
tcagaagaat ggacacgata aatccggcaa ccacctcatg atatttgatg atggtgctgg   7500
ctattgcaac cgtggtcact tccatgataa tggcaagccc tactatcaca agccagaggg   7560
tggcatcgag ataaccgaat tgcctattac tggcaatatc aaatatacac cttctcaatt   7620
caaagagatg gagaaggaag ggaagataag cgaccctaag ttgcgcgcca tcgcacttgg   7680
tggtatgcgt atgaaagacc gttgggaggt catgaatgag caagaaaggg cagaccaaga   7740
agcagagtgg aaacttgatg ttgaatggtt cctcacgctt aagcgtaaga accttgtgtc   7800
ccgtcacatt cgaggtgaca tcgcagcaat gtacgatgtg cgcgttggac acgatgaaga   7860
```

```
gggaagagtc aaccgtcact attatccacg atatgaaaag ggtgtgcttg ttggagcaaa   7920
atgccggacg ttgccgaagg attttaagtt cggacaccta ggtaaactct ttggtatgca   7980
agaccttttc ggtatgaata ctttgtctca cgtgttagac aagggaagac gaaaggattg   8040
cttgcttatt gtgggcggcg aactggatgc actagcagca cagcaaatgc tccttgattc   8100
tgccaagggt actaagtggg aaggccagcc ttaccatgta tggtctgcca ataaaggtga   8160
gtcttgcctt gaagagatag tgcaaaaccg tgagcacata gcccaattca agaagattat   8220
atggggcttt gatggcgacg aggtggggca gaagcagaac caacaagctg ctcgcctgtt   8280
tcctggcaaa tcctacatcc tcgaatatcc ctctggttgc aaagatgcta acaaggcatt   8340
gatggctggc aaggctaaag agtttgttga tgcttggttt aatgccaagt catctgatga   8400
agtctttggt agccagatta aatctatcgc atctcaaagg gataagctca aggctgcacg   8460
tccagagcaa ggactatcat ggccttggcc taagctgaac aaggtaacgc taggtattcg   8520
taagaaccag cttatcattg taggtgcagg ctctggtgta ggtaagactg agttccttcg   8580
tgaagtagtt aagcacctca ttgaagaaca cggtgaatct gtaggcatca tttctacaga   8640
agacccgatg gtcaaggtgt cccgtgcttt tatcggcaag tggattgata agcgtattga   8700
gttaccgcca accaacgacc cgaaagaaga cggataccgt gaggtgttcg actacaccga   8760
ggaagaagct aacgctgcca ttgattatgt ggctgataca ggaaagttat ttgtggctga   8820
cctagaaggc gactattcta tggagaaggt agagcaaact tgcctagagt ttgaggctat   8880
gggcatttct aatatcatca ttgataactt aacggggatt aaattagatg agcgtgcttt   8940
tggtgggaag gttggtgcac ttgatgaatg cgtcaaacga attggtacta tcaaagaccg   9000
acatgcggtt acgattttcc ttgtctctca ccttacacgt cctccggcaa accgtaccca   9060
acacgaagaa ggtggcgaag ttatcctttc tgacttccga ggctcaggcg ctatcggatt   9120
ctgggcatct tacgccttgg ggattgagcg taatacaaga gctgaaacgc ttgacgaaag   9180
gactaccacg tacatctcat gtgtcaaaga ccgcgaccaa ggtatctgga ctggaaccaa   9240
ggtcatgctt aagggtgaca ttcaaaccgg acgtttaatg gaaccacaag cccgtactaa   9300
gtcatttgat acaggtgaag caaggcaaca agaagtgccg gatttaccgg acactataga   9360
agagacaacc tttgacgatg aacaggagtt ttaatggaaa ttattaaacc agtattgaat   9420
atcggtattg agatcctatt catgcttgtg atcgcagatt atgctgcacg atatggattc   9480
aagaaagctg tgaaacttat cgttgcatct ggttttctta tgtcaatgtt ctttattgta   9540
acacgcctta tctagtgtat ttatcagggc ttgtctcaca tgtgagacag gctcttatta   9600
agtacattaa ataactggag attgattatg tatagattag tattgaatgt aggtgattat   9660
gttcgtaaca tcaatgaagc ctcacgtcgt tatcgttgcc gtggtgtagt ggctcgtgta   9720
agtgagaaca tgtatcatgt agaatatgag gatggtatta aggcttctta ccacaagaaa   9780
acagcacata aatatcttga aaagattgta gagataaaca atcaatgtaa gtgcatacat   9840
gatgaggttt gcgataaatg tgctcgccag atgcttaaga atttcctagc tcctctttat   9900
tatggtgctg gtcctcaaac actagcagag tacatggcag aaaagaaaac cacactcaag   9960
aaagagcgtc gcaatgtaat cactggtaag actcaaagtg aaatgattaa gcaatgtggc  10020
actgcattag gtgttacaca gttcaatact cgtgcattgg gtaaatccac agggcaagct  10080
atggtgaaaa ttggtgaagc tatgatgcac ccaaatgtgc ctgtgcgaat cttggatgtt  10140
gaccatgcaa tcacagagca tggcacacca cggcgtgtag ctaataatca tttcgccgac  10200
```

```
actatagaag gtattattcg taagcaaggg ttgaagggtc ttcacatctt aaatggtgaa  10260
gaattactgt acctacctat cgttactgaa gaaacctacg tgaatatcta aggagttaat  10320
catgactaag gtattaattt atatgcgtgg acctcataaa tgctatgcag ttgtagcacc  10380
agatggtgtc aagacatatg gtacttcaaa ggggtttgca ttaataggtg ccagtcttag  10440
tgcaagtttt cagatggaac ttttcggtca ttggactgaa aaagagttcc gtgaggagtt  10500
taatgtaatc ggcagcttta tggtgaaaca tgcaaaataa acacagtctt aagatgtttg  10560
atggtcacga agacctgcaa gcacaaatta ctaaccaagc cttcctgttt gcacagttaa  10620
ctatggctga agcaaagaag aatagcctga cgcgcgagca agttatcaaa gaggcaactt  10680
gggagccaca ccaaggcaaa tacatgggcc agaaattaac tgtaacacgc agtcgataag  10740
taaagggttg tctcacacgt gagacagcct ttcatcatat tgattggagg tgcattatgc  10800
cacgtgatta tgattctgat tgggatttcc aagattcaat gaactcaaaa cctgaacgtt  10860
cagatgacta ctacgaaaca gaggcaatgt atgaaagcta ttaaagtcag taaggtttgc  10920
tcttgcggta aaggttatcg cagtcgtatt gatggtaagt gtgggcattg caggtctaag  10980
aaagaggctg ctttgtttga taagtaccac aatgaattag catataacta tcctcatcta  11040
acacctaatt ctttattagg acttggttat agggttaaat actttggagc aatctatgaa  11100
atcaattgat tggaagaagg aagcagaagg ccgcatctta gtgatggatt ctgaggctaa  11160
aggcctgctg gatgctatcc gatatggcca ccgcgaagat gtgcacatca tttgctgcat  11220
ggatttgctt actacagagg agttcctctt ctttgaccca tacgagatgc gtgaccctga  11280
agcaagagaa cgcctaaaag aatgggaagg ccatcaagat ggaacattgg ttgacggtgt  11340
taacttcctt aaacactgcg aagccatcgt ctcacagaac ttcctagggt acgacggcct  11400
tctatttgag aaagcattcc ctgatatctg gaaaggcttt aactataccg agagacgcgg  11460
caagggcaga ctccgcgctg acctgtgtcc ggtacgcgtc atggatacgc tggtcatgag  11520
tcgcctgtta aaccccgata gacgcctccc tccgcaagca tacgccaaag gcatgggtaa  11580
cgtagcccct cactcaattg aggcgcacgg cattcgtata ggccgttata agccggagaa  11640
cgaggattgg tctaaactaa ctgaccacat ggtacatcgt gtacgcgagg acgtggcgat  11700
aggccgtgac ctattcctct ggctatttaa cggagaatgg acggagcaca aacgccgtgg  11760
cgtgaataaa cgcactggcc taggtattga gacagccttc cacatggagt ccattgtggc  11820
gctggagatg agccgtcagg ccgagcgtgg attccgtctg gatatagata aagcattagc  11880
acgatgcgag gaattggacg ctaagattga tgagacagtc gcagcgttcc gtccgcacat  11940
gcctatgcgt atcaagtcta aaccttttaa accggaagaa aagaatgaag tatgccaacg  12000
cgcaaatgag tatggagcta gcaacaatat acctactgtc cttgacccct ctcactttct  12060
tcacgcagag agacgaggag atcgcaagac agtatggagt gtcactacta agtctggtga  12120
ttggtcggct agcgtcaaga aagactttcc tcaccttaga ggaaaccgta atgacacgcc  12180
aagcatcaag tggattggcg cttactcgcc tgttactttc gaagagattc ccttgggtaa  12240
cagggataca gttaagcaag tgctctatga ttatggatgg aaaggtgttg aatttaacga  12300
taccgagcaa gcgcatctcg atgagcatgg cgtattaccc aagccttgga gtgggaagat  12360
aaatgaaaag tcccttactt tatggcaaga gagagccgca cgtgaaggta aaacagtccc  12420
tgattggtgc ttgggtatcg ctgcatggta catactcgta tcccgtcgtg gtcagatcct  12480
caaccgtggt gacgttgaag ccttcgacca gaagggggtg tggccttcgc aagctggtat  12540
acgaaagtgt cgcggccttg tacctgtagc atttaacaag gagttaggaa tcaatgcgca  12600
```

```
gcaatactac gaaaggtacg gatgctggcc tacgtcagac aaggatgacg gagaatggcg  12660
tgtgccagct attgctatta gtattggaac ttctacgttc cgtatgcgtc atcgtaacgt  12720
ggttaatatt cctgcccgtg gtttgtatcc tttacgtgat ttattcatag ccggtaaagg  12780
taagctaatc cttggttgtg atggtgctgg tcttgaacta cgtgtactgt ctcacttcat  12840
gaatgaccct gaatatcaag atattgtact gcatggtgac attcacaccc ataatcaaat  12900
gaaggctggt cttcctaagc gtgacatggc gaagacattt atatatgcct tcctatatgg  12960
gtctggtata gctaaccttg cagcagtatg tggtgttact gaggaagaaa tggaggaagt  13020
tgtggcaaga tttgaggttg aactaccatc tcttgcacgt cttcgtgaga atgttatcgc  13080
acaaggtaac aagtttggct acctacaagc acctgatggt cattggggtc gcatccgtat  13140
gtctggtggt gaacttaaag agcacactat gcttaacgta ctactccaga tgactggttc  13200
tctgtgtatg aaatacgcat tggtcagagc gtttgcagtg atgcgcaagg aaggtgtggc  13260
cttagatagc atgggaaacc cttgcggtat agctaacgtg cacgatgaaa tccagatgga  13320
agtccctgaa gatgaggtct tgtatctcaa ctacgacttg cctttcacct tagaagggtt  13380
cgaaacagag aaggctgctg tgaaagcagt gttcgatgca gaggagaaac gtgttcatgt  13440
ggattctgaa ggacgtatgt ggtctgctgc aaatctcgtt agcgttgatg ctgatgctgg  13500
tgtacttcat tgccagcgtc gctatcaccg tgcagggcat atcattgccg acgcaatgac  13560
ttgggcgggt cagtatctga agatgcgttg tccgatggca ggtgagtata agattggtgc  13620
aagttggaag gaaacacact gatggacagg tttgatattg tttgcctatt ctccaccttc  13680
tttcttatat tccttatgct tgcttgctat ggaagtatgc gattagatat acctgatgaa  13740
gaggagggtt acgattgatg caggcatctt ttattattct tggagtcata ttatttatgg  13800
tagtattctg ggctttctct ggcattgacc cagattgtga tggtaactac gactgagtta  13860
tactcaaggt cacttacgag tggcctttat gaataactta ttcctactta ttttgtctaa  13920
catgatttac tggacactat agaaggaaag cctaggtaat ctaggtttat aaggtagtat  13980
aggtaattaa ataaatatag gagatataaa tatgtctatg gtaactactc tggtattcgt  14040
ggctcaatac tttcgtggtc ttgctaataa gttcaagtcc aaggctatca aagctattga  14100
ggctcgcatc gaagcagtac aggcagagca agttaaagtt gaagaacatc gtagttctca  14160
aatgattgac tgtcataacc gctactatgc atctcgtgat gaactaaatg cacgtcaagt  14220
caaagaggta gaagatatgc tggcacgtca ccagcaagag cgtgacagcc tgaaagctga  14280
atttgaagag aacaaggcat caattgctct tgtaaatcaa gctgcatctg acagcctgaa  14340
gaaagagatt gttatgctgg aaatagaact ggacaacttg actaaataag gagttatgat  14400
ggaagaagtg attcaagcta aacatgtagg tatcatcttt cgtgacctag agcagcgtaa  14460
agttgcaggt cacactcgtc tggctaaaga agacgataca gcaatcacta ctgtggaaca  14520
agcagatgcc tatcgtggtc cagagtttac tcaaggtgaa acttgtcatc aattgagcct  14580
ttcactttgt gacactatgg ctagtgtaaa tgtacaagag gttgaagatg gtgaatgtgt  14640
tagttatgtc taccctctcg atactattgc acgtattaag gtagttcata agtaattact  14700
ggacactata gaacaatagg tcggcttagt tcggcctatg attgtaaagt gtcgttgatg  14760
ttgaaccatt gtgcaccttg cacaacccga taccgtatcg ggctttctag tgagcacatg  14820
cttgtgctca gtacaaagct aactgacaat aggagactaa ataaatggca cgtggtgatt  14880
tcgattttgg tgcttccgta tctaaagctg aaggtaaagt ctttaagaat ccagaagtag  14940
```

```
gtgatcatga agcagtaatc tctggcatca ttcatgttgg ttccttccaa gacatcttta  15000
agaaaggtaa taccactgaa gttaagaagc cagcaaactt tgttctggtt aagattgtcc  15060
tgatgggtga cgatgacaag aacgaagatg gttctcgcat ggaacaatgg atggctgtgc  15120
ctctgaagtc tggtgataag gcaacactga ctaagttcct gaatgcagtt gaccctaaag  15180
agttgctggg tggcttcgat gattttatcg gtgaatgtct gactgcaact atggttggct  15240
ctggcgacaa gaatgatgat ggtactttca agtatgttaa ctggaaaggc tttggcggta  15300
tgcctgataa gttgaagaag cttgtactgg ctcaggtaga agaggaaggt ctgtctatga  15360
caggtcatat caccttcgac aagctgacca aagaaatcat tgatgacatc ccagctaact  15420
tggtacgtca atacttcctg aacgagacac ctcgtggtaa gaacctgtct gttgctggct  15480
ctcacgtaga agctattatc aaagctgctc gtgaagaaga ccctgaatgg aagaaggcta  15540
agaagaaaga cgaggaagat gctaccccag ctaatcgtaa atctctggat actggtgagt  15600
ctgttccgca ggaagtacct gaagcagaag atacgcctgc accggagatg gatgaggacg  15660
cggaatatta aggagaacgg atgaaagtac aaatcgtaac tctgcattgc aagaaaggaa  15720
tcaccacact tggcggcaat acttttcact ccttctctga aggggagaca tacgccgacc  15780
ttcactatat ctggcgtgac gggcagcacg tggtgaacta cagcgaccct gcgactggta  15840
aacgccacgg cgtgtcgctt ccggcgcacg acattgctca ggtgaacaca gttttataaa  15900
gtctcacgtg tgagacaaat cggtgtccgg tatttactgg acactataga agagaagaat  15960
tttaatcggc gataatgcca taaccaacaa aaggagaatt taatatgttc aagattgaaa  16020
ctatcgtaaa ccgtgttgtt aaaggtgctg ctctggtatc cgttgagtct ttcattatcg  16080
tcgatgaagc tgatcaactg gtagctggta ctaaggctta cgatacccgt gaagaagctc  16140
aggctaagat tgacagcatg ggtaacttcg ctgctggtct ggagtttgct cgtgcttgct  16200
tccctgagca ggctgacaaa gcccagatcg gtaaggctaa catcgtagct gaatatctgg  16260
attggattgc tgctggtaaa ccagtgaaag aagttaaagc tgctgaagaa gctgaagctc  16320
cggcagtaga agtgtctgca ccggaagctc cggttagcga agaggaagag ttttgataat  16380
agcaggtgta gcctctgtta gtcctagttg actatcacgc tcacctcatc taatgccctg  16440
tctgccttag tgtaggcagg gtcttttgcg taatagttat tggagaatga attatgccga  16500
ctattgaatc tcgaattgaa ctggacatta gctacaatgc aatcaccaga cagtatattg  16560
gggttgccta tgattacaaa actggtgaga agctagtgga ggtgagacaa tgggatgact  16620
attggttaag acagaacctc catgatgcgg tgtcctcctt cttgaaggag tggcctacat  16680
gcgaccaaac ttcgacttcg gagctacagt atcggaagac aataatctca tcctgtggcc  16740
aactgaaggt aatcgaatcg ctttaataga tgctgatatg ttaccctaca tcgtaggtta  16800
tacaatcagt gacatgactt atttacgagc cacaactcgt gttaagtcag gacaagtccc  16860
atcaatcaaa gatacacctg agtgtaagca agcatgtgac cgtgtgaact ccttgcttaa  16920
ctcttgggtg tatgcagcag agtgtgatgc agctaagcta ttcatgacga aatcagaagc  16980
taacttccgt gtccgcctag cattcacaaa gccttataag ggtcaacgta agaccgagaa  17040
gcctccgttc ttctatgaat tgcgagagca tctcttagag gttcacggtg caatcttggc  17100
agatggtgag gaagctgatg acctcatgag catcgcacaa tgggatagcc accgccgctt  17160
ccagcaagat acaggtaacg agttcgctat cggtagtcca gagcataaag cattctctga  17220
tacttgcatc gtttccttag ataaggattt gatgattgtt cccggttggc atctacagcc  17280
gggtcaagag aagaagtggg tagagcctat gggctggctt gagctacgcc gtaaggttaa  17340
```

```
tgggcaagtc aaagatctaa aaggtgctgg cctcatgttc cactatgcac agatgattat  17400
cggtgatgat attgataact atgctggcat accaggtcgt ggtgctaaat atgcctatga  17460
tcttctcaaa gattgtaaga cagagaaaga gttgtacatg gcagtgctgg gtgcttacaa  17520
ggctaagttc gggcatggac aagttaaaat taagaattac cgaggtggtt atcgtatcgg  17580
caaagccttt gacctaatgc ttgagtgtgg tcgcttagct cacatggcaa gattcaaggg  17640
tgatatatgg cgagccgata agaacccaat cttgtgggga gatgaaggat ggctacaaag  17700
ttaaaagcat ctgaagttgc tgcttataag aaagagttgc tagagaagca gggctggaaa  17760
tgtcctattt gtggagcacc tcttaaagca gtggccgaga ttaaccgagt actagaccat  17820
tgccatcgca gaggttactg tagagcggta ctctgtcgtg ggtgcaatgg cggtatcggg  17880
aagatagaaa acctagtaaa gacttattgt aaggctgggg ataatgagta tttcattatc  17940
aagacattgc gaaacattgc agattatcta gacttacata gtaagcctca gactgataag  18000
atttatcata aacatcaaac ggaggcagag aagcgcgagg ctaagaaccg taaggcacgc  18060
cttgcttatg caagaaagaa gaaggaggtt aaagttgggt aagcttcgca gcttgtacaa  18120
agactccgag gtacttgatg caatcgagca agctaccgac gagaaaggta atgttaatta  18180
caatgagatg gcacggatat tatcgtgcca ccctgtgggt aagaagatta cccgccagtt  18240
ggctagatac tggcatggtc aattcaagaa gaccaagaag aatggtgatt actaccagac  18300
ccttctgcaa gaggataagc gtatcaagga agagcgtaag ctcaggactc ctgaccgcta  18360
cgaggatttg gctattgtac cattgcctga ctcgcctcat cgaagtgtac tggtaatccc  18420
tgatacccat gcaccgtatg agcacccaga taccttagag ttccttgcag cagtggcagc  18480
acgttaccgt cctgatacgg tggttcatct tggagatgag gcagacaaac atgccttatc  18540
gttccacgat tcggacccaa atctggacag tgctggcatg gagttagaga aggcccgtgt  18600
ctttatgcat aaattacaca agatgtttcc tgtgatgcgc ctgtgtcatt ctaatcacgg  18660
ctctatgcac ttccgtaagg caagcgccaa aggtattcct gtacaatatc tgcgtaccta  18720
tcgtgaagtc ttctttccgc atgggggtgg cgaccagtgg gattggcagc atacacacgt  18780
tcttgagttg ccgaatggtg aacaggttgc atttaagcat caacccgcag gctcagtctt  18840
agcagatgca gcgcatgagc gcatgaactt agtgtgcggt cacttgcatg gtaagatgtc  18900
ggtggagtat gcacgtaata cacatgaaca gtattgggct gtgcagggcg gctgtttgat  18960
tgatgagtca tctcgtgcat ttgcctatgg tcgtgagtcc aaatacaagc cagcattagg  19020
ttgtgtggtt attctggagg gtgtgccgca cattgtcccg atgcagacca atagtgacaa  19080
tcgctggatt ggtaagattt agttgacact atagaacaaa gggtaggtat tagcttaccc  19140
ttgattgtat agtgaatgga ggaattaata tgtcacaata tgtatgtgag aaatgcggca  19200
atcgatatga taactgcacc tgtgattata ataaaggtaa aaggattaaa tcaggtgatt  19260
atgttatacg acgtgcaggc tgccgcgacc cagagtgggg cagggtgtgt aaactattag  19320
gcaagaaatc agatgcaaca ttcaaagtta taaaggatga gtctgtcggc agcgccatta  19380
tacttgaagg tatcgaaaag cgagaatggt atgcacctta tttcgagaga gtggcaaccc  19440
caccagttgt acctgagtct aataactcaa acgataatat ggttacgcaa cctaagcact  19500
acgagttctt cgatggggta gaggcaatca ctatcattgc tcgtagtatg accgagaagc  19560
aatttgctgg atattgcatg ggtaatgctt tgaagtatcg tctgcgtgca gggaagaaat  19620
tcaacacgga agaagacctg aagaaagcag actactacaa agagctattc cagaagcatc  19680
```

```
gtcacgaatg tattgatgag gatatttaat atggaaggta aactgtatag agggtacttc  19740
ggtaacttat ataaagtaag ccctcgcggt tttgtattga cctctgatga tgaaggtgca  19800
atgtggttcc taagtgccta tggttctgac ttagcatact ttaaagaggc aatagttaaa  19860
ggtgtgatga aggaggtgaa atgaatatct tccaattcct aggtcttcca gaagaccacc  19920
gcaatcaccc attcatgctg gtgaaacatc gcggtgaagt acctgagaag aaattaactt  19980
ttccatgtta tgcacaggta aaacgagatg gtatatttag tgctgtggtt gttcgcaacg  20040
atggtgtcgt tggtgtcttt ggacgcactg gaaagaaact ggctaacacg gaaaccttgg  20100
aagaatctta ttcagctttc cctactggca tttatctcgg tgagttgcaa tctatggcta  20160
ttgatgtcta ccttgaagca ctttctggag tagttaaccc taaccgcact gagccactgg  20220
atttcatagg ccagcagatt aaagacaacc tgtatattga cttcttcgat atgttaacta  20280
ttaaggcatt ccatgatgga ttcactgatg tttcttatct caaacgttac gatgctttac  20340
atcgtcgcat cggcgctcat cttagcgggc acaacgctat ccttcctatt actccttgcc  20400
ataatgagcg agaagttgaa gcgtttgcgc aagagcaaat agatgcaggc cgagagggtg  20460
ctgtgttcaa actggactgc gattatgaag caggccacaa aggttatcgt caaactaaga  20520
ttgtacgcat ggtgtcttat gacctaacct gtattggttg ggaagagggt aaaggaaaat  20580
acaagggtaa ggttgctaac ctgatcttta aatggaaagg aggcaagtct gttaaggcta  20640
tgctgggtcg tggctggtcg catgaggatg cagcccaaat gtatcacgat attaaacacg  20700
gtggcgaact gaacgtcatt gggaaaatct tcgctgtcaa ggcgttgcag gaatctagca  20760
agggagtcct gagacttccc aaggtttctg agttgcgcca cgataaggag gttcctgatg  20820
tctattgatt tgaacgaaga gcagcttgaa ttgttaatag aagccattga gcaatactat  20880
tacatgtgtg gctatcaatc agaagaacta gactccttat attcacaatt aaaaggaggt  20940
taattatgtc ttttgattct atgaaggcaa ctcgtgcggt tgaggtagca gaggctatct  21000
tcgaaacttt atcctgtggt atggaagtac catatacttt actggctgat gcagaagagc  21060
ttggtctttc tatagaggcc atccaagaga aggttgagga actctatggt acagacgaag  21120
aagaaaccga cgatttcatt tgagggtatg gagatgcttg agatgattct caagccttct  21180
tctccgaagg tgactaagac tcacgaagaa ttaatcgtag atgaagtgaa gcgttacata  21240
atggattgtg tcagagcaca actggtggtc caatgatacg tccagcttca ttcttagata  21300
ttcctgagat tataaacctt gggaataagt acgtggaaga ggaagtcaag gttgtagccc  21360
atcactcagc ctcatggaat gcagaacaaa gcgcacataa cctttgtgca tctcttagta  21420
gagaagattt attcctatgg gtggctgtag atgaagggca gattgtaggt tttctgtggg  21480
ccggctatca tgagttagcc ccttggacac ctgtaagagt tgcatctgac attctctttt  21540
atattgtacc agagaagcga gggacactgc tcggtatgcg cctcatcaaa gccttgaagc  21600
aatgggctaa tgatagtggg tgttccgagg tccgcctgtc tatcgcttct ggtattaatg  21660
aagaacgtgt cggacgtatg tataagcgac ttggctttga acagtttggc actgtgtata  21720
acctgaagtt ctaaggagat cacatgggta ttgtaaagaa agcatttaag gctgtcggtc  21780
ttgctcaaga tgcaccgcgt attgaagcca aggttcctgc tcagcagctt gagcgtaagc  21840
ctgagactga agctgaagat atacagattg gtgcaggtgg tgatgatgcg actgcatctg  21900
caaaaggtaa gcgcgggctt gtccgtccgg tagcttctag cttgaaggtg taatatgaaa  21960
cagagcacag atttggagta tggaggtaag cggtctaaga tacctaagct atgggagaag  22020
ttctccacta aacgtagctc tttccttgat agggcgaagc attactccaa attaaccttg  22080
```

```
ccctatctga tgaatgacaa aggtgataac gagacttcgc agaacggatg gcaaggtgta  22140
ggtgctcagg caactaacca cctagccaac aagctagcgc aagtgctatt ccctgcacag  22200
cgctccttct tccgtgtaga cctaactgca caaggtgaga aggttcttaa tcagcgtggc  22260
ctgaagaaga cagagctagc tactatcttt gctcaagtgg aaacacgggc aatgaaagag  22320
ttagagcaac gtcaattccg gcctgctgta gtagaagcat tcaagcatct tattgttgct  22380
ggtagctgta tgctatacaa gccaagcaaa ggtgcaatca gtgcaatccc aatgcatcac  22440
tatgtagtta atcgtgacac taatggcgac ctgttagaca ttatcttact gcaagaaaaa  22500
tccttgcgta catttgaccc tgctacacgt gctgtagtag aggttggctt gaaaggtaag  22560
aaatgcaagg aagatgacag cattaagctg tacacacatg ctaagtatct tggtgagggt  22620
ttttgggaac tcaagcaatc tgctgatgat atccctgttg gtaaggtaag taaaatcaaa  22680
tcagaaaagc taccatttat cccgctaact tggaagcgaa gctatggtga ggattggggt  22740
cgtcctttag cagaggatta ctccggtgat ttattcgtta tccaattctt atctgaagca  22800
gttgcccgtg gtgctgcact gatggcagac attaagtacc tgattcgtcc gggtgctcag  22860
actgatgttg accactttgt taactctggc actggtgagg ttgtcactgg tgtagaagaa  22920
gatatccata ttgtacagtt aggtaagtac gcagacctca cacctattag cgcggttcta  22980
gaggtataca ctcgccgtat cggtgtagtc ttcatgatgg agacaatgac acgtcgtgac  23040
gctgaacgtg ttactgctgt agaaatccag cgagatgcgt tagaaattga gcagaacatg  23100
ggtggtgtat attccctctt tgctactact atgcaatcgc cagtagcgat gtggggtctg  23160
ctggaggcag gagactcctt cactagtgac ctagtggacc ctgtgattat cacaggtatt  23220
gaagctttag gacgcatggc tgagttggat aaactggcaa actttgctca gtacatgtca  23280
ctgccattac aatggcctga gcctgtacta gctgctgtga aatggcctga ctatatggat  23340
tgggtacgag gtcaaatctc tgctgaactg ccgttcctta aatcggctga agagatggaa  23400
caagaacagg aagcacagat gcaagcacag caagcacaga tgcttgaaga aggtgtggct  23460
aaggccgtgc cgggtgtaat tcaacaagaa cttaaggagg cgtaatgtct ttctcattta  23520
ctgaaccgtc aaccactcat cctactgctg aagaaaatcc ggtagaaacc aaggaggtaa  23580
caactgatgc tgctactact gatgttcctg ctgatgctgg cactgctgta caagatgaca  23640
atgctggtgc acaatctact gaagacgccg gaggagaagc ttctggacag ccttcagaag  23700
aaggagacaa tggcggagag aatggtgaat ctaagccaga tgataccgcg accgacactg  23760
aggaagtgca gtacttcttc ggagaatatg aagtaacagt agatatacca caggatgtta  23820
cggatagcct taaagagaag ggtattgatg ctaagcaggt tgccaaggaa ctctatgcca  23880
aagatggcaa gtttgagctg tctgatgcaa ccaagcagaa attgtatgat gcttttggca  23940
agtttgcggt agatgcttac ctgtcaggtc ttaaggctca aaatgaagcc ttcttcctga  24000
aagaagccaa cgcagctaaa gagttggaag cagctaatac ccaacgcttc tctgatgttt  24060
ctaaggaaat tggtggagaa gaaggttggt cccgtcttga ggcgtgggcg cttgaaacgc  24120
tatccaatga cgaactcacg gcattcaatg cggtgatgga gtctggcaac caatacctcc  24180
agcaatatgc tgtgcgtgaa ctagaaagcc gccgtaaagc tgcacagggt gatgacaagc  24240
caaacttgat tgagccatct gcacctgctg ccgcatctga ggataatgga cctctgtctc  24300
gcgagcagta tctccgtgag atgatgacgc tgggttcccg cttcggtaca gacaagaaag  24360
ctgctgctga gtatcaggct aagctggatg ctcgccgccg tgcgggtatg gctcgcggac  24420
```

-continued tttaatcagt atttactgga cactatagaa gggagaaatg tctccctaaa ttatcaattt 24480
gatttataag gaggtttatt aatgtctacg ccgaataacc tgaccaacgt tgcagtttcc 24540
gcttccggtg aggtagacag ccttctcatt gagaaattca atggtaaggt aaatgagcag 24600
tacctgaaag gtgagaatat catgtcttac ttcgatgttc agactgtaac tggtactaac 24660
actgtaagca acaagtactt gggtgaaacc gagttgcagg ttctagcacc gggccagtct 24720
ccggctgcaa cctccactca ggccgataaa aaccagctgg taattgatgc cactgttatc 24780
gcgcgtaaca ccgttgcaca cctgcatgat gtacagggtg atattgacag cctgaaaccg 24840
aagctggcta ccaaccaagc taagcagctt aagaagatgg aagacgagat gcttattcag 24900
cagatgctgc tgggcggtat tgccaacact caggccaagc gcacaaatcc tcgtgtgaaa 24960
ggtcatggct tctctgtaaa cgtagaggtc aatgaaggag aagcactggt taacccacag 25020
tatgtaatgg cagctgtaga gtttgctctg gagcagcagc ttgagcagga agttgatatc 25080
tctgatgtag ctattctgat gccatggcgt tacttcaacg tactgcgtga cgcagaccgt 25140
attgttgata agagctacac gattagccag tccggtgcta ctatccaggg cttcgtactg 25200
tcttcctaca attgtccggt gatcccgtct aaccgcttcc ctaaatattc tcaggggcag 25260
aaacatcacc ttttgtctaa cgaagataac ggctatcgtt atgacccgat tgcagaaatg 25320
aacggtgcta tcgctgttct gttcactgct gatgcattgc tggttggtcg ctctatcgac 25380
gtaattggtg atatcttcta tgagaagaaa gagaagacct actacatcga caccttcatg 25440
tcagaaggtg caatccctga ccgttgggag gctgtgtcgg ttgttactac caagcgtcaa 25500
agcactggag cagttgactc tggtaatgct gcacagcaca ctcaggttct gaaccgtgca 25560
cagcgcaaag ctgtctacgt taagaatgct gcccctgcag gtgctttcgc tgctgctagc 25620
ttgtctgctg aagacttggt tgctgctgta cgtgcagtga tggctaatga cattaagccg 25680
actgcaatga aacctactga gtaataccta tgccctatct accttgcgta ggtagggttc 25740
tttttgttag gaggattcat gcctgtaatt agacaaacca gtaaagtagg acatatgatg 25800
gaagatgtgg ccttccagat tattgatagt aagctggaag cggtaaactt gtgtatgcga 25860
gctattggtc gtgagggtgt ggattctctc gactcaggtg acttggacgc agaagatgca 25920
agcaagatga tcgacatcgt atcccagcga ttccagtaca acaaaggagg tggctggtgg 25980
ttcaatcgtg aaccaaactg gcagattgca cctgatacca atggtgaagt caatctacct 26040
aacaactgcc tagcagtatt gcagtgttat gctttgggtg agaagaaagt acccatgact 26100
atgcgagcag gtaagctcta ctctacatgg agtcatacct ttgatatgcg taagcatgtg 26160
aatgctaatg gtatgattcg tcttacctta cttaccttac ttccatatga gcatctacct 26220
actagtgtaa tgcaggctat tgcctatcaa gctgctgtag agtttattgt gtctaaggat 26280
gcagatcaga ctaagctagc cactgcacag cagattgcca ctcagcttct aatggatgtg 26340
caatcagaac aaatgtcaca aaagcgattg aatatgcttg tacataatcc tacgcagcgt 26400
cagttcggta ttatggcagg tggttctcag aatgtacctg cttactctca ttcaccatat 26460
gacagttggg cacttcgtcc gtgggaggat cgttaatgga agtacaaggt tcattaggga 26520
ggcaaatcca agggattagc cagcaacctc cagcggtacg tcttgatggt caatgtacga 26580
ctatggtgaa catggtccct gatgtagtga atggaactca atcccgcatg ggtacaactc 26640
acattgctaa gctcttggat gaaggtacag ataatatggc aacgcaccat tatcgcaggg 26700
gtgaggggga tgaagagtat ttcttcacct taaagaaggg gcaagtgcca gagatatttg 26760
ataagcatgg acgcaagtgc aatgtcatct ctcaagatgc acctatgacc tacctttctg 26820

-continued

```
aagttgttaa ccctagggaa gatgtgcaat tcatgactat agctgatgtt acttttatgc  26880
ttaaccgtag gaaagtggtt aaagttagta ataggaagtc acctaaagtt ggagataaag  26940
ccattgtgtt ttgtgcatat ggtcaatacg gtacatctta ttctatcata attaatggaa  27000
ctacagctgc tagttttaaa acaccagatg gggaagtgc agaacatgtt gaacaaatac  27060
gaacggaacg tatcacttct gaattgtact ccaagttgca gcaatggagt ggtgtgaatg  27120
actatgaaat acaaagagat ggtacgagca tatttataga gagacgcgat ggtaaaagtt  27180
tcacagtaac aactaccgat ggtgcaaaag gtaaggactt agtggctatc aagaataaag  27240
ttagctctac tgacctactc ccttctcgtg cgcctgctgg ttataaagta caagtgtggc  27300
ctactggcag caaacctgag tctcgttact ggctgcaagc tgagcctaaa gagggaaacc  27360
ttgtgtcttg gaaagaaaca atagctgctg atgtattact tgggtttgat aaaggcacaa  27420
tgccttacat tattgaacgt acaggtatca tcgacggcat agctcaattc aagataagac  27480
aaggtgattg ggaagatcgt aaagtagggg atgacttgac taaccctatg ccctctttta  27540
ttgatgagga agtaccccag acaataggtg gaatgttcat ggtgcagaac cgcctatgct  27600
ttacagcagg tgaagcggtt attgcttctc gtacatcata cttcttcgat ttctttcgtt  27660
atacggttat ctctgcattg gcaactgacc catttgatat tttctcagat gcgagtgaag  27720
tctaccagct aaaacatgca gtgaccttag atggcgctac cgtattgttc tctgataagt  27780
cacaattcat actgccagga gataagcctt tagagaagtc aaatgcattg cttaagcctg  27840
ttacaacatt tgaagtgaac aataaagtga agccagtagt aactggtgaa tcggtaatgt  27900
ttgccactaa tgatggttct tactctggtg tacgagagtt ctatacggac tcttatagtg  27960
acactaagaa ggcacaagca atcacaagtc atgtgaataa actcatcgaa ggtaacatta  28020
ccaacatggc agcaagcacc aatgtcaata ggctacttgt cactactgat aagtatcgta  28080
acataattta ctgctatgat tggttatggc aaggtacaga ccgtgtacaa tcagcatggc  28140
atgtatggga gtggcctatg ggtacaaagg tgcgaggtat gttttattct ggtgaattac  28200
tttatctact ccttgagcga ggcgatggcg tctatctgga gaagatggac atgggtgatg  28260
cactaaccta tggtttgaat gaccgcatca gaatggatag gcaagcagag ttgatcttca  28320
agcattttaa agcagaagat gaatggatat ctgaaccact tccttggact cctactaacc  28380
cagaactttt ggattgcatc ttaatagaag ggtgggattc atatattgga ggttctttcc  28440
tgttcaaata taaacctagt gataacacct tgtctacaac ctttgacatg catgatgata  28500
accacgtaaa agcgaaggtt attgttggtc agatttaccc tcaagagttt gaacctacac  28560
ctgtagttat cagagatagg caagaccgtg tatcctatat tgatgtacct gttgtggggt  28620
tggttcacct taatcttgat atgtatcctg atttctccgt ggaagttaag aatgtgaaga  28680
gtggtaaagt acgcagggtg ctagcgtcaa accgtatagg tggtgctctc aacaacacag  28740
taggttatgt tgaaccaagg gagggtgtct tcagattccc actgagggct aagagtacgg  28800
atgctgttta tcgtattatt gtagaatcac ctcatacatt ccagcttcgc gatattgagt  28860
gggaagggag ctacaatcca accaaaagga gggtctaatg gctataggtt cagccgttat  28920
ggctggtatg tcttctattg gtagcatgtt tgcaggcagt ggtgcagcag ccgctgctgg  28980
aggtgctgcc gcaggtggcg gaggtttgct aggttcacta ggtggattcc taagtggctc  29040
cactgctggt ttctctaatg ctggccttct tggtgctggc cttcaagggt taggcttgat  29100
tggtgatcta tttggtggaa gtgatgaagc caaggcgatg aagaaagcac aagaagagca  29160
```

-continued

```
atggcggcag cagcttattg ctacacaaga ggcgtacaag acagtggcag acgcagaacg  29220
ttctgctgct aaacaatatc atgcagatgc aatcagtaat caggcttcac tgctacagca  29280
gcgagcacag gttgcattac ttgctggggc tactggtact ggtggtaatt ctgtgtcctc  29340
tatgcttaat gacttagcag cagatggcgg caggaaccag agtaccatca ttgataacta  29400
tgagaatcag aagattaatt tcaccaacca acttaagtct atccaacgtg gtggtcagat  29460
gcagatgcgt gagtttaaga agccttctgc tatgagtacc ttggttcaag gtattccaag  29520
tctggcatct gcctatgtaa ctggtagtaa gtctggcaag gcattgggta aagccttaac  29580
tgattctcgt acatattcat ctggaacaag aggtatttaa tggcaattga gcgacaagca  29640
gtacaaggtc tgccacaagt gcaggccact tctcctaatg tcatgacctt tgcacctcaa  29700
caagtgggag gtgtggaggc tggcgtggct tctacctccg gtagtaggtt tatcgaagac  29760
cttattcgtg cagccagcag tgtggctgat gttaccactg gtatccttaa tcagaagatt  29820
gaggaagata aggttgttca aatggaacgg gcatataacg gactaatgcc ttctgaggat  29880
gcaactcgtg gtggcgctcg tgctaacatg cttgtcaaag ctcaactgct agctaatgat  29940
gaagcagcac gaatgaaaga catggctact cgtttccaag ggacggatga cgagtggaca  30000
caacttatgg ttgactctcg taatgagatg cagaataagc tgttccagca ataccctgag  30060
ttgcaaggtg acaaagatac tatgcgtatg gtcactaatg tcttccaaga acagcagcct  30120
cagatttggg ctacacgaac ccagcataaa cttgaccgtg aacaagcaga ccgggaggat  30180
acctttgacg ggcgagtggc ttctacttgg gatcctaata ttgaccctga agcatctggc  30240
tatgctttac aggaacgaat ccgcgaaggt cttactcaag gattactacc tgaacagatg  30300
cacaagaagt tagtccagcg agcaatttca cttgcacaag gcggtgatgt tagcatggct  30360
gaagccctga agtatgtgaa ggacgataag ggtgtttctg tttatgctaa gaatccacag  30420
cttatcacag ccatcactag tggtaatgca gtttgggcta ggaataatgt agctgatgta  30480
actcgtatgt ctttcgaagt taaagaatca taccttgcag gtgatttaac tgatgaagaa  30540
ttgttggaac gagcacagca cattaataat ctgacaggta actctgtctt ctctaatcca  30600
gaactagagg cactgatgcg ccaacgggct aagcagaatg cagagctagg tgcaatgcag  30660
gatatgcgac gtgagcttta ctccgaccgc ctgactggct tccaaggtaa gactgataaa  30720
gagaagaagg cttacattga tgttatcaaa caggatagcc aactttatgc agaccagcaa  30780
atcaaacaac gtggcttgga cccttacagt caagaggctg aagctattcg tggtgcagtg  30840
gaagtgcagc gcctgcaatt catgaactcc aaaggtttag tggatgatac ctttgaatct  30900
cgtatcaagg ctatggaatc catgctatca cctgagcact ttgctaaagg tgaaccacag  30960
gagttaatga ccattcgtca gttgtgggag cagttacctg aagaaagtcg aggtgtcttc  31020
ggtgacactg tgaacggtta tatggataac tacaatactg cattacaaat gggagagaca  31080
cctttgcagg ctgcaaggtt tgcccgtgaa gcacagcaga aattctctcg tactgagaag  31140
gaaaccaaga agttcaactc cgctattgga gatgcactgg atgaggtatc tggtgctggc  31200
tggtttgatg gtaaaaccga ggtgtcagac ttaggtaaag ctattgcgga agaagagtta  31260
cgagctaagg ccaatatgtt gtggtctagc ggtatgcgta acatggattc tatcaagaag  31320
gctttaatca cttggggcaa taaacgctac actcaatcag aggatgcaaa gacttccggt  31380
ggctatttca ttaaaggtga ttacacttct gcatctgata tgcttatgtc agttgggaaa  31440
ggtgtaaacc ctaccgatgt ccctctggcg cttggtaggt atgtagaaac acagatgcca  31500
gaattgaaga aggagcttca agagtgggaa actaaggatg atgtgtacat tgattacaat  31560
```

```
gaacagaaag gaacttttgt gattcgtgct ggtgcagcag gtcgccctct ttctggagta  31620
atccctgtaa cttctttgga taccacttca ctactggatt ctgcctatca gaagaaagta  31680
gaagaacgag ataaaggcga gtatgttcat ccctatcgta cagatatcgg tgcacaagaa  31740
ccaatgccag ctaagccaac tgccaaagat attggtaaat taggattagc taacttcctc  31800
atgtcttctg cttttgcttc tggtgagaat ctaccttcta acttcgagat taactatcga  31860
ggcaatatgc aacaattcta tgacaagcta gctatggatg agaataaaga taaagttggc  31920
tttaataagg caactggaac ctttactcca tataaagacg ctcacggtga gtctatcggt  31980
tacggtcatt tcttaacgga agaagagaag cgagacgggt atattaagat tggcgatgaa  32040
ctagttccct atcgagggtc tatgtctcag cttacagaga gtaaggctcg cgctcttatg  32100
gagcaagatg ctaggaagca tgtgcctcct actcgtgact ggaagattcc gtttgaccag  32160
atgcatcctg cacagcaacg tggcttgatg gatttaacct acaatttagg taaaggtgga  32220
atccagaact caccgcgtgc tcttgctgca ttcaaagctg gtaagcttac ggaaggcttt  32280
atcgaaatgc tgggtactgc atcaagtgaa ggtaaacgta ttccgggcct actgaagcga  32340
cgcgctgagg catacaatat ggcagctgct ggtggtgtac ctaagatcac agaagtggag  32400
acgagggaag atggctctat gtgggttaag tttggtggac ctatgccagc aggctctgtt  32460
tctgcgtgga cgcataaacg tattggagcc gatggctggt atcaggttta tgaggctgca  32520
cctaccaagt tagctaaaga ctctaaggta ggtaaagtta aattgtagta cctaactcaa  32580
ggcttgtctc acatgtgaga caggtcttta tgataggcac tatggaggaa ctatggaaca  32640
agatattaag actaattggg ctggatatgt ccagtctact cctgagccgt tttctattga  32700
ggcggctccg gtatcggctc ctacgatacg ccagcgtaat gagttacaag agcaagttct  32760
tgaagccaaa gctgatgcgg acatcttagg tgctgtaggt gctgccttcc agaatgaatg  32820
gttggcattc ggaggtaagc gatggtatga ccgtgccact gctgatttca caccccaacc  32880
tgactttgaa atccaaccag agcaacgtga agcactacgt ttcaaatatg gtacggatat  32940
gatgcagaca atcactgagg gtgttcgttc tgaggatgaa ttgaacttcc gtattcagaa  33000
tgctgatgaa gaccttgagc gcaataagcg cattgctcag gctggatggg ccggctctgt  33060
ggcaacgatt ggcgctgctg tgcttgaccc agtgggttgg gttgcctcta ttccaaccgg  33120
tggtgcagct aaagttggac tcgtaggccg tgctgtgcgt ggcgctatcg ccgctggcgt  33180
gagtaatgcc gctattgaat ccgtattggt ccaaggtgac atgactcgtg atttagatga  33240
cattatggta gcactaggtt ccggtatggc tatgggtggc gttattggag ctgtagcgcg  33300
tggtagggcc actaagctca gtgagcaagg ggatgacagg gctgcgagca ttgtgcgcag  33360
tgcagacgca ggggaccgct atgtgcgtgc tgttgctgat gacagtatcg gtgcgatgcg  33420
tgttaagggc gaagaggtac tcactgaggg tgcatttgat atctctagca aaggtgaaga  33480
tttgctgaaa accctacagc gggaaggtaa tgcaattgat atgacacctc gccgctgggc  33540
cggaactatg tctgcccttg ggactgtcgt gcactcctct caggatgcta gtgttcgtgg  33600
cctcggtgct cgcctgtttg agtctccgca aggtttaggt atgcaaaagg catctgccag  33660
tcttatgcag aataccaact tgaatcgact gaagtctgct gatatgaacc gtttcaatga  33720
cgggtttgac ttatggctca aagaaaataa tatcaatcca gttgcaggcc atactaactc  33780
tcactatgtg cagcaatata atgagaaggt atgggaagct gtacgcatcg gtatggatga  33840
ggctacgcct aagtctatcc gtatggcagc agaggggcag caagctatgt atcgtgaagc  33900
```

```
attagcatta cgtcaacgct ctggtgaagc tgggtttgaa aaggttaaag cagatgataa  33960
gtacatgcct gatatttttg acagtatgaa ggctcgtcgt caattcggta tgcacgataa  34020
agaagatatc attgagttat tctctcgtgc ttatcagaac ggcgctcgta aaattccaaa  34080
agaagtagcg gatgaaattg cacgagcaca agtaaaccgt gttgtggatg ccactctgac  34140
aggacgtatg agtttcgaaa aggctatgtc tggtcagact aaagcagagt atgaagcaat  34200
aatgcgcaag gcaggcttca gtgatgaaga aattgaaaag atggtagaag ctctggataa  34260
taaagaaacc aaagataata tctctaaccg agctaagatg agtttaggct tagatgttac  34320
tcaagagtac aatggcattc gtatgcgtga ctttatgaat actaacgtgg aagagttaac  34380
agataactac atgaaggaag cggcaggtgg tgctgccttg gctcgtcaag gtttctctac  34440
ctatcaggct gcacttaatg caattgacct tgtagagcga aatgcacgaa atgcagctaa  34500
agatacaaaa gcacacgcac aatttgaagc ggagtctgct aagattcgtc aatcagagcc  34560
tgattacaag aaggcacaag agaagattga agagctaaag aagcgactta aattgaaaga  34620
gaaagatgaa gcagcaggtc tggctattga tgaagaaatc cgtcagatgc gagaagggct  34680
tcgcttgatt atgggtaaat ctatcgatgc agacccacag gctttgtcta ctaaaatgct  34740
gcgtcgtggt cgtgacatca caggcgtact tcgcttaggt cagatgggtt tcgcacagct  34800
aggtgaactt gctaacttca tgggtgagtt tggtattgct gcaaccacta tagctttagg  34860
taagcaattc cgctttacat ctaaggcttt gcggagcggt gatggcttct tccgagataa  34920
gaacttggca gaagtagaga ggatggtagg ttacattggt gaggataact ggctaacaac  34980
caagggtgca cgtccagatg agtttggtga tgtaaccaca gtaaaaggaa tgatggctca  35040
ctttgaccaa tccatgaact caatacgtcg tgctcaaacc aacctatcac tcttccgcat  35100
ggcacagggt tctctggagc gaatgaccaa taggcaaata gctttgtctt tcattgacca  35160
ccttgaaggc aagaagatta ttcctcagaa gaaactggag gaacttggtc ttactcagga  35220
gttcatgact aacctacaga agcactatga tgctaactct aaaggttctg gcttgcttgg  35280
ctttgataca atgccttatg ccatgggtga aactttagct aatgctattc gtcgtaagtc  35340
aggtctaatt atccaacgta acttcattgg tgatgaaggt atctggatga acaaagcact  35400
aggtaagaca tttgcacagc ttaagtcatt ctctcttgta tctggtgaga agcaatttgg  35460
tcgagggatt cgccacgata aaattggtct tgctaagaag acagcttacg ggtttgcttt  35520
gggttcaata gtgtatgcgg caaaagccta tgtgaactct attgggcgag aagaccaaga  35580
tgaatatttg gaagagaagt tatcgcctaa agggttggcc tttggtgcaa tgggtatgat  35640
gagtacaact gctgtattta gtctaggtgg agatttctta ggtggcctag gtgttctacc  35700
ttctgagtta gtacaatccc gttatgaggc tggctttcag actaaaggtt tgatagacca  35760
aataccacta gtaggtgttg gtcaagatgc atatcgttta gcagattcta taactaaata  35820
tgcagagggt gatacagaag gtgtagatgt ggcacgtagg gctttacgct tagtgcctct  35880
aactaatgta ataggaatcc agaacgcatt gcgttatggc ttagatgaac tggaggattg  35940
atgagttata ctttcacaga acatatagcc aacggtacgc aagtaaccta tccctttagc  36000
tttgctggca gggataaagg ctatcttcgt gcctcagatg tgatagtgga atctcttcaa  36060
ggtaacactt ggattgagat tacatctggc tggcaattaa ctggtacgca tcaaatcact  36120
tttgatgtag cacccgttgc aggtttgaag ttccgtattc gaagggaagt acaaaaggaa  36180
tatccatacg ctgagtttga ccgtggtgtt accttggata tgaagtcttt aaatggttct  36240
ttcattcata tactggagat tacacaggag ttacttgatg ggttttatcc agaaggatac  36300
```

ttcattaagc agaatgtaag ctggggcggc aataagatta ctgacctagc tgatggtgag 36360
aatccaaaag atgcagtaaa taaatcacag ctagatgcta tcgacaagaa gcatactgat 36420
tggaactctg cacaagatat agagattgct ggtattaaga gagggatggt gtctggtgtg 36480
tcgcatcgaa ctattccttg gtatatggtt gcctccggtg gagagcaaat cattcgacca 36540
ccttactcat ttgatgatgc tatggtgttt ataaacggtg tattccagca tgaactagca 36600
ggtgcagtat ccgtggggta tgatgttata accctgtcca agccattaca ggctggggat 36660
gaagtttatg tgcttatcgg tagtcgctta accccaccta caagtgcgga tactatcctc 36720
tttacacaag cagtgagtga aggcacacaa tctatcgaca ttgtaacggc tttccaacgt 36780
cttgatgtat acttggatgg cctgtatcaa cctaataatg cttatgaaat cgtagggtct 36840
actatcactt tcagtgagcc attacctgag tgtgtcgtaa gtatgaagct acaactagtg 36900
taaggaggtg agatgattaa ctccgaactg gtagatagtg gtgtgaagct tgcgccacct 36960
gcattagtct caggtgggta cttcctcggt atcagttggg ataattgggt gttaatagca 37020
acattcattt ataccgtgtt gcaaattgga gactggtttt ataccaagat taaactatgg 37080
aggaagaacc gtgagcgtcc acaataaaca tgcagctaca gaagatgagg ttggcatcct 37140
gcatggtgct attaccaaaa tctttaataa gaaagcacag gcaatactgg acactataga 37200
agaagaccca gatgcagcac tgcatttagt ctctggtaaa gacattggag ctatgtgtaa 37260
gtgggttctt gataatggta ttaccgctac acctgctgca cagcaggagg agtccaagct 37320
atctaagcgc ctcaaggcta tccgagaggc atcaagtggc aagattattc aattcactaa 37380
ggaggattga tggctaaggc aagagaatca caagcggagg ctcttgccag atgggagatg 37440
ctacaggagt tacagcagac ctttccttac acagcggaag gtttgcttct ctttgcagac 37500
acagttattc ataacttaat tgcaggcaac cctcatctga ttcgtatgca ggctgatatc 37560
ttgaagttcc tattctacgg acacaagtat cgcctcatcg aagcgcctcg tggtatcgct 37620
aagacaacac tatcagcaat ctatacagta ttccgtatca ttcatgaacc gcataagcgt 37680
atcatggttg tatcccaaaa cgccaagcga gcagaggaaa tcgcaggttg ggtagttaaa 37740
atcttccgtg gcctagactt tcttgagttt atgctaccgg acatctacgc aggggaccgt 37800
gcctcagtta aggcatttga gattcattac accctacgtg gcagtgacaa gtcgccttct 37860
gtgtcttgtt actcaatcga agcaggtatg cagggtgcgc gtgcagatat catcctagca 37920
gatgacgttg agtcaatgca gaatgctcgt acagcggcag gacgtgcctt gcttgaggaa 37980
ctgaccaagg agtttgaatc tattaaccag tttggtgata ttatctacct tggtactcct 38040
cagaacgtaa actctatcta caataaccta cctgctcgtg gttactctgt tcgtatctgg 38100
actgcacgtt atccctcagt ggagcaggag caatgctatg gtgacttcct tgcacctatg 38160
attgtgcagg atatgaagga caacccagca cttcgctcag ggtatggctt ggatggcaat 38220
agtggtgccc cttgtgcacc tgaaatgtat gatgatgatg tgctgattga gaaggaaatc 38280
tcgcagggtg cggctaagtt ccagcttcag ttcatgctta acactcgcat gatggatgct 38340
gaccgctatc cgctacgcct gaacaacctc atcttcactt cattcggtac agaggaagtc 38400
cctgtgatgc ctacgtggag caatgattcc atcaatatta ttggcgatgc accgaagtat 38460
ggcaataagc ctacagactt catgtatcga cctgtggctc gcccgtatga atggggcgct 38520
gtcactcgta agattatgta tattgaccct gctggtaaac acctctgcca gcgtaaaacc 38580
ctcttaattc ggtggaactc tcactgagac aataccgagc gaagcctgtt gcaataacag 38640

```
gaacgtgtag agactaactg taaggccaag cggtctgaaa cagagggagg cgcaagccta  38700
agatatagtc cgacctacta ggtgactagt agaagttaaa gtagcgaatt aacgtaacaa  38760
ttgaagggag ttaaatatga cagagcataa agtttatcat attcgtgttg ttggtgaaac  38820
tgatgtaatg caaggttata ttggtgtaac ctccgatatt aagaagcgta tgagagagca  38880
caagtgtgca ggccgtcttt gtgatggccg cgagtacgtt atcttattca ctggtagcaa  38940
agaagagtgt tatgcactag aagagaagct acgcccacat gacaacatgg gttggaataa  39000
gggtaaaggt ggttatcgca aagcaggtaa catcgagaaa ggtgaacgca taagtattgc  39060
cactgaaatc aagaaaggac agcacttgtc tgttgccact gagttcaaga aaggcatgac  39120
accttacaac aaaggtactg gcaaagatta catattcact tctccagatg gtgaagagtt  39180
tcttgtaact tgcattactg acttctgtaa agagcacaac ctaacacctc agaatatgcg  39240
taaggtggca cgtggtttac gtaaacacca caagggttgg ctcgcacgtc acgttcaaac  39300
cgggaggtaa gaatggggat gaaacgggtg tggctatcgt cttcctgcac ggcacattca  39360
tttatgtgta tcagtgcttt ggtgtgccgg gaggataccg cgaatcgtcc ctgaatcgca  39420
ttgtgcaggc cgcaaagcag gcaggtgtta aagaggtatt cattgaaaag aactttggtc  39480
atggcgcgtt tgaggccgtt ataaagccat actttgaacg agagtggcct gtgactctgg  39540
aggaagatta cgccaccgga cagaaagagt tgcgtatcat tgaaacacta gagccactaa  39600
tggcggccca caggctcatc ttcaacgcag agatggtcaa gtctgatttt gagtcggtac  39660
agcactatcc gcttgagcta cgcatgtcat acagcctttt caatcaaatg tcgaacatca  39720
cgattgagaa gaacagccta cgacacgatg accgcttaga cgctctgtat ggcgctatac  39780
ggcaattaac ttctcagata gactatgacg aggttacacg gattaatcgc ctcagagcgc  39840
aggagatgcg cgattacatc catgctatga acacacctca cctccgtagg gcaatgctct  39900
atggagatta tggcactgag cgaagagtaa ccaacacttc cgtggctatg cagcaaagag  39960
tatacggtca gaattacagg agtaaatcgg caagcagaaa tacactttct gcaaggattt  40020
caaggactta ttaattaccg gacactatag aaggaaggcc cagataataa gagaaataac  40080
aaggataata taggttaacc taggttatat aggtattcct tagtatgggt gtactcctgt  40140
acaccctatt ccttacttcc ttactatact tacataatag gagagagaga gagagagaat  40200
gtctaatagt tatagtacac aacctcttac aggtaagtct gctcgtaagc agatacaacc  40260
tgttagtgaa gcccttatgc ttcctgtagt ttacgaggac actgttgaga agaaaggtga  40320
tgttattaat gatgccacca aatcaggtaa gcagaaaggg gccatggtgt gtcttgatac  40380
acatgataac ctggttattg ctatcgcagt tgatggcaaa gaagattcca attggttgac  40440
agctaataaa gcggtcacta ctattacccc agcttaagag gagagttaca tgtctaaata  40500
tggaaccgca ggtactgtta ctggtcaggc ttttcgagta aaaactgtac aaaccactgc  40560
aacggcaatc cctttgccta ttgttgctga agcagacctt aagaagaaag atcatcctat  40620
caacattaaa cacctctctg gtaaacagaa aggtgccatg gttgctgtag agaaaacaga  40680
ccaatccttg tacatcgcta ttgcacgtgg gagtgaaccc accgacaagt gggatgcaac  40740
tactatggag ttggaccctg taacacctgc ggcttaattg taaagacgaa ggagattcaa  40800
catggtcttc acactcgaag atttcgttgg ggactggcga cagacagccg gctacaacct  40860
ggaccaagtc cttgaacagg gaggtgtgtc cagtttgttt cagaatctcg ggtgtccgt  40920
aactccgatc caaaggattg tcctgagcgg tgaaaatggg ctgaagatcg acatccatgt  40980
catcatcccg tatgaaggtc tgagcggcga ccaaatgggc cagatcgaaa aaatttttaa  41040
```

```
ggtggtgtac cctgtggatg atcatcactt taaggtgatc ctgcactatg gcacactggt  41100
aatcgacggg gttacgccga acatgatcga ctatttcgga cggccgtatg aaggcatcgc  41160
cgtgttcgac ggcaaaaaga tcactgtaac agggaccctg tggaacggca acaaaattat  41220
cgacgagcgc ctgatcaacc ccgacggctc cctgctgttc cgagtaacca tcaacggagt  41280
gaccggctgg cggctgtgcg aacgcattct ggcgtaaagg tcaatagtgc ttaacaaaca  41340
cttcaagcgc cgtgagttcg cttgccgttg tgggtgcggt acatccacag tagatgctga  41400
gttactacag gtagtcacag atgtacgtga gcactttggt gctcctgtag ttattacttc  41460
tggacaccgc tgtgctaagc acaatgctaa tgtgggaggt gctaagaact ccatgcatct  41520
tactggtaag gctgctgaca ttaaggtaca aggtattaca ccttaccgtg tatggtccta  41580
tctaacagca cgctacccca ataaatatgg cattgggtct tatcctaatt tcacccacat  41640
tgatgtaaga gagggatgtg cacgatggta agatgtattg aatggtgcga gcgcatggtt  41700
gctcaagctg ccgaggatgg caactatgat gactggaaga actactctga cttgttagct  41760
caatggaaag ggagatgcaa tgaaaaagct gtttaagtct aagaaagtgg taggtgcact  41820
ggttgcacta gtgattgctc ttgtttctgt aggtcttggc gtagacctag gtgaaggtgc  41880
ggaaggttcc gtcactgacg tggtatgcca agtaatcacc tgtgaataag gtgctagagg  41940
tggtagcagg tcttattggc ctgctgcttg ccgctaagaa gaagaaggaa gagaaggagg  42000
cacaaagtga ggcgaatcat gctagcgaca atcctgctga ttggttcact gatcacttca  42060
gggtgtcaga cggcgttacc agagaatcca aaggtgaagc ctctgaagcc gacgcttacg  42120
gcagtctacg aggtggacga taaagtctgc ttcagtaagc ctgacgctac aaaattaggt  42180
ctgtacattc tctcgctaga acgcgggtat aattaataca tagttttatg tatcagtgtc  42240
ttacgattta ctggacacta tagaagagat aagatagtgc cgttcttttg agcggcctat  42300
tactagccaa tcttcatagg gagggttggg aagtaatagg agagtatatg gctaagttaa  42360
ctaaacccaa gacaacgggc ttactacata gagatactgt actagctacc ttattagata  42420
atttactatc taaaaggcgt gttacatttg aaggtgtagt tccaagtgaa gatactaaaa  42480
ttgagataga agtacctaca gcatgggatt tagattcttc gtgggcatca cttgtatcat  42540
taagtacacc tacactttgt acagcttgga ttactaaagt gtcagatact agattagaag  42600
tacatgtgtt ccatacagca caagttgaaa tagacataga tgtagatgtt tacattctag  42660
gtaaacacat tgtcagtgcg taagcactgc ttttcgcgca acttttctta aaggttatca  42720
tgatggtagc ctttcagaaa aggaggttac atgattcaaa gactaggttc ttcattagtt  42780
aaattcaaga gtaaaatagc aggtgcaatc tggcgtaact tggatgacaa gctcaccgag  42840
gttgtatcgc ttaaagattt tggagccaaa ggtgatggta agacaaacga ccaagatgca  42900
gtaaatgcag cgatggcttc aggtaagaga attgacggtg ctggtgctac ttacaaagta  42960
tcatctttac ctgatatgga gcgattctat aacacccgct tcgtatggga acgtttagca  43020
ggtcaacctc tttactatgt gagtaaaggt tttatcaatg gtgaactcta taaaatcacg  43080
gataaccctt attacaatgc ttggcctcaa gacaaagcgt ttgtatatga gaacgtgata  43140
tatgcacctt acatgggtag cgaccgtcat ggtgttagtc gtctgcatgt atcatgggtt  43200
aagtctggtg acgatggtca aacatggtct actccagagt ggttaactga tatgcatcca  43260
gattacccta cagtgaacta tcattgtatg agtatgggtg tatgtcgcaa ccgtctgttt  43320
gccatgattg aaacacgtac tttagccaag aacgaactaa ccaattgtgc attgtgggat  43380
```

-continued

```
cgccctatgt ctcgtagtct gcatcttact ggtggtatca ctaaggctgc aaatcagaga  43440
tatgcaacaa tccatgtacc tgatcacgga ctcttcgttg gtgattttgt taacttctct  43500
aactctgcgg taacaggtgt atctggtgat atgaaggttg caacagtaat agataaggac  43560
aacttcacgg ttcttacacc taaccagcag acttcagatt tgaataacgc tggaaagaat  43620
tggcacatgg gtacttcttt ccataagtct ccgtggcgta agacagatct tggtctaatc  43680
cctcgtgtca cagaggtgca tagctttgct actattgata acaatggctt tgttatgggc  43740
tatcatcaag gtgatgtagc tccacgagaa gttgggcttt tctacttccc tgatgctttc  43800
aatagcccat ctaattatgt tcgtcgtcag ataccatctg agtatgaacc agatgcggca  43860
gagccatgca tcaagtacta tgacggtgta ttatacctta tcactcgtgg tactcgtggc  43920
gaccgactag gaagctctct gcatcgtagt agagatatag gtcagacttg ggagtcacta  43980
agatttccac ataatgtgca tcatactact ttaccgtttg ctaaggtagg agatgacctt  44040
attatgtttg gttcagaacg tgcagaaaat gaatgggaag caggtgcacc agatgatcgt  44100
tacaaggcat cttatcctcg taccttctat gcacgattga atgtaaacaa ttggaatgca  44160
gatgatattg aatgggttaa catcacagac caaatctatc agggtgacat tgtgaactct  44220
agtgtaggtg taggttctgt tgtagttaaa gacagcttca tttactatat ctttggtggt  44280
gaaaaccatt tcaacccaat gacttatggt gacaacaaag acaaagaccc atttaaaggt  44340
catggacacc ctactgatat atactgctat aagatgcaga ttgcaaatga caatcgtgta  44400
tctcgtaagt ttacatatgg tgcaactcca ggtcaagcta tacctacttt catgggtact  44460
gatggaatac gaaatatccc tgcacctttg tatttctcag ataacattgt tacagaggat  44520
actaaagttg gacacttaac acttaaagca agcacaagtg ccaatatacg atctgaaatg  44580
cagatggaag gtgagtatgg ctttattggc aagtctgttc caaaggacaa accaacaggt  44640
caacgtttga ttatttgtgg tggagaaagg acttcatcat cttcaggtgc acagataact  44700
ttgcacggtt ctaattcaag taaggctaag cgtatcactt ataacggaaa cgagcaccta  44760
ttccaaggtg caccaatcat gcctgctgta gataaccagt ttgctgctgg tggacctagt  44820
aaccgattca ctaccatcta cctaggcagt gaccctgtta caacttcaga tgctgaccac  44880
aagtacggta tctctagtat taataccaag gtgttaaagg cttggagcag ggttggtttt  44940
aaacagtatg gtttgaatag tgaagcagag aggaaccttg atagcataca cttcggtgtc  45000
ttggctcagg atattgtagc tgcttttgaa gctgaagggt tggatgccat taagtatgga  45060
attgtgtcct tcgaagaagg taggtatggt gtgagatata gtgaagttct aatcctagag  45120
gctgcctata ctcgccatcg tcttgataaa ttagaggaga tgtatgccac taataaaatc  45180
agttaagcaa tctgctgcac gccagaacac ataagaactt atacaatcag gacgtgaccc  45240
taagcaggca tacgccattg ccaaggatgt acaacgtcgt gccatgaaga aaccttctgc  45300
atcttctgcg taagcaggtt aatatcttag tgtacacaag ggcagactta ggtttgctct  45360
tagtgtaatc caaggaggta acatgcaaga ggagaattgg gatgtgtaat gttggatatg  45420
gagaaggttg aacctcagtg ttgtacaagg attaaccaaa gtaaaaattt tgatataggc  45480
gtgtgtcagc tctctcgccc tcgccctcgc cggattttcc ccatatgggg ccgcgctgcg  45540
gttggcttgg ggattgggct aggctgggcc gtcttcaacc tgctgccgca ggaagctcga  45600
tgggttggct gagggttgcc gagggctgcg cttagtggta cacaagtaga acgcctagga  45660
agcgctaggg cacgccttag tgttggacaa ggtgattgcc ttagtgcaac cgtttagggc  45720
ttacacaggc cgttttaggg caattcctga gtgtttgaca gggtgtgagg gtgtgggcta  45780
```

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
acgaaggaga ttcaacatgg tcttcacact cgaagatttc gttggggact ggcgacagac 60
agc 63

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
gagtaaccat caacggagtg accggctggc ggctgtgcga acgcattctg gcgtaaagg 59

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cttaagaaga aagatcatcc tatcaac 27

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gttcttagca cctcccacat 20

<210> SEQ ID NO 8
<211> LENGTH: 228
<212> TYPE: DNA
<213> ORGANISM: Enterobacteria phage K1E

<400> SEQUENCE: 8
gttgctgtag agaaaacaga ccaatccttg tacatcgcta ttgcacgtgg gagtgaaccc 60
accgacaagt gggatgcaac tactatggag ttggaccctg taacacctgc ggcttaattg 120
taaagacgag gtcaatagtg cttaacaaac acttcaagcg ccgtgagttc gcttgccgtt 180
gtgggtgcgg tacatccaca gtagatgctg agttactaca ggtagtca 228

<210> SEQ ID NO 9
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

```
<400> SEQUENCE: 9

tactatggag ttggaccctg taacacctgc ggcttaattg taaagacgaa ggagattcaa     60

catggtcttc acactcgaag atttcgttgg ggactggcga cagacagc                108


<210> SEQ ID NO 10
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (27)..(27)
<223> OTHER INFORMATION: a, c, t, g, unknown or other

<400> SEQUENCE: 10

tactatggag ttggaccctg taacacntgc ggcttaattg taaagacgaa ggagattcaa     60

catggtcttc acactcgaag atttcgttgg ggactggcga cagacagc                108


<210> SEQ ID NO 11
<211> LENGTH: 107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

gagtaaccat caacggagtg accggctggc ggctgtgcga acgcattctg gcgtaaggtc     60

aatagtgctt aacaaacact tcaagcgccg tgagttcgct tgccgtt                 107


<210> SEQ ID NO 12
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gagtaaccat caacggagtg accggctggc ggctgtgcga acgcattctg gcgtaaaggt     60

caatagtgct taacaaacac ttcaagcgcc gtgagttcgc ttgccgtt                108
```